United States Patent
Lynn et al.

(10) Patent No.: US 9,042,952 B2
(45) Date of Patent: *May 26, 2015

(54) SYSTEM AND METHOD FOR AUTOMATIC DETECTION OF A PLURALITY OF SPO2 TIME SERIES PATTERN TYPES

(75) Inventors: Lawrence A. Lynn, Columbus, OH (US); Eric N. Lynn, Villa Ridge, MO (US)

(73) Assignee: Lawrence A. Lynn, Columbus, OH (US)

( * ) Notice: Subject to any disclaimer, the term of this patent is extended or adjusted under 35 U.S.C. 154(b) by 392 days.

This patent is subject to a terminal disclaimer.

(21) Appl. No.: 11/351,961

(22) Filed: Feb. 10, 2006

(65) Prior Publication Data

US 2006/0149144 A1  Jul. 6, 2006

Related U.S. Application Data

(63) Continuation-in-part of application No. 11/280,559, filed on Nov. 16, 2005, and a continuation-in-part of application No. 11/274,960, filed on Nov. 16, 2005, now abandoned, and a continuation-in-part of (Continued)

(51) Int. Cl.
*A61B 5/1455* (2006.01)
*A61B 5/08* (2006.01)
*A61B 7/00* (2006.01)

(Continued)

(52) U.S. Cl.
CPC . *A61B 7/003* (2013.01); *A61B 5/00* (2013.01); *A61B 5/0205* (2013.01); *A61B 5/087* (2013.01); *A61B 5/145* (2013.01); *A61B 5/14551* (2013.01); *A61B 5/412* (2013.01); *A61B 5/4818* (2013.01); *A61B 5/726* (2013.01); *A61B 5/7275* (2013.01)

(58) Field of Classification Search
USPC .................. 600/323, 324, 484, 529
See application file for complete search history.

(56) References Cited

U.S. PATENT DOCUMENTS

| 3,638,640 A | 2/1972 | Shaw |
| 3,646,606 A | 2/1972 | Buxton |

(Continued)

FOREIGN PATENT DOCUMENTS

| DE | 2450900 | 5/1975 |
| DE | 9 200 422.9 | 7/1992 |

(Continued)

OTHER PUBLICATIONS

Downs, John B., Has Oxygen Administration Delayed Appropriate Respiratory Care? Fallacies Regarding Oxygen Therapy, Respiratory Care, Jun. 2003, vol. 48, No. 6.

(Continued)

*Primary Examiner* — Etsub Berhanu
(74) *Attorney, Agent, or Firm* — International IP Law Group, PLLC

(57) ABSTRACT

The disclosed embodiments relate to pulse oximetry. An exemplary pulse oximeter comprises a probe that is adapted to be attached to a body part of a patient to create a signal indicative of an oxygen saturation of blood of the patient, and a processor that is adapted to receive the signal produced by the probe, to calculate an SPO2 value based on the signal, to detect a plurality of pattern types of SPO2 indicative of pathophysiologic events, and to produce an output indicative of a detected one of the plurality of pattern types.

53 Claims, 30 Drawing Sheets

Related U.S. Application Data application No. 11/280,653, filed on Nov. 16, 2005, said application No. 11/280,559 is a continuation-in-part of application No. 10/150,582, filed on May 17, 2002, now Pat. No. 7,081,095, said application No. 11/274,960 is a continuation-in-part of application No. 10/150,582, said application No. 11/280,653 is a continuation-in-part of application No. 10/150,582, and a continuation-in-part of application No. 10/150,842, filed on May 17, 2002, now Pat. No. 7,758,503.

(60) Provisional application No. 60/921,687, filed on May 17, 2001, provisional application No. 60/291,691, filed on May 17, 2001, provisional application No. 60/295,484, filed on Jun. 10, 2001, provisional application No. 60/291,687, filed on May 17, 2001.

(51) Int. Cl.
*A61B 5/00* (2006.01)
*A61B 5/087* (2006.01)
*A61B 5/145* (2006.01)
*A61B 5/0205* (2006.01)

(56) References Cited

U.S. PATENT DOCUMENTS

| | | |
|---|---|---|
| 3,884,219 A | 5/1975 | Richardson et al. |
| 3,926,177 A | 12/1975 | Hardway et al. |
| 3,999,537 A | 12/1976 | Noiles |
| 4,022,353 A | 5/1977 | Hamlin et al. |
| 4,036,211 A | 7/1977 | Veth et al. |
| 4,106,503 A | 8/1978 | Rosenthal et al. |
| 4,141,354 A | 2/1979 | Ismach |
| 4,340,044 A | 7/1982 | Levy et al. |
| 4,365,636 A | 12/1982 | Barker |
| 4,523,279 A | 6/1985 | Sperinde |
| 4,630,614 A | 12/1986 | Atlas |
| 4,651,746 A | 3/1987 | Wall |
| 4,696,307 A | 9/1987 | Montgieux |
| 4,714,341 A | 12/1987 | Hamaguri |
| 4,738,266 A | 4/1988 | Thatcher |
| 4,757,824 A | 7/1988 | Chaumet |
| 4,765,340 A | 8/1988 | Sakai et al. |
| 4,800,495 A | 1/1989 | Smith |
| 4,802,485 A | 2/1989 | Bowers et al. |
| 4,805,623 A | 2/1989 | Jobsis |
| 4,807,631 A | 2/1989 | Hersh et al. |
| 4,838,275 A | 6/1989 | Lee |
| 4,846,195 A | 7/1989 | Alt |
| 4,869,253 A | 9/1989 | Craig |
| 4,911,167 A | 3/1990 | Corenman et al. |
| 4,913,150 A | 4/1990 | Cheung et al. |
| 4,936,679 A | 6/1990 | Mersch |
| 4,938,218 A | 7/1990 | Goodman et al. |
| 4,971,062 A | 11/1990 | Hasebe et al. |
| 4,972,331 A | 11/1990 | Chance |
| 4,974,591 A | 12/1990 | Awazu et al. |
| 4,995,400 A | 2/1991 | Boehringer et al. |
| 5,028,787 A | 7/1991 | Rosenthal et al. |
| 5,065,749 A | 11/1991 | Hasebe et al. |
| 5,066,859 A | 11/1991 | Karkar et al. |
| 5,072,737 A | 12/1991 | Goulding |
| 5,084,327 A | 1/1992 | Stengel |
| 5,092,326 A | 3/1992 | Winn et al. |
| 5,094,246 A | 3/1992 | Rusz et al. |
| 5,119,815 A | 6/1992 | Chance |
| 5,122,974 A | 6/1992 | Chance |
| 5,123,420 A | 6/1992 | Paret |
| 5,134,995 A | 8/1992 | Gruenke et al. |
| 5,143,078 A | 9/1992 | Mather et al. |
| 5,167,230 A | 12/1992 | Chance |
| 5,190,038 A | 3/1993 | Polson et al. |
| 5,199,424 A | 4/1993 | Sullivan |
| 5,206,807 A | 4/1993 | Hatke |
| 5,218,962 A | 6/1993 | Mannheimer et al. |
| 5,233,983 A | 8/1993 | Markowitz |
| 5,238,001 A | 8/1993 | Gallant et al. |
| 5,246,003 A | 9/1993 | DeLonzor |
| 5,247,931 A | 9/1993 | Norwood |
| 5,253,645 A | 10/1993 | Friedman et al. |
| 5,263,244 A | 11/1993 | Centa et al. |
| 5,269,310 A | 12/1993 | Jones et al. |
| 5,275,159 A | 1/1994 | Griebel |
| 5,279,295 A | 1/1994 | Martens et al. |
| 5,285,783 A | 2/1994 | Secker |
| 5,297,548 A | 3/1994 | Pologe |
| 5,303,699 A | 4/1994 | Bonassa et al. |
| 5,309,908 A | 5/1994 | Friedman et al. |
| 5,312,454 A | 5/1994 | Roline et al. |
| 5,318,597 A | 6/1994 | Hauck et al. |
| 5,329,931 A | 7/1994 | Clauson et al. |
| 5,335,654 A | 8/1994 | Rapoport |
| 5,353,788 A | 10/1994 | Miles |
| 5,355,880 A | 10/1994 | Thomas et al. |
| 5,368,026 A | 11/1994 | Swedlow et al. |
| 5,372,136 A | 12/1994 | Steuer et al. |
| 5,385,143 A | 1/1995 | Aoyagi |
| 5,385,144 A | 1/1995 | Yamanishi et al. |
| 5,390,666 A | 2/1995 | Kimm et al. |
| 5,390,670 A | 2/1995 | Centa et al. |
| 5,398,682 A | 3/1995 | Lynn |
| 5,413,099 A | 5/1995 | Schmidt et al. |
| 5,423,327 A | 6/1995 | Clauson et al. |
| 5,469,845 A | 11/1995 | DeLonzor et al. |
| 5,482,036 A | 1/1996 | Diab et al. |
| 5,483,646 A | 1/1996 | Uchikoga |
| 5,483,969 A | 1/1996 | Testerman |
| 5,485,851 A | 1/1996 | Erickson |
| 5,490,502 A | 2/1996 | Rapoport et al. |
| 5,520,176 A | 5/1996 | Cohen |
| 5,535,739 A | 7/1996 | Rapoport et al. |
| 5,540,733 A | 7/1996 | Testerman et al. |
| 5,549,106 A | 8/1996 | Gruenke et al. |
| 5,551,419 A | 9/1996 | Froehlich et al. |
| 5,553,614 A | 9/1996 | Chance |
| 5,558,086 A | 9/1996 | Smith et al. |
| 5,564,417 A | 10/1996 | Chance |
| 5,575,285 A | 11/1996 | Takanashi et al. |
| 5,584,298 A | 12/1996 | Kabal |
| 5,605,151 A | 2/1997 | Lynn |
| 5,611,337 A | 3/1997 | Bukta |
| 5,619,991 A | 4/1997 | Sloane |
| 5,630,413 A | 5/1997 | Thomas et al. |
| 5,632,270 A | 5/1997 | O'Mahony et al. |
| 5,645,053 A | 7/1997 | Remmers et al. |
| 5,645,054 A | 7/1997 | Cotner et al. |
| 5,645,059 A | 7/1997 | Fein et al. |
| 5,645,060 A | 7/1997 | Yorkey |
| 5,660,171 A | 8/1997 | Kimm et al. |
| 5,680,857 A | 10/1997 | Pelikan et al. |
| 5,682,878 A | 11/1997 | Ogden |
| 5,692,503 A | 12/1997 | Kuenstner |
| 5,704,345 A | 1/1998 | Berthon-Jones |
| 5,716,384 A | 2/1998 | Snell |
| 5,724,580 A | 3/1998 | Levin et al. |
| 5,730,124 A | 3/1998 | Yamauchi |
| 5,730,144 A | 3/1998 | Katz et al. |
| 5,740,795 A | 4/1998 | Brydon |
| 5,743,250 A | 4/1998 | Gonda et al. |
| 5,749,900 A | 5/1998 | Schroeppel et al. |
| 5,751,911 A | 5/1998 | Goldman |
| 5,758,644 A | 6/1998 | Diab et al. |
| 5,765,563 A | 6/1998 | Vander Schaaf |
| 5,769,082 A | 6/1998 | Perel |
| 5,769,084 A | 6/1998 | Katz et al. |
| 5,779,631 A | 7/1998 | Chance |
| 5,782,240 A | 7/1998 | Raviv et al. |
| 5,782,757 A | 7/1998 | Diab et al. |
| 5,786,592 A | 7/1998 | Hok |
| 5,794,614 A | 8/1998 | Gruenke et al. |
| 5,794,615 A | 8/1998 | Estes |
| 5,800,348 A | 9/1998 | Kaestle |

(56) References Cited

U.S. PATENT DOCUMENTS

| | | |
|---|---|---|
| 5,803,065 A | 9/1998 | Zdrojkowski et al. |
| 5,803,066 A | 9/1998 | Rapoport et al. |
| 5,822,544 A | 10/1998 | Chaco et al. |
| 5,823,187 A | 10/1998 | Estes et al. |
| 5,827,179 A | 10/1998 | Lichter et al. |
| 5,830,135 A | 11/1998 | Bosque et al. |
| 5,830,136 A | 11/1998 | DeLonzor et al. |
| 5,830,139 A | 11/1998 | Abreu |
| 5,831,598 A | 11/1998 | Kauffert et al. |
| 5,840,019 A | 11/1998 | Wirebaugh |
| 5,842,981 A | 12/1998 | Larsen et al. |
| 5,845,636 A | 12/1998 | Gruenke et al. |
| 5,846,190 A | 12/1998 | Woehrle |
| 5,853,364 A | 12/1998 | Baker, Jr. et al. |
| 5,862,802 A | 1/1999 | Bird |
| 5,865,173 A | 2/1999 | Froehlich |
| 5,865,736 A | 2/1999 | Baker, Jr. et al. |
| 5,871,442 A | 2/1999 | Madarasz et al. |
| 5,873,821 A | 2/1999 | Chance et al. |
| 5,891,022 A | 4/1999 | Pologe |
| 5,891,023 A | 4/1999 | Lynn |
| 5,902,250 A | 5/1999 | Verrier et al. |
| 5,920,263 A | 7/1999 | Huttenhoff et al. |
| 5,931,790 A | 8/1999 | Peel, III |
| 5,935,099 A | 8/1999 | Peterson et al. |
| 5,957,885 A | 9/1999 | Bollish |
| 5,995,855 A | 11/1999 | Kiani et al. |
| 5,995,856 A | 11/1999 | Mannheimer et al. |
| 5,995,859 A | 11/1999 | Takahashi |
| 6,002,952 A | 12/1999 | Diab et al. |
| 6,004,276 A | 12/1999 | Wright et al. |
| 6,006,379 A | 12/1999 | Hensley |
| 6,011,986 A | 1/2000 | Diab et al. |
| 6,015,388 A | 1/2000 | Sackner et al. |
| 6,024,699 A | 2/2000 | Surwit et al. |
| 6,050,951 A | 4/2000 | Friedman et al. |
| 6,064,898 A | 5/2000 | Aldrich |
| 6,067,462 A | 5/2000 | Diab et al. |
| 6,070,098 A | 5/2000 | Moore-Ede et al. |
| 6,081,742 A | 6/2000 | Amano et al. |
| 6,083,156 A | 7/2000 | Lisiecki |
| 6,083,172 A | 7/2000 | Baker, Jr. et al. |
| 6,088,607 A | 7/2000 | Diab et al. |
| 6,095,984 A | 8/2000 | Amano et al. |
| 6,102,038 A | 8/2000 | DeVries |
| 6,102,870 A | 8/2000 | Edwards |
| 6,105,575 A | 8/2000 | Estes et al. |
| 6,120,441 A | 9/2000 | Griebel |
| 6,120,460 A | 9/2000 | Abreu |
| 6,134,460 A | 10/2000 | Chance |
| 6,138,675 A | 10/2000 | Berthon-Jones |
| 6,141,590 A | 10/2000 | Renirie et al. |
| 6,144,877 A | 11/2000 | De Petrillo |
| 6,148,814 A | 11/2000 | Clemmer et al. |
| 6,150,951 A | 11/2000 | Olejniczak |
| 6,151,516 A | 11/2000 | Kiani-Azarbayjany et al. |
| 6,154,667 A | 11/2000 | Miura et al. |
| 6,163,715 A | 12/2000 | Larsen et al. |
| 6,171,258 B1 | 1/2001 | Karakasoglu et al. |
| 6,181,958 B1 | 1/2001 | Steuer et al. |
| 6,181,959 B1 | 1/2001 | Schollermann et al. |
| 6,190,324 B1 | 2/2001 | Kieval et al. |
| 6,215,403 B1 | 4/2001 | Chan et al. |
| 6,216,032 B1 | 4/2001 | Griffin et al. |
| 6,223,064 B1 | 4/2001 | Lynn et al. |
| 6,230,035 B1 | 5/2001 | Aoyagi et al. |
| 6,230,142 B1 | 5/2001 | Benigno et al. |
| 6,230,708 B1 | 5/2001 | Radko |
| 6,266,546 B1 | 7/2001 | Steuer et al. |
| 6,285,895 B1 | 9/2001 | Ristolainen et al. |
| 6,286,508 B1 | 9/2001 | Remmers et al. |
| 6,299,581 B1 | 10/2001 | Rapoport et al. |
| 6,305,374 B1 | 10/2001 | Zdrojkowski et al. |
| 6,312,393 B1 | 11/2001 | Abreu |
| 6,322,515 B1 | 11/2001 | Goor et al. |
| 6,342,039 B1 | 1/2002 | Lynn et al. |
| 6,345,619 B1 | 2/2002 | Finn |
| 6,353,750 B1 | 3/2002 | Kimura et al. |
| 6,360,114 B1 | 3/2002 | Diab et al. |
| 6,363,270 B1 | 3/2002 | Colla et al. |
| 6,364,834 B1 | 4/2002 | Reuss et al. |
| 6,367,474 B1 | 4/2002 | Berthon-Jones et al. |
| 6,371,113 B1 | 4/2002 | Tobia et al. |
| 6,371,114 B1 | 4/2002 | Schmidt et al. |
| 6,375,623 B1 | 4/2002 | Gavriely |
| 6,385,589 B1 | 5/2002 | Trusheim et al. |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,099 B1 | 5/2002 | Chance |
| 6,398,727 B1 | 6/2002 | Bui et al. |
| 6,401,713 B1 | 6/2002 | Hill et al. |
| 6,411,833 B1 | 6/2002 | Baker, Jr. et al. |
| 6,415,166 B1 | 7/2002 | Van Hoy et al. |
| 6,415,175 B1 | 7/2002 | Conley et al. |
| 6,415,236 B2 | 7/2002 | Kobayashi et al. |
| 6,419,671 B1 | 7/2002 | Lemberg |
| 6,425,861 B1 | 7/2002 | Haberland et al. |
| 6,438,399 B1 | 8/2002 | Kurth |
| 6,449,501 B1 | 9/2002 | Reuss |
| 6,461,305 B1 | 10/2002 | Schnall |
| 6,463,326 B1 | 10/2002 | Hartley et al. |
| 6,466,809 B1 | 10/2002 | Riley |
| 6,475,153 B1 | 11/2002 | Khair et al. |
| 6,487,439 B1 | 11/2002 | Skladnev et al. |
| 6,488,634 B1 | 12/2002 | Rapoport et al. |
| 6,501,974 B2 | 12/2002 | Huiku |
| 6,501,975 B2 | 12/2002 | Diab et al. |
| 6,502,572 B1 | 1/2003 | Berthon-Jones et al. |
| 6,519,486 B1 | 2/2003 | Edgar, Jr. et al. |
| 6,526,301 B2 | 2/2003 | Larsen et al. |
| 6,529,752 B2 | 3/2003 | Krausman et al. |
| 6,532,960 B1 | 3/2003 | Yurko |
| 6,539,940 B2 | 4/2003 | Zdrojkowski et al. |
| 6,542,764 B1 | 4/2003 | Al-Ali et al. |
| 6,544,193 B2 | 4/2003 | Abreu |
| 6,546,267 B1 | 4/2003 | Sugiura et al. |
| 6,549,795 B1 | 4/2003 | Chance |
| 6,553,242 B1 | 4/2003 | Sarussi |
| 6,571,622 B2 | 6/2003 | Koch |
| 6,572,557 B2 | 6/2003 | Tchou et al. |
| 6,579,242 B2 | 6/2003 | Bui et al. |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,606,511 B1 | 8/2003 | Ali et al. |
| 6,609,016 B1 | 8/2003 | Lynn |
| 6,609,517 B1 | 8/2003 | Estes et al. |
| 6,615,064 B1 | 9/2003 | Aldrich |
| 6,618,042 B1 | 9/2003 | Powell |
| 6,622,095 B2 | 9/2003 | Kobayashi et al. |
| 6,622,726 B1 | 9/2003 | Du |
| 6,637,434 B2 | 10/2003 | Noble |
| 6,640,806 B2 | 11/2003 | Yurko |
| 6,641,542 B2 | 11/2003 | Cho et al. |
| 6,654,621 B2 | 11/2003 | Palatnik et al. |
| 6,654,624 B2 | 11/2003 | Diab et al. |
| 6,658,276 B2 | 12/2003 | Kianl et al. |
| 6,658,277 B2 | 12/2003 | Wasserman |
| 6,659,961 B2 | 12/2003 | Robinson |
| 6,661,161 B1 | 12/2003 | Lanzo et al. |
| 6,662,030 B2 | 12/2003 | Khalil et al. |
| 6,662,032 B1 | 12/2003 | Gavish et al. |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,675,797 B1 | 1/2004 | Berthon-Jones |
| 6,678,543 B2 | 1/2004 | Diab et al. |
| 6,684,090 B2 | 1/2004 | Ali et al. |
| 6,690,958 B1 | 2/2004 | Walker et al. |
| 6,691,705 B2 | 2/2004 | Dittmann et al. |
| 6,697,658 B2 | 2/2004 | Al-Ali |
| 6,699,194 B1 | 3/2004 | Diab et al. |

(56) References Cited

U.S. PATENT DOCUMENTS

| | | |
|---|---|---|
| 6,708,048 B1 | 3/2004 | Chance |
| 6,711,424 B1 | 3/2004 | Fine et al. |
| 6,711,425 B1 | 3/2004 | Reuss et al. |
| 6,714,245 B1 | 3/2004 | Ono |
| 6,721,584 B2 | 4/2004 | Baker, Jr. et al. |
| 6,723,077 B2 | 4/2004 | Pickup et al. |
| 6,731,274 B2 | 5/2004 | Powell |
| 6,738,666 B1 | 5/2004 | Park et al. |
| 6,745,764 B2 | 6/2004 | Hickle |
| 6,748,252 B2 | 6/2004 | Lynn |
| 6,752,150 B1 | 6/2004 | Remmers et al. |
| 6,760,608 B2 | 7/2004 | Lynn |
| 6,761,167 B1 | 7/2004 | Nadjafizadeh et al. |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes |
| 6,804,656 B1 | 10/2004 | Rosenfeld et al. |
| 6,807,965 B1 | 10/2004 | Hickle |
| 6,810,277 B2 | 10/2004 | Edgar, Jr. et al. |
| 6,814,074 B1 | 11/2004 | Nadjafizadeh et al. |
| 6,816,266 B2 | 11/2004 | Varshneya et al. |
| 6,817,361 B2 | 11/2004 | Berthon-Jones et al. |
| 6,820,618 B2 | 11/2004 | Banner et al. |
| 6,822,564 B2 | 11/2004 | Al-Ali |
| 6,829,496 B2 | 12/2004 | Nagai et al. |
| 6,830,549 B2 | 12/2004 | Bui et al. |
| 6,832,200 B2 | 12/2004 | Greevan et al. |
| 6,836,679 B2 | 12/2004 | Baker, Jr. et al. |
| 6,839,581 B1 | 1/2005 | El-Solh et al. |
| 6,850,053 B2 | 2/2005 | Daalmans et al. |
| 6,863,652 B2 | 3/2005 | Huang et al. |
| 6,869,402 B2 | 3/2005 | Arnold |
| 6,873,865 B2 | 3/2005 | Steuer et al. |
| 6,889,153 B2 | 5/2005 | Dietiker |
| 6,896,660 B2 | 5/2005 | Jelliffe et al. |
| 6,898,451 B2 | 5/2005 | Wuori |
| 6,918,878 B2 | 7/2005 | Brodnick |
| 6,928,370 B2 | 8/2005 | Anuzis et al. |
| 6,931,268 B1 | 8/2005 | Kiani-Azarbayjany et al. |
| 6,931,269 B2 | 8/2005 | Terry |
| 6,932,084 B2 | 8/2005 | Estes et al. |
| 6,934,570 B2 | 8/2005 | Kiani et al. |
| 6,939,307 B1 | 9/2005 | Dunlop |
| 6,947,780 B2 | 9/2005 | Scharf |
| 6,948,497 B2 | 9/2005 | Zdrojkowski et al. |
| 6,949,081 B1 | 9/2005 | Chance |
| 6,961,598 B2 | 11/2005 | Diab |
| 6,963,767 B2 | 11/2005 | Rantala et al. |
| 6,983,178 B2 | 1/2006 | Fine et al. |
| 6,985,762 B2 | 1/2006 | Brashears et al. |
| 6,988,498 B2 | 1/2006 | Berthon-Jones |
| 6,993,371 B2 | 1/2006 | Kiani et al. |
| 6,994,675 B2 | 2/2006 | Sharrock |
| 6,996,427 B2 | 2/2006 | Ali et al. |
| 7,013,898 B2 | 3/2006 | Rashad et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,031,857 B2 | 4/2006 | Tarassenko et al. |
| 7,034,692 B2 | 4/2006 | Hickle |
| 7,035,679 B2 | 4/2006 | Addison et al. |
| 7,035,697 B1 | 4/2006 | Brown |
| 7,040,315 B1 | 5/2006 | Stromberg |
| 7,044,917 B2 | 5/2006 | Arnold |
| 7,047,056 B2 | 5/2006 | Hannula et al. |
| 7,081,095 B2 | 7/2006 | Lynn et al. |
| 7,090,648 B2 | 8/2006 | Sackner et al. |
| 7,118,534 B2 | 10/2006 | Ward et al. |
| 7,123,950 B2 | 10/2006 | Mannheimer et al. |
| 7,127,278 B2 | 10/2006 | Melker et al. |
| 7,130,671 B2 | 10/2006 | Baker |
| 7,139,599 B2 | 11/2006 | Terry |
| 7,153,263 B2 | 12/2006 | Carter et al. |
| 7,161,484 B2 | 1/2007 | Tsoukalis |
| 7,162,306 B2 | 1/2007 | Caby et al. |
| 7,171,269 B1 | 1/2007 | Addison et al. |
| 7,181,264 B2 | 2/2007 | Wiesmann |
| 7,186,217 B2 | 3/2007 | Kawasaki |
| 7,188,621 B2 | 3/2007 | DeVries et al. |
| 7,190,261 B2 | 3/2007 | Al-Ali |
| 7,190,995 B2 | 3/2007 | Chervin et al. |
| 7,209,775 B2 | 4/2007 | Bae et al. |
| 7,218,966 B2 | 5/2007 | Haefner |
| 7,220,220 B2 | 5/2007 | Stubbs et al. |
| 7,222,623 B2 | 5/2007 | DeVries et al. |
| 7,222,624 B2 | 5/2007 | Rashad et al. |
| 7,225,013 B2 | 5/2007 | Geva et al. |
| 7,230,529 B2 | 6/2007 | Ketcherside et al. |
| 7,231,240 B2 | 6/2007 | Eda et al. |
| 7,236,811 B2 | 6/2007 | Schmitt |
| 7,239,905 B2 | 7/2007 | Kiani-Azarbayjany et al. |
| 7,263,395 B2 | 8/2007 | Chan et al. |
| 7,267,652 B2 | 9/2007 | Coyle et al. |
| 7,272,426 B2 | 9/2007 | Schmid et al. |
| 7,277,752 B2 | 10/2007 | Matos |
| 7,297,119 B2 | 11/2007 | Westbrook et al. |
| 7,309,314 B2 | 12/2007 | Grant et al. |
| 7,338,447 B2 | 3/2008 | Phillips |
| 7,353,054 B2 | 4/2008 | Kawasaki et al. |
| 7,355,512 B1 | 4/2008 | Al-Ali |
| 7,366,569 B2 | 4/2008 | Belalcazar |
| 7,367,339 B2 | 5/2008 | Hickle |
| 7,367,954 B2 | 5/2008 | Starr et al. |
| 7,370,650 B2 | 5/2008 | Nadjafizadeh et al. |
| 7,373,193 B2 | 5/2008 | Al-Ali et al. |
| 7,398,115 B2 | 7/2008 | Lynn |
| 7,407,485 B2 | 8/2008 | Huiku |
| 7,407,486 B2 | 8/2008 | Huiku et al. |
| 7,421,296 B1 | 9/2008 | Benser et al. |
| 7,431,696 B1 | 10/2008 | Brady et al. |
| 7,447,541 B2 | 11/2008 | Huiku et al. |
| 7,460,909 B1 | 12/2008 | Koh et al. |
| 7,465,555 B2 | 12/2008 | Anderson et al. |
| 7,488,293 B2 | 2/2009 | Marchovecchio |
| 7,499,835 B2 | 3/2009 | Weber |
| 7,539,537 B2 | 5/2009 | Hickle |
| 7,544,190 B2 | 6/2009 | Pickup et al. |
| 7,635,337 B2 | 12/2009 | Huiku et al. |
| 7,640,055 B2 | 12/2009 | Geva et al. |
| 7,645,573 B2 | 1/2010 | Ivey et al. |
| 7,647,185 B2 | 1/2010 | Tarassenko et al. |
| 7,668,579 B2 | 2/2010 | Lynn |
| 7,674,230 B2 | 3/2010 | Reisfeld |
| 7,725,146 B2 | 5/2010 | Li et al. |
| 7,758,503 B2 | 7/2010 | Lynn et al. |
| 7,767,395 B2 | 8/2010 | Garrett et al. |
| 7,785,262 B2 | 8/2010 | Melker et al. |
| 7,794,406 B2 | 9/2010 | Reisfeld et al. |
| 7,803,118 B2 | 9/2010 | Reisfeld et al. |
| 7,803,119 B2 | 9/2010 | Reisfeld |
| 7,806,832 B2 | 10/2010 | Gallagher et al. |
| 7,970,725 B2 | 6/2011 | Armstrong et al. |
| 8,274,360 B2 | 9/2012 | Sampath et al. |
| 8,414,488 B2 | 4/2013 | Colman et al. |
| 8,428,966 B2 | 4/2013 | Green, III et al. |
| 8,438,041 B2 | 5/2013 | Green, III et al. |
| 2001/0005773 A1 | 6/2001 | Larsen et al. |
| 2001/0018557 A1 | 8/2001 | Lynn et al. |
| 2001/0020122 A1 | 9/2001 | Steuer et al. |
| 2001/0039376 A1 | 11/2001 | Steuer et al. |
| 2001/0044588 A1 | 11/2001 | Mault |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0082488 A1 | 6/2002 | Al-Ali et al. |
| 2002/0085952 A1 | 7/2002 | Ellingboe et al. |
| 2002/0091326 A1 | 7/2002 | Hashimoto et al. |
| 2002/0095090 A1 | 7/2002 | Caro et al. |
| 2002/0111748 A1 | 8/2002 | Kobayashi et al. |

(56) References Cited

U.S. PATENT DOCUMENTS

| | | |
|---|---|---|
| 2002/0117173 A1 | 8/2002 | Lynn et al. |
| 2002/0128544 A1 | 9/2002 | Diab et al. |
| 2002/0133068 A1 | 9/2002 | Huiku |
| 2002/0138014 A1 | 9/2002 | Baura et al. |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0165462 A1 | 11/2002 | Westbrook et al. |
| 2002/0190863 A1 | 12/2002 | Lynn |
| 2002/0198443 A1 | 12/2002 | Ting |
| 2003/0000522 A1 | 1/2003 | Lynn et al. |
| 2003/0023140 A1 | 1/2003 | Chance |
| 2003/0055324 A1 | 3/2003 | Wasserman |
| 2003/0055331 A1 | 3/2003 | Kotmel et al. |
| 2003/0060693 A1 | 3/2003 | Monfre et al. |
| 2003/0101076 A1 | 5/2003 | Zaleski |
| 2003/0127097 A1 | 7/2003 | Yurko |
| 2003/0135127 A1 | 7/2003 | Sackner et al. |
| 2003/0139687 A1 | 7/2003 | Abreu |
| 2003/0144584 A1 | 7/2003 | Mendelson |
| 2003/0150842 A1 | 8/2003 | Mikame |
| 2003/0158466 A1 | 8/2003 | Lynn et al. |
| 2003/0181815 A1 | 9/2003 | Ebner et al. |
| 2003/0220548 A1 | 11/2003 | Schmitt |
| 2003/0220576 A1 | 11/2003 | Diab |
| 2003/0228625 A1 | 12/2003 | Toh et al. |
| 2004/0010188 A1 | 1/2004 | Wasserman |
| 2004/0039295 A1 | 2/2004 | Olbrich et al. |
| 2004/0044276 A1 | 3/2004 | Arnold |
| 2004/0054270 A1 | 3/2004 | Pewzner et al. |
| 2004/0064020 A1 | 4/2004 | Diab et al. |
| 2004/0073098 A1 | 4/2004 | Geva et al. |
| 2004/0078219 A1 | 4/2004 | Kaylor et al. |
| 2004/0078228 A1 | 4/2004 | Fitzgerald et al. |
| 2004/0087846 A1 | 5/2004 | Wasserman |
| 2004/0087916 A1 | 5/2004 | Pickup et al. |
| 2004/0107065 A1 | 6/2004 | Al-Ali |
| 2004/0111014 A1 | 6/2004 | Hickle |
| 2004/0117204 A1 | 6/2004 | Mazar et al. |
| 2004/0127779 A1 | 7/2004 | Steuer et al. |
| 2004/0158135 A1 | 8/2004 | Baker, Jr. et al. |
| 2004/0163648 A1 | 8/2004 | Burton |
| 2004/0170154 A1 | 9/2004 | Carter et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0181134 A1 | 9/2004 | Baker, Jr. et al. |
| 2004/0181196 A1 | 9/2004 | Pickup et al. |
| 2004/0204637 A1 | 10/2004 | Diab et al. |
| 2004/0230105 A1 | 11/2004 | Geva et al. |
| 2004/0230106 A1 | 11/2004 | Schmitt et al. |
| 2004/0249299 A1 | 12/2004 | Cobb |
| 2004/0254481 A1 | 12/2004 | Brodnick |
| 2004/0254490 A1 | 12/2004 | Egli |
| 2005/0001728 A1 | 1/2005 | Appelt et al. |
| 2005/0016536 A1 | 1/2005 | Rapoport et al. |
| 2005/0017864 A1 | 1/2005 | Tsoukalis |
| 2005/0027207 A1 | 2/2005 | Westbrook et al. |
| 2005/0033129 A1 | 2/2005 | Edgar, Jr. et al. |
| 2005/0043616 A1 | 2/2005 | Chinchoy |
| 2005/0065556 A1 | 3/2005 | Reghabi et al. |
| 2005/0070774 A1 | 3/2005 | Addison et al. |
| 2005/0080323 A1 | 4/2005 | Kato |
| 2005/0081854 A1 | 4/2005 | Nadjafizadeh et al. |
| 2005/0085735 A1 | 4/2005 | Baker, Jr. et al. |
| 2005/0101850 A1 | 5/2005 | Parker |
| 2005/0113651 A1 | 5/2005 | Wood et al. |
| 2005/0113656 A1 | 5/2005 | Chance |
| 2005/0113709 A1 | 5/2005 | Millet |
| 2005/0119586 A1 | 6/2005 | Coyle et al. |
| 2005/0119708 A1 | 6/2005 | Haefner |
| 2005/0143665 A1 | 6/2005 | Huiku et al. |
| 2005/0154422 A1 | 7/2005 | Band et al. |
| 2005/0168722 A1 | 8/2005 | Forstner et al. |
| 2005/0177034 A1 | 8/2005 | Beaumont |
| 2005/0187480 A1 | 8/2005 | Kario et al. |
| 2005/0192488 A1 | 9/2005 | Bryenton et al. |
| 2005/0192500 A1 | 9/2005 | Caro et al. |
| 2005/0203357 A1 | 9/2005 | Debreczeny et al. |
| 2005/0209521 A1 | 9/2005 | Kettunen et al. |
| 2005/0222503 A1 | 10/2005 | Dunlop et al. |
| 2005/0228248 A1 | 10/2005 | Dietiker |
| 2005/0240091 A1 | 10/2005 | Lynn |
| 2005/0245830 A1 | 11/2005 | Hutchinson |
| 2005/0247311 A1 | 11/2005 | Vacchiano et al. |
| 2005/0251056 A1 | 11/2005 | Gribkov et al. |
| 2005/0267346 A1 | 12/2005 | Faber et al. |
| 2005/0277819 A1 | 12/2005 | Kiani et al. |
| 2005/0283059 A1 | 12/2005 | Iyer et al. |
| 2006/0009688 A1 | 1/2006 | Lamego et al. |
| 2006/0009809 A1 | 1/2006 | Marcovecchio et al. |
| 2006/0015021 A1 | 1/2006 | Cheung |
| 2006/0020181 A1 | 1/2006 | Schmitt |
| 2006/0030763 A1 | 2/2006 | Mannheimer et al. |
| 2006/0042631 A1 | 3/2006 | Martin et al. |
| 2006/0052680 A1 | 3/2006 | Diab |
| 2006/0058683 A1 | 3/2006 | Chance |
| 2006/0064024 A1 | 3/2006 | Schnall |
| 2006/0081259 A1 | 4/2006 | Bruggeman et al. |
| 2006/0084854 A1 | 4/2006 | Cho et al. |
| 2006/0137577 A1 | 6/2006 | Chang et al. |
| 2006/0149144 A1 | 7/2006 | Lynn et al. |
| 2006/0155176 A1 | 7/2006 | Ebner et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0167363 A1 | 7/2006 | Osypka et al. |
| 2006/0189872 A1 | 8/2006 | Arnold |
| 2006/0189880 A1 | 8/2006 | Lynn et al. |
| 2006/0195028 A1 | 8/2006 | Hannula et al. |
| 2006/0195041 A1 | 8/2006 | Lynn et al. |
| 2006/0195149 A1 | 8/2006 | Hopper et al. |
| 2006/0200016 A1 | 9/2006 | Diab et al. |
| 2006/0217614 A1 | 9/2006 | Takala et al. |
| 2006/0217615 A1 | 9/2006 | Huiku et al. |
| 2006/0217628 A1 | 9/2006 | Huiku |
| 2006/0224058 A1 | 10/2006 | Mannheimer |
| 2006/0235324 A1 | 10/2006 | Lynn |
| 2006/0235726 A1 | 10/2006 | Paraison |
| 2006/0247501 A1 | 11/2006 | Ali |
| 2006/0258921 A1 | 11/2006 | Addison et al. |
| 2006/0276695 A9 | 12/2006 | Lynn et al. |
| 2006/0287590 A1 | 12/2006 | McEowen |
| 2007/0004957 A1 | 1/2007 | Hilburg |
| 2007/0010723 A1 | 1/2007 | Uutela et al. |
| 2007/0015976 A1 | 1/2007 | Miesel et al. |
| 2007/0027369 A1 | 2/2007 | Pagnacco et al. |
| 2007/0027375 A1 | 2/2007 | Melker et al. |
| 2007/0037873 A1 | 2/2007 | Zurier et al. |
| 2007/0073361 A1 | 3/2007 | Goren et al. |
| 2007/0093701 A1 | 4/2007 | Myers et al. |
| 2007/0093721 A1 | 4/2007 | Lynn et al. |
| 2007/0129647 A1 | 6/2007 | Lynn |
| 2007/0142719 A1 | 6/2007 | Kawasaki et al. |
| 2007/0149860 A1 | 6/2007 | Lynn et al. |
| 2007/0179350 A1 | 8/2007 | Nadeau |
| 2007/0179369 A1 | 8/2007 | Baker, Jr. |
| 2007/0191688 A1 | 8/2007 | Lynn |
| 2007/0191697 A1 | 8/2007 | Lynn et al. |
| 2007/0203406 A1 | 8/2007 | Anderson et al. |
| 2007/0208269 A1 | 9/2007 | Mumford et al. |
| 2007/0213619 A1 | 9/2007 | Linder |
| 2007/0213620 A1 | 9/2007 | Reisfeld |
| 2007/0213621 A1 | 9/2007 | Reisfeld et al. |
| 2007/0213622 A1 | 9/2007 | Reisfeld |
| 2007/0213624 A1 | 9/2007 | Reisfeld et al. |
| 2007/0225606 A1 | 9/2007 | Naghavi et al. |
| 2007/0225614 A1 | 9/2007 | Naghavi et al. |
| 2007/0238937 A1 | 10/2007 | Chang et al. |
| 2007/0240723 A1 | 10/2007 | Hong et al. |
| 2007/0255146 A1 | 11/2007 | Andrews et al. |
| 2007/0255322 A1 | 11/2007 | Gerber et al. |
| 2007/0282212 A1 | 12/2007 | Sierra et al. |

(56) References Cited

U.S. PATENT DOCUMENTS

| | | |
|---|---|---|
| 2008/0009689 A1 | 1/2008 | Benaron et al. |
| 2008/0014115 A1 | 1/2008 | Johns |
| 2008/0027368 A1 | 1/2008 | Kollar et al. |
| 2008/0036752 A1 | 2/2008 | Diab et al. |
| 2008/0051764 A1 | 2/2008 | Dent et al. |
| 2008/0064965 A1 | 3/2008 | Jay et al. |
| 2008/0066753 A1 | 3/2008 | Martin et al. |
| 2008/0082018 A1 | 4/2008 | Sackner et al. |
| 2008/0091088 A1 | 4/2008 | Kiani |
| 2008/0167540 A1 | 7/2008 | Korhonen et al. |
| 2008/0177163 A1 | 7/2008 | Wang et al. |
| 2008/0183058 A1 | 7/2008 | Mannheimer |
| 2008/0183083 A1 | 7/2008 | Markowitz et al. |
| 2008/0188729 A1 | 8/2008 | Sato et al. |
| 2008/0200775 A1 | 8/2008 | Lynn |
| 2008/0200781 A1 | 8/2008 | Van Herpen et al. |
| 2008/0200824 A1 | 8/2008 | Kane et al. |
| 2008/0208012 A1 | 8/2008 | Ali |
| 2008/0235049 A1 | 9/2008 | Morita et al. |
| 2008/0235057 A1 | 9/2008 | Weidenhaupt et al. |
| 2008/0269583 A1 | 10/2008 | Reisfeld |
| 2008/0269626 A1 | 10/2008 | Gallagher et al. |
| 2008/0269832 A1 | 10/2008 | Wong et al. |
| 2008/0275349 A1 | 11/2008 | Halperin et al. |
| 2008/0281168 A1 | 11/2008 | Gibson et al. |
| 2008/0287756 A1 | 11/2008 | Lynn |
| 2008/0300471 A1 | 12/2008 | Al-Ali et al. |
| 2008/0312533 A1 | 12/2008 | Balberg et al. |
| 2009/0082641 A1 | 3/2009 | Giftakis et al. |
| 2009/0083072 A1 | 3/2009 | Osawa et al. |
| 2009/0143694 A1 | 6/2009 | Krauss et al. |
| 2009/0177493 A1 | 7/2009 | Narayan |
| 2009/0281838 A1 | 11/2009 | Lynn et al. |
| 2009/0281839 A1 | 11/2009 | Lynn et al. |
| 2009/0299154 A1 | 12/2009 | Segman |
| 2009/0318775 A1 | 12/2009 | Michelson et al. |
| 2010/0026510 A1 | 2/2010 | Kiani et al. |
| 2010/0066540 A1 | 3/2010 | Theobald et al. |
| 2010/0079292 A1 | 4/2010 | Lynn et al. |
| 2010/0088346 A1 | 4/2010 | Urness et al. |
| 2010/0113909 A1 | 5/2010 | Batchelder et al. |
| 2010/0234705 A1 | 9/2010 | Lynn |
| 2010/0261977 A1 | 10/2010 | Seely |
| 2011/0009722 A1 | 1/2011 | Amundson et al. |
| 2011/0015501 A1 | 1/2011 | Lynn et al. |
| 2011/0208018 A1 | 8/2011 | Kiani |
| 2011/0208539 A1 | 8/2011 | Lynn |
| 2012/0145152 A1 | 6/2012 | Lain et al. |
| 2012/0328594 A1 | 12/2012 | McKenna et al. |
| 2013/0211214 A1 | 8/2013 | Olsen |
| 2013/0254717 A1 | 9/2013 | Al-Ali et al. |
| 2013/0262730 A1 | 10/2013 | Al-Ali et al. |
| 2013/0274572 A1 | 10/2013 | Al-Ali et al. |
| 2013/0276785 A1 | 10/2013 | Melker |

FOREIGN PATENT DOCUMENTS

| | | |
|---|---|---|
| EP | 0178197 A1 | 4/1986 |
| EP | 0934723 A1 | 8/1988 |
| EP | 0459647 B1 | 10/1991 |
| EP | 0459284 A1 | 12/1991 |
| EP | 0615723 | 3/1993 |
| EP | 0666056 A1 | 7/1994 |
| EP | 0459284 B1 | 1/1995 |
| EP | 0392503 B1 | 5/1995 |
| EP | 0684011 A1 | 5/1995 |
| EP | 0651971 A1 | 10/1995 |
| EP | 0700690 A2 | 3/1996 |
| EP | 0709107 A1 | 5/1996 |
| EP | 0714670 A2 | 6/1996 |
| EP | 0722747 A2 | 7/1996 |
| EP | 0759791 A1 | 3/1997 |
| EP | 0788805 A2 | 6/1997 |
| EP | 0788805 A3 | 5/1998 |
| EP | 0875258 A2 | 11/1998 |
| EP | 0968734 A3 | 1/2000 |
| EP | 1004325 A3 | 6/2000 |
| EP | 1172123 A2 | 1/2002 |
| EP | 0700690 | 2/2002 |
| EP | 0700690 B1 | 2/2002 |
| EP | 0759791 | 8/2002 |
| EP | 0759791 B1 | 8/2002 |
| EP | 0934723 B1 | 9/2004 |
| EP | 1172123 B1 | 10/2004 |
| EP | 0875258 B1 | 11/2004 |
| EP | 1488743 A2 | 12/2004 |
| EP | 1905356 | 9/2007 |
| GB | 1554829 | 2/1978 |
| JP | 63275325 | 11/1988 |
| JP | 05266002 | 3/1992 |
| JP | 2000-042111 | 2/2000 |
| JP | 2004145853 | 5/2004 |
| JP | 2005034472 | 2/2005 |
| JP | 2006519626 | 8/2006 |
| WO | WO 86/00234 | 1/1986 |
| WO | WO 88/01149 | 2/1988 |
| WO | WO 90/09146 | 8/1990 |
| WO | WO 90/14121 | 11/1990 |
| WO | WO 92/11054 | 7/1992 |
| WO | WO 92/12750 | 8/1992 |
| WO | WO 92/22244 | 12/1992 |
| WO | WO 93/16629 | 9/1993 |
| WO | WO 94/06499 | 3/1994 |
| WO | WO 94/23780 | 10/1994 |
| WO | WO 95/32016 | 11/1995 |
| WO | WO 96/39927 | 12/1996 |
| WO | WO 97/14462 | 4/1997 |
| WO | WO 97/19719 | 6/1997 |
| WO | WO 97/28838 | 8/1997 |
| WO | WO 98/12965 | 4/1998 |
| WO | WO 98/43071 | 10/1998 |
| WO | WO 99/13766 | 3/1999 |
| WO | WO 99/24099 | 5/1999 |
| WO | WO 99/45989 | 9/1999 |
| WO | WO 00/21438 | 4/2000 |
| WO | WO 00/67827 | 11/2000 |
| WO | WO 00/74551 A2 | 12/2000 |
| WO | WO0074551 | 12/2000 |
| WO | WO 01/40776 | 6/2001 |
| WO | WO 01/76461 | 10/2001 |
| WO | WO 01/76471 | 10/2001 |
| WO | WO 01/82099 A1 | 11/2001 |
| WO | WO 01/87149 | 11/2001 |
| WO | WO 02/41771 | 5/2002 |
| WO | WO 02/41771 A1 | 5/2002 |
| WO | WO 03/000125 A1 | 1/2003 |
| WO | WO 03/039326 | 5/2003 |
| WO | WO 03/053780 | 7/2003 |
| WO | WO 2004/047621 A2 | 6/2004 |
| WO | 2004056301 A2 | 7/2004 |
| WO | 2004080300 A1 | 9/2004 |
| WO | WO2004075746 | 9/2004 |
| WO | WO2004105601 | 12/2004 |
| WO | WO 2005/037077 | 4/2005 |
| WO | WO 2005/056087 | 6/2005 |
| WO | WO 2005/065540 A1 | 7/2005 |
| WO | WO 2005/065757 A1 | 7/2005 |
| WO | WO 2005/096931 A1 | 10/2005 |
| WO | WO 2005/110215 A2 | 11/2005 |
| WO | WO 2006/086010 A2 | 8/2006 |
| WO | WO 2006/116469 A2 | 11/2006 |
| WO | 2007013708 | 2/2007 |
| WO | WO 2007/013708 | 2/2007 |
| WO | WO 2007/051006 A2 | 5/2007 |
| WO | WO2007051066 | 5/2007 |
| WO | WO 2007/131064 | 11/2007 |
| WO | WO 2007/131066 | 11/2007 |

(56) References Cited

FOREIGN PATENT DOCUMENTS

| WO | WO 2008/008163 A2 | 1/2008 |
|---|---|---|
| WO | WO2008097411 | 8/2008 |
| WO | WO2008117338 | 10/2008 |

OTHER PUBLICATIONS

Downs, John B., Is Supplemental Oxygen Necessary, Journal of Cardiothoracic and Vascular Anesthesia, vol. 20, No. 2, Apr. 2006.
Fu, Eugene S., et al., Supplemental Oxygen Impairs Detection of Hypoventilation by Pulse Oximetry, Chest 2004; vol. 126, pp. 1552-1558.
Simmons, Richard L. et al.; The Role of the Central Nervous System in Septic Shock: II. Hemodynamic, Respiratory and Metabolic Effects of Intracisternal or Intraventricular Endotoxin; Annals of Surgery; Feb. 1968; pp. 158-167.
Siggaard-Andersen O. et al.; The Bohr Effect and the Haldane Effect; Scand J Clin Lab Invest; vol. 3 (1); 1973; pp. 1-8.
Neuman, Michael R.; Pulse Oximetry: Physical Principles, Technical Relization and Present Limitations; Adv Exp Med Biol 1987;220; pp. 135-144.
O'Donovan, Richard et al.; Acid-Base Disturbances in Cardiogenic Polmonart Edema; Nephron; 1991; 57; pp. 416-420.
Moller, J.T. et al.; Hypoxaemia is Reduced by Pulse Oximetry Monitoring in the Operating Theatre and in the Recovery Room; British Journal of Anaesthesia; 1992; vol. 68; pp. 146-150.
Moller, Jakob T. et al.; Randomized Evaluation of Pulse Oximetry in 20,802 Pateints: I; Anesthesiology, vol. 78, No. 3; Mar. 1993; pp. 436-444; US.
Moller, Jakob T. et al.; Randomized Evaluation of Pulse Oximetry in 20,802 Patients: II; Anesthesiology, vol. 78, No. 3; Mar. 1993; pp. 445-453; US.
Murray, Carol B. et al.; Making the most of pulse oximetry; Contemporary Pediatrics; Jul. 1995; pp. 45-62.
Tang, et al.; Perepheral neural modulation of endotoxin-induced hyperventilation; Critical Care Medicine; vol. 26, Issue 9; Sep. 1998, pp. 1558-1563.
Sinex, James E.; Pulse Oximetry: Principles and Limitations; American Journal of Emergency Medicine; vol. 17, No. 1; Jan. 1999; pp. 59-66.
Manley,G.T.; Cerebral Oxygenation During Hemorrhagic Shock: Perils of Hyperventilation and the Therapeutic Potential of Hypoventilation, J Trauma: 2000; 48: 1025-1032.
Mackenzie, I.M.J.; The haemodynamics of human septic shock; Anaesthesia; 2001; 56; pp. 130-144; UK.
Soubani, Ayman O.; Noninvasive Monitoring of Oxygen and Carbon Dioxide; American Journal of Emergency Medicine; vol. 19, No. 2; Mar. 2001; pp. 141-146.
Howell, Mandy et al.; Pulse oximetry: an audit of nursing and medical staff understanding; British Journal of Nursing, 2002, vol. 11, No. 3; pp. 191-197.
Attin, M. et al.; An Educational Project to Improve Knowledge Related to Pulse Oximetry; American Journal of Critical Care, Nov. 2002, vol. 11, No. 6; pp. 529-534; US.
Alattar, M.A. et al.; Opioid-associated central sleep apnea: a case series, Sleep Breath, 2009, vol. 13, pp. 201-206.
Alchanatis, M et al., Left ventricular function in patients with obstructive sleep apnoea syndrome before and after treatment with nasal continuous positive airway pressure, Respiration, 2000, vol. 67, No. 4, p. 367- (Abstract).
Al-Shawwa, Baha et al., Defining Common Outcome Metrics Used in Obstructive Sleep Apnea, Sleep Medicine Reviews, 2008, pp. 449-461.
Anderson, R. et al., Data logging technology in ambulatory medical instrumation, Physiological Measurement, 2001, pp. R1-R13.
Antic, Nick et al., PHOX2B Mutation-confirmed Congenital Central Hypoventilation Syndrome, American Journal of Respiratory and Critical Care, 2006, vol. 174, pp. 923-927.
Augusto, Juan Carlos, Temporal Reasoning for Decision Support in Medicine, Artificial Intelligence in Medicine, 2005, vol. 33, pp. 1-24.

Author Unknown, $FiO_2$, Wikipedia Encyclopedia, modified Oct. 30, 2007 . . . http://en.wikipedia.org/wiki/FiO2.
Author Unknown, News Bulletin, Lack of sleep America's top health problem, doctors say, Health Story Page, CNN, htto://cnn.com/HEALTH/9703117/nfm/sleep.deorivation/index.html, Mar. 17, 1997.
Barker, Steven, "Motion-Resistant" Pulse Oximetry: A Comparison of New and Old Models, Anesthesia & Analgesia, 2002, vol. 95, pp. 967-972.
Bell, Linda, Monitor Alarm Fatigue, American Journal of Critical Care, Jan. 2010, vol. 19 No. 1, pp. 37-38.
Bellomo, Rinaldo et al., Prospective controlled trial of effect of medical emergency team on postoperative morbidity and mortality rates, Critical Care Medicine, 2004, vol. 32 No. 4, pp. 916-921.
Berry, Richard et al., Triazolam in Patients with Obstructive Sleep Apnea, American Journal of Respiratory and Critical Care, 1995, vol. 151, pp. 450-454.
Berwick, Donald et al., IHI Replies to "The 100,000 Lives Campaign: A Scientific and Policy Review", Joint Commission Journal on Quality and Patient Safety, Nov. 2006, vol. 32, No. 11, pp. 628-633.
Blair, Emil, Acid-Base Balance in Bacteremic Shock, The Archives of Internal Medicine, Apr. 1971, vol. 127, pp. 731-739.
Blair, Emil, Hypocapnia and Gram-Negative Bacteremic Shock, The American Journal of Surgery, Apr. 1970, vol. 119, pp. 433-439.
Blanc, Victor Faria et al., Computerized photoplethysmography of the finger, Canadian Journal of Anaesthesia, 1993, vol. 40, No. 3, pp. 271-278.
Bossink, Ailko et al., Prediction of Mortality in Febrile Medical Patient: How Useful Are Systemic Inflammatory Response Syndrome and Sepsis Criteria?, Chest Journal, Jun. 1998, vol. 113 No. 6, pp. 1533-1541.
Bouillon, T. et al., Opioid-induced respiratory depression is associated with increased tidal volume variability, Europen Journal of Anaesthesiology, 2003, vol. 20, pp. 127-133.
Busquet, Xavier et al., Decreased Plasma Levels of Orexin-A in Sleep Apnea, Respiration, 2004,vol. 71, pp. 575-579.
Cacho, G et al., Capnography is superior to pulse oximetry for the detection of respiratory depression during colonoscopy, Revista Española De Enfermedades Digestivas, 2010, vol. 102, No. 2, pp. 86-89.
Caruso, Antonello L.G. et al., On the modeling of drug induced respiratory depression in the non-steady-state, 30th Annual International IEEE EMBS Conference, Aug. 20-24, 2008, pp. 5564-5568.
Casey, Kenneth et al., Sleep-Related Hypoventilation/Hypoxemic Syndromes, Chest Journal, 2007, vol. 131, pp. 1936-1948.
Catley, D.M., Pronounced, Episodic, Oxygen Desaturation in the Postoperative Period: Its Association with Ventilatory Pattern and Analgesic Regimen, Anesthesiology, Jul. 1985, vol. 63, No. 1, pp. 20-28.
Catling, J A et al., Respiratory effects of analgesia after cholecystetomy: comparison of continuous and intermittent papavveretum, British Medical Journal, Aug. 16, 1980, pp. 478-480.
Chan, Paul et al., Hospital-wide Code Rates and Mortality Before and After Implementation of a Rapid Response Team, Journal of the American Medical Association, Dec. 3, 2008, vol. 300, No. 21, pp. 2506-2513.
Chan, Paul et al., Rapid Response Teams, Archieves of Internal Medicine, Jan. 11, 2010, vol. 170, No. 1, 18-26.
Chugh, Sumeet et al., A Community-Based Evaluation of Sudden Death Associated with Therapeutic Levels of Methadone, American Journal of Medicine, Jan. 2008, vol. 121, pp. 66-71.
Cirignotta, Fabio, Cerebral Anoxic Attacks in Sleep Apnea Syndrome, Sleep, 1989, pp. 400-404, vol. 12 No. 5.
Curry, J. Paul, Threshold Monitoring, Alarm Fatigue, and the Patterns of Unexpected Hospital Death, APSF Newsletter, Fall 2011, pp. 32-35.
Davidson Ward, Sally et al., Responses to hypoxia and hypercapnia in infants of substance-abusing mothers, The Journal of Pediatrics, 1992, pp. 704-709, vol. 121 No. 5 Pt. 1.
Davis, David et al., Radio Telemetry in Patient Monitoring, Current Comment, 1961, vol. 22, No. 6, pp. 1010-1013.

(56) References Cited

OTHER PUBLICATIONS

Decker, Michael J et al., Ambulatory Monitoring of Arterial Oxygen Saturation, Chest, vol. 95, No. 4, Apr. 1989, pp. 717-722, Northbrook, Illinois, USA.
Dempsey, Jerome A et al., Pathophysiology of Sleep Apnea, Physiological Reviews, 2010, vol. 90, No. 1, pp. 47-112.
Devita, M.A. et al., Findings of the First Consensus Conference on Medical Emergency Teams, Critical Care Medicine, 2006, vol. 34, No. 9, pp. 2463-2478.
Devita, M.A. et al., Use of medical emergency team responses to reduce hospital cardiopulmonary arrests, 2004, vol. 13, pp. 251-254.
Diagnostic Apparatus, Bibliographic Data: JP63275325A, Publication Date Nov. 14, 1988, 12 pages.
Dojat, Michel et al., Scenario recognition for temporal reasoning in medical domains, Artificial Intelligence in Medicine, 1998, vol. 14, pp. 139-155.
Duckitt, R.W. et al., Worthing physiological scoring system: derivation and validation of a physiological early-warning system for medical admissions. An observational, population-based single-centre study, The British Journal of Anaethesia, 2007, vol. 98, No. 6, pp. 769-774.
Eckert, Danny, Central Sleep Apnea: Pathophysiology and Treatment, Chest Journal, 2007, vol. 131, pp. 595-607.
Eckert, Danny et al., Pathophysiology of Adult Obstructive Sleep Apnea, Proceedings of American Thorac Society, 2008, vol. 5, pp. 144-153.
Edworthy, J. et al., "Fewer but better auditory alarms will improve patient safety," Qual. Saf. Health Care., 2005, vol. 14(3), pp. 212-215.
Elhefnawy, Ahmed, et al., Stability Analysis of C02 Control of Ventilation, Journal of Internal Medicine, 0161-7567/90, pp. 498-503, Publisher: The American Physiological Society, 1990.
Esbenshade, Aaron et al., "Respiratory failure after endotoxin infusion in sheep: Lung mechanics and lung fluid balance," Journal of Applied Physiology, 1982, vol. 53(4), pp. 967-976.
Escourrou, P et al., Heart failure and sleep respiratory disorders. Prevalence, physiopathology and treatment, [Article in French], Rev Mal Respir, Jun. 2000, vol. 17, Suppl 3, pp. S31-S40 (Abstract).
Farney et al., "Sleep-Disordered Breathing Associated with Long-Term Opioid Therapy," Chest, 2003, vol. 123, pp. 632-639.
Finck, A. D. et al., "Pharmacokinetics of Morphine; Effects of Hypercarbia on Serum and Brain Morphine Concentrations in the Dog," Anesthesiology, 1977, vol. 47(5), pp. 407-410.
Fletcher, Eugene et al., Pulmonary Edema Develops after Recurrent Obstructive Apneas, American Journal of Respiratory and Critical Care Medicine, 1999, vol. 160, pp. 1688-1696.
Franklin, Cory et al., Developing strategies to prevent in hospital cardiac arrest: Analyzing responses of physicians and nurses in the hours before an event, Critical Care Medicine, 1994, vol. 22, No. 2, pp. 244-247.
Freeman, Roy, M.D., "Neurogenic Orthostatic Hypotension," The New England Journal of Medicine, 2008, vol. 358, pp. 615-624.
Gami et al., "Obstructive sleep apnea, obesity, and the risk of incident atrial fibrillation," Journal of the American College of Cardiology, 2007, vol. 49(5), pp. 565-571.
Gillard, C., M.D. et al., "Operating characteristics of the Finapress system to predict elevated left ventricular filing pressure," Clin. Cardiol., 2006, vol. 29(3), pp. 107-111.
Giuliano, Karen, et al., "New-generation pulse oximetry in the care of critically ill patients," Am. J. Crit. Care, 2005, vol. 14(1), pp. 26-37.
Giuliano, Karen, "Physiological Monitoring for Critically Ill Patients: Testing a Predictive Model for the Early Detection of Sepsis," American Journal of Critical Care, 2007, vol. 16, pp. 122-130.
Gold, Avram R et al., Impact of Basic Research on Tomorrow's Medicine, The Pharyngeal Critical Pressure, The Whys and Hows of Using Nasal Continuous Positive Airway Pressure Diagnostically, Chest, vol. 110, No. 4, Oct. 1996, pp. 1077-1088, Northbrook, IL, USA.
Goldhill et al., "A physiologically-based early warning score for ward patients: the association between score and outcome," Anaesthesia, 2005, vol. 60, pp. 547-553.
Graham, Kelly Creighton et al., "Monitor alarm fatigue: standardizing use of physiological monitors and decreasing nuisance alarms," Am. J. Crit. Care., 2010, vol. 19(1), pp. 28-34.
Greer, Ruari, "The temporal evolution of acute respiratory distress syndrome following shock," European Journal of Anaesthesiology, 2010, vol. 27(3), pp. 226-232.
Guo et al., "Early recognition of myxedematous respiratory failure in the elderly," American Journal of Emergency Medicine, 2009, vol. 27(2), pp. 212-215.
Guyenet, Patrice, "The 2008 Carl Ludwig Lecture: retrotrapezoid nucleus, C02, homeostasis, and breathing automaticity," J. Appl. Physiol., 2008, vol. 105, pp. 404-416.
Hajiha, Mohammad et al., "Opioid receptor mechanisms at the hypoglossal motor pool and effects on tongue muscle activity in vivo," The Journal of Physiology, 2009, vol. 587(11), pp. 2677-2692.
Hallowell, Peter et al., "Potentially life-threatening sleep apnea is unrecognized without aggressive evaluation," The American Journal of Surgery, 2007, vol. 193, pp. 364-367.
Harris, Richard et al., "Manifestations of Sepsis," Arch. Intern. Med., 1987, vol. 147, pp. 1895-1906.
Heitman, Steven et al., "Validation of Nasal Pressure for the Identification of Apneas/ Hypopneas during Sleep," American Journal of Respiratory and Critical Care Medicine, 2002, vol. 166, pp. 386-391.
High Resolution Pulse Oximetry (HRPO) Case Report, Patient Safety, Inc., Nov. 23, 2008, 7 pages.
Hillman, D.R. et al., "The upper airway during anaesthesia," British Journal of Anaesthesia, 2003, vol. 91(1), pp. 31-39.
Hillman, David et al., "Sleep, anesthesia, and the upper airway," Seminars in Anesthesia, Perioperative Medicine and Pain, 2007, vol. 26, pp. 65-72.
Hinshaw, Lerner, "Sepsis/septic shock: participation of the microcirculation: an abbreviated review," Critical Care Medicine, 1996, vol. 24(6), pp. 1072-1078.
Horne, Rosemary S.C. et al., Arousal responses and risk factors for sudden infant death syndrome, Sleep Medicine 3, 2002, Supplement, pp. S61-S65.
Horne, Rosemary S.C. et al., Effects of Prematurity on Arousal from Sleep in the Newborn Infant, Pediatric Research, 2000, pp. 468-474, vol. 47 No. 4.
Hravnak et al., "Defining the Incidence of Cardiorespiratory Instability in Patients in Step-Down Units Using an Electronic Integrated Monitoring System," Arch Intern Med., 2008, vol. 168(12), pp. 1300-1308.
Hutchison, Rob et al., "Capnography and Respiratory Depression," American Journal of Nursing, 2008, vol. 108(2), pp. 35-39.
Hwang et al., "Association of Sleep-Disordered Breathing With Postoperative Complications," Chest, 2008, vol. 133, pp. 1128-1134.
Imholz, Ben et al., "Continuous non-invasive blood pressure monitoring: reliability of Finapres device during the Valsalva manoeuvre," Cardiovascular Research, 1988, vol. 22, pp. 390-397.
Imholz, Ben et al., "Non-Invasive continuous finger blood pressure measurement during orthostatic stress compared to intra-arterial pressure," Cardiovascular Research, 1990, vol. 24, pp. 214-221.
Intensive Care Ventilators, Product Comparrison by Healthcare Product Comparison Systems, Inc. published by ECRI, Apr. 2006, 71 pages.
International Application No. PCT/US2009/059102, Written Opinion of the International Searching Authority, date of Issue Apr. 5, 2011.
Iscimen, Remzi et al., "Risk factors for the development of acute lung injury in patients with septic shock: an observational cohort study," Crit. Care Med., 2008, vol. 36(5), pp. 1518-1522.
Ismail, F. et al., "Integrated monitoring and analysis for early warning of patient deterioration," British Journal of Anaesthesia, 2007, vol. 98(1), pp. 149-152.
Isono, Shiroh, "Obstructive Sleep Apnea of Obese Adults," Anesthesiology, 2009, vol. 110, pp. 908-921.
Jabre. Patricia et al., "Capnography monitoring in non intubated patients with respiratory distress," Am. J. Emerg. Med., 2009, vol. 27(9), pp. 1056-1059.

(56) References Cited

OTHER PUBLICATIONS

Jacques, Theresa et al., "Signs of critical conditions and emergency responses (SOCCER): A model for predicting adverse events in the inpatient setting," Resuscitation, 2006, vol. 69, pp. 175-183.
Jobin, V. et al., "Predictive value of automated oxygen saturation analysis for the diagnosis and treatment of obstructive sleep apnoea in a home-based setting," Thorax, 2007, vol. 62, pp. 422-427.
Johnston, Renea et al., "Repetitive hypoxia rapidly depresses cardio-respiratory responses during active sleep but not quiet sleep in the newborn lamb," The Journal of Physiology, 1999, vol. 519, pp. 571-579.
Kato, Inrko et al., "Incomplete Arousal Processes in Infants Who Were Victims of Sudden Death," American Journal of Respiratory and Critical Care Medicine, 2003, vol. 168, pp. 1298-1303.
Kause, Juliane et al., A comparison of antecedents to cardiac arrests, deaths, and emergency intensive care admissions in Australia and New Zealand, and the United Kingdom—the ACADEMIA study, Resuscitation, 2004, vol. 62(3), pp. 275-282.
Kelleher, "Pulse oximetry," J. Clin. Monit., 1989, vol. 5(1), pp. 37-62.
Khoo, See Meng et al., "Obstructive Sleep Apnea Presenting as Recurrent Cardiopulmonary Arrest," Sleep and Breathing, 2009, vol. 13, pp. 89-92.
Landrigan, Christopher et al., "Temporal Trends in Rates of Patient Harm Resulting from Medical Care," The New England Journal of Medicine, 2010, vol. 363, pp. 2124-2134.
Lang, Charles et al., "Sustained hypermetabolic sepsis in rats: characterization of the model," Journal of Surgical Research, 1983, vol. 35(3), pp. 201-210.
Lanone, Sophie et al., "Diaphragmatic fatigue during sepsis and septic shock," Intensive Care Medicine, 2005, vol. 31(12), pp. 1611-1617.
Lejemtel, Thierry et al., "Seek and Treat Obstructive Sleep Apnea in Heart Failure," Journal of the American College of Cardiology, 2007, vol. 49(15), pp. 1632-1633.
Lightdale, Jenifer et al., "Microstream Capnography Improves Patient Monitoring During Moderate Sedation: A Randomized, Controlled Trial," Pediatrics, 2006, vol. 117(6), pp. 1170-1178.
Littleton, Stephen et al., "The pickwickian syndrome-obesity hypoventilation syndrome," Clinics in Chest Medicine, 2009, vol. 30(3), pp. 467-478.
Litvak, Eugene et al., "Rethinking Rapid Response Teams," JAMA, 2010, vol. 304(12), pp. 1375-1376.
Lung Volumes, Wikipedia, available at http://en.wikipedia.org/wiki/Tidal_volume, printed on Nov. 15, 2007, 4 pages.
MacLean, Lloyd et al., "Patterns of septic shock in man: A detailed study of 56 patients," Annals of Surgery, 1967, vol. 166, pp. 543-562.
Maddox, Ray et al., "Clinical Experience with Patient-Controlled Analgesia Using Continuous Respiratory Monitoring and a Smart Infusion System," Am. J. Health-Syst. Pharm., 2006, vol. 63, pp. 157-164.
Manzke, Till et al., "5-HT$_{4(a)}$ Receptors Avert Opioid-induced Breathing Depression without Loss of Analgesia," Science, 2003, vol. 301, pp. 226-229.
Marini, Carlo et al., "Arterial base deficit in pulmonary embolism is an index of severity and diagnostic delay," Intern. Emerg. Med., 2010, vol. 5(3), pp. 235-243.
Matsuoka, Y et al., "Pulmonary embolism during laparoscopic cholecystectomy detected by sudden decrease in end-tidal carbon dioxide pressure," Masui, 2001, vol. 50(1), pp. 42-45 (abstract only).
Mayer., Pierre, et al., Peripheral Neuropathy in Sleep Apnea, A Tissue Marker of the Severity of Nocturnal Desaturation, American Journal Respiratory Critical Care Medicine, vol. 159, pp. 213-219, 1999, Internet address: www.atsjournals.org.
McEwen, James et al., Detection of Interruptions in the Breathing Gas of Ventilated Anaesthetized Patients, Canidian Journal of Anaesthology, 1988, vol. 35, No. 6, pp. 549-561.
McGaughey et al., "Outreach and Early Warning Systems (EWS) for the prevention of intensive care admission and death of critically ill adult patients on general hospital wards," Cochrane Database Syst Rev., 2007, vol. 3, 23 pages.
McGillicuddy, Daniel et al., "Evaluation of end-tidal carbon dioxide role in predicting elevated SOFA scores and lactic acidosis," Intern. Emerg. Med., 2009, vol. 4(1), pp. 41-44.
McKinney, "Alarm fatigue sets off bells, Mass. incident highlights need for protocols check," Modern Healthcare, 2010, vol. 40(15), pp. 14.
McQuilan, Peter et al., Confidential Inquiry into Quality of Care Before Admission to Intensive Care, Jun. 20, 1998, BMJ, vol. 316, pp. 1853-1858.
Michaelson, Peter, MD et al., et al., "Validations of a Portable Home Sleep Study With Twelve-Lead Polysomnography: Comparisons and Insights Into a Variable Gold Standard," Annals of Otology, Rhinology & Laryngology, 2006, vol. 115(11), pp. 802-809.
Mikkelsen, Mark et al., "Serum lactate is associated with mortality in severe sepsis independent of organ failure and shock," Crit. Care Med., 2009, vol. 37(5), pp. 1670-1677.
Mildh, Leena et al., "The concentration-effect relationship of the respiratory depressant effects of alfentanil and fentanyl," Anesthesia Analgesia, 2001, vol. 93(4), pp. 939-946.
Moldenhauer, Kendra et al., "Clinical triggers: an alternative to a rapid response team," 2009, vol. 35(3), pp. 164-174.
Mora, Christina et al., "Sedative and ventilatory effects of midazolam infusion: effect of flumazenil reversal," Can. J. Anaesth., 1995, vol. 42(8), 677-684.
Moses, James et al., "The correlation and level of agreement between end-tidal and blood gas pCO$_2$ in children with respiratory distress: a retrospective analysis," BMC Pediatrics, 2009, vol. 9(20), 6 pages.
Muller, Nestor L. et al., Mechanism of Hemoglobin Desaturation During Rapid-Eye-Movement Sleep in Normal Subjects and in Patients with Cystic Fibrosis, American Review of Respiratory Disease, vol. 121, 1980, pp. 463-469.
Nakano, Hiroshi et al., "A New Oximetry Algorithm for Screening of Sleep-Disordered Breathing," Therapeutic Research, 2005, vol. 26(5), pp. 1-7.
Newman, N. M., Arousal defect: Mechanism of the Suddent Infant Death Syndrome?, Australian Pediatric Journal, 1989, pp. 196-201.
Newman-Toker, David et al., "Diagnostic Errors—the Next Frontier for Patient Safety," The Journal of the American Medical Association, 2009, vol. 301 (10), pp. 1060-1062.
Nigro et al., "Validation of the WristOx 3100™ oximeter for the diagnosis of sleep apnea/hypopnea syndrome," Sleep Breath, 2008, 10 pages.
Ochroch, Andrew et al., "The impact of continuous pulse oximetry monitoring on intensive care unit admissions from a postsurgical care floor," Anesth Analg, 2006, vol. 1 02(3), pp. 868-875.
Overdyk, Frank et al., "Continuous Oximetry/ Capnometry Monitoring Reveals Frequent Desaturation and Bradypnea During Patient-Controlled Analgesia," Anesthesia & Analgesia, 2007, vol. 105(2), pp. 412-418.
Palsson, Jan et al., "Changes in central hemodynamics during experimental septic shock in conscious rats," Circulatory Shock, 1987, vol. 22(1), pp. 65-72.
Pass, Lawrence et al., "Cardiopulmonary response of the rat to gram-negative bacteremia," Am. J. Physiol., 1984, vol. 246, H344-350.
Patil, Susheel et al., "Neuromechanical control of upper airway patency during sleep," Journal of Applied Physiology, 2007, vol. 102, pp. 547-556.
Pedersen, T. et al., "Pulse oximetry for perioperative monitoring," Cochrane Database of Systematic Reviews, 2009, vol. 7(4), CD002013.
Peppard, Paul et al., "The impact of obesity on oxygen desaturation during sleep-disordered breathing," Am. J. Respir. Crit. Care Med., 2009, vol. 180(8), pp. 788-793.
Photoplethysmograph, Wikipedia, available at http://en.wikipedia.org/wiki/Photoplethysmography, printed on Dec. 8, 2010, 4 pages.
Qadeer, Mohammed et al., "Capnographic Monitoring of Respiratory Activity Improves Safety of Sedation for Endoscopic Cholangiopancreatography and Ultrasonography," Gastroenterology, 2009, vol. 136, pp. 1568-1576.
Redline et al., "The Scoring of Respiratory Events in Sleep: Reliability and Validity," Journal of Clinical Sleep Medicine, 2007, vol. 3(2), pp. 169-200.

(56) References Cited

OTHER PUBLICATIONS

Remmers et al., "Pathogenesis of Upper Airway Occlusion During Sleep," Journal of Applied Physiology, 1978, vol. 44(6), pp. 931-938.
Rivera, Luis, MD et al., Dynamic Ventilatory Characteristics During Weaning in Postoperative Critically Ill Patients, Anesthesia & Analgesia, 1997, vol. 84, pp. 1250-1255.
Rothschild, Jeffrey et al., "A Controlled Trial of a Rapid Response System in an Academic Medical Center," The Joint Commission Journal on Quality and Patient Safety, 2008, vol. 34(7), pp. 417-425.
Sakurai, Shigeru et al., "Low Plasma Orexin-A Levels Were Improved by Continuous Positive Airway Pressure Treatment in Patients with Severe Obstructive Sleep Apnea-Hypopnea Syndrome," Chest, 2005, vol. 127, pp. 731-737.
Saper, Clifford et al., "The Sleep Switch: Hypothalamic Control of Sleep and Wakefulness," Trends in Neurosciences, 2001, vol. 24(12), pp. 726-731.
Schein, R.M. et al., Clinical Anecedents to in-hospital cardiopulmonary arrest. Chest Journal, 1990, pp. 1388-1392.
Schwab, Richard j et al., Upper Airway and Soft Tissue Structural Changes Induced by CPAP in Normal Subjects, American Journal Respiratory Critical Care Medicine, 1996, vol. 154, pp. 1106-1116.
Seifer, Colette et al., "Mointoring Devices for Falls and Syncope," Clinics in Geriatric Medicine, 2002, Seifer et al., "Mointoring Devices for Falls and Syncope," Clinics in Geriatric Medicine, 2002, vol. 18, pp. 295-306.
Shelley, Kirk, "Photoplethysmography: Beyond the Calculation of Arterial Oxygen Saturation and Heart Rate," The International Anesthesia Research Society, 2010, 30 pages.
Sieker, Herbert et al., "Carbon dioxide intoxication: the clinical syndrome, its etiology and management with particular reference to the use of mechanical respirators," Medicine, 1956, vol. 35(4), pp. 389-423.
Simmons, Daniel et al., "Hyperventilation and respiratory alkalosis as signs of gram-negative bacteremia," JAMA, 1960, vol. 174(18), pp. 2196-2199.
Smith, Gary et al., "Hospital-wide physiological surveillance—a new approach to the early identification and management of the sick patient," Resuscitation, 2006, vol. 71, pp. 19-28.
Smith, Gary et al., "Review and performance evaluation of aggregate weighted 'track and trigger' systems," Resuscitation, 2008, vol. 77, pp. 170-179.
Stacey, Michael et al., "Temporal abstraction in the intelligent clinical data analysis: A survey," Artificial Intelligence in Medicine, 2007, vol. 19, pp. 1-24.
Stead, William et al., "Computational Technology for Effective Health Care: Immediate Steps and Strategic Directions," National Research Council of the National Academies, 2009, 113 pages.
Stock, Christine et al., "The PaC02 rate of rise in anesthetized patients with airway obstruction," J. Clin. Anesth., 1989, vol. 1(5), pp. 328-332.
Taenzer, Andreas et al., "Impact of pulse oximetry surveillance on rescue events and intensive care unit transfers: a before-and-after concurrence study," Anesthesiology, 2010, vol. 112(2), pp. 282-287.
Tarassenko et al., "Integrated monitoring and analysis for early warning of patient deterioration," British Journal of Anaesthesia, 2006, vol. 97, pp. 64-68.
Tee, Augustine et al., "Bench-to-bedside review: The MET syndrome—the challenges of researching and adopting medical emergency teams," Critical Care, 2008, vol. 12(1), 6 pages.
The Doctor's Advocate, The Doctors Company, Third Quarter 2010, 8 pages.
Tibballs, J. et al., "Reduction of paediatric in-patient cardiac arrest and death with a medical emergency team: preliminary results," Arch. Dis. Child., 2005, vol. 90, pp. 1148-1152.
Valipour, A et al., "Some factors affecting cerebral tissue saturation during obstructive sleep apnoea," European Respiratory Journal, 2002, vol. 20, pp. 444-450.
Van Lieshout, Johannes et al., "Physical manoeuvres for combating orthostatic dizziness in autonomic failure," The Lancet, 1992, vol. 339, pp. 897-898.
Vandercar, D.H. et al., "Sleep apnea syndromes: a potential contraindication for patient-controlled analgesia," Anesthesiology, 1991, vol. 74(3), pp. 623-624.
Vázquez, Juan-Carlos et al., "Automated Analysis of Digital Oximetry in the Diagnosis of Obstructive Sleep Apnoea," Thorax, 2000, vol. 55, pp. 302-307.
Ventetuolo, Corey et al., "Sepsis: A Clinical Update," Clinical Journal of the American Society of Nephrology, 2008, vol. 3, pp. 571-577.
Walker, James et al., "Chronic Opioid Use is a Risk Factor for the Development of Central Sleep Apnea and Ataxic Breathing," Journal of Clinical Sleep Medicine, 2007, vol. 3(5), pp. 455-462.
Wang, Hanqiao et al., "Influence of Obstructive Sleep Apnea on Mortality in Patients with Heart Failure," Journal of the American College of Cardiology, 2007, vol. 49(15), pp. 1625-1631.
Watkinson, P.J. et al., "A randomised controlled trial of the effect of continuous electronic physiological monitoring on the adverse event rate in high risk medical and surgical patients," Anaesthesia, 2006, vol. 61(11), pp. 1031-1039.
Weiss, YG et al., Computer Assisted Physiological Monitoring and Stability Assessment in Vascular Surgical Patients Undergoing General Anesthesia—Preliminary Data, Journal of Clinical Monitoring and Computing, 2000, vol. 16, pp. 107-113.
White, David, "Opioid-induced suppression of genioglossal muscle activity: is it clinically important?" J. Physiol., 2009, vol. 587, pp. 3421-3422.
Wiedemann et al., The effect of sedation on pulmonary function Anaesthesist, 1995, vol. 44 Suppl 3, pp. S588-S593 (Abstract only).
Winters, Bradford et al., "Rapid Response Systems: A systemic review," Crit. Care Med., 2007, vol. 35, pp. 1238-1243.
Winters, Bradford et al., "Rapid response teams: Walk, don't run," JAMA, 2006, vol. 296, pp. 1645-1647.
Witting, Michael et al., "The sensitivity of room-air pulse oximetry in the detection of hypercapnia," Am. J. Emerg. Med., 2005, vol. 23(4), pp. 497-500.
Wittwer et al., "Role of Morphine's Metabolites in Analgesia: Concepts and Controversies," The AAPS Journal, 2006, vol. 8(2), Article 39, E348-E352.
Yegneswaran, "The importance of screening for obstructive sleep apnea before surgery," Letter to the Editor, Sleep Medicine, 2008, 1 page.
Younes, Magdy, "Contributions of Upper Airway Mechanics and Control Mechanisms to Severity of Obstructive apnea," Am. J. Respir. Crit. Care Med., 2003, vol. 168, pp. 645-658.
Younes, Magdy, "Role of Arousals in the Pathogenesis of Obstructive Sleep Apnea," American Journal of Respiratory and Critical Care Medicine, 2004, vol. 169, pp. 623-633.
Zhang, Zhenxiong et al., "Activation of opioid μ receptors in caudal medullary raphe region inhibits the ventilatory response to hypercapnia in anesthetized rats," Anesthesiology, 2007, vol. 1 07(2), pp. 288-297.
Abelson, Harold et al., Structure and Interpretation of Computer Programs, MIT Press, 2nd Edition, 1996, p. 99-107, 113-126.
Agronsky, Dominik, et al., Diagnosing Community-Acquired Pneumonia with a Bayesian Network, AMIA, Inc., 1998, pp. 632-636.
Appeal Brief for U.S. Appl. No. 11/351,961, filed Sep. 24, 2009.
Brabrand, Mikkel, et al., Risk scoring systems for adults admitted to the emergency department: a systematic review, Scandinavian Journal of Trauma, Resuscitation & Emergency Medicine, Retrieved from <http://www.sjtrem.com/content/18/1/8>, 2010, pp. 1-8.
Caines et al: "Overlooking orthostatic hypotension with routine blood-pressure equipment" 1 Lancet The Lancet Limited. London, GB, vol. 352, No. 9126, Aug. 8, 1998, p. 458, DXP004832973, ISSN:0140-6736, the whole document.
Capuano, Terry Ann, et al., Remote Telemetry, Nursing Management, Vo. 26, No. 7, Jul. 1995, p. 26.
Charbonnier et al., "A trend-based alarm system to improve patient monitoring in intensive care units," Control Engineering Practice, Pergamon Press, Oxford, GB, vol. 15, No. 9, May 12, 2007; pp. 1039-1050.
Crowe, Colleen A., et al., Comparison of severity of illness scoring systems in the prediction of hospital mortality in severe sepsis and septic shock, Journal of Emergencies, Trauma, and Shock, Oct.-Dec. 2010, pp. 342-347, Oak Lawn, IL, USA.

(56) References Cited

OTHER PUBLICATIONS

Diep, Binh An, et al., Polymorphonuclear leukocytes mediate *Staphylococcus aureus* Panton-Valentine leukocidin-induced lung inflammation and injury, PNAS, Mar. 23, 2010, vol. 107, No. 12, pp. 5587-5592.
Doctors use 'remote control' to monitor ICU patients, CNN.com. technology>computing, Aug. 21, 2000, http://www.cnn .com/2000/ TEC H/computing/08/21/icu. t_t 1.
Earthrowi-Gould, T., et al.; "Chest and abdominal surface motion measurement for continuous monitoring of respiratory function," Proc. Instn Mech Engrs, V215, Part H; pp. 515-520 (2001).
East, Christine E., et al.; "Fetal Oxygen Saturation and Uterine Contractions During Labor," American Journal of Perinatology, vol. 15, No. 6, pp. 345-349 (Jun. 1998).
Examiner's Answer for U.S. Appl. No. 11/351,961, mailed Jan. 4, 2010.
Ferrari, A U, et al., Inverse Relationship between heart rate and blood pressure variabilities in rats. Hypertension. Nov. 1987, vol. 10, No. 5, pp. 533-537.
Finding Value in Intensive Care, From Afar, The New York Times on the Web, Jul. 27, 1999, www.Visicu.com/ companynews/0799_ nytimes.htm.
Fry, Donald, et al., The Changing Face of *Staphylococcus aureus*: A Continuing Surgical Challenge, Surgical Infections, 2011, vol. 12, No. 3, pp. 191-203.
Ghanem-Zoubi, Nesrin 0., et al., Assessment of disease-severity scoring systems for patients with sepsis in general internal medicine departments, Critical Care, Retrieved from <http://ccforum.com/ content/15/2/R95>, 2011, pp. 1-7.
Grundy, Betty L., et al., Telemedicine in Critical Care: An Experiment in Health Care Delivery, JACEP, vol. 6, Oct. 1977, pp. 439-444.
Hornero, Roberto, et al.; "Utility of Approximate Entropy From Overnight Pulse Oximetry Data in the Diagnosis of the Obstructive Sleep Apnea Syndrome,"; IEEE Transactions on Biomedical Engineering, vol. 54, No. 1, pp. 107-113, Jan. 2007.
International Preliminary Report on Patentability Including Written Opinion for International (PCT) Patent Application No. PCT/ US2009/043150, issued Nov. 9, 2010 9 pages.
International Preliminary Report on Patentability including Written Opinion for International (PCT) Patent Application No. PCT/ US2009/064312, issued May 31, 2011 10 pages.
International Search Report and Written Opinion for application No. PCT/082010/001624 dated Dec. 7, 2010.
International Search Report for International (PCT) Patent Application No. PCT/US2009/043150, mailed Aug. 4, 2009 2 pages.
International Search Report for International (PCT) Patent Application No. PCT/US2009/064312, mailed Feb. 26, 2010 3 pages.
International Search Report for International (PCT) Patent Application No. PCT/US2012/065124, mailed Mar. 25, 2013, 10 pages.
International Search Report for International (PCT) Patent Application No. PCT/US2012/065129, mailed Mar. 20, 2013, 12 pages.
International Search Report, PCT/US2008/002253; Date of mailing: Jun. 9, 2008.
International Search Report, PCT/US2008/002254, Date of Mailing: Jul. 28, 2008.
Johansson, A.; "Neural network for photoplethysmographic respiratory rate monitoring," Medical & Biological Engineering & Computing, vol. 41, pp. 242-248 (2003).
Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.
Kaplan, Simon M. and Geraldine Fitzpatrick, Designing Support for Remote Intensive-Care Telehealth Using the Locales Framework, ACM, 1997, pp. 173-184.
Kellett, J., et al., The Simple Clinical Score predicts mortality for 30 days after admission to an acute medical unit, Retrieved from <http:// qjmed.oxfordjornals.org>, Q J Med, Received Apr. 17, 2006 and in revised form Jul. 3, 2006, pp. 771-781, vol. 99, Published by Oxford University Press on behalf of the Association of Physicians, Nenagh, Ireland.
Kreisel. Kristen, et al., USA300 Methicillin-resistant *Staphylococcus aureus* bacteremia and the risk of severe sepsis: is USA300 Methicillin-resistant *Staphylococcus aureus* associated with more severe infections?, Diagnostic Microbiology and Infectious Disease, 2011, vol. 70, pp. 285-290.
Lappin, Emma, et al., Gram-Positive Toxic Shock Syndromes, The Lancet, May 2009, vol. 9, pp. 281-290.
Lee, Ho Sung, et al., Remote Patient Monitoring Service through World-Wide Web, Proceedings—19th International Conference— IEEE/EMBS, Oct. 3D-Nov. 2, 1997, pp. 928-931.
Levy, Mitchell M., et al., 2001 SCCM/ESICM/ACCP/ATS/SIS International Sepsis Definitions Conference, Critical Care Medicine, 2003, pp. 1250-1256, vol. 31 No. 4.
Mabry, Susan L., et al., Integrated Medical Analysis System, Proceedings of the 1997 Winter Simlation Conferece, , 1997, pp. 1167-1168.
Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).
Members of the American College of Chest Physicians/Society of Critical Care Medicine Consensus Conference Committee, Definitions for sepsis and organ failure and guidelines for the use of innovative therapies in sepsis, Critical Care Medicine, 1992, pp. 864-874, vol. 20 No. 6.
Miksch, Silvia, Artificial Intelligence for Decision Support: Needs, Possibilities, and Limitations in ICU, 10th Postgraduate Course in Critical Care Medicine A.P.I.C.E. '95, Springer, 1995, pp. 1-11.
Nenov, Valeriy and John Klopp, Remote Access to Neurosurgical ICU Physiological Data using the World Wide web, health Care in the Information Age, 1996, pp. 242-249.
Nguyen, H. Bryant, et al., Severe Sepsis and Septic Shock: Review of the Literature and Emergency Department Management Guidelines, Annals of Emergency Medicine, Jul. 2006, vol. 48, No. 1, pp. 28-55.
Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).
Non-Final Office Action for U.S. Appl. No. 11/351,961, mailed Aug. 19, 2008.
Notice of Allowability for U.S. Appl. No. 10/150,582, mailed Feb. 13, 2006.
Notice of Allowance for U.S. Appl. No. 11/455,408, mailed Jan. 23, 2012 8 pages.
Notice of Allowance for U.S. Appl. No. 11/455,488, mailed Aug. 22, 2011 8 pages.
Notice of Allowance for U.S. Appl. No. 11/455,488, mailed Nov. 29, 2011 8 pages.
Official Action for Canada Patent Application No. 2,678, 776, dated Feb. 8, 2012.
Official Action for Canada Patent Application No. 2,678,856, mailed Feb. 2, 2012 3 pages.
Official Action for U.S. Appl. No. 10/150,582, mailed Jun. 20, 2005.
Official Action for U.S. Appl. No. 11/274,960, mailed Jun. 8, 2010.
Official Action for U.S. Appl. No. 11/274,960, mailed Oct. 20, 2010.
Official Action for U.S. Appl. No. 11/280,559, mailed Mar. 21, 2011 13 pages.
Official Action for U.S. Appl. No. 11/280,559, mailed Oct. 5, 2011 12 pages.
Official Action for U.S. Appl. No. 11/280,653, mailed Dec. 1, 2010 9 pages.
Official Action for U.S. Appl. No. 11/280,653, mailed Jun. 13, 2011 8 pages.
Official Action for U.S. Appl. No. 11/280,653, mailed Mar. 31, 2010.
Official Action for U.S. Appl. No. 11/351,787, mailed Apr. 22, 2011 11 pages.
Official Action for U.S. Appl. No. 11/351,787, mailed Nov. 12, 2010.
Official Action for U.S. Appl. No. 11/351,961, mailed Apr. 24, 2009.
Official Action for U.S. Appl. No. 11/351,961, mailed Aug. 19, 2008.
Official Action for U.S. Appl. No. 11/351,961, mailed Jan. 4, 2010.

(56) References Cited

OTHER PUBLICATIONS

Official Action for U.S. Appl. No. 11/369,355, mailed Aug. 18, 2011 8 pages Restriction Requirement.
Official Action for U.S. Appl. No. 11/369,355, mailed Jan. 6, 2012 8 pages.
Official Action for U.S. Appl. No. 11/369,379, mailed Jun. 20, 2011 8 pages.
Official Action for U.S. Appl. No. 11/455,408, mailed Dec. 27, 2010.
Official Action for U.S. Appl. No. 11/455,408, mailed Jul. 27, 2011 6 pages.
Official Action for U.S. Appl. No. 11/455,488, mailed Dec. 28, 2010.
Official Action for U.S. Appl. No. 12/437,385, mailed Apr. 5, 2011 22 pages.
Official Action for U.S. Appl. No. 12/437,385, mailed Nov. 25, 2011 18 pages.
Official Action for U.S. Appl. No. 12/437,417, mailed Mar. 4, 2011 24 pages.
Official Action for U.S. Appl. No. 12/839,177, mailed Nov. 21, 2011 12 pages.
Patel, M.S., et al., Does the use of a "track and trigger" warning system reduce mortality in trauma patients?, Injury, D May 25, 2011, doi:1 0.1 016/j.injury.2011.05.030, pp. 1-5, Elsevier Ltd., United Kingdom.
Perednia, Douglas A., Telemedine Technology and Clinical Applications, JAMA, vol. 6, Feb. 8, 1995, p. 483.
Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.
Remote Monitoring of ICU Patients Lowers Mortality Rates, Complications, Johns Hopkins Newsrelease, Mar. 20, 2001 , http ://www. newswise. com/areticles/2001/3/ICU.JHM.html.
Response to Non-Final Office Action for U.S. Appl. No. 11/351,961, filed Dec. 19, 2008.
Restriction Requirement for U.S. Appl. No. 11/369,355, mailed Sep. 2, 2010.
Restriction Requirement for U.S. Appl. No. 11/274,960, mailed Feb. 3, 2010.
Restriction Requirement for U.S. Appl. No. 11/280,559, mailed Mar. 4, 2010.
Restriction Requirement for U.S. Appl. No. 11/280,559, mailed Oct. 18, 2010.
Restriction Requirement for U.S. Appl. No. 11/351,787, mailed Jul. 9, 2010.
Restriction Requirement for U.S. Appl. No. 11/369,355, mailed Dec. 8, 2010.
Restriction Requirement for U.S. Appl. No. 11/369,379, mailed Dec. 27, 2010.
Restriction Requirement for U.S. Appl. No. 11/369,379, mailed Sep. 20, 2010.
Restriction Requirement for U.S. Appl. No. 11/455,408, mailed Sep. 30, 2010.
Restriction Requirement for U.S. Appl. No. 11/455,488, mailed Sep. 16, 2010.
Rosenfeld, M.D., Brian A., FCCM, FCCP, et al., Intensive care unit telemedicine: Alternate paradigm for providing continuous intensivist care, Critical Care Medicine, vol. 28, No. 12, 2000 p. 3925.
Sawyer, Amber M., et al., Implementation of a real-time computerized sepsis alert in nonintensive care unit patients, Critical Care Medicine, 2011, pp. 469-4 73, vol. 39, No. 3 D.
Seelbach-Gobel, Birgit, et al.; The prediction of fetal acidosis by means of intrapartum fetal pulse oximetry, Am J. Obstet. Gynecol., vol. 180, No. 1, Part 1, pp. 73-81 (1999).
Seigel, Todd A., et al., Inadequacy of Temperature and White Blood Cell Count in Predicting Bacteremia in Patients D with Suspected Infection, 2010, Elsevier, Inc., The Journal of Emergency Medicine, pp. 1-6, 2010.
Spigulis, Janis, et al.; "Optical multi-channel sensing of skin blood pulsations," Optical Sensing, Proceedings of SPIE, vol. 5459, pp. 46-53 (2004).

Subbe, C. P., et al., Validation of a modified Early Warning Score in medical admissions, Original Papers, Q J Med, D May 17, 2001 and in revised form Jul. 9, 2001, pp. 521-526, vol. 94, Association of Physicians.
Tufte, Edward R., The Visual Display of Quantitative Information (Graphics Press, 1983), p. 17, 21, 153.
USPTO, U.S. Appl. No. 11/431,686, Amendment and Response to NF Office Action, Filed Jun. 21, 2011.
USPTO, U.S. Appl. No. 11/431,686, Final Office Action, dated Oct. 12, 2011.
USPTO, U.S. Appl. No. 11/431,686, NF Office Action, dated Jan. 21, 2011.
USPTO, U.S. Appl. No. 11/431,686, Office Action (Restriction Requirement), dated Sep. 30, 2010.
USPTO, U.S. Appl. No. 11/431,686, Request for Continued Examination and Preliminary Amendment, Filed Feb. 29, 2012.
USPTO, U.S. Appl. No. 11/431,686, Response to Restriction Requirement, filed Oct. 29, 2010.
USPTO, U.S. Appl. No. 12/437,385, Amendment and Response to NF Office Action, dated Jan. 15, 2013.
USPTO, U.S. Appl. No. 12/437,385, Amendment and Response to NF Office Action, dated Sep. 6, 2011.
USPTO, U.S. Appl. No. 12/437,385, NF Office Action, dated Apr. 5, 2011.
USPTO, U.S. Appl. No. 12/437,385, NF Office Action, dated Aug. 17, 2012.
USPTO, U.S. Appl. No. 12/437,385, Request for Continued Examination and Preliminary Amendment, Filed Feb. 7, 2012.
USPTO, U.S. Appl. No. 12/437,417, Amendment and Response to NF Office Action, dated Nov. 5, 2012.
USPTO, U.S. Appl. No. 12/437,417, Amendment and Response to NF Office Action, dated Sep. 6, 2011, 13 pages.
USPTO, U.S. Appl. No. 12/437,417, Final Office Action, dated Feb. 14, 2013.
USPTO, U.S. Appl. No. 12/437,417, NF Office Action, dated Aug. 3, 2012.
USPTO, U.S. Appl. No. 12/437,417, NF Office Action, dated Nov. 29, 2011.
USPTO, U.S. Appl. No. 12/437,417, Request for Continued Examination and Preliminary Amendment, Filed Feb. 29, 2012.
USPTO, U.S. Appl. No. 12/629,407, Amendment and Response to NF Office Action dated Sep. 25, 2012, filed Feb. 21, 2013.
USPTO, U.S. Appl. No. 12/629,407, NF Office Action, dated Aug. 16, 2012.
USPTO, U.S. Appl. No. 12/629,407, NF Office Action, dated Sep. 25, 2012.
USPTO, U.S. Appl. No. 12/629,407, Response to Requirement for Restriction, filed Sep. 14, 2012.
Wile, Michael J., et al., Manual Differential Cell Counts Help Predict Bacterial Infection, A Multivariate Analysis, D Hematopathology, 2001, pp. 644-649, vol. 115, Am J Clin Pathol.
Yoon, Gilwon, et al.; Multiple diagnosis based on Photoplethysmography: hematocrit, $SpO_2$, pulse and respiration, Optics in Health Care and Biomedical optics: Diagnostics and Treatment; Proceedings of the SPIE, vol. 4916; pp. 185-188 (2002).
Abraham, Howard et al., Sequential Cardiorespiratory Patterns in Septic Shock, Critical Care Medicine, vol. 11, No. 10, Oct. 1983, pp. 799-803.
Agilent Technologies, Agilent M1165/66/67/75/76/77A Component Monitoring System and Agilent M1205A V24 & V26, User's Reference Manual, vol. 1, System Information, Part No. M1046-9101L, First Ed., Printed Nov. 2000.
Agilent Technologies, Agilent M1165/66/67/75/76/77A Component Monitoring System and Agilent M1205A V24 & V26, User's Reference Manual, vol. 2, Parameter Information, Part No. M1046-9101L, First Ed., Printed Nov. 2000.
Alaris System, Brochure, Medication Safety System Focused at the Point of Care, Cardinal Health, Alaris Products, pp. 8.
Aubry, et al., The $SaO_2$/t Diagram as a Useful Means to Express Nocturnal Hypoxemia, Chest, 1989; 96: 1341-45.
Bartolo, Anton, et al., An Arrhythmia Detector and Heart Rate Estimator for Overnight Polysomnography Studies, conditionally accepted for IEEE Transactions, 19 pages.

(56) References Cited

OTHER PUBLICATIONS

Benumof, Jonathan L., Creation of Observational Unit May Decrease Sleep Apnea Risk, Letters to the Editor, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp.

Blackshear et al., Nocturnal Dyspnea and Atrial Fibrillation Preset Cheyne-Stokes Respirations in Patients With Congestive Heart Failure, Jun. 26, 1995, Arch Intern Med. vol. 155, p. 1296-1302.

Buckle, Patricia, et al., Polysomnography in Acutely Ill Intensive Care Unit Patients, Chest, v. 102 n. 1, p. 288 (4), American College of Chest Physicians.

Daley, Denise M., MD, Beware of All Sedatives in Patients With Sleep Apnea, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp.

Dowdell, WT; Javaheri, S; McGinnis, W, Cheyne-Stokes Respiration Presenting as Sleep Apnea Syndrome. Clinical and Polysomnographic Features, Am Rev Respir Dis, Apr. 1990, pp. 871-879.

Dyken, Mark Eric et al., Obstructive Sleep Apnea Associated with Cerebral Hypoxemia and Death, Neurology 2004; 62, pp. 491-493.

Epstein et al., "Cost-Effectiveness Analysis of Nocturnal Oximetry as a Method of Screening for Sleep Apnea-Hypopnea Syndrome," Jan. 1, 1998, Chest, vol. 113, p. 97-103.

Evans, et al., A Microcomputer System for Monitoring and Analysing Oxyhemolobin Saturation During Sleep. Computer Programs in Biomedicine, 1984; 18: 227-234.

Fisher, Kyle S., MD, Value of Pulse Oximetry Monitoring on the Ward is Questioned, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp.

Fletcher et al., Effect of Cardiac Output Reduction on Rate of Desaturation in Obstructive Apnea; Chest, 99:452-456, 1991.

Fletcher et al., Rate of Oxyhemolglobin Desaturation in Obstructive versus Nonobstructive Apnea; Am Rev Respi Dis. 143:657-660; 1990.

Fletcher et al., The Rate of Fall of Arterial Oxyhemoglobin Saturation in Obstructive Sleep Apnea, Chest, 1989; 96: 717-722.

Forster, Robert E., The Lung: Physiologic basis of Pulmonary Function Tests (Book), 1986 Year Book medical Publishers, Inc., Chapter 3, I. Volume of Pulmonary Ventilation, pp. 32-64.

Gagnadoux, Fredrick et al., Home Unattended vs Hospital Telemonitored Polysomnography in Suspected Obstructive Sleep Apnea Syndrome: A Randomized Crossover Trial, Chest 2002; 121; 753-758.

Gami, Apoor S. et al., Day-Night Pattern of Sudden Death in Obstructive Sleep Apnea, The New England Journal of Medicine, 2005; 352, pp. 1206-1214.

George et al., Identification on Qualification of Apneas by Computer-based Analysis of Oxygen Saturation, American Review of Respiratory Disease, 1988; 137; 1238-1240.

Griffiths, et al., A Video System for Investigating Breathing Disorders During Sleep, Thorad, 1991; 46: 136-140.

Guilleminault et al., Sleep Apnea Syndrome: Can It Induce Hemodynamic Changes?, Western Journal of Medicine, vol. 123, Jul. 1975, pp. 7-16.

Guilleminault, C. et al., Unattended CPAP Titration: Toward a Smart Machine, May 20, Stanford University Sleep Research Center, 1 page.

Gyulay et al., A Comparison of Clinical Assessment and Home Oximetry in the Diagnosis of Obstructive Sleep Apnea, American Review of Respiratory Disease, 1993; 147: 50-53.

Hoch, et al., Uberprufung der Fruherkennungsmethode MESAM und Biox 3700 zur Erfassung Schlafbezogener Atmmgmsergulationsstorungen bei jungen Mannern, Pneumologie, 1991; 45: 217-222 (and translation).

Hoffarth, et al., Beuteilung Pulsoximetrisch Erfasster zklisheer . . . and translation (Hoffarth et al. Assessment of Cyclic and Phasic Oxygen Desaturations Measured via Pulsoxymetry in Nocturnal Diagnosis of Respiratory Regulation Disorders, Peumologie, May 1991; 45: 229-232.

Jain, Sanjay S., et al., Perioperative Treatment of Patients with Obstructive Sleep Apnea, Current Opinion Pulmonary Medicine 10, pp. 482-488.

Keyl, C., et al., Spektralanalyse von Arterieller Sauerstoff-sättigung und RR-Intervallen bei Patienten mit obstrukitver Schlafapnoe, Wein Med Wschr 1995, pp. 515-516 (vol. 145).

Kirby et al., Computer Quantitation of Saturation Impairment Time as an Index of Oxygenation During Sleep, Com Meth, 1992: 107-115.

Koehler, U., et al., Nocturnal Myocardial Ischemia and Cardiac Arrhythmia in Patients with Sleep Apnea with and Without Coronary Heart Disease (1991) 69; 474-482.

Longobardo et al., Sleep Apnea Considered as a Control System Instability, Sep. 1982, Respiratory Physiology 50: 311-333.

Lynn, Lawrence A., Cluster Analysis: A New Technology for the Evaluation of Oximetry and Airflow Waveforms in Obstructive Sleep Apnea, Accepted after revision on Dec. 20, 1997, 17 total pages.

Pae, Eung-Kwon, et al., Neuroscience Letters 375, 2005, pp. 123-128.

Patil, Ramesh S. et al., Application of an Artificial Intelligence Program to Therapy of High-Risk Surgical Patients, New Horizons, vol. 4, No. 4, pp. 541-550.

Pepin et al., Does Oximetry contribute to the Detection of Apneic Events? Mathematical. Processing of the $SaO_2$ Signal, Chest, May 1991; 99: 1151-1157.

Rapoport, et al., CO2 Homeostasis During Periodic Breathing: Predictions From a Computer Model, The American Journal of Applied Physiological, 1993, vol. 75, Issue 5, pp. 2302-2309.

Rauscher et al., Computerized Detection of Respiratory Events During Sleep from Rapid Increases in Oxyhemoglobin Saturation, Lung, 1991; 169: 355-42.

Rauscher et al., Quantification of sleep-disordered breathing by computerized analysis of oximetry, heart rate, and snoring, Eur Respir J. Jun. 1991; 4: 655-659.

Ryan, Clodagh M., et al., Periodicity of Obstructive Sleep Apnea in Patients With and Without Heart Failure, Chest 2005; 127, pp. 536-542.

Salmi, et al., Evaluation of Automatic Analysis of SCSB, Airflow and Oxygen Saturation Signals in Patients with Sleep Related Apneas, Chest, 1989; 96: 255-61.

Sanders et al., Obstructive Sleep Apnea Teated by Independently Adjusted Inspiratory and Expiratory Positive Airway Pressures via Nasal Mask, Chest, 1990: 98: 317-24.

Scharf, Steven M., et al., Cardiovascular Effects of Periodic Occlusions of the Upper Airways in Dogs, American Review of Respiratory Disease, pp. 321-329.

Series, et al., Influence of Continuous Positive Airways Pressure on Sleep Apnea-Related Desaturation in Sleep Apnea Patients, Lung, 1992; 170: 281-290.

Series et al., Utility of Nocturnal Home Oximetry for Case Finding in Patients with Suspected Sleep apnea Hypopnea Syndrome, Sep. 15, 1993, Annals of Internal Medicine, col. 119, p. 449-453.

Shepard, J., Gas Exchange and Hemodynamics During Sleep, Medical Clinics of North America, vol. 69, No. 6, Nov. 1985, pp. 1243-1265.

Shoemaker, W. C. et al., Incidence, Physiologic Description, Compensatory Mechanisms, and Therapeutic Implications of Monitored Events, Critical Care Medicine, Dec. 1989, vol. 17, No. 12, pp. 1277-1285.

Shoemaker, W. C. et al., Multicenter study of noninvasive monitoring systems as alternatives to invasive monitoring of acutely ill emergency patients, Chest, 1998; vol. 114; pp. 1643-1652.

Shoemaker, W. C. et al., Noninvasive Physiologic Monitoring of High-Risk Surgical Patients, Archives of Surgery, vol. 131, No. 7, Jul. 1996, pp. 732-737.

(56) References Cited

OTHER PUBLICATIONS

Shoemaker, W. C. et al., Prediction of Outcome and Severity of Illness by Analysis of the Frequency Distributions of Cardiorespiratory Variables, Critical Care Medicine, vol. 5, No. 2, Mar.-Apr. 1977, pp. 82-88.
Shoemaker, W. C. et al., Sequence of Physiologic Patterns in Surgical Septic Shock, Critical Care Medicine, Dec. 21, 1993 (12): pp. 1821.
Shoemaker, W. C., Cardiorespiratory Patterns in Complicated and Uncomplicated Septic Shock: Physiologic Alterations and Their Therapeutic Implications, Ann. Surg., Jul. 1971, vol. 174, No. 1, pp. 119-125.
Shoemaker, W. C., Early Physiologic Patterns in Acurate Illness and Accidents: Toward a Concept of Circulatory Dysfunction and Shock Based on Invasive and Noninvasive Hemodynamic Monitoring, New Horizons, Nov. 1996, vol. 4, No. 4, pp. 395-412.
Shoemaker, W.C., Oxygen Transport and Oxygen Metabolism in Shock and Critical Illness, Invasive and Noninvasive Monitoring of Circulatory Dysfunction and Shock, Critical Care Clinics, vol. 12, No. 4, Oct. 1996, pp. 939-969.
Shoemaker, W. C., Temporal Physiologic Patterns of Shock and Circulatory Dysfunction Based on Early Descriptions by Invasive and Noninvasive Monitoring, New Horizons, vol. 4, No. 2, May 1996, pp. 300-318.
Slutsky et al., Quantification of Oxygen Saturation During Episodic Hypoxemia, American Review of Respiratory Disease, 1980; 121:893-895.
Staniforth, AD; Kinnear, WJ; Starling, R; Cowley AJ, Nocturnal desaturation in Patients with Stable Heart Failure, Heart, Apr. 1998; pp. 394-399.
Strohl et al., Oxygen Saturation During Breath Holding and During Apneas in Sleep, Chest, Feb. 1984: 85, No. 1; 181-186.
Svanborg, et al., A Limited diagnostic Investigation for Obstructive Sleep Apnea Syndrome: Oximetry and Static Charge Sensitive Bed, Chest, 1990; 98: 1341-45.
Tan and T. H. Koh, Evaluation of Obstructive Sleep Apnea in Singapore Using Computerized Polygraphic Monitoring, Annals Academy of Medicine, Mar. 1991, vol. 20 No. 2, pp. 196-200.
Tatevossian, Raymond G., et al., Noninvasive Hemodynamic Monitoring for Early Warning of Adult Respiratory Distress Syndrome in Trauma Patients, Journal of Critical Care, vol. 15, No. 4 (Dec. 2000), pp. 151-159.
Tatevossian, Raymond G., et al., Transcutaneous oxygen and C02 as early warning of tissue hypoxia and hemodynamic shock in critically ill emergency patients.
Timms et al., Oxygen Saturation by Oximetry: analysis by Microcomputer, Journal of Polysomographic Technology, Spring 1988: 13-21.
Timms, et al., and Profox Associates, Inc., Profox for the Bedside, Version 8SP 11/92, Programs for Oximetry [IBM], User's Manual, Nov. 1992, 20 total pages.
White, D. P., et al., Assessment of Accuracy and Analysis Time of a Novel Device to Monitor Sleep and Breathing in the Home, Sleep, vol. 18, No. 2, Feb. 1995, pp. 115-126.
Wilkins, Robert L., et al., Egan's Fundamentals of Respiratory Care, Analysis and Monitoring of Gas Exchange, Book, Eighth Edition, Chapter 16, Section III, Capnography/Capnometry During Mechanical Ventilation, pp. 383-389.
Wilkinson, M. H., et al., Effect of Venous Oxygenation on Arterial Desaturation Rate During Repetitive Apneas in Lambs, Respiration Physiology 101 (19950 321-331.
Williams, et al., Screening for Sleep Apnea Using Pulse Oximetry and a Clinical Score, Chest, 100/3, Sep. pp. 631-635.
Aboyans, V., et al., Sleep Apnoea Syndrome and the Extent of Atherosclerotic Lesions in Middle-Aged Men with Myocardial Infarction, International Angiology, Mar. 1999, vol. 18, No. 1, pp. 70-73.
Aittokallio, Tero, et al., Analysis of Inspiratory Flow Shapes in Patients with Partial Upper-Airway Obstruction During Sleep, Chest, vol. 119, No. 1, Jan. 2001, pp. 37-44, Northbrook, IL, USA.
Alchanatis, M., et al., Left ventricular function in patients with obstructive sleep apnoea syndrome before and after treatment with nasal continuous positive airway pressure, Respiration, 2000, vol. 67, No. 4, p. 367—(Abstract).
Andreas, Stefan, et al., Prevalence of Obstructive Sleep Apnoea in Patients with Coronary Artery Disease, Coronary Artery Disease, Jul. 1996, vol. 7, No. 7, pp. 541-545.
Author Unknown, 1998 New Survey Reports More Than 168 Million American Adults Fail Sleep IQ Test, 132 Million Suffer Sleep Problems, Feb. 1998, Life Magazine.
Author Unknown, Background of Oximetry Utilization for Sleep Apnea Diagnosis, Publication information unknown, Undated.
Author Unknown, Chapter IV Oxygen Consumption During ADO, Introduction, pp. 40-46, Book Title Unknown, Date Unknown.
Author Unknown, Chapter X Effects of a 6-minute Period of ADO, Introduction, pp. 108-113, Book Title Unknown, Date Unknown.
Author Unknown, Excessive Daytime Sleepiness, News Bulletin, http://www.websciences.org/nsf/pressarchives/leadpressrelease_g.html, Jun. 3, 1997, Washington, DC, USA.
Author Unknown, Guidance Article, (No Author), Critical Alarms and Patient Safety, Health Devices, vol. 31, No. 11, Nov. 2002, pp. 397-417, 2002 ECRI.
Author Unknown, News Bulletin, Lack of sleep America's top health problem, doctors say, Health Story Page, CNN, http://cnn.com/HEALTH/9703/17/nfm/sleep.deprivation/index.html, Mar. 17, 1997.
Author Unknown, Sleep Apnea & Heart Problems, News Channel WTVC, Chattanooga, Tennessee, USA, Jun. 3, 1999, News Bulletin.
Author Unknown, The Physiologic Parameters Defining the Oximetry Waveform Patterns in Sleep Apnea, Undated, Publication Unknown.
Author Unknown, The Ventilation Instability Detection Trial, Hospital Protocol, Early Discussion Draft, 4 pages, Facsimile dated Jul. 23, 2003, From SDC.
Ayas, Najib, et al., Unrecognized Severe Postoperative Hypercapnia: A Case of Apneic Oxygenation, Case Report, Mayo Clinic Proceedings, 1998, vol. 73, pp. 51-54, Minneapolis, Minnesota, USA.
Badoual, T., et al., Sleep Apnoea Syndrome and Cardiac Failure, Arch Mal Coeur Vaiss., Mar. 2005, vol. 98, No. 3, pp. 198-2, [Article in French] (Abstract).
BaHammam, A., Comparison of nasal prong pressure and thermistor measurements for detecting respiratory events during sleep, Respiration, Jul.-Aug. 2004, vol. 71, No. 4, pp. 385-390 (Abstract).
Baker, Clark R., et al., Nellcor 04 Algorithm Summary, Copyright 1999 Mallinckrodt Inc., pp. 1-8.
Ball, Eric M., et al., Diagnosis and Treatment of Sleep Apnea Within the Community, The Walla Walla Project, Arch Intern Med, vol. 157, Feb. 24, 1997, pp. 419-424.
Barach, Alvan L., et al., The Physiologic Action of Oxygen and Carbon Dioxide on the Coronary Circulation, as Shown by Blood Gas and Electrocardiographic Studies, The American Heart Journal, Received for publication Aug. 14, 1940, pp. 13-38.
Barker, Steven J., The Effects of Motion on the Performance of Pulse Oximeters in Volunteers (Revised Publication), Anesthesiology, Lippincott-Raven Publishers, American Society of Anesthesiologists, Inc.(Revised Publication) 1997, vol. 86, pp. 101-108 (Both paper and Abstract).
Barnum, P. T., et al., Novel Pulse Oximetry Technology Capable of Reliable Bradycardia Monitoring in the Neonate, Respiratory Care, 1997, vol. 42, No. 11, pp. 1072 (Abstract).
Bassetti, Claudio L., Sleep and Stroke, Seminars in Neurology, vol. 25, No. 1, Nov. 1, 2005, pp. 19-32.
Berg, Sören, et al., Continuous Intrathoracic Pressure Monitoring with a New Esophageal Microchip Catheter in Sleep-Related Upper Airway Obstructions, The Journal of Otolaryngology, vol. 24, No. 3, 1993, pp. 160-164.
Bernet-Buettiker, Vera et al., Evaluation of New Combined Transcutaneous Measurement of PCO2/Pulse Oximetry Oxygen Saturation Ear Sensor in Newborn Patients, Dec. 15, 2004, DOI: I0.1542/peds.2004-0946, Pediatrics Official Journal of the American Academy of Pediatrics, published online, pp. e-64-e-68, Elk Grove Village, IL 60007, USA.

(56) References Cited

OTHER PUBLICATIONS

Berry, Richard B., et al., Comparison of Respiratory Event Detection by a Polyvinylidene Fluoride Film Airflow Sensor and a Pneumotachograph in Sleep Apnea Patients, Chest, The Cardiopulmonary and Critical Care Journal, Chest/128/3/Sep. 2005, pp. 1331-1338, Northbrook, IL, USA.
Berry, Richard B., Positive Nasal Airway Pressure Eliminates Snoring as Well as Obstructive Sleep Apnea, Chest, vol. 85, No. 1, Jan. 1984, pp. 15-20.
Berthon-Jones, M., et al., Time Course of Change in Ventilatory Response to $CO_2$ with Long-Term CPAP Therapy for Obstructive Sleep Apnea, American Review Respiratory Disease, 1987, vol. 135, pp. 144-147.
Berthon-Jones, Michael, Feasibility of a Self-Setting CPAP Machine, Sleep, vol. 16, pp. S120-S123, 1993.
Bixler, E. O., et al., Effects of age on sleep apnea in men: I. Prevalence and Severity, American Journal of Respiratory & Clinical Care Medicine, vol. 157, No. 1, pp. 144-148, Jan. 1998 (Abstract)o.
Blankfield, R. P., et al., Bilateral leg edema, obesity, pulmonary hypertension, and obstructive sleep apnea, Arch Intern Med., Aug. 14, 2000, vol. 28, 160(15), pp. 2357-2362 (Abstract).
Blankfield, R. P., et al., Bilateral leg edema, pulmonary hypertension, and obstructive sleep apnea: a cross-sectional study, Family Practice, Jun. 2002, vol. 51, No. 6, pp. 561-564 (Abstract).
Block, A. Jay, et al., Sleep Apnea, Hypopnea and Oxygen Desaturation in Normal Subjects, A Strong Male Predominance, The New England Journal of Medicine, vol. 300, Mar. 8, 1979, pp. 513-517.
Blumen, M., et al., Dilator muscles of the pharynx and their implication in the sleep apnea syndrome of obstructive type. Review of the literature., [Article in French], Ann Otolaryngol Chir Cervicofac, May 1998, p. 115 (Abstract).
Bock, A. V. et al., The Oxygen and Carbon Dioxide Dissociation Curves of Human Blood (This is study No. 37 of a series of studies on the physiology and pathology of blood form the Harvard Medical School and allied Hospitals, a part of the expense of which has been defrayed by the Proctor Fund for the study of chronic disease, Journal of Biologic Chemistry, vol. 29, 1924, pp. 353-377.
Bohnhorst, B., et al., Major Reduction in Alarm Frequency With a New Pulse Oximeter, Intensive Care Medicine, 1998, vol. 24, No. 3, pp. 277-278 (Abstract).
Bordier, P., et al., Death during polysomnography of a patient with cheyne-stokes respiration, respiratory acidosis, and chronic heart failure, Chest, Nov. 2004, vol. 126, No. 5, pp. 1698-1700 (Abstract).
Botelho, R. V., et al., Adult Chiari malformation and sleep apnoea, Neurosurg Review, Jul. 2005, vol. 28, No. 3, pp. 169-176 (Abstract).
Botelho, Ricardo Vieira, et al., Adult Chiari Malformation and Sleep Apnoea, Published online May 21, 2005, Neurosurgeon Review, vol. 28, pp. 169-176, 2005.
Boushra, N. N., Anaesthetic management of patients with sleep apnoea syndrome, Canadian Journal Anaesth, Jun. 1996, vol. 45, No. 6, pp. 599-616 (Abstract).
Bowton, David L., et al., The Incidence and Effect on Outcome of Hypoxemia in Hospitalized Medical Patients, The American Journal of Medicine, Vo. 97, Jul. 1994, pp. 38-46.
Bradley, Douglas T., et al., Daytime Hypercapnia in the Development of Nocturnal Hypoxemia in COPD, Chest, vol. 97, No. 2, Feb. 1990, pp. 308-312.
Brooks, L. J., et al., Adenoid size is related to severity but not the number of episodes of obstructive apnea in children, Journal of Pediatrics, vol. 132, No. 4, pp. 682-686, Apr. 1998 (Abstract).
Broughton, Roger J., et al., Practice Parameters for the Use of Stimulants in the Treatment of Narcolepsy, ASDA Standards of Practice, Sleep, vol. 17, No. 4, pp. 348-351, American Sleep Disorders Association and Sleep Research Society 1994.
Brown, D. L., et al., Screening for obstructive sleep apnea in stroke patients: a cost-effectiveness analysis, Stroke, Jun. 2005, pp. 1291-1293, Epub May 12, 2005 (Abstract).
Brown, Lee K., "Dephlogisticated air" revisited: oxygen treatment for central sleep apnea, 1997 American College of Chest Physician, Physician Information, No. 8, Rev. 01, Nov. 1997.
Burk, John R., et al., Auto-CPAP in the Treatment of Obstructive Sleep Apnea: A New Approach, Sleep Research 21, 1992, p. 182, Abstract.
Cain, S. M., Breaking Point of Two Breath Holds Separated by a Single Inspiration, Journal of Appl. Physiol., vol. II(I), Jul. 1957, pp. 87-90.
Campos-Rodriguez, Francisco, et al., Mortality in Obstructive Sleep Apnea-Hypopnea Patients Treated With Positive airway Pressure, Chest, The Cardiopulmonary and Critical Care Journal, 2005, vol. 128, pp. 624-633, Northbrook, Illinois, USA (plus Abstract).
Cannesson, Maxime et al., Relation between respiratory variations in pulse oximetry plethsmographic waveform amplitude and arterial pulse pressure in ventilated patients, Critical Care 2005, vol. 9, #5, pp. R562-R568, Available online http://ccforum.com/content/9/5/R562.
Chaoquat, Ari, et al., Association of Chronic Obstructive Pulmonary Disease and Sleep Apnea Syndrome, American Journal Respiratory Critical Care Medicine, 1995, vol. 151, pp. 82-86.
Cherniack and Longobardo, Periodic Breathing During Sleep, pp. 158-190, New Jersey Medical School, Dean's Office, ID 9739727104, May 26, 1999, 14:23, No. 010, (first page missing).
Cherniack, N. S., Introduction to Session on the Pathophysiology of Breathing Control and Breathing: Awake and Asleep, Modeling and Control of Ventilation, Plenum Press, New York, USA, 1995, pp. 87-88.
Cherniack, N. S., New mechanisms for the cardiovascular effects of sleep apnea, American Journal Medicine, Nov. 1, 2000, vol. 109, No. 7, pp. 592-594 (Abstract).
Cherniack, Neil S., Oxygen Sensing: applications in humans, Highlighted Topic: Oxygen Sensing in Health and Disease, Journal Appl. Physiol., vol. 96, pp. 352-358, 2004, The American Physiological Society, http://www.jap.org.
Christiansen, J., et al., Carbon Dioxide in Blood, pp. 266-271, Proceedings of the Physiological Society, This Journal, XLVII, p. ii, 1913, pp. 266-271.
Cilli, Aykut, et al., Nocturnal Oxygen Desaturation in Coronary Artery Disease, JPN Heart Journal, Jan. 1999, pp. 23-28.
CNS Poly G, Printout Examples, CNS, Inc., Chanhassen, Minnesota, USA, Undated, Test Date Feb. 10, 1992.
Conte, G., et al., Acute cardiovascular diseases and respiratory sleep disorders, Minerva Cardioangiol, Jun. 1999, vol. 47, No. 6, pp. 195-202 (Abstract).
Cooper, B. G., et al., Value of Nocturnal Oxygen Saturation as a Screening Test for Sleep Apnoea, Thorax, 1991, vol. 46, pp. 586-588.
Coppola, Michael P., et al., Management of Obstructive Sleep Apnea Syndrome in the Home, The Role of Portable Sleep Apnea Recording, Chest, vol. 104, No. 1, Jul. 1993, pp. 19-24, Northbrook, IL, USA.
Coy, Timothy V., Sleep Apnoea and Sympathetic Nervous System Activity: A Review, Journal Slep Res., 1996, No. 5, pp. 42-50, European Sleep Research Society.
Decker, Michael J., et al., Ambulatory Monitoring of Arterial Oxygen Saturation, Chest, vol. 95, No. 4, Apr. 1989, pp. 717-722, Northbrook, Illinois, USA.
Deegan, P. C., et al., Predictive Value of Clinical Features for the Obstructive Sleep Apnoea Syndrome, European Respiratory Journal, vol. 9, pp. 117-124, 1996.
DeLeeuw, P.W., On sleep and death: cardiovascular risk the obstructive sleep apnea syndrome, Neth Journal Medicine, May 1999, vol. 54, No. 5, pp. 188-190 (Abstract).
Dement, William C., Chairman, National Commission on Sleep Disorders Research, Wake Up America: A National Sleep Alert, vol. 1, Executive Summary and Executive Report, Report of the National Commission on Sleep Disorders Research, Submitted to the United States Congress and to the Secretary, u.s. department of Health and Human Services, Jan. 1993, pp. 1-76.
Demeter, P., et al., The relationship between gastroesophageal reflex disease and obstructive sleep apnea, Gastroenterology, Sep. 2004, vol. 39, No. 9, pp. 815-820 (Abstract).
Dempsey, Jerome A., et al., Sleep and Breathing State of the Art Review Sleep-Induced Breathing Instability, Sleep, vol. 19, No. 3, pp. 236-247, American Sleep Disorders Association and Sleep Research Society.

(56) References Cited

OTHER PUBLICATIONS

Den Herder, Cindy et al., Risks of general anaesthesia in people with obstructive sleep apnea, BMJ, vol. 329, Oct. 23, 2004, pp. 955-959, Downloaded from bmj.com.
Dhonneur, G., et al., Postoperative Obstructive Apnea, Anesth Analg., Sep. 1999, vol. 89, No. 3, pp. 762-767 (Abstract).
Doherty, L. S, et al., Long-term effects of nasal continuous positive airway pressure therapy on cardiovascular outcomes in sleep apnea syndrome, Chest, Jun. 2005, vol. 127, No. 6, pp. 2076-2084 (Abstract).
Douglass, A. B., et al., The Sleep Disorders Questionnaire. I: Creation and multivariate structure of SDQ, Sleep, Mar. 1994, vol. 17, No. 2, pp. 160-167 (Abstract).
Douglass, Alan B., et al., The Sleep Disorders Questionnaire I: Creation and Multivariate Structure of SDQ, Clinical Research, Sleep, vol. 17, No. 1, pp. 160-167, 1994 American Sleep Disorders Association and Sleep Research Society.
Dumas, Constantine, et al., Clinical Evaluation of a Prototype Motion Artifact Resistant Pulse Oximeter in the Recovery Room, Anesth Analg 1996, vol. 83, pp. 263-272.
Dursunoglu, D., et al., Impact of obstructive sleep apnoea on left ventricular mass and global function, European Respiratory Journal, Aug. 2005, vol. 26, No. 2, pp. 283-288 (Abstract).
Dyken, M. E., et al., Obstructive sleep apnea associated with cerebral hypoxemia and death, Neurology, Feb. 10, 2004, vol. 62, No. 3, pp. 491-493 (Abstract).
Dziewas, R., et al., Capnography screening for sleep apnea in patients with acute stroke, Neurology Res. Jan. 2005, vol. 27, No. 1, pp. 83-87 (Abstract).
Dziewas, R., et al., Increased Prevalence of Sleep Apnea in Patients with Recurring Ischemic stroke Compared with First Stroke Victims, Journal Neurology, Nov. 2005, vol. 252, No. 11, pp. 1394-1398. Epub Jul. 20, 2005 (Abstract).
Edge City Hospital Sleep Disorders Center, Sleep Summary of Patient, Houston, Texas, USA, pp. 1-3, Feb. 17, 1997.
Elfadel, I. M., et al., Motion-Resistant Pulse Oximetry, Abstract Only, Journal of Clinical Monitoring, vol. II, No. 4, Jul. 1995, p. 262.
Eihefnawy, Ahmed, et al., Stability Analysis of CO2 Control of Ventilation, Journal of Internal Medicine, 0161-7567/90, pp. 498-503, Publisher: The American Physiological Society, 1990.
Escourrou, P., et al., Heart failure and sleep respiratory disorders. Prevalence, physiopathology and treatment, [Article in French], Rev Mal Respir, Jun. 2000, vol. 17, Suppl 3, pp. S31-S40 (Abstract).
Farhi, Leon E., et al., Dynamics of Changes in Carbon Dioxide Stores, Anesthesiology, Nov.-Dec. 1960, vol. 21, pp. 604-614 (last page missing).
Farney, Robert J., et al., Ear Oximetry to Detect Apnea and Differentiate Rapid Eye Movement (REM) and Non-REM (NREM) Sleep, Screening for the Sleep Apnea Syndrome, Chest, vol. 89, No. 4, Apr. 1986, pp. 533-539, Northbrook, IL, USA.
Farre, R., et al., Importance of the Pulse Oximeter Averaging time When Measuring Oxygen Desaturation in Sleep Apnea, Sleep, Jun. 15, 1998, vol. 21, No. 4, pp. 386-390 Missing pp. 386 and 390.
Feinsilver, Steven H., Current and Future Methodology for Monitoring Sleep, Sleep Disorders, Clinics in Chest Medicine, vol. 19, No. 1, Mar. 1998, Published from the Division of Pulmonary Medicine, North Shore University Hospital, Manhasset, New York, NY, USA.
Ferber, Richard, et al., Portable Recording in the Assessment of Obstructive Sleep Apnea, ASDA Standards of Practice, American Sleep Disorders Association, 1610 14th Street, NW, Suite 300, Rochester, MN 55901-2200, USA.
Findley, Larry J., et al., Cheyne-Stokes Breathing During Sleep in Patients With Left Ventricular Heart Failure, Southern Medical Journal, vol. 78, No. 1, Jan. 1985, pp. 11-15.
Findley, Larry J., et al., Sleep Apnea and Auto Crashes, What is the Doctor to do?, Chest, vol. 94, No. 2, Aug. 1988, pp. 225-226.
Fiz, J. A., et al., Acoustic Analysis of Snoring Sound in Patients with Simple Snoring and Obstructive Sleep Apnoea, European Respiratory Journal, 1996, vol. 9, pp. 2365-2370, Printed in the United Kingdom.
Flemons, W. Ward, et al., Sleep Apnea and Cardiac Arrhythmias, Is There a Relationship?, American Review Respiratory Disease, vol. 148, pp. 618-621, 1993.
Fletcher, Eugene C., et al., Nocturnal Oxyhemoglobin Desaturation in COPD Patients with Arterial Oxygen Tensions Above 60 mm Hg, Chest, vol. 92, No. 4, Oct. 1987, pp. 604-608.
Forster, R. E., et al., Time course of exchages between red cells and extracellular fluid during $CO_2$ uptake, Journal of Applied Physiology, vol. 38, No. 4, Apr. 2975, Printed in U.S.A.
Franklin, K. A., et al., Reversal of Central Sleep Apnea with Oxygen, Chest, Jan. 1997, vol. 111, No. 1, pp. 163-169 (Abstract).
Freid, E. B., The rapid sequence induction revisited: obesity and sleep apnea syndrome, Anesthesiol Clin North America, Sep. 2005, vol. 23, No. 3, pp. 551-564 (Abstract).
Frumin, Jack M., Apneic Oxygenation in Man, Anesthesiology, vol. 20, pp. 789-798, 1959.
Gami, A. et al., Day-night pattern of sudden death in obstructive sleep apnea, New England Journal Medicine, Mar. 24, 2005, vol. 352, No. 12, pp. 1206-1214 (Abstract).
Gangitano, E. S., et al., Near Continuous Pulse Oximetry During Newborn ECLS, ASAI Journal, 1999, vol. 45, No. 1, p. 125 (Abstract).
Gaultier, C., Upper airway muscles and physiopathology of obstructive sleep apnea syndrome, [Article in French], Neurophysiol Clin, Jun. 1994, vol. 24, No. 3, pp. 195-206 (Abstract).
Gavin, T. P., et al., The effect of exercise modality on exercise-induced hypoxemia, Respiration Physiology, May 3, 1999, vol. 115, No. 3, pp. 317-323 (Abstract).
Gentil, Benoit, et al., Enhancement of Postoperative Desaturation in Heavy Snorers, Anesth Analg 1995, vol. 81, pp. 389-392.
George, Charles Frederick Petersen, Diagnostic Techniques in Obstructive Sleep Apnea, Progress in Cardiovascular Diseases, vol. 41, No. 5, Mar./Apr. 1999, pp. 355-366.
Glerant, J. C., et al., Intensive care and respiratory sleep disorders, [Article in French], Rev Mal Respir, Dec. 1999, vol. 16, No. 6, pp. 1091-1104 (Abstract).
Gold, Avram R., et al., Impact of Basic Research on Tomorrow's Medicine, The Pharyngeal Critical Pressure, The Whys and Hows of Using Nasal Continuous Positive Airway Pressure Diagnostically, Chest, vol. 110, No. 4, Oct. 1996, pp. 1077-1088, Northbrook, IL, USA.
Goldberger, Ary L., et al., Components of a New Research Resource for Complex Physiologic Signals, PhysioBank, PhysioToolkit, and PhysioNet, American Heart Association Journals, Circulation, vol. 101, No. 23, pp. 1-9, 2000, Circulation, 2000:101:e215, http://circ.ahajournals.org/cgi/content/ful/101/23/e215.
Goldstein, M. R., et al., Pulse Oximetry in Transport of Poorly-Perfused Babies, Abstract only, Pediatrics, 1998, vol. 102, No. 3, p. 818.
Goode, Richard L., Who needs a sleep test? The value of the history in the diagnosis of obstructive sleep apnea, http://www.findarticles.com/p/articles/mi_m0BUM/is_9_78/ai_56229331/print, Sep. 1999.
Goodfriend, Theodore L., et al., Resistant Hypertension, Obesity, Sleep Apnea, and Aldosterone: Theory and Therapy, Hypertension, Journal of the American Heart Association, published online Jan. 19, 2004, Print ISSN: 0194-911X. Online ISSN: 1524-4563, pp. 518-524, Dallas, Texas, USA.
Grap, Mary Jo, Protocols for Practice, Applying Research at the Bedside, Critical Care Nurse, vol. 18, No. 1, Feb. 1998, pp. 94-99.
Greco, J. M., et al., Long-term Airway Space Changes after Mandibular Setback Using Bilateral Sagittal Split Osteomy, Internal Journal Oral Maxillofac. Surg. 1990, vol. 19, pp. 103-105.
Greco, Joan M., Cephalometric Analysis of Long-Term Airway Space Changes with Maxillary Osteotomies, Oral Surg Oral Med Oral Pathol, Nov. 1990, vol. 70, No. 5, pp. 552-554.
Grimm, W., et al., Outcome of patients with sleep apnea-associated severe bradyarrhythmias after continuous positive airway pressure therapy, American Journal Cardiology, Sep. 15, 2000, vol. 86, No. 6, pp. 688-692 (Abstract).

(56) References Cited

OTHER PUBLICATIONS

Grote, Ludger, et al., Finger Plethysmography—A Method for Monitoring Finger Blood Flow During Sleep Disordered Breathing, Respiratory Physiology & Neurobiology, vol. 136, 2003, pp. 141-152, Publisher: Elsevier.

Grunstein, Ronald R., et al., Treatment of Sleep Disordered Breathing, Position Statement, The Medical Journal of Australia, vol. 154, Mar. 4, 1991, pp. 355-359, Australia.

Gugger, M., Comparison of ResMed AutoSet (version 3.03) with polysomnography in the diagnosis of the sleep apnoea/hypopnoea syndrome, European Respiratory Journal, Mar. 1997, vol. 10, No. 3, pp. 587-591 (Abstract).

Guilleminault, C., et al., Maxillo-mandibular surgery for obstructive sleep apnoea, European Respiratory Journal, 1989, vol. 2, pp. 604-612.

Guilleminault, C., et al., Sleep-disordered breathing in children, Annals of Medicine, vol. 30, No. 4, pp. 350-356, Aug. 1998 (Abstract).

Guilleminault, Christian, et al., A Cause of Excessive Daytime Sleepiness, The Upper Airway Resistance Syndrome, Chest, vol. 104, No. 3, Sep. 1993, pp. 781-787.

Guilleminault, Christian, et al., The Sleep Apnea Syndromes, Copyright 1976, Citation Annual Review of Medicine, vol. 27: 465-484 (Volume publication date Feb. 1976).

Guilleminault, Christian, Obstructive Sleep Apnea, The Clinical Syndrome and Historical Perspective, Medical Clinics of North America, vol. 69, No. 6, Nov. 1985, pp. 1187-1203, Stanford, California, USA.

Gupta, R. M., et al., Perioperative cardiopulmonary evaluati and management: are we ignoring obstructive sleep apnea syndrome?, chest, Dec. 1999, vol. 116, No. 6, p. 1843 (Abstract).

Gupta, Rakesh M., et al., Postoperative Complications in Patients with Obstructive Sleep Apnea Syndrome Undergoing Hip or Knee Replacement: A Case-Control Study, Mayo Clinic Proceedings, 2001, vol. 76, pp. 897-905, Rochester, MN, USA.

Gyulay, Stephen, et al., Evaluation of a Microprocessor-Based Portable Home Monitoring System to Measure Breathing During Sleep, Sleep, vol. 10, No. 2, pp. 130-142, Raven Press, New York, USA, 1987, Association of Professional Sleep Societies.

Hanley, Patrick, et al., Pathogenesis of Cheyne-Stokes Respiration in Patients with Congestive Heart Failure, Relationship to Arterial $Pco_2$, Chest, vol. 104, No. 4, Oct. 1993, pp. 1079-1084.

Hanly, P. J., et al., Increased Mortality Associated with Cheyne-Stokes Respiration in Patients with Congestive Heart Failure, American Journal Respiratory Critical Care Medicine, Jan. 1996, vol. 153, No. 1, 272-6 (Abstract).

Hanly, Patrick J., et al., Respiration and Abnormal Sleep in Patients with Congestive Heart Failure, Chest, vol. 96, No. 3, Sep. 1989, pp. 480-488.

Hanly, Patrick, et al., ST-Segment Depression During Sleep in Obstructive Sleep Apnea, The American Journal of Cardiology, vol. 71, Jun. 1, 1993, pp. 1341-1345.

Harbison, J., et al., Cardiac rhythm disturbances in the obstructive sleep apnea syndrome: effects of nasal continuous positive airway pressure therapy, Chest, Sep. 2000, vol. 118, No. 3, pp. 591—(Abstract).

Hatta, K., et al., Prolonged upper airway instability in the parenteral use of benzodiazepine with levomepromazine, Journal Clin Psychopharmacol, Feb. 2000, vol. 20, No. 1, pp. 99—(Abstract).

He, Jiang, et al., Mortality and Apnea Index in Obstructive Sleep Apnea, Experience in 385 Male Patients, Clinical Investigations, Chest, vol. 94, No. 1, Jul. 1988, pp. 9-14.

Health Devices, Next-Generation Pulse Oximetry, Special Issue, Feb. 2003, vol. 32, No. 2, Plymouth Meeting, PA, USA.

Henderson, L. J., et al., Blood as a Physicochemical System. II, pp. 426-431, Paper.

Hillman, David R., et al., Obstructive Sleep Apnoea and Anaesthesia, Sleep Medicine Reviews, 2004, vol. 8, pp. 459-472, Publisher: Elsevier.

Hoffman, Eric A., et al., Multimodality Imaging of the Upper Airway: MRI, MR Spectroscopy, and Ultrafast X-ray CT, Sleep and respiration, 1990 Wiley-Liss, Inc., pp. 291-301.

Hoffmann, M., et al., Sleep apnea and hypertension, Minerva Med., Aug. 2004, vol. 95, No. 4, pp. 281-290 (Abstract).

Hoffstein, Victor, Blood Pressure, Snoring, Obesity, and Nocturnal Hypoxaemia, The Lancet, vol. 344, Sep. 3, 1994, pp. 643-645.

Hoffstein, Victor, et al., Cardiac Arrhythmias, Snoring, and Sleep Apnea, Chest, 1994, vol. 106, pp. 466-471, Northbrook, IL, USA.

Hoffstein, Victor, et al., Snoring and Arousals: A Retrospective Analysis, Sleep, vol. 18, No. 10, pp. 866-882, 1995 American Sleep Disorders Association and Sleep Research Society.

Holmes, Michael, et al., Co-Oximetry Validation of a New Pulse Oximeter in Sick Newborns, Respiratory Care, 1998, vol. 43, No. 10, pp. 860 (Abstract).

Hung, Joseph, et al., Association of Sleep Apnoea with Myocardial Interfarction in Men, The Lancet, vol. 336, pp. 261-264, Jul. 28, 1990, Abstract only, p. 261.

Isono, S., et al., Anatomy of pharynx in patients with obstructive sleep apnea and in normal subjects, Journal Appl Physiol, Apr. 1997, vol. 82, No. 4, pp. 1319-1326 (Abstract).

Isono, S., et al., Interaction of cross-sectional area, driving pressure, and airflow of passive velopharynx, Journal Appl Physiol, Sep. 1997, vol. 83, No. 3, pp. 851-859 (Abstract).

Isono, S., et al., Static mechanics of the velopharynx of patients with obstructive sleep apnea, Journal Appl Physiol, Jul. 1999, vol. 75, No. 1, pp. 148-154 (Abstract).

Jarrell, L., Preoperative diagnosis and postoperative management of adult patients with obstructive sleep apnea syndrome: a review of the literature, Journal Perianesth Nursing, Aug. 1999, vol. 14, No. 4, pp. 193-200 (Abstract).

Javaheri, S., Effects of continuous positive airway pressure on sleep apnea and ventricular irritability in patients with heart failure, Circulation, Feb. 1, 2000, vol. 101, No. 4, pp. 392-397 (Abstract).

Javaheri, S., et al., Occult Sleep-Disordered Breathing in Stable Congestive Heart Failure, Annuals Internal Medicine, Apr. 1995, vol. 122, No. 7, pp. 487-492 (Abstract).

Javaheri, S., et al., Sleep Apnea in 81 Ambulatory Male Patients With Stable Heart Failure, Types and Their Prevalences, Consequences, and Presentations, Received Nov. 20, 1997; revision received Jan. 23, 1998, accepted Jan. 28, 1998, From the Sleep Disorders Laboratory, Department of Veterans Affairs Medical Center, and the Department of Medicine, University of Cincinatti, College of Medicine, Cincinnati, Ohio.

Johnson, J. T., et al., Preoperative, Intraoperative, and postoperative management of patients with obstructive sleep apnea syndrome, Otolaryngol Clin North America, Dec. 1998, vol. 31, No. 6, pp. 1025-1030 (Abstract).

Jones, N. L., et al., The Estimation of Carbon Dioxide Pressure of Mixed Venous Blood During Exercise, Clinical Science (1967), vol. 32, pp. 311-327.

Juhász, János, et al., Unattended Continuous Positive Airway Pressure Titration, Clinical Relevance and Cardiorespiratory Hazards of the Method, American Journal Respiratory Critical Care Medical, vol. 154, pp. 359-365, 1996.

Kabeli, Cheryl, Obstructive Sleep apnea and Modifications in Sedation, Critical Care Nursing Clinics of North America, vol. 17, 2005, pp. 269-277, ccnursing.theclinics.com, Publisher: Elsevier Saunders.

Kalra, Maninder, et al., Obstructive Sleep Apnea in Extremely Overweight Adolescents Undergoing Bariatric Surgery, Obesity Research, vol. 13, No. 7, Jul. 2005, pp. 1175-1179.

Kanagala, Ravi, et al., Obstructive Sleep Apnea and the Recurrence of Atrial Fibrillation, Circulation, May 27, 2003, pp. 2589-2594, American Heart Association, Inc.

Kaplan, Joseph, Beginner's Atlas of Overnight Oximetry, Apr. 10, 1995, Mayo Clinic, Jacksonville, Florida, USA, Copyright 1986, PROFOX Associates, Inc.

Kaplan, Joseph, et al., Home Pulse Oximetry as a Screening Test for Sleep-Disordered Breathing, Chest, vol. 103, pp. 322S, Northbrook, IL, USA.

Kapur, V. K., et al., Association of hypothyroidism and obstructive sleep apnea, American Journal of Respiratory & Critical Care Medicine, vol. 158, No. 5 Pt. 1, pp. 1379-1383, Nov. 1998 (Abstract).

(56) References Cited

OTHER PUBLICATIONS

Kapur, V., et al., The medical cost of undiagnosed sleep apnea, Sleep, Sep. 1999, vol. 22, No. 6, pp. 749-755 (Abstract).
Katchen, Marc, et al., Evaluation of the Sleepy Crewmember: USAFSAM Experience and a Suggested Clinical Approach, Aviation, Space and Environmental Medicine, Mar. 1989, pp. 263-267.
Kaw, Roop, et al., Unrecognized Sleep Apnea in the Surgical Patient, Implications for the Perioperative Setting, Chest, 2006, vol. 129, pp. 198-205.
Kawai, Mitsuru, et al., Nocturnal hypoxia index: A new pulse oximetry index of nocturnal hypoventilation in neuromuscular disorders, Clinical Neurology, vol. 35, pp. 1003-1007, 1995 (Abstract).
Kimmel, Paul L., et al., Sleep Apnea syndrome in Chronic renal Disease, The American Journal of Medicine, vol. 86, Mar. 1989, pp. 308-314.
King, E. D., et al., A model of obstructive sleep apnea in normal humans. Role of the upper airway., American Journal Respiratory Critical Care Medicine, Jun. 2000, vol. 161, No. 6, pp. 1979-1984 (Abstract).
Kirby, S.D., et al., Neural network prediction of obstructive sleep apnea from clinical criteria, Chest, vol. 116, No. 2, pp. 409-415, Aug. 1999 (Abstract).
Kirby, Stan C., et al., Section II. Systems and programs, Computer quantitation of saturation impairment time as an index of oxygenation during sleep, Computer Methods and Programs in Biomedicine, vol. 38, 1992, pp. 107-115, Elsevier Science Publishers B.V.
Klocke, F. J., et al., Breath holding after breathing of oxygen, Journal Appl. Physiol., vol. 14, No. 5, pp. 689-693, 1959.
Koehler, U., et al., Heart Block in Patients with Obstructive Sleep Apnoea: Pathogenetic Factors and Effects of Treatment, European Respiratory Journal, 1998, vol. 11, pp. 434-439, Printed in United Kingdom.
Kolobow, Theodor, et al., Intratracheal Pulmonary Ventilation (ITPV); Control of Positive End-Expiratory Pressure at the Level of the Carina Through the Use of a Novel ITPV Catheter Design, Anesth Analg, 1994, vol. 78, pp. 455-461.
Koopmann, Charles F., et al., Surgical Management of Obstructive Sleep Apnea, Otolaryngologic Clinics of North America, vol. 23, No. 4, Aug. 1990, pp. 787-808.
Krachman, S. L., et al., Comparison of oxygen therapy with nasal continuous positive airway pressure on Cheyne-Stokes respiration during sleep in congestive heart failure, Chest, Dec. 1999, vol. 116, No. 6, pp. 1550-1557 (Abstract).
Kribbs, Nancy Barone, et al., Effects of One Night without Nasal CPAP Treatment on Sleep and Sleepiness in Patients with Obstructive Sleep Apnea, American Review Respiratory Disease, vol. 147, pp. 1162-1168, 1993.
Kribbs, Nancy Barone, et al., Objective Management of Patterns of Nasal CPAP Use by Patients with Obstructive Sleep Apnea, American Review Respiratory Disease, vol. 147, pp. 887-895, 1993.
Krieger, Jean, et al., Breathing During Sleep in Normal Middle-Aged Subjects, Sleep, vol. 13, No. 2, pp. 143-154, Raven Press, Ltd. New York, NY, USA, 1990 Association of Professional Sleep Societies.
Krieger, Jean., et al., Dangerous Hypoxaemia During Continuous Positive Airway Pressure Treatment of Obstructive Sleep Apnoea, The Lancet, Dec. 17, 1983, pp. 1429-1430.
Krieger, Jean., et al., Left Ventricular Ejection Fraction in Obstructive Sleep Apnea, Effects of Long-term Treatment with Nasal Continuous Positive Airway Pressure, Chest, vol. 100, No. 4, Oct. 1991, pp. 917-921.
Kuna, S. T., et al., Pathophysiology of upper airway closure during sleep, JAMA, Sep. 11, 1991, vol. 266, No. 10, pp. 1384-1389 (Abstract).
Kyzer, S., et al., Obstructive Sleep Apnea in the obese, World Journal Surg, Sep. 1988, vol. 22, No. 9, pp. 998-1001 (Abstract).
Lafontaine, Victoria M., et al., Pulse Oximetry: Accuracy of Methods of Interpreting Graphic Summaries, Pediatric Pulmonology, vol. 21, 1996, pp. 121-131.
Lanfranchi, P. A., et al., Prognostic value of nocturnal Cheyne-Stokes respiration in chronic heart failure, Circulation, Mar. 23, 1999, vol. 99, No. 11, pp. 1435-1440, Italy (Abstract).
Lanfranchi, P., et al., The assessment of breathing during sleep: a curiosity or clinical necessity?, Italian Heart Journal, May 2000, vol. 1, No. 5 Suppl., pp. 641-654 (Abstract).
Lawrence, Nancy, Treatment for Sleep Apnea shows promise in reducing deaths from congestive heart failure: Nation-wide study to determine long-term benefits, London Health Sciences Centre, Jun. 3, 1999, News Bulletin.
Lertzman, Morley, et al., [Letters—Correspondence], Sleep Apnea A Risk Factor for Poor Driving, Canadian Medical Association Journal, Oct. 15, 1995; vol. 153(8), p. 1063.
Letters, Obstructive Sleep Apnoea, BMJ, 1997, pp. 315-367 (Aug. 9); http://bmj.com/Shneerson et al. (7104).
Lichstein, K. L., et al., Occult sleep apnea in a recruited sample of older adults with insomnia, Journal of Consulting & Clinical Psychology, vol. 67, No. 3, pp. 405-410, Jun. 1999 (Abstract).
Little, S. A., et al., Predictors of nocturnal oxygen desaturation in patients with COPD, Respir Med., Mar. 1999, vol. 93, No. 3, pp. 202-207, United Kingdom (Abstract).
Lofsky, Ann, Sleep Apnea and Narcotic Postoperative Pain Medication: A Morbidity and Mortality Risk, APSF Newsletter Summer 2002, pp. 24-25.
Longobardo, G. S., et al., Sleep Apnea Considered as a Control System Instability, Elsevier Biomedical Press, 1982, 0034-5687/82/0000-0000.
Lowton, K., Pulse oximeters for the detection of hypoxaemia, Professional Nurse, Feb. 1999, vol. 14, No. 5, pp. 343-347 (Abstract).
Lugaresi, E., et al., Breathing During sleep in Man in Normal and Pathological Conditions, Proceedings of the Symposium on Regulation of Respiration during Sleep and Anesthesia held at the Faculte de Medecine Saint-Antoine, Paris, France, Jul. 14-16, 1977, 1978 Plenum Press, New York, USA, pp. 35-45.
Lynn, Lawrence A. et al., Diagnostic Evaluation of OSA Utilizing Analysis of Frequency and Spatial Relationships of Clustered, Sequential Oximetry Waveform Events, Vth World Congress on Sleep Apnea, Marburg, Germany, Sep. 17-20, 1997.
Lynn, Lawrence A., Interpretive Oximetry: Future Directions for Diagnostic Applications of the $SpO_2$ Time-Series, Anesth Analg 2002, vol. 94, pp. S84-S88.
Lynn, Lawrence, PROFOX Associates, Inc., Version 12S (12 hours SpO2), Demonstration disk for Dr. Lawrence Lynn, Columbus, Ohio, Copyright 1986 PROFOX Associates, Inc., Version 12S, Nov. 1992, p. 1.
Lyznicki, James M., Sleepiness, Driving and Motor Vehicle Crashes, JAMA, Jun. 17, 1998, vol. 279, No. 23, pp. 1908-1913.
Magalang, Ulysses J. et al., Prediction of the Apnea-Hypopnea Index From Overnight Pulse Oximetry, Chest the Cardiopulmonary and Critical Care Journal, 2003; vol. 124; pp. 1694-1701, Northbrook, IL, USA.
Marin, Jose M., et al., Long-Term Cardiovascular Outcomes in Men with Obstructive sleep apnoea-hypopnoea with or without treatment with continuous positive airway pressure: an observational study, The Lancet, vol. 365, Issue 9464, Mar. 19, 2005-Mar. 25, 2005, pp. 1046-1053.
Marin, José M., et al., Obstructive Sleep Apnea and Acute Myocardial Infarction: Clinical Implications of the Association, Sleep, vol. 21, No. 8, 1998, pp. 809-815.
Mayer, Pierre, et al., Peripheral Neuropathy in Sleep Apnea, A Tissue Marker of the Severity of Nocturnal Desaturation, American Journal Respiratory Critical Care Medicine, vol. 159, pp. 213-219, 1999, Internet address: www.atsjournals.org.
McDannold, M. D., et al., Night-to-Night variability in Optimal CPAP Pressures Using Auto CPAP Titration in a Single Patient, Sleep Research No. 23, 1994, p. 453 (Abstract).
McEvoy, R. D., et al., Ventilatory responses to sustained eucapnic hypoxia in healthy males during wakefulness and NREM sleep, Sleep, vol. 20, No. 11, Nov. 1997, pp. 1008-1011 (Abstract).
McGregor, Christine D. et al., Performance of Pulse Oximeter Technologies in a Pediatric Sleep Lab Setting, OF-901-191, dated Nov. 2, 2001, Abstract.

(56) References Cited

OTHER PUBLICATIONS

McNicholas, W. T., et al., Diagnostic Criteria for the Sleep Apnoea Syndrome: Time for Consensus?, European Respiratory Journal, vol. 9, pp. 634-635, 1996, United Kingdom.
Mehra, Reena, et al., Association of Nocturnal Arrhythmias with Sleep-Disordered Breathing: The Sleep Heart Health Study, AJRCCM Articles in Press, Published Jan. 19, 2006, as doi: 10.1164/rccm.200509-1442OC, Copyright 2006 by the American Thoracic Society.
Mehta, Y., et al., Obstructive sleep apnea syndrome: anesthetic implications in the cardiac surgical patient, Journal Cardiothorac Vasc Anesth, Aug. 2000, vol. 14, No. 4, pp. 449-453 (Abstract).
Mendelson, W. B., et al., Effects of Hemodialysis on Sleep Apnea Syndrome in End-Stage Renal Disease, Clinical Nephrology, vol. 33, No. 5, 1990, pp. 247-251.
Middlekoop, Huub, et al., The Value of Nocturnal Motor Activity Monitoring as a Screening Tool for Obstructive Sleep Apnoea, Letter to the Editor, Journal Sleep Res., 1996, vol. 5, pp. 66-67.
Miles, L. E., et al., Development and Application of Automatic Nasal CPAP Calibration Procedures for Use in the Unsupervised Home Environment, Sleep, vol. 16, pp. S118-S119, 1993 American Sleep Disorders Association and Sleep Research Society.
Miles, Laughton E., Optimization of Nasal-CPAP Airflow Pressure by Use of Home Oximetry Recordings, Clinical Monitoring Center, Palo Alto, California, USA, Sleep Research, p. 568, 1987, Abstract.
Millard, R. K., Inductive plethysmography components analysis and improved non-invasive postoperative apnoea monitoring, Physiol Meas, May 1999, vol. 20, No. 2, pp. 175-186, United Kingdom (Abstract).
Mitler, Merrill M., et al., Narcolepsy and Its Treatment With Stimulants, ASDA Standards of Practice, Sleep, vol. 17, No. 4, pp. 352-371, 1994, American Sleep Disorders Association and Sleep Research Society.
Miyamura, Miharu, et al., $CO_2$ Dissociation Curves of Oxygenated Whole Blood Obtained at Rest and in Exercise, European Journal Applied Physiology, vol. 39, pp. 37-45, 1978, European Journal of Applied Physiology and Occupation Physiology.
Morelot-Panzini, Capucine et al., Simplified Method to Measure Respiratory-Related Changes in Arterial Pulse Pressure in Patients Receiving Mechanical Ventilation, Chest 2003, vol. 124, pp. 665-670, Northbrook, IL, USA.
Muller, Nestor L., et al., Mechanism of Hemoglobin Desaturation During Rapid-Eye-Movement Sleep in Normal Subjects and in Patients with Cystic Fibrosis, American Review of Respiratory Disease, vol. 121, 1980, pp. 463-469.
Myatt, H. M., et al., Snoring—a simple surgical solution, Clin. Otolaryngol., 1996, vol. 21, pp. 419-424, Publisher: Blackwell Science Ltd.
Narkiewicz, Krzysztof, et al., Altered Cardiovascular Variability in Obstructive Sleep Apnea, Copyright 1998, American Heart Association, Inc., Iowa City, Iowa, USA, pp. 1071-1077, Published Sep. 15, 1998.
Naughton, Matthew T., Cycling Sleep Apnea, The Balance of Compensated and Decompensated Breathing, American Journal of Respiratory and Critical Care Medicine, vol. 168, 2003, Editorials, pp. 624-625.
Naughton, Matthew T., et al., Sleep Apnea in Congestive Heart Failure, Clinics in Chest Medicine, vol. 19, No. 1, Mar. 1998, pp. 99-113.
Netzer, Nikolaus, et al., Overnight Pulse Oximetry for Sleep-Disordered Breathing in Adults, A Review, Chest, vol. 120, #2, Aug. 2001, pp. 625-633, Northbrook, IL, USA.
Neumann, Cristina et al., Nocturnal oxygen desaturation in diabetic patients with severe autonomic neuropathy, Diabetes Research and Clinical Practice, Publisher: Elsevier Science Ireland Ltd, vol. 28, 1995, pp. 97-102.
Nobili, L., et al., Morning increase of whole blood viscosity in obstructive sleep apnea syndrome, Clinical Hemorheol Microcirc, 2000, vol. 22, No. 1, pp. 21-27 (Abstract).
Noda, A., et al., Daytime sleepiness and automobile accidents in patients with obstructive sleep apnea syndrome, Psychiatry & Clinical Neurosciences, vol. 52, No. 2, pp. 221-222, Apr. 1988 (Abstract).
Noda, Akiko, et al., Circadian Rhythm of Autonomic Activity in Patients with Obstructive Sleep Apnea Syndrome, Clinical Cardiology, vol. 21, pp. 271-276, 1998, Japan.
Ogan, O. U., et al., Anesthetic safety always an issue with obstructive sleep apnea, Journal Clin Monit Comput, Jan. 1998, vol. 14, No. 1, pp. 69-70 (Abstract).
Ogretmenoglu, O., et al., Body fat composition: a predictive factor for obstructive sleep apnea, Laryngoscope, Aug. 2005, vol. 115, No. 8, pp. 1493-1498 (Abstract).
Ohga, Eijiro, et al., Increased Levels of Circulating ICAM-1, VCAM-1, and L-selectin in obstructive sleep apnea syndrome, Address for reprint requests and other correspondence: T. Nagase, Dept. of Geriatric Medicine, Faculty of Medicine, Univ. of Tokyo, 7-3-1, Hongo, Bunkyo-Ku, Tokyo 113, Japan, Received Nov. 13, 1998, accepted in final form Mar. 9, 1999.
Olson, L. G., et al., Prediction of Sleep-disordered breathing by unattended overnight oximetry, Journal Sleep Res., 1999, vol. 8, pp. 51-55, European Sleep Research Society.
Olson, Leslie G., et al., Chapter 10, A Biomechanical View of Upper Airway Function, pp. 359-389, 1988, Publisher, Marcel Dekker, Inc., New York-Basel, Book: Respiratory Function of the Upper Airway.
Ostermeier, A. M., et al., Three sudden postoperative respiratory arrests associated with epidural opioids in patients with sleep apnea, Anasth Analg., Aug. 1997, vol. 85, No. 2, pp. 452-460.
Owen, G. O., et al., Overnight Pulse Oximetry in Normal Children and in Children Undergoing Adenotonsillecomy, Clinical Otolaryngology, 1996 vol. 21, pp. 59-65, Blackwell Science Ltd.
Owen, G. O., et al., Overnight Pulse Oximetry in Snoring and Non-Snoring Children, Clinical Otolaryngology, 1995, vol. 20, pp. 402-406, Blackwell Science Ltd.
OxiScan, AirSep Corporation, 800/874-0202, Oxiscan Sample Report/Explanation and the Delta Sleep Apnea Index, OxiScan Sample Report, vol. 1, Rev. 1, Nov. 1997.
Pae, E. K., et al., Intermittent hypoxia damages cerebellar cortex and deep nuclei, Neurosci Lett., Feb. 28, 2005, vol. 375, No. 2, pp. 123-128 (Abstract).
Partinen, Markku, et al., Daytime Sleepiness and Vascular Morbidity at Seven-Year Follow-up in Obstructive Sleep Apnea Patients, Chest, vol. 97, No. 1, Jan. 1990, pp. 27-32.
Payne, J. P., Apnoeic Oxygenation in Anaesthetised Man, Acta Anaesth. Scandinav., 1962, vol. 6, pp. 129-142.
Peker, Y., et al., An independent association between obstructive sleep apnoea and coronary artery disease, European Respiratory Journal, 1999, vol. 14, No. 1, pp. 179-184 (Abstract).
Peker, Y., et al., Reduced hospitalization with cardiovascular and pulmonary disease in obstructive sleep apnea patients on nasal CPAP treatment, Sleep, 1997, vol. 20, No. 8, pp. 45-53 (Abstract).
Peled, N., et al., Nocturnal ischemic events in patients with obstructive sleep apnea syndrome and ischemic heart disease: effects of continuous positive air pressure treatment, Journal American Coll Cardiology, Nov. 1999, vol. 15, p. 34 (Abstract).
Pelttari, Lisa H., et al., Little Effect of Ordinary Antihypertensive Therapy on Nocturnal High Blood Pressure in Patients with Sleep Disordered Breathing, American Journal of Hypertension, 1998, vol. 11, No. 3, Part 1, pp. 272-279.
Penzel, T., et al., Systematic Comparison of Different Algorithms for Apnoea Detection Based on Electrocardiogram Recordings, Medical & Biological Engineering and Computing 2002, vol. 40, pp. 402-407.
Peppard, Paul E., et al., Prospective Study of the Association Between Sleep-Disordered Breathing and Hypertension, May 11, 2000, vol. 342, No. 19, pp. 1378-1384.
Peters, John P. Jr., et al., Studies of the Carbon Dioxide Absorption Curve of Human Blood, Book: The Journal of Biological Chemistry, pp. 709-716, Received for publication, Feb. 7, 1923.
Peters, John P. Jr., et al., The Carbon Dioxide Absorption Curve and Carbon Dioxide Tension of the Blood of Normal Resting Individuals, Book: Carbon Dioxide Absorption Curve, pp. 489-547, Received for publication, Dec. 2, 1920 (missing pp. 490, 491, 538-541).

(56) References Cited

OTHER PUBLICATIONS

Phillips, Barbara A., et al., Catching Up on Sleep, The National Sleep Disorders Research Plan, Editorial, Chest, vol. 110, No. 5, Nov. 1996, pp. 1132-1133.
Phillips, Susan, et al., Obstructive Sleep Apnoea: Diagnosis and Management, Nursing Standard, vol. 11, No. 17, pp. 43-46, 1997.
Phillipson, Eliot A., Sleep Apnea—A Major Public Health Problem, Editorials, The New England Journal of Medicine, Editorials, vol. 328, No. 17, pp. 1271-1273, Apr. 29, 1993.
Plastiras, James, Sleep disorders create need for more sleep labs, Capital District Business Review, Mar. 9, 1998.
Poets, C. F., Apparent life-threatening events and sudden infant death on a monitor, Paediatr Respiratory Review, 2004, Suppl. A, pp. S383-S386 (Abstract).
Poets, C. F., et al., Arterial oxygen saturation and breathing movements during the first year of life, Journal Developmental Physiology, Jun. 1991, vol. 15, No. 6, pp. 341-345 (Abstract).
Poets, C. F., et al., Home monitoring of transcutaneous oxygen tension in the early detection of hypoxaemia in infants and young children, Arch Dis Child, Jun. 1991, vol. 66, No. 6, pp. 676-682 (Abstract).
Poets, C. F., et al., Patterns of oxygenation during periodic breathing in preterm infants, Early Human Development, Jul. 1991, vol. 26, No. 1, pp. 1-12 (Abstract).
Poets, C. F., et al., Oxygen saturation and breathing patterns in infancy. 2: Preterm infants at discharge from special care, Arch Dis Child, May 1991, vol. 66, No. 5, pp. 574-578 (Abstract).
Pradhan, Pratik S., et al., Screening for Obstructive Sleep Apnea in Patients Presenting for Snoring Surgery, Laryngoscope, vol. 106, Nov. 1996, pp. 1393-1397.
Principe-Rodriguez, K., et al., Sleep symptoms and clinical markers of illness in patients with heart failure, Sleep Breath., Sep. 2005, vol. 9, No. 3, pp. 127-133 (Abstract).
Quinn, S. J., et al., The Differentiation of Snoring Mechanisms Using Sound Analysis, Clinical Otolaryngol., 1996, vol. 21, pp. 119-123, Publisher: Blackwell Science Ltd.
Randerath, Winfried J., et al., Autoadjusting CPAP Therapy Based on Impedance Efficacy, Compliance and Acceptance, American Journal Respiratory Critical Care Medicine, vol. 163, pp. 652-657, 2001, Internet address: www.atsjournals.org.
Rapoport, David M., et al., Reversal of the "Pickwickian Syndrome" by Long-Term Use of Nocturnal Nasal-Airway Pressure, The New England Journal of Medicine, Oct. 7, 1982, vol. 307, No. 15, pp. 931-933.
Rauscher, Helmuth, et al., Computerized Detection of Respiratory Events During Sleep from Rapid Increases in Oxyhemoglobin Saturation, Lung, 1991, vol. 169, pp. 335-342.
Redline, Susan, et al., Hypopnea, a Floating Metric: Implications for Prevalence, Morbidity Estimates, and Case Finding, Sleep, vol. 20, No. 12, pp. 1209-1217.
Redline, Susan, et al., Recognition and Consequences of Obstructive Sleep Apnea Hypopnea Syndrome, Sleep Disorders, Clinics in Chest Medicine, vol. 19, No. 1, Mar. 1998, Cleveland, Ohio, USA (Article and Abstract).
Reite, Martin, et al., The Use of Polysomnography in the Evaluation of Insomnia, An American Sleep Disorders Association Review, Sleep, vol. 18, No. 1, 1995, pp. 58-70, American Sleep Disorders Association and Sleep Research Society 1995.
Remmers, John E., et al., Nasal Airway Positive Pressure in Patients with Occlusive Sleep Apnea, Methods and Feasibility, American Review Respiratory Disorders, Dec. 1984, vol. 130, No. 6, pp. 1152-1155.
Rennotte, M. T., Epidural opioids and respiratory arrests, Anesth Analg., Aug. 1997, vol. 85, No. 2, pp. 452-460 (Abstract).
Resta, O., et al., Sleep-related breathing disorders in acute respiratory failure assisted by non-invasive ventilatory treatment: utility of portable polysomnographic system, Respir Medicine, Feb. 2000, vol. 94, No. 2, pp. 128-134 (Abstract).
Riley, Robert W., et al., Maxillofacial Surgery and Nasal CPAP, A Comparison of Treatment for Obstructive Sleep Apnea Syndrome, Chest, vol. 98, No. 6, Dec. 1990, pp. 1421-1425.
Riley, Robert W., et al., Maxillofacial Surgery and Obstructive Sleep Apnea: A Review of 80 Patients, Otolaryngology—Head and Neck Surgery, vol. 101, No. 3, Sep. 1989, pp. 353-361.
Riley, Robert W., et al., Maxillofacial Surgery and Obstructive Sleep Apnea Syndrome, Otolaryngologic Clinics of North America, vol. 23, No. 4, Aug. 1990, pp. 809-824.
Rosenberg, J., et al., Ventilatory Pattern and Associated Episodic Hypoxaemia in the Late Postoperative Period in the General Surgical Ward, Anaesthesia, 1999, vol. 54, pp. 323-328, Publisher: Blackwell Science Ltd.
Roux, Francoise, et al., Sleep-related Breathing Disorders and Cardiovascular Disease, The American Journal of Medicine, Apr. 1, 2000, vol. 108, pp. 396-400.
Ruchala, Joanna B., Chapter 13, Applications of Pulse Oximetry, Book: Design of Pulse Oximeters, pp. 214-236.
Ruhle, K. H., et al., Monitoring at Home, Lung, 1990, Suppl, pp. 927-932, Lung, Springer-Verlag, New York, Inc. 1990.
Rundell, O. H., et al., Polysomnography Methods and Interpretations, Sleep Apnea, Otolaryngologic Clinics of North America, vol. 23, No. 4, Aug. 1990, pp. 583-592.
Rusch, T. L., et al., Signal Processing Methods for Pulse Oximetry, Computers in Biology & Medicine, vol. 26, No. 2, pp. 143-159, Mar. 1996 (Abstract).
Ryan, C. Francis, et al., Mechanical Properties of the Velopharynx in Obese Patients with Obstructive Sleep Apnea, American Journal Respiratory Critical Care Medicine, 1996, vol. 154, pp. 806-812.
Saarelainen, Seppo, et al., Effect of Nasal CPAP Treatment on Plasma Volume, Aldosterone and 24-h Blood Pressure in Obstructive Sleep Apnoea, Journal Sleep Research, 1996, vol. 5, pp. 181-185.
Sadeh, Avi, et al., The Role of Actigraphy in the Evaluation of Sleep Disorders, An American Sleep Disorders Association and Sleep Research Society, Sleep, vol. 18, No. 4, pp. 288-302.
Sadrmoori, Bijan, Evaluation of Self Adjusting Nasal CPAP (DPAP) in the Treatment of Adult Obstructive Sleep Apnea, Sleep Research No. 23, 1994, p. 386 (Abstract).
Saito, Toshiyuki, et al., Sleep Apnea in Patients with Acute Myocardial Infarction, Critical Care Medicine, vol. 19, No. 7, pp. 938-941, Printed in USA, Copyright 1991 by Williams and Wilkins.
Sajkov, Dimitar, et al., Daytime Pulmonary Hemodynamics in Patients with Obstructive Sleep Apnea without Lung Disease, American Journal Respiratory Critical Care Medicine, 1999, vol. 159, pp. 1518-1526.
Sanders, Mark H., et al., Obstructive Sleep Apnea Treated by Independently Adjusted Inspiratory and Expiratory Positive Airway Pressures via Nasal Mask, Physiologic and Clinical Implcations, Chest, vol. 98, No. 2, Aug. 1990, pp. 317-324.
Sanders, Mark H., Nasal CPAP Effect on Patterns of Sleep Apnea, Chest, vol. 86, No. 6, Dec. 1984, pp. 839-844.
Sangal, R. Bart et al., P300 Latency: Abnormal in Sleep Apnea with Somnolence and Idiopathic Hypersomnia, but Normal in Narcolepsy, Clinical Electroencephalography, 1995, vol. 26, No. 3, pp. 146-153, Troy, Michigan, USA.
Sanna, A., et al., Apport de la Polysomnographie à la mise au point des maladies atteints d'une bronchopneumopathie chronique obstructive (BPCO), Travail Original, Rev. Mèd. Brux., vol. 12, pp. 315-320, 1991, Belgium.
Sanner, B. M., et al., Sleep-related respiration disorders: their relevance in intensive care medicine, [Article in German], Dtsch Med Wochenschr, Mar. 1999, vol. 12, p. 124 (Abstract).
Sarodia, B.D., et al., Prevalence of obstructive sleep apnea in patients admitted to the intensive care unit with cardiovascular events, Sleep Research, 1996, vol. 25, pp. 356.
Schafer, H., et al., Cardiovascular morbidity in patients with obstructive sleep apnea in relation to the severity of respiratory disorder, Dtsch Med Wochenschr, 1998, vol. 123, No. 39, pp. 1127-1133 (Abstract).
Schafer, H., et al., Pulmonary Haemodynamics in Obstructive Sleep Apnoea: Time Course and Associated Factors, European Respiratory Journal, 1998, vol. 12, pp. 679-684, Printed in United Kingdom.

(56) References Cited

OTHER PUBLICATIONS

Schagatay, E., et al., Diving Response and Apneic Time in Humans, Undersea Hyper Med., 1998, vol. 25, No. 1, pp. 13-19, Copyright 1988 Underseas and Hyperbaric Medical Society, Inc.

Scharf, Martin B., et al., Cyclic Alternating Pattern Sequences in Non-Apneic Snorers With and Without Nasal Dilation, ENT—Ear, Nose & Throat Journal, Sep. 1996, vol. 75, No. 9, pp. 617-619.

Scheers, N. J., et al., Sudden Infant Death With External Airways Covered, Case-Comparison Study of 206 Deaths in the United States, Arch Pediatric Adolescent Medicine, 1998, vol. 152, pp. 540-547.

Schmidt-Notwara, Wolfgang, et al., Oral Appliances for the Treatment of Snoring and Obstructive Sleep Apnea: A Review, An American Sleep Disorders Association Review, Sleep, vol. 18, No. 6, pp. 501-510, 1995, American Sleep Disorders Association and Sleep Research Society.

Schnader, Jeff, Increase of Pulmonary Artery Occlusion Pressure During Upper Airway Obstruction in Sleep Apnea, Case Reports, Critical Care Medicine, 1996, vol. 24, No. 2, pp. 354-358.

Schnapp, Lynn M., et al., Pulse Oximetry Uses and Abuses, Critical Care, Chest, vol. 98, No. 5, Nov. 1990, pp. 1244-1250.

Schneider, H., et al., Neural and local effects of hypoxia on cardiovascular responses to obstructive apnea, Journal Appl Physiol., Mar. 2000, vol. 88, No. 3, pp. 1093-1092 (Abstract).

Schoenberg, R., et al., Making ICU Alarms Meaningful: A Comparison of Traditional vs. Trend-Based Algorithms, AMIA 1999, Annual Symposium (Abstract).

Schwab, Richard J., et al., Upper Airway and Soft Tissue Structural Changes Induced by CPAP in Normal Subjects, American Journal Respiratory Critical Care Medicine, 1996, vol. 154, pp. 1106-1116.

Senn, Oliver et al., Monitoring Carbon Dioxide Tension and Arterial Oxygen Saturation by a Single Earlobe Sensor in Patients With Critical Illness or Sleep Apnea, Chest 2005, vol. 128, pp. 1291-1296, Northbrook, IL, USA.

Series, Frederic, et al., Prospective Evaluation of Nocturnal Oximetry for Detection of Sleep-Related Breathing Disturbances in Patients With Chronic Heart Failure, Chest 2005, vol. 127, pp. 1507-1514, Northbrook, IL, USA.

Severinghaus, John W., et al., Recent Developments in Pulse Oximetry, Anesthesiology, vol. 76, pp. 1018-1038, 1992.

Shamir, M. et al., Pulse oximetry plethsymographic waveform during changes in blood volume, British Journal of Anaesthesia, vol. 82(2), pp. 178-181, 1999, Great Britain.

Shephard, John W. Jr., et al., Relationship of Ventricular Ectopy to Oxyhemoglobin Desaturation in Patients with Obstructive Sleep Apnea, Chest, vol. 88, No. 3, Sep. 1985, pp. 335-340, Northbrook, IL, USA.

Shephard, John W., Jr., et al., Uvulopalatopharyngoplasty for Treatment of Obstructive Sleep Apnea, Mayo Clinic Proceedings, vol. 65, pp. 1260-1267, 1990.

Sher, Aaron E., et al., The Efficacy of Surgical Modifications of the Upper Airway in Adults With Obstructive Sleep Apnea Syndrome, An American Sleep Disorders Association Review, Sleep, vol. 19, No. 2, pp. 156-177, Nov. 1995.

Shinohara, E., et al., Visceral Fat Accumulation as an Important Risk Factor for Obstructive Sleep Apnoea Syndrome in Obese Subjects, Journal of Internal Medicine, vol. 241, pp. 11-18, Publisher: Blackwell Science Ltd., 1997.

Silverberg, D. S., et al., Essential and Secondary Hypertension and Sleep-Disordered Breathing: A Unifying Hypothesis, Journal of Human Hypertension, 1996, vol. 10, pp. 353-363.

Silverberg, D., et al., Sleep apnoea and hypertension. Active approach to detection of obstructive sleep apnoea is imperative, BMJ, Jul. 2000, vol. 22, pp. 321 (Abstract).

Silverberg, Donald, The Joint National Committee on Prevention, Detection, Evaluation, and Treatment of High Blood Pressure and Obstructive Sleep Apnea: Let Their Silence Not Be Matched by the Silence of the Ordinary Physician, Arch Intern Med., Jun. 8, 1998, vol. 158, pp. 1272-1273.

Sin, D. D., et al., Effects of continuous positive airway pressure on cardiovascular outcomes in heart failure patients with and without Cheyne-Stokes respiration, Circulation, Jul. 2000, vol. 102, No. 1, pp. 61-66 (Abstract).

Skjodt, N. M., et al., Screening for hypothyroidism in sleep apnea, American Journal of Respiratory & Critical Care Medicine, vol. 160, No. 2, pp. 732-735, Aug. 1999 (Abstract).

Smith, Philip E. M., et al., Hypoxemia During Sleep in Duchenne Muscular Dystrophy, American Review Respiratory Disorders, 1988, vol. 137, pp. 884-888.

Smyth, Edward, et al., Apneic Oxygenation Associated with Patient-Controlled Analgesia, Journal of Clinical Anesthesia, vol. 10, pp. 499-501, 1998, Publisher: Elsevier Science, Inc., New York, NY, USA.

Soto, F., Cardiovascular manifestations of obstructive sleep apnea. Effects of the treatment, Rev Med Chil., [Article in Spanish], Sep. 1998, vol. 126, No. 9, pp. 1112-1116 (Abstract).

Spector, Rosanne, Low-tech Screening for high-risk breathing disorder, http://healthlink.stanford.edu/healthlink/news2/lowtech.thml, Copyright 1996 Stanford University Medical Center News Bureau.

Staniforth, A. D., et al., Nocturnal desaturation in patients with stable heart failure, Heart, Apr. 1998, vol. 79, No. 4, pp. 394-399, United Kingdom (Abstract).

Stebbens, V. A., Oxygen saturation and breathing patterns in infancy. 1: Full term infants in the second month of life, Arch Dis Child, May 1991, vol. 66, No. 5, pp. 569-573 (Abstract).

Stegman, S. S., et al., Asymptomatic bradyarrhythmias as a marker for sleep apnea: appropriate recognition and treatment may reduce the need for pacemaker therapy, Pacing Clin Electrophysiol, Jun. 1996, vol. 19, No. 6, pp. 899-904 (Abstract).

Stradling, J. R., et al., Automatic Nasal Continuous Positive Airway Pressure Titration in the Laboratory: Patient Outcomes, Thorax, 1997, vol. 52, pp. 72-75.

Stradling, J. R., et al., Predictors and Prevalence of Obstructive Sleep Apnoea and Snoring in 1001 Middle Aged Men, Thorax, 1991, vol. 46, pp. 85-90.

Stradling, John R., et al., Relation between systemic hypertension and sleep hypoxaemia or snoring: analysis in 748 men drawn from general practice, BMJ, vol. 300, Jan. 13, 1990, pp. 75-78.

Strohl, Kingman P., Consequences of Sleep-Disordered Breathing, Respiratory Care, Apr. 1998, vol. 43, No. 4, pp. 277-282.

Strohl, Kingman P., et al., Physiologic Basis of Therapy for Sleep Apnea, State of Art: Physiologic Basis of Therapy for Sleep Apnea, pp. 791-802.

Sullivan, Colin E., et al., Reversal of Obstructive Sleep Apnoea by Continuous Positive Airway Pressure applied through the Nares, The Lancet, Apr. 18, 1981, pp. 862, 865.

Sullivan, Mary Anna et al., PCA Update, Unexpected Deaths of Patients Receiving Patient-Controlled Analgesia, Nov. 2001.

Svatikova, A., et al., Plasma brain natriuretic peptide in obstructive sleep apnea, American Journal Cardiology, Aug. 15, 2004, vol. 94, No. 4, pp. 529-532 (Abstract).

Szaboova, E., et al., Obstructive Sleep Apnea as a Cause of Dysrhythmia in Sudden Cardiac Death, Bratisl Lek Listy, Jul.-Aug. 1997, vol. 98, No. 7-8, pp. 448-453 (Abstract).

Tanchaiswad, Waran, Is Sudden Unexplained Nocturnal Death a Breathing Disorder?, Review Article, Psychiatry and Clinical Neurosciences, 1995, vol. 49, pp. 111-114.

Tanigawa, T., et al., Screening for sleep-disordered breathing at workplaces, Ind. Health, Jan. 2005, vol. 43, No. 1, pp. 53-57 (Abstract).

Teramoto, S., et al., Does the altered cardiovascular variability associated with obstructive sleep apnea contribute to development of cardiovascular disease in patients with obstructive sleep apnea syndrome?, Circulation, Dec. 21, 1999, vol. 100, No. 25, pp. e136-e137 (Abstract).

Teschler, H., et al., Influence of Moderate Alcohol Consumption on Obstructive Sleep Apnoea with and without AutoSet™ Nasal CPAP Therapy, European Respiratory Journal, 1996, vol. 9, pp. 2371-2377, Printed in United Kingdom.

(56) References Cited

OTHER PUBLICATIONS

Teschler, Helmut, et al., Automated Continuous Positive Airway Pressure Titration for Obstructive Sleep Apnea Syndrome, American Journal Respiratory Critical Care Medicine, vol. 154, pp. 734-740, 1996.

The American Sleep Disorders Association Accreditation Committee, Standards for Accreditation of Sleep Disorders Centers, American Sleep Disorders Association, Rochester, MN, Mar. 1997, Revised Edition, pp. 1-17 (p. 16 missing).

Thorpy, Michael J., The Clinical Use of the Multiple Sleep Latency Test, Report From the American sleep Disorders Association, Sleep, vol. 15, No. 3, 1992, pp. 268-276, American Sleep Disorders Association and Sleep Research Society.

Thorpy, Michael, et al., ASDA Standards of Practice, Practice Parameters for the Use of Portable Recording in the Assessment of Obstructive Sleep Apnea, Standards of Practice Committee of the American Sleep Disorders Associate, Sleep, vol. 17, No. 4, pp. 372-377.

Thorpy, Michael, et al., Practice Parameters for the Treatment of Obstructive Sleep Apnea in Adults: The Efficacy of Surgical Modifications of the Upper Airway, An American Sleep Disorders Association Review, Sleep, vol. 19, No. 2, pp. 152-155, 1996, American Sleep Disorders Association and Sleep Research Society.

Thorpy, Michael, et al., Practice Parameters for the Treatment of Snoring and Obstructive Sleep Apnea with Oral Appliances, An American Sleep Disorders Association and Sleep Research Society, Sleep, vol. 18, No. 6, pp. 511-513, 1995.

Thorpy, Michael, et al., Practice Parameters for the Use of Actigraphy in the Clinical Assessment of Sleep Disorders, An American Sleep Disorders Association Report, Sleep, vol. 18, No. 4, pp. 285-287, 1995 American Sleep Disorders Association and Sleep Research Society.

Thorpy, Michael, et al., Practice Parameters for the Use of Laser-assisted Uvulopalatoplasty, An American Sleep Disorders Association and Sleep Research Society, Sleep, vol. 17, No. 8, pp. 744-748, 1994.

Thorpy, Michael, et al., Practice Parameters for the Use of Polysomnography in the Evaluation of Insomnia, An American Sleep Disorders Association Report, Sleep, vol. 18, No. 1, pp. 55-57, 1995 American Sleep Disorders Association and Sleep Research Society.

Tkacova, R., et al., Continuous positive airway pressure improves nocturnal barareflex sensitivity of patients with heart failure and obstructive sleep apnea., Journal Hypertension, Sep. 2000, vol. 18, No. 9, pp. 1257-1262 (Abstract).

Tkacova, R., et al., Effects of continuous positive airway pressure on obstructive sleep apnea and left ventricular afterload in patients with heart failure, Circulation, 1998, vol. 98, No. 21, pp. 2269-2275 (Abstract).

Tobert, Daren G., et al., Laboratory Medicine and Pathology, New Directions for Pulse Oximetry in Sleep Disorders, Mayo Clinic Proceedings, 1995, vol. 70, pp. 591, Rochester, Minnesota, USA.

Tobin, Martin J., et al., Breathing Abnormalities During Sleep, Arch Intern Med, vol. 143, Jun. 1983, pp. 1221-1228.

Trang, H., et al., [B20] [Poster: 904] Masimo SetR Pulse Oximetry Improves Detection of Sleep Apnea-Related Hypoxemia, Nov. 2, 2001, C:/Masimo/Biblio, p. 1 of 1.

Tremel, F., et al., High prevalence and persistence of sleep apnoea in patients referred for acute left ventricular failure and medically treated over 2 months, European Heart Journal, Aug. 1999, vol. 20, No. 16, pp. 120-129.

Trinder, J., et al., Pathiophysiological interactions of ventilation, arousals, and blood pressure oscillations during Cheyne-Stokes respiration in patients with heart failure, American Journal Respiratory Critical Care Medicine, Sep. 2000, vol. 162, No. 3 Pt. 1, pp. 808-813 (Abstract).

Trupp, R. J., et al., Prevalence of sleep disordered breathing in a heart failure program, Congestive Heart Failure, Sep.-Oct. 2004, vol. 10, No. 5, pp. 217-220 (Abstract).

Trupp, R. J., The heart of sleep: sleep-disordered breathing and heart failure, Journal Cardiovascular Nursing, Nov.-Dec. 2004, vol. 19, No. 6 Suppl, S67-74 (Abstract).

Ullmer, E., et al., Cheyne-stokes respiration or obstructive sleep apnoea: patterns of desaturation, Respiration, 2000, vol. 67, No. 2, p. 203 (Abstract).

VanBoxem, T. J., et al., Prevalence and severity of sleep disordered breathing in a group of morbidly obese patients, Netherlands Journal of Medicine, vol. 54, No. 5, pp. 202-206, May 1999 (Abstract).

VanSlyke, Donald D., et al., Studies of Gas and Electrolyte Equilibria in Blood, pp. 781-798, Journal Biol. Chem., Oct. 1928, vol. 79, No. 2.

Verbraecken, J., et al., Chronic $CO_2$ Drive in Patients with Obstructive Sleep Apnea and Effect of CPAP, Respiration Physiology, vol. 101, pp. 279-287, 1995, Publisher: Elsevier.

Vgontzas, Alexandros N., et al., Obesity Without Sleep Apnea Is Associated with Daytime Sleepiness, Arch Intern Med., Jun. 22, 1998, vol. 158, pp. 1333-1337.

Vidhani, K., et al., Obstructive sleep apnoea syndrome: is this an overlooked cause of desaturation in the immediate postoperative period?, British Journal Anaesth, Apr. 1997, vol. 78, No. 4, pp. 442-443 (Abstract).

Visser, B.F., Pulmonary Diffusion of Carbon Dioxide, Med. Biol. vol. 5, pp. 155-166, Issue 2, Oct. 1960.

Waldhorn, Richard E., Surgical Treatment of Obstructive Sleep Apnea, Is Mandibular Surgery an Advance?, Chest, 1998, vol. 6, Dec. 1990, pp. 1315-1316.

Walker, Regina Paloyan, et al., Uvulopalatopharyngoplasty Versus Laser-Assisted Uvulopalatoplasty for the Treatment of Obstructive Sleep Apnea, Laryngoscope, vol. 107, Jan. 1997, pp. 76-82.

Weber, W., et al., Low-Perfusion Resistant Pulse Oximetry, Abstract Only, Journal of Clinical Monitoring, vol. II, No. 4, Jul. 1995, p. 284.

Weiss, J. Woodrow, et al., Cardiovascular Morbidity in Obstructive Sleep Apnea, Progress in Cardiovascular Diseases, vol. 41, No. 5, Mar./Apr. 1999, pp. 367-376.

Wessendorft, T. E., et al., Sleep-disordered breathing among patients with first-ever stroke, Journal Neurology, Jan. 2000, vol. 247, No. 1, pp. 41-47 (Abstract only).

West, Peter, et al., Dynamic in Vivo Response Characteristics of Three Oximeters: Hewlett-Packard 47201A, Biox III, and Nellcor N-100, Sleep, vol. 10, No. 3, 1987, pp. 263-271, Raven Press, New York, USA.

Westesson, Per-Lennart, et al., Morbidity after temporomandibular joint arthrography is lower than after removal of lower third molars, Oral Surgery Oral Medical Oral Pathol., 1990, vol. 70, pp. 2-4.

Wheatley, J. R., et al., Mechanical properties of the upper airway, Curr Opin Pulm Medicine, Nov. 1998, vol. 4, No. 6, pp. 363-369 (Abstract).

White, David P., Pathophysiology of Obstructive Sleep Apnoea, Sleep-Related Breathing Disorder—2, Thorax, 1995, vol. 50, pp. 797-804.

Whitelaw, William A., et al., Clinical Usefulness of Home Oximetry Compared with Polysomnography for Assessment of Sleep Apnea, American Journal Respiratory Critical Care Medicine, vol. 171, pp. 188-193, 2005, Internet address: www.atsjournals.org.

Whitman, R. A., et al., Comparison of the New Masimo SET V3 Technology with a Conventional Pulse Oximeter during Polysomnography, Sleep, 2001, vol. 24, pp. A412 (730.R).

Wiater, A., et al., Polysomnographic Standards for Infants and Children, Somnologie, vol. 4, pp. 39-42, 2000, Berlin—Wien.

Wieczorek, Paul M., et al., Obstructive Sleep Apnea Uncovered After High Spiral Anesthesia: A Case Report, Cardiothoracic Anesthesia, Respiration and Airway, Canadian Journal of Anesthesia, 2005, vol. 52, No. 7, pp. 761-764.

Wilhoit, Stephen C., et al., Comparison of Indices Used to Detect Hypoventilation during Sleep, Respiration, vol. 47, pp. 237-242, 1985.

Williams, Adrian J., et al., Clinical Value of Polysomnography, The Lancet, vol. 339, May 2, 1992, p. 1113.

Wright, John, et al., Health effects of obstructive sleep apnoea and the effectiveness of continuous positive airways pressure: a systematic review of the research evidence, BMJ, vol. 314, Mar. 22, 1997, pp. 851-860.

Wright, John, et al., Letters, Obstructive Sleep Apnoea, Authors' reply, bmj.com, Jun. 26, 2001.

(56) References Cited

OTHER PUBLICATIONS

Wynne, James W., et al., Disordered Breathing and Oxygen Desaturation During Sleep in Patients with Chronic Obstructive Lung Disease (COLD), The American Journal of Medicine, vol. 66, Apr. 1979, pp. 573-579.
Yamakage, M., et al., Changes in respiratory pattern and arterial blood gases during sedation with propofol or midazolam in spinal anesthesia, Journal Clinical Anesth, Aug. 1999, vol. 11, No. 5, pp. 375-379 (Abstract).
Yantis, M. A., Decreasing surgical risks for patients with obstructive sleep apnea, AORN Journal, Jul. 1998, vol. 68, No. 1, pp. 50-55 (Abstract).
Younes, Magdy, et al. Chemical Control Stability in Patients with Obstructive Sleep Apnea, American Journal Respiratory Critical Care Medicine, vol. 163, pp. 1181-1190, 2001.
Young, Terry, et al., The Gender Bias in Sleep Apnea Diagnosis, Are Women Missed Because They Have Different Symptoms?, Original Investigation, Arch Intern Medicine, vol. 156, Nov. 25, 1996, pp. 2445-2451.
Zafar, Subooha, et al., Choice of Oximeter Affects Apnea-Hypopnea Index, Chest, vol. 127/1, Jan. 2005, pp. 80-88, Clinical Investigations, www.chestjournal.org.
Zamarron, C., et al., Oximetry Spectral Analysis in the Diagnosis of Obstructive Sleep Apnoea, Clinical Science, 1999, vol. 97, pp. 467-473, Printed in Great Britain.
Zoccali, Carmine, et al., Nocturnal Hypoxemia, Night-Day Arterial Pressure Changes and Left Ventricular Geometry in Dialysis Patients, Kidney International, vol. 53, 1998, pp. 1078-1084, International Society of Nephrology.
Zou, Ding, et al., Obstructive Apneic Events Induce Alpha-Receptor Mediated Digital Vasoconstriction, Sleep, vol. 27, No. 3, 2004, pp. 485-489.
Zucconi, M., et al., An unattended device for sleep-related breathing disorders: validation study in suspected obstructive sleep apnoea syndrome, European Respiratory Journal, 1996, vol. 9, pp. 1251-1256, Printed in United Kingdom.
Alaris System, Brochure, Medication Safety System Focused at the Point of Care, Cardinal Health, Alaris Products, pp. 8, 2004.
Alian, Aymen et al., Evaluation of Rapid Response Team Flag-Alert Parameters, Published on www.cardiopulmonarycorp.com/pdf/rapidresponsealert paramers.pdf referenced in 2008, Internet Publication 2010.
Author Unknown, Chapter IV Oxygen Consumption During ADO, Introduction, pp. 40-46, Book Title Unknown, Study published 1980.
Author Unknown, Chapter X Effects of a 6-minute Period of ADO, Introduction, pp. 108-113, Book Title Unknown, Study published 1980.
Avance Innovating with you, shaping exceptional care, Brochure, GE Healthcare, pp. 8, 2006.
Bartolo, Anton et al., An Arrhythmia Detector and Heart Rate Estimator for Overnight Polysomnography Studies, conditionally accepted for IEEE Transactions, 19 pages, Nov. 3, 2000.
Benumof, Jonathan L., Creation of Observational Unit May Decrease Sleep Apnea Risk, Letters to the Editor, Anesthesia Patient Safety Foundation Newsletter and posted on the Malpractice company's web site. The Doctors Company | Sleep Apnea and Narcotic Postoperative Paln . . . http://www.thedoctors.com/risk/bulletins/sleepapnea.asp, 2002: 17:39.
Buckle, Patricia et al., Polysomnography in Acutely Ill Intensive Care Unit Patients, Chest, v. 102 n. 1, p. 288(4), American College of Chest Physicians, Jul. 1992.
Centiva/5 Critical Care Ventilator, Brochure, GE Healthcare, pp. 8, Oct. 2005.
Chi, Time-Series Matrices, University of Minnesota, http://www-users.cs.umn.edu/-echi/papers/infovis97/spread/node13.html, 1997, pp. 1-3.
Critical Care Therapy and Respiratory Care Section Policy, National Institute of Health, pp. 7, revised Mar. 2000.

Daley, Denise M., MD, Beware of All Sedatives in Patients With Sleep Apnea, Anesthesia Patient Safety Foundation Newsletter and posted on the Malpractice company's web site. The Doctors Company, Sleep Apnea and Narcotic Postoperative Pain . . . http://www.thedoctors.com/risk/bulletins/sleepapnea.asp, Letters to the Editor 2002-2003.
Datex-Phmeda Output Protocols Ohmeda Corn 1.0 Serial Protocol, Brochure, Datex-Ohmeda, Version 1.5, pp. 31. Aug. 14, 2001.
Dempsey, Jerome A. et al., Sleep and Breathing State of the Art Review Sleep-Induced Breathing Instability, Sleep, vol. 19, No. 3, pp. 236-247, American Sleep Disorders Association and Sleep Research Society, 1996.
Ferber, Richard et al., Portable Recording in the Assessment of Obstructive Sleep Apnea, ASDA Standards of Practice, American Sleep Disorders Association, vol. 17, No. 4, pp. 378-392, 1610 14th Street, NW, Suite 300, Rochester, MN 55901-2200, USA, 1994.
Fisher, Kyle S., MD, Value of Pulse Oximetry Monitoring on the Ward is Questioned, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp, Fall 2002.
Henderson, L. J. et al., Blood as a Physicochemical System. II, pp. 426-431, Paper, 1924.
Jain, Sanjay S. et al., Perioperative Treatment of Patients with Obstructive Sleep Apnea, Current Opinion Pulmonary Medicine 10, pp. 482-488, 2004.
Kaplan, Joseph et al., Home Pulse Oximetry as a Screening Test for Sleep-Disordered Breathing, Chest, vol. 103, pp. 322S, Northbrook, IL, USA, 1993.
Lynn, Lawrence, Background of Oximetry Utilization for Sleep Apnea Diagnosis, Publication information unknown, Article Written 1994, Not published.
Lynn, Lawrence A. et al., History of Threshold Oximetry, First viewing of Article Apr. 11, 2009, not published.
Lynn, Lawrence A. et al., Piercing the Panacea of Pulse Oximetry, Article Written Jul. 24, 2006, 8 pages, Not published.
Lynn, Lawrence, The Physiologic Parameters Defining the Oximetry Waveform Patterns in Sleep Apnea, Article Written 1994, Not published.
Lynn, Lawrence et al., Patterns of Unexpected In-Hospital Deaths: A Root Cause Analysis, Patient Safety in Surgery, vol. 5, No. 3, pp. 1-25, Feb. 11, 2011.
Final Official Action for U.S. Appl. No. 12/629,407, mailed Jul. 17, 2013 14 pages.
Final Official Action for U.S. Appl. No. 13/603,659, dated Sep. 25, 2013, 8 pages, English.
Non-Final Official Action for U.S. Appl. No. 11/369,355, dated Sep. 17, 2013 8 pages, English.
Patil, Ramesh S. et al., Application of an Artificial Intelligence Program to Therapy of High Risk Surgical Patients, New Horizons, vol. 4, No. 4, pp. 541-550, 1996.
Redline, Susan et al., Hypopnea, a Floating Metric: Implications for Prevalence, Morbidity Estimates, and Case Finding, Sleep, vol. 20, No. 12, pp. 1209-1217, 1997.
Ruchala, Joanna B., Chapter 13, Applications of Pulse Oximetry, Book: Design of Pulse Oximeters, pp. 214-236, Oct. 1997.
Sadeh, Avi et al., The Role of Actigraphy in the Evaluation of Sleep Disorders, An American Sleep Disorders Association and Sleep Research Society, Sleep, vol. 18, No. 4, pp. 288-302, 1995.
Scharf, Steven M. et al., Cardiovascular Effects of Periodic Occlusions of the Upper Airways in Dogs, American Review of Respiratory Disease, pp. 321-329, Aug. 1992.
Shneerson J, Obstructive Sleep Apnoea, BMJ, pp. 315-367 (Aug. 9, 1997); http://bmLcom/Shneerson et al. (7104).
Siggaard-Anderson, O et al., Editorial: The Bohr Effect and the Haldane Effect, Publication information unknown, 1973.
Strohl, Kingman P. et al., Physiologic Basis of Therapy for Sleep Apnea, State of Art: Physiologic Basis of Therapy for Sleep Apnea, pp. 791-802, 1986.

(56) References Cited

OTHER PUBLICATIONS

Tatevossian, Raymond G. et al. Noninvasive Hemodynamic Monitoring for Early Warning of Adult Respiratory Distress Syndrome in Trama Patients, Journal of Critical Care, vol. 15, No. 4 (Dec. 2000), pp. 151-159.

Thorpy, Michael et al., ASDA Standards of Practice, Practice Parameters for the Use of Portable Recording in the Assessment of Obstructive Sleep Apnea, Standards of Practice Committee of the American Sleep Disorders Associate, Sleep, vol. 17, No. 4, pp. 372-377, 1994.

Wilkins, Robert L. et al., Egan's Fundamentals of Respiratory Care, Analysis and Monitoring of Gas Exchange, Book, Eighth Edition, Chapter 16, Section III, Capnography/Capnometry During Mechanical Ventilation, pp. 383-389, 2003.

Williams et al., Screening for Sleep Apnea Using Pulse Oximetry and a Clinical Score, Chest, 100/3, Sep. 1991, pp. 631-635.

Campbell, Beverly, Arterial Waveforms: Monitoring Changes in Configuration, Hemodynamics, Heart & Lung, May/Jun. 1997, vol. 26, No. 3, pp. 204-214.

Inflection Point | Slope$^N$ - Slope$^{N-1}$ | > Selected Deviaton

Polarity Change

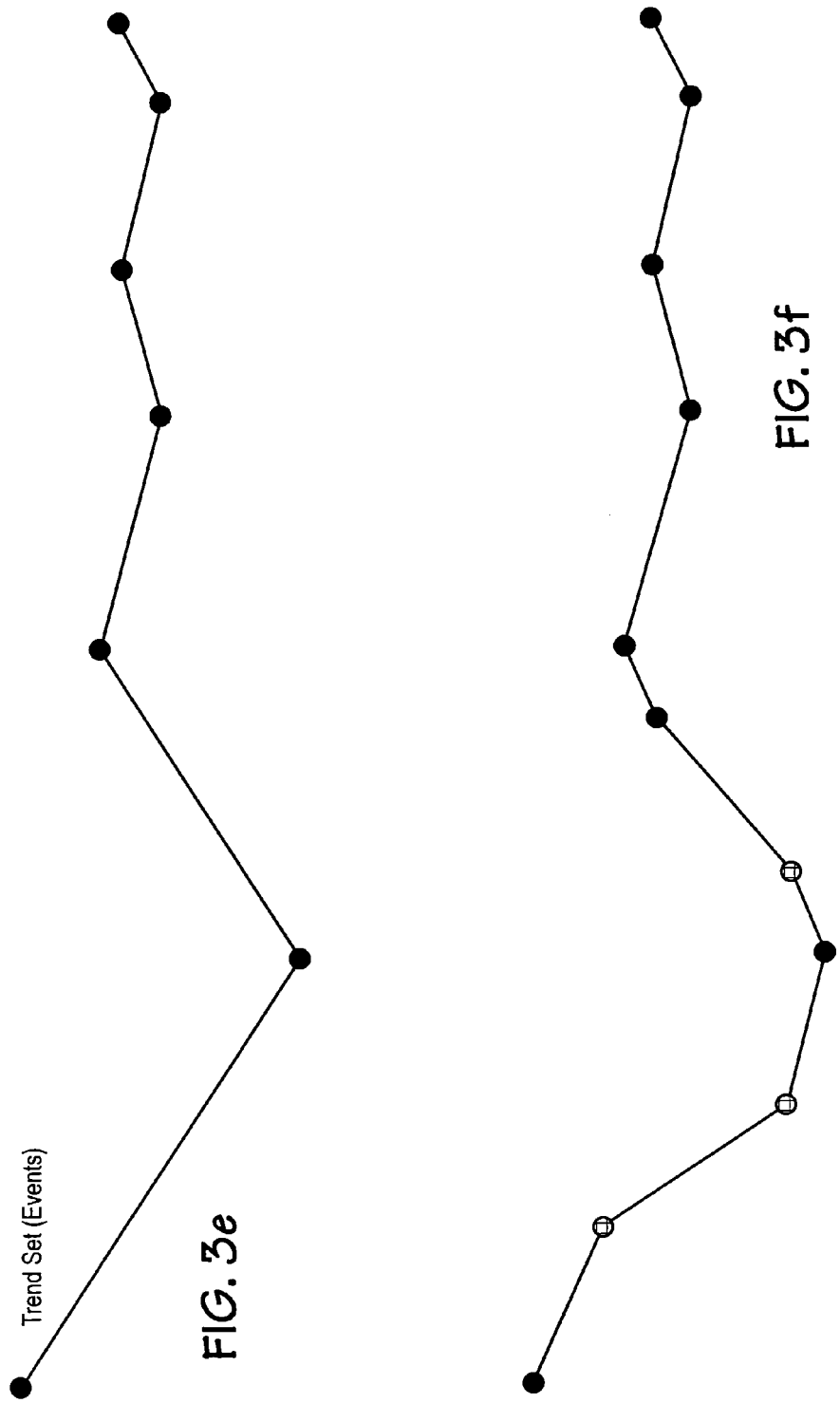

SYSTEM AND METHOD FOR AUTOMATIC DETECTION OF A PLURALITY OF SPO2 TIME SERIES PATTERN TYPES

CROSS-REFERENCE TO RELATED APPLICATIONS

This application is a continuation-in-part of U.S. patent application Ser. No. 11/280,559 ("the '559 application") filed Nov. 16, 2005, the contents of which are hereby incorporated herein by reference, and U.S. patent application Ser. No. 11/274,960 ("the '960 application") filed Nov. 16, 2005 now abandoned, the contents of which are hereby incorporated herein by reference, and U.S. patent application Ser. No. 11/280,653 ("the '653 application") filed Nov. 16, 2005, the contents of which are hereby incorporated herein by reference. The '559 application, the '960 application and the '653 application are each continuations-in-part of U.S. patent application Ser. No. 10/150,582 filed May 17, 2002 now U.S. Pat. No. 7,081,095 (which claims the benefit of U.S. Provisional Application Ser. No. 60/291,687 filed May 17, 2001, the contents of which are hereby incorporated herein by reference, and the benefit of U.S. Provisional Application Ser. No. 60/291,691, filed May 17, 2001, the contents of which are hereby incorporated herein by reference, and the benefit of U.S. Provisional Application Ser. No. 60/295,484 filed Jun. 10, 2001, the contents of which are hereby incorporated herein by reference), the contents of which are hereby incorporated herein by reference, and a continuation-in-part of U.S. patent application Ser. No. 10/150,842 filed May 17, 2002 now U.S. Pat. No. 7,758,503 (which claims the benefit of U.S. Provisional Application Ser. No. 60/291,687 filed May 17, 2001, the contents of which are hereby incorporated herein by reference), the contents of which are hereby incorporated herein by reference, and the benefit of U.S. Provisional Application Ser. No. 60/291,691, filed on May 17, 2001), the contents of which are hereby incorporated herein by reference), the contents of which are hereby incorporated herein by reference.

FIELD OF THE INVENTION

This invention relates to an object based system for the organization, analysis, and recognition of complex timed processes and the analysis, integration and objectification of time series outputs of data sets and particularly physiologic data sets, and to the evaluation of the financial and physiologic datasets and the determination of relationships between them.

BACKGROUND

The analysis of time series data is widely used to characterize the behavior of a system. The following four general categories of approaches are commonly applied to achieve characterization of such a system and these provide a general background for the present invention. The approaches are illustrative both in their conceptualization, application, and limitations.

The first such approach represents a form of mathematical reductionism of the complexity through the application of a cascade of rules based on an anticipated relationship between the time series output and a given set of system mechanisms. In this approach the operative mechanisms, data set characteristics, and intruding artifact are a priori defined to the best extent possible. Then a set of rules is applied to characterize and analyze the data set based on predicted relationships between the data set and the systems being characterized.

Such systems often include cascading branches of decision-based algorithms, the complexity of which increase greatly in the presence of multiple interactive mechanisms. The reductionism approach is severely limited by the uncertainty and complexity, which rapidly emerges when a cascade of rules is applied to a highly interactive data set, when the signal to noise ratio is low, and/or when multiple data sets generated by complex and dynamically interactive systems are evaluated. These methods become inordinately more cumbersome as the complexity and number of time series increases. In addition the subtlety of the interactive and dynamic relationships along and between datasets and the variations associated with the technique or tools of data collection often makes the cascading rules very difficult to define a priori.

The weakness of simplification the analysis through mathematical reductionism to adequately characterize the complex systems generating such data sets, led to the perception that this failure resulted from specific limitations of a particular data format (usually the time domain format). In other words, the time series was perceived to contain sufficient information to characterize the system but, it was thought, that the recognition of this information required reformatting into a different mathematical representation, which emphasized other hidden components which were specific for certain important system characteristics. This approach is exemplified by frequency processing methods, which reformat the time series into frequency components, such as its sine components or wavelets, with the hope that patterns of specific frequency relationships within the system will emerge to be recognized. While often uncovering considerable useful information, this approach is remains quite limited when applied to highly complex and interactive systems, because many complex relationships are poorly characterized by their frequency components, and it is often difficult to relate an output derived from frequency-based primitives to specific mechanisms operative within the system. In other words, the advantages associated with mathematically defined linkages between system mechanisms and the rules based analysis provided by reductionism is reduced by the data reformatting process for the purpose of frequency based signal processing as, for example, is provided by Fourier or wavelet transforms.

A third approach seeks to identify the patterns or relationships by repetitively reprocessing the time series with a set of general comparative rules or by statistical processing. As with the data reformatting approach, the utility of this method in isolation (as embodied in neural network based analysis), is severely limited by dissociation of the output from the complex and interactive operative mechanisms, which define the output. With such processing, the relevant scope and characterization of the relationships of the output to the actual behavior of the dynamic interactions of the system is often quite limited. This limits the applicability of such processing in environments wherein the characterization of behavior of the system as a function by the output may be as important as the actual output values themselves.

A fourth approach has been to apply chaotic processing to the time series. Again, like that of conventional signal processing this alternative method is applied the expectation that some predictive pattern will emerge to be recognized. This technique shares several of the limitations noted for both frequency and statistical based data reformatting. In addition as, will be discussed, the application of this type of processing to physiologic signals is limited by, redundant and interactive higher control which greatly limits the progression of the system to a state of uncontrolled chaotic behavior. Such systems operate in environments of substantial interactive control until the development of a severe disease state, a point at which the diagnostic information provided by processing often has less adjective utility relevant timely intervention.

The human physiologic system derives a large array of time series outputs, which have substantial relevance when monitored over a finite time interval. The human can be considered the prototypic complex interactive system. These interactions and the mechanisms defining, them have been the subject of intense research for over one hundred years and most of this work has been performed the time domain. For this reason any approach toward the characterization of such a system needs to consider the value of engaging the body of knowledge, which relates to these mechanisms. This has been one of the reasons that the reductionism has predominated in the analysis of physiologic signals. U.S. Pat. No. 5,765,563 to Vander Schaff, U.S. Pat. No. 5,803,066 to Rapoport, and U.S. Pat. No. 6,138,675 to Berthon-Jones show such simple cascade decision systems for processing physiologic signals. U.S. Pat. No. 5,751,911 to Goldman shows a real-time waveform analysis system, which utilizes neural networks to perform various stages of the analysis. U.S. Pat. No. 6,144,877 to Depetrillo shows a processor based method for determining statistical information for time series data and for detecting a biological condition of a biological system from the statistical information. U.S. Pat. Nos. 5,782,240 and 5,730,144 to Katz shows a system, which apply chaos analysers, which generate a time series, vector representation of each monitored function and apply chaotic processing to identify certain events. All of these systems are deficient in that they are not able to adequately organize, order and analyze the true state of dynamic interaction operative in the generation of these signals.

Critical illness is one example of a dynamic timed process, which is poorly characterized by the above noted conventional methods. When human physiologic stability is under threat, it is maintained by a complex array of interactive physiologic systems, which control the critical time dependent process of oxygen delivery to the organism. Each system (e.g. respiratory, cardiac or vascular) has multiple biochemical and/or mechanical controls, which operate together in a predictable manner to optimize oxygen delivery under conditions of threat. For example an increased oxygen requirement during infection causes the patient to increase oxygen delivery by lowering lung carbon dioxide through hyperventilation and the fall in carbon dioxide then causes the hemoglobin molecule to increase its affinity for oxygen thereby further enhancing oxygen delivery. In addition to the basic control of a single system, other systems interact with the originally affected system to producing a predictable pattern of response. For example, in the presence of infection, the cardiac system interacts with the respiratory system such that both the stroke volume and heart rate increase. In addition, the vascular system may respond with a reduction in arterial tone and an increase in venous tone, thereby both reducing impedance to the flow of oxygen to the tissues and shifting more blood into the arterial compartment.

Each system generally also has a plurality of predicable compensation responses to adjust for pathologic alteration or injury to the system and these responses interact between systems. For example the development of infectious injury to the lung will result in an increase in volume of ventilated gas to compensate for the loss of functional surface area. This increase in ventilation can then induce a synergistic increase in both stroke volume and heart rate.

Finally a pathologic process altering one system will generally also induce an alteration in one or more other systems and these processes are all time dependent. Sub acute or acute life threatening conditions such as sepsis, pulmonary embolism, or hemorrhage generally affect the systems in cascades or predictable sequences which may have a time course range from as little as 20 seconds or more than 72 hours. For example, the brief development of airway collapse induces a fall in oxygen saturation, which then causes a compensatory hyperventilation response, which causes a rise in heart rate over as little as 20-30 seconds. An infection, on the other hand, has a more prolonged time course inducing a rise in respiration rate, a rise in heart rate, and then a progressive fall in oxygen saturation and finally a fall in respiration rate and a finally a terminal fall in heart rate often over a course of 48-72 hours.

It can be seen therefore that each disease process engaging the organism causes the induction of a complex and interactive time series of pathophysiologic perturbation and compensation. At the onset of the disease (such as early in the course of infection) the degree of physiologic change may be very slight and limited to one or two variables. As a disease progresses both the magnitude of perturbation and the number of system involved increases. In addition to inducing a predictable range of perturbation, a particular disease process generally produces a specific range of progression and pattern of evolution as a function of injury, compensation, and system interaction. Furthermore, this multi-system complexity, which can be induced by initial pathologic involvement of a single system, is greatly magnified when a plurality of pathologic processes is present Despite the fact that these conditions represent some of the most important adversities affecting human beings, these pathologic processes are poorly characterized by even the most sophisticated of conventional monitors, which greatly oversimplify the processing and outputs. Perhaps this is due to the fact that this interactive complexity overwhelmed the developers of substantially all of the conventional physiologic signal-processing methods in the same way that it overwhelms the physicians and nurses at the bedside everyday. Hospital critical care patient monitors have generally been applied as warning devices upon threshold breach of specific critical parameters with the focus on the balance between timely warning of a potentially life threatening threshold breach and the mitigation of false alarms. However, during the pivotal time, early in the process of the evolution of critical illness, the compensatory responses limit the change in primary critical variables so that the user, monitoring these parameters in isolation, is often given a false sense of security. For this reason it cannot be enough to recognize and warn of the occurrence of a respiratory arrest, or hypotension, or hypoxia, or of a particular type of cardiac arrhythmia. To truly engage and characterize the processes present, a patient monitor must have capability to properly analyze, organize, and output in a quickly and easily understood format the true interactive state of critical illness. As discussed below, it is one of the purposes of the present invention to provide such a monitor.

BRIEF DESCRIPTION OF THE DRAWINGS

FIG. 3e is a diagram of a time series of trend parameters calculated to provide the trend (or polarity) analysis in accordance with embodiments of the present invention;

FIG. 3f is a diagram of a wave pattern shown in FIG. 3d, which can be derived from the utilization of user-defined object boundaries in accordance with embodiments of the present invention;

FIG. 5b is a diagram of a raw data set comprising a plurality of signals derived from the mechanism shown in FIG. 5a and from which, according to embodiments of the present invention, may be represented as multi-signal three-dimensional hierarchal object as shown in FIG. 5a;

DETAILED DESCRIPTION

Figure 1A:
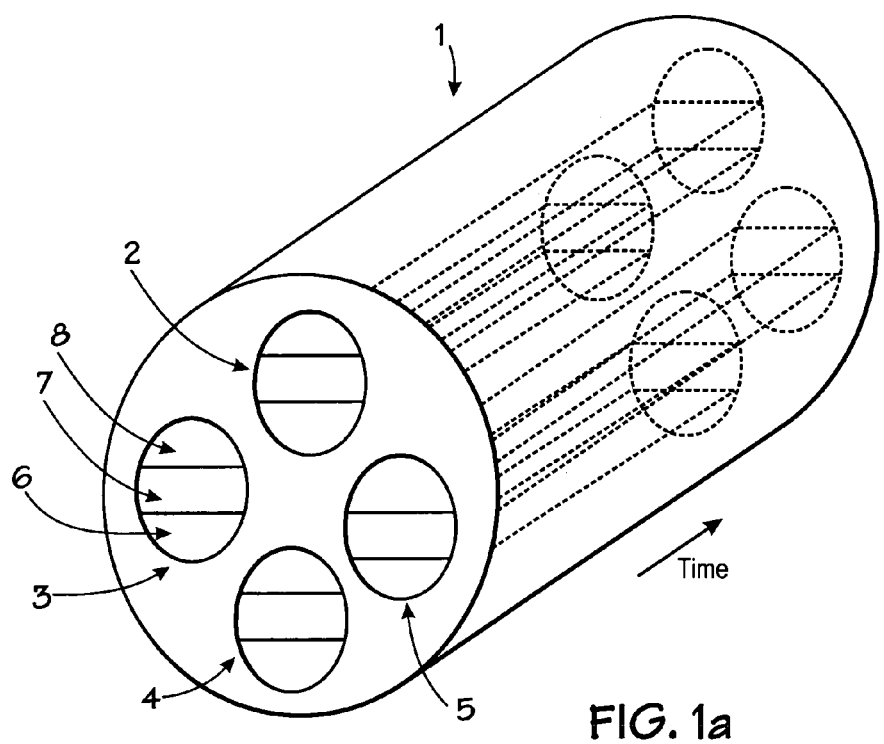
FIG. 1a is a diagram of a three-dimensional cylindrical data matrix in accordance with embodiments of the present invention comprising corresponding, streaming, time series of objects from four different timed data sets.

The present invention comprises a system and method of providing comprehensive organization and analysis of interactive complexity along and between pluralities of time series. An embodiment of the present invention comprises an object-based method of iterative relational processing of time series fragments or their derivatives along and between corresponding time series. The system then applies an iterative comparison process of those fragments along and between a plurality time series. In this way, the relationship of a wide range of characteristics of substantially any dynamic occurrence in one time series can be compare to the same or other characteristics of substantially any dynamic occurrence along another portion of the same time series or any of the processed corresponding time series.

In accordance with embodiments of the present invention, a first time series is processed to render a time series first level derived from sequential time series segments the first series, the time series first level is stored in a relational database, object database or object-relational database. The first time series level is processed to render a second time series level derived from the sequential time series component of the first time series level and these are stored in the relational database, object database or object-relational database. Additional levels are then derived as desired. The compositions of sequential time series, which make up the first and second levels, are determined by the definitions selected for the respective segments from which each level is derived. Each time series fragment is represented as a time series object, and each more complex time series object inherits the more basic characteristics of time series objects from which they are derived.

The time course of sub acute and acute critical illness to point of death is highly variable and can range from 24-72 hours with toxic shock, to as little as 30 seconds with neonatal apnea. The present inventors recognized that, regardless of its time course, such a pathological occurrence will have a particular "conformation", which according to the present invention can be represented spatially by an object-based processing system and method as a particular object or time series of objects, as a function of the specific progression of the interactive components for the purpose of both processing and animation. The present inventors also recognized that the development of such a processing system would be capable of organizing and analyzing the inordinate degree of dynamic complexity associated with the output from the biologic systems through the automatic incorporation of these time series outputs into a highly organized relational, layered, object based data structure. Finally, the inventors further recognized that because of the potentially rapid time course of these illnesses and the irreversible endpoint, that patient care monitors must provide a quickly and easily understood output, which gives the medical personnel a simplified and succinct analysis of these complex relationships which accurately reflects the interactive complexity faced by the patient's physiologic systems.

It has been suggested that the development of periodicity in a human physiologic system represents a simplification of that system. This concept is based on the perception that the human interactive physiologic systems operates in an environment of chaos and that a partial loss of control, simplifies the relationships, allowing simpler periodic relationships to emerge. However, there is considerable reason to believe that this is not the case. Patients centering an environment of lower partial pressure of oxygen, as at altitude, will develop periodicity of ventilation. This does not indicate a general simplification of the system but rather, one proposed operative mechanism for the emergence of this new pattern is that the pattern reflects the uncovering of a preexisting dynamic relationship between two controllers, which now, together determine ventilation in this new environment. At sea level, the controller responding to oxygen was subordinate the controller responding to carbon dioxide so that the periodicity was absent. This simple illustration serves to demonstrate the critical linkage between patient outputs and higher control and the criticality of comprehensively comparing dynamic relationships along and between signals to achieve a true picture of the operative physiology. While periodicities are, at times, clearly pathologic, their development in biologic systems, rather than a manifestation of simplification of physiological behavior often represents the engagement of more rudimentary layers of protection of a particular organ function or range built into the control system. This illustration further demonstrates that a given physiologic signal, when monitored in isolation, may appear to exhibit totally unpredictable and chaotic behavior, but when considered in mathematical or graphical relation (as in phase space) to a plurality of corresponding interactive signals, and to the interactive control mechanisms of those corresponding signals, the behavior of the original, chaotic appearing, signal often becomes much more explicable.

By way of example, consider a timed plot of oxygen saturation ($SPO_2$) under heavy sedation during sleep. This state is often associated with a loss of the maintenance of a narrow control range of ventilation during sleep and with the loss of stability of the airway so that a plot of the oxygen saturation, in the presence of such deep sedation, shows a highly variable pattern, which often appears grossly unpredictable, with sustained falls in oxygen saturation intermixed with rapid falls and often seemingly random rapid corrections. However, there are definable limits or ranges of the signal, and generally definable patterns, which are definable within the background of a now highly variable $SPO_2$ signal. It may be tempting to define this behavior statistically or by a chaotic processor in the hope of defining some emerging patterns as a function of the mathematical behavior of that signal. However, when analyzed with the partial pressure of $CO_2$, the minute ventilation, and a plot of EEG activity the oxygen saturation values are seen as a subordinate signal to the airflow which is now being controlled by a dysfunctional control process, which process is being salvaged by a more coarse and rudimentary survival response mechanism such as an arousal response. The apparently chaotic behavior is now seen as driven by a complex but predictable sequence of a plurality of dynamic interactive relationships between corresponding signals and the forces impacting them. Therefore, in the presence of a pathophysiologic process, the behavior and ranges of any given signal are optimally defined by the dynamic patterns of the interactive behavior of corresponding signals and their respective dynamic ranges.

A biologic system actually exploits the chaotic output of simple nonlinear relationships by defining control ranges, which are affected by variations in corresponding signals.

This produces a great degree in diversity of dynamic physiologic response, which is beneficial in that it may favor survival of a particular subgroup, in the presence of a certain type of pathophysiologic threat. The present inventors noted that, while this diversity imparts greater complexity, this complexity can be ordered by the application of iterative processing in which a given signal is defined as a function of a range "dynamic normality." According to one embodiment of the present invention, each signal is defined as a function of its own dynamic range (and in relation to a predicted control range) and as a function of contemporaneously relevant relationships of the dynamic ranges of other corresponding signals (with respect to their respective control ranges).

Embodiments of the present invention may comprise a system and method for organizing and analyzing multiple time series of parameters generated by a patient (as during critical illness) and outputting this analysis in readily understandable format. The system may include the capability of simultaneously processing dynamic time series of physiologic relationships in real time at multiple levels along each parameter and across multiple levels of different parameters. Embodiments of the present invention provide this level of interactive analysis specifically to match the complexity occurring during a pathologic occurrence. More specifically, embodiments of the present invention may provide an analysis system and method that analyzes the true dynamic state of a biologic system and the interactive primary and compensatory perturbations defining that state. During health the output of physiologic systems are maintained within tight variances. As will be discussed, a signal processing system in accordance with embodiments of the present invention may expose the extent to which the signals are held within these tight variances and may be characterized as a function of their dynamic ranges of variance. The signals may be further characterized as a function their dynamic relationships along the time series within a given signal and between a plurality of additional corresponding signals. A monitor of the human physiologic state during critical illness in accordance with embodiments of the present invention may be adapted to analyze time series relationships along and between a plurality signals with the similar degree of analytic complexity as is operative in the biologic systems controlling the interactive responses which are inducing those signals and of outputting an indication based on the analysis in a readily understandable format. Such a format may comprise a dynamic format such as a two-dimensional or three-dimensional object animation, the configuration of which is related to the analysis output. The configurations of the animation changes with the analysis output, as this output changes over time in relation to changes in the patient's physiologic state. The animation thereby provides a succinct and dynamic summary rendering which organizes the complexity of the interactive components of the output so that they can be more readily understood and used at the bedside and for the purpose of patient management and education of medical staff relevant the application of time series analysis in the assessment of disease. According to an exemplary embodiment of the present invention the process proceeds by organizing the multiple data streams defining the input into a hierarchy of time series objects in an object based data structure, analyzing and comparing objects along and across time series, organizing and summarizing the output, animating and presenting the summarized output and taking action based on the output. Embodiments of the present invention may comprise analyzing and comparing new objects derived subsequent the previous actions, adjusting the action and repeating the process.

Additionally, embodiments of the present invention may comprise calculating the expense and resource utilization related to said output.

Figure 2A:
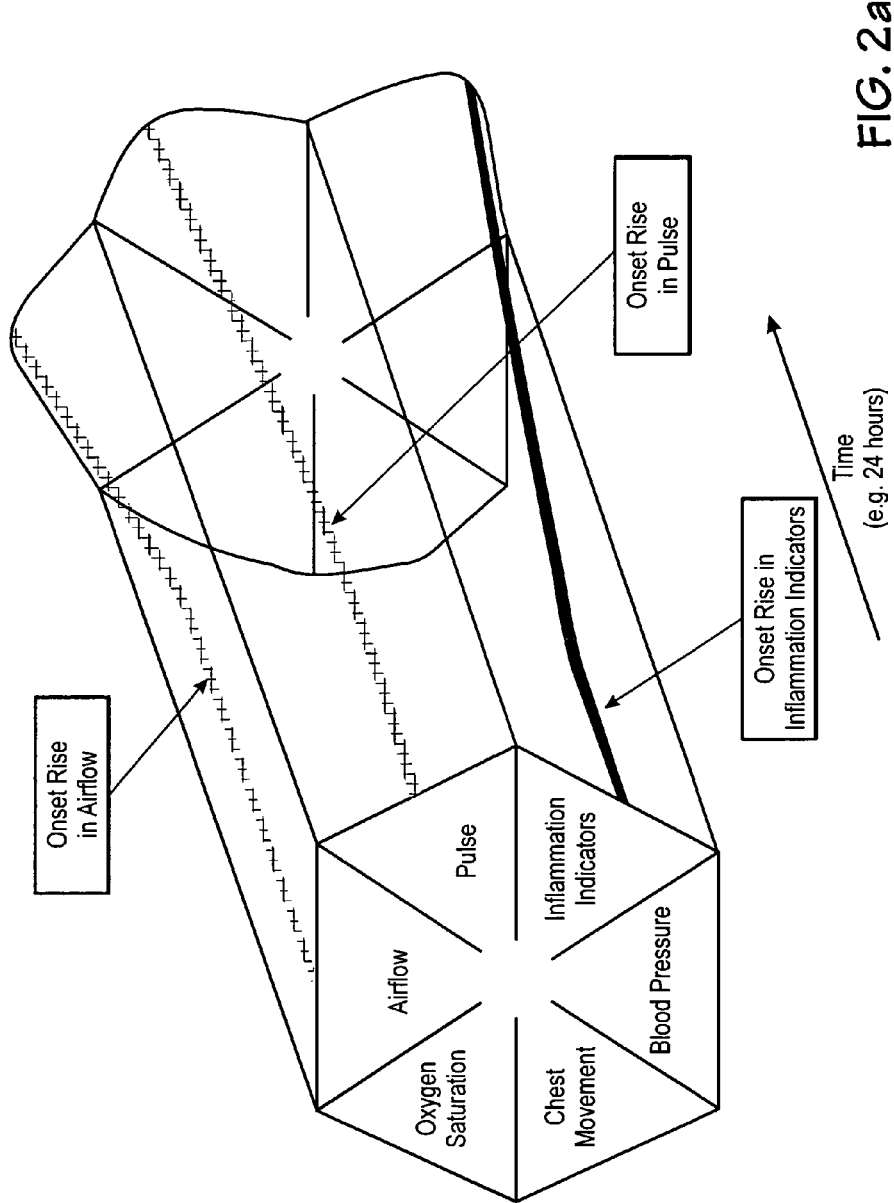
FIG. 2a is a diagram of a three-dimensional representation of collective conformation of corresponding time series of objects of pulse (which can be heart rate and/or pulse amplitude), oxygen saturation, airflow, chest wall movement, blood pressure, and inflammatory indicators during early infection, organized in accordance with embodiments of the present invention.
Figure 2B:
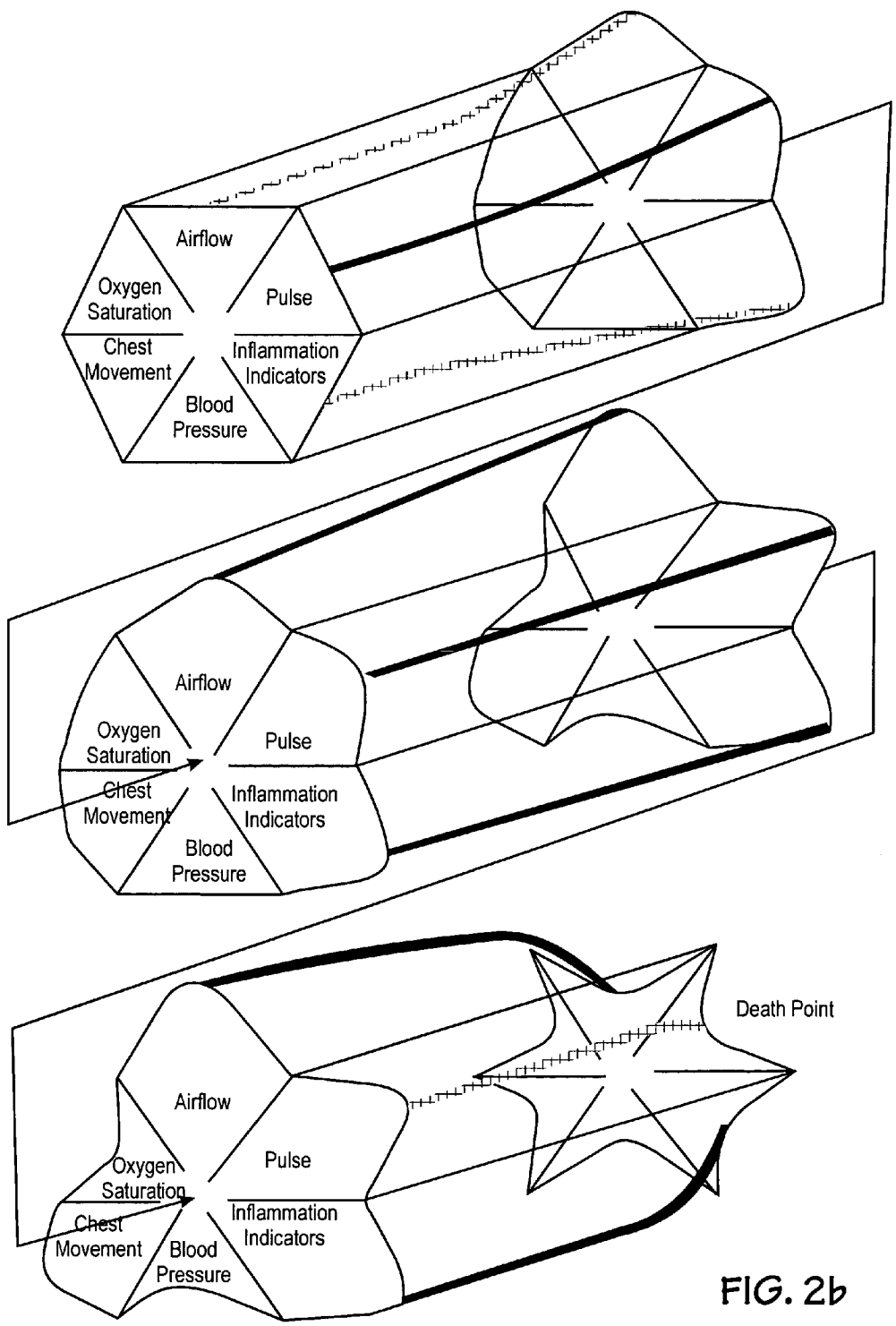
FIG. 2b is a diagram of a representation of the dynamic multi-parameter conformation shown in FIG. 2a, but extended through the evolution of septic shock to the death point.

In accordance with embodiments of the present invention, a plurality of time series of physiologic signals (including timed laboratory data) of a given physiologic process (such as sepsis) can have a particular conformational representation in three-dimensional space (as is shown in FIGS. 2a and 2b). This spatial representation comprises a summary of the relational data components, as analyzed, to diagnose a specific pathophysiologic process, to determine its progression, to define its severity, to monitor the response to treatment, and to simplify the representative output for the health care worker.

Two exemplary pathophysiologic processes (airway instability and sepsis) will be discussed below and exemplary patient monitoring systems and methods according to the present invention, for processing, organizing, analyzing, rendering and animating output, and taking action (including additional testing or treatment based on said determining) will be disclosed.

Figure 5A:
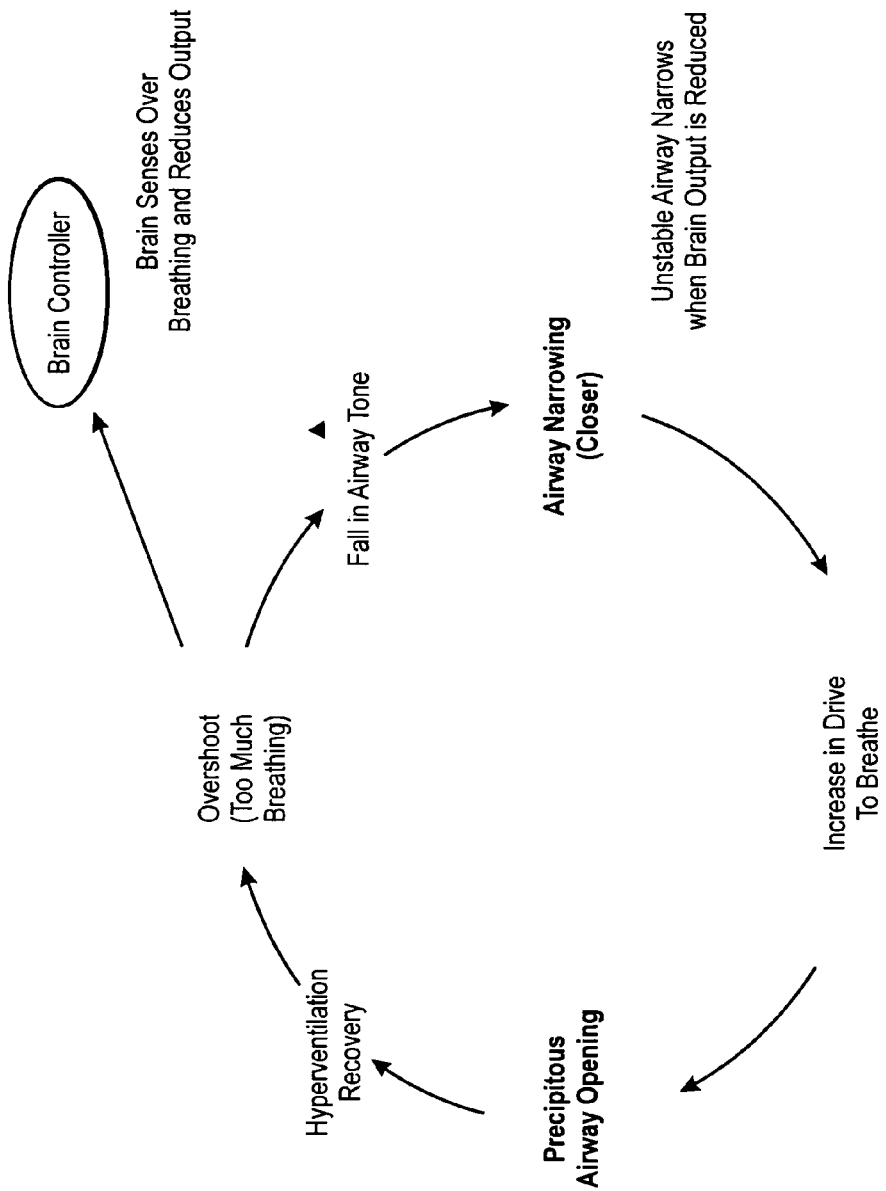
FIG. 5a is a diagram of a cyclic process of sleep apnea that shows the complexity of the mechanisms defining the timed interactions of physiologic systems induced by upper airway instability, which may be referred to as an "apnea cluster reentry cycle"
Figure 5B:
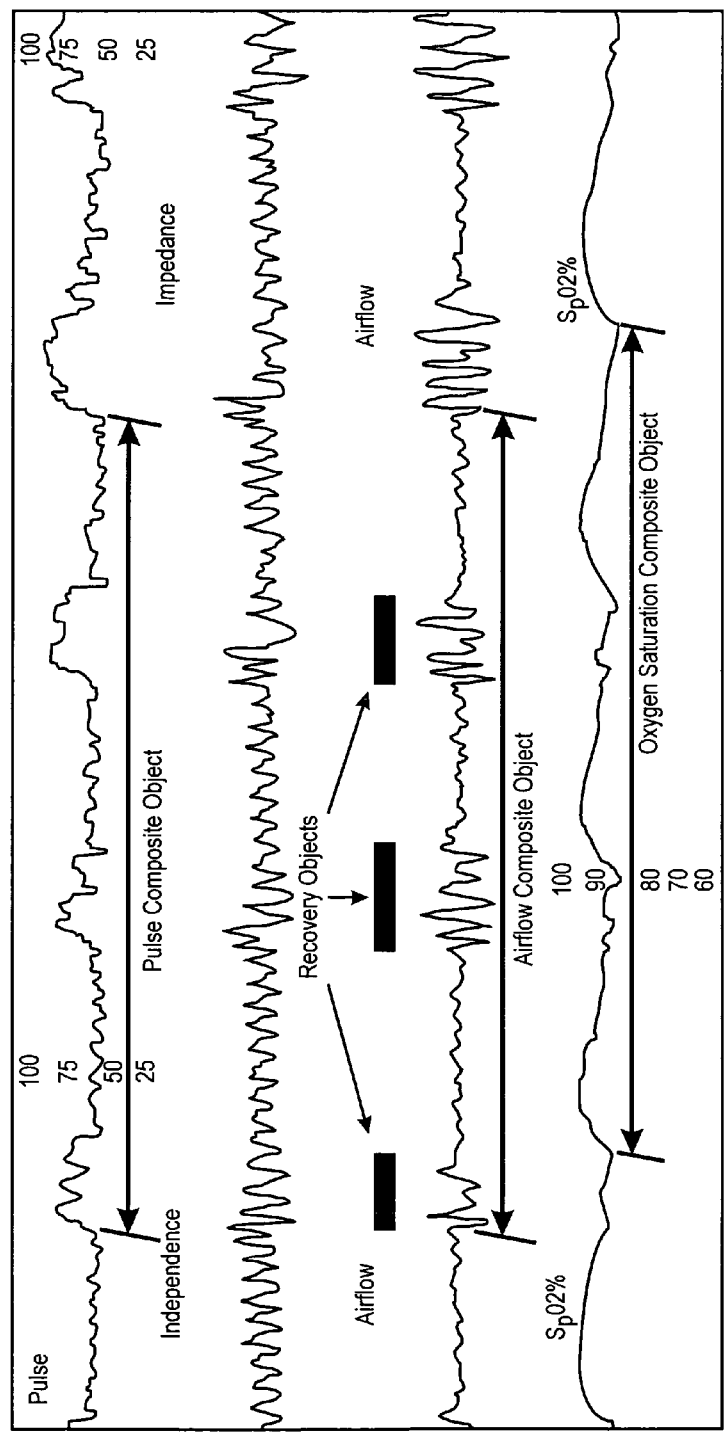

An important factor in the development of respiratory failure is airway instability, which results in air-way collapse during sedation, stroke, narcotics, or stupor. As illustrated in FIGS. 5a and 5b, such collapse occurs in dynamic cycles called apnea clusters affecting a range of physiologic signals. These apnea clusters are an example of a common and potentially life threatening process, which, perhaps due to the dynamic interactive complexity of the time series, is not recognized by conventional hospital processors. Yet subgroups of patients in the hospital are at considerable risk from this disorder. Patients with otherwise relatively, stable airways may have instability induced by sedation or narcotics and it is critical that this instability be recognized in real time in the hospital so that the dose can be adjusted or the drug withheld upon the recognition of this development. Conventional patient monitors are neither configured to provide interpretive recognition the cluster patterns indicative of airway and ventilation instability nor to provide interpretative recognition of the relationship between apnea clusters. In fact, such monitors often apply averaging algorithms, which attenuate the clusters. For these reasons thousands of patients each day enter and leave hospital-monitored units with unrecognized ventilation and airway instability.

Conventional hospital-based central patient monitors such as Agilent CMS, or the GE-Marquette Solar 8000, do not automatically detect and quantify obstructive sleep apnea or the cluster patterns indicative of airway instability. Because sleep apnea is so common, it is possible that many patients who unknowingly have sleep apnea have passed through hospitals over the past decade without being diagnosed. Many of these patients may never be diagnosed in their lifetime, which could result in increased suffering and medical costs. Also, other patients may develop complications while in the hospital due to the failure to recognize obstructive sleep apnea or airway instability. If automatic detection of sleep apnea is not performed, an opportunity to improve the efficiency of the diagnosis of obstructive sleep apnea, and to increase the revenue for the critical care monitoring companies marketing may remain unrealized. Further, an opportunity to increase hospital and/or physician revenue has been missed. Automatic detection of airway instability and/or obstructive sleep apnea by observing data clusters indicative of those conditions may reduce the occurrences of respiratory failure, arrest, and/or death related to the administration of IV sedation and narcotics to patients in the hospital with unrecognized airway instability.

The importance of recognizing airway instability in real-time may be appreciated by those of ordinary skill in the art based on consideration of the combined effect that oxygen therapy and narcotics or sedation may have in the patient care environment in the hospital. By way of example, consider the management of a post-operative obese patient after upper abdominal surgery. Such a patient may be at particular risk for increased airway instability in association with narcotic therapy in the first and second post-operative day due to sleep deprivation, airway edema, and sedation. Indeed, many of these patients have significant sleep apnea prior to admission to the hospital which is unknown to the surgeon or the anesthesiologist due to the subtly of symptoms. These patients, even with severe sleep apnea, may be relatively safe at home because of an arousal response. However, in the hospital, narcotics and sedatives often undermine the effectiveness of the arousal response. The administration of post-operative narcotics can significantly increase airway instability and, therefore, place the patient at risk. Many of these patients are placed on electrocardiographic monitoring but the alarms are generally set at high and low limits. Hypoxemia, induced by airway instability generally does not produce marked levels of tachycardia; therefore, airway instability is poorly identified by electrocardiographic monitoring without the identification of specific clusters of the pulse rate. In addition, oximetry evaluation may also be a poor method of identifying airway instability if an averaging interval, which may result in the attenuation of dynamic desaturations, is employed. Even when clustered desaturations occur, they may be thought to represent false alarms if they are brief. When desaturations are recognized as potentially real, a frequent result is the administration of nasal oxygen by a caregiver, which may produce undesirable results. For example, nasal oxygen may prolong the apneas and potentially increase functional airway instability. From a monitoring perspective, the addition of oxygen therapy can be seen to potentially hide the presence of significant airway instability by attenuation of the level of desaturation and reduction in the effectiveness of the oximeter as a monitoring tool in the diagnosis of this disorder.

Oxygen and sedatives can produce undesirable results in patients with severely unstable airways since the sedatives increase the apneas and the oxygen hides them from the oximeter. For all these reasons, as will be shown, according to the present invention, it is important to monitor and identify specific cluster patterns indicative of airway instability or sleep apnea. This may be particularly true during the administration of narcotics or sedatives in patients with increased risk of airway instability.

The central drive to breathe, which is suppressed by sedatives or narcotics, basically controls two muscle groups. The upper airway "dilator muscles" and the diaphragm "pump muscles". The tone of both these muscle groups must be coordinated. A fall in tone from the brain controller to the airway dilators results in upper airway collapse. Alternatively, a fall in tone to the pump muscles causes hypoventilation.

Two major factors contribute to respiratory arrest in the presence of narcotic administration and sedation. The first and most traditionally considered potential effect of narcotics or sedation is the suppression of the drive to the pump muscles. In this situation, airway instability may be less important than the reduced stimulation of the pump muscles, such as the diaphragm and chest wall, resulting in inadequate tidal volume, which results in an associated fall in minute ventilation and a progressive rise in carbon dioxide levels. The rise in carbon dioxide levels causes further suppression of the arousal response, therefore, potentially causing respiratory arrest. This first cause of respiratory arrest associated with sedation or narcotics has been the primary focus of previous efforts to monitor patients postoperatively for the purpose of minimization of respiratory arrests. Both oximetry and tidal $CO_2$ monitoring have been used to attempt to identify and prevent this development. However, in the presence of oxygen administration, oximetry is likely to be a poor indicator of ventilation. In addition, patients may have a combined cause of ventilation failure induced by the presence of both upper airway instability and decreased diaphragm output. In particular, the rise in $CO_2$ may increase instability of the respiratory control system in the brain and, therefore potentially increase the potential for upper airway instability.

The second factor causing respiratory arrest due to narcotics or sedatives relates to depression of drive to upper airway dilator muscles causing a reduction in upper airway tone. This reduction in airway tone results in dynamic airway instability and precipitates cluster cycles of airway collapse and recovery associated with the arousal response as the patient engages in a recurrent and cyclic process of arousal based rescue from each airway collapse. If, despite the development of a significant cluster of airway collapses, the narcotic administration or sedation is continued, this can lead to further prolongation of the apneas and eventual respiratory arrest. There is, therefore, a dynamic interaction between suppression of respiratory drive, which results in hypoventilation, and suppression of respiratory drive, which results in upper airway instability. At any given time, a patient may have a greater degree of upper airway instability or a greater degree of hypoventilation. The relative combination of these two events will determine the output of the monitor, with the former producing a simple trending rise (as with end tidal $CO_2$) or fall (as with minute ventilation or oxygen saturation) and the latter producing a cluster output pattern.

Unfortunately, this has been one of the major limitations of carbon dioxide monitoring. The patients with significant upper airway obstruction tend to be the same patients who develop significant hypoventilation. The upper airway obstruction may result in drop out of the nasal carbon dioxide signal due to both the upper airway obstruction, on one hand, or be due to conversion from nasal to oral breathing during a recovery from the upper airway obstruction, on the other hand. Although breath by breath monitoring may show evidence of apnea, conversion from nasal to oral breathing can reduce the ability of the $CO_2$ monitor to identity even severe hypoventilation in association with upper airway obstruction, especially if the signal is averaged or sampled at a low rate. For this reason, conventional tidal $CO_2$ monitoring when applied with conventional monitors may be least effective when applied to patients at greatest risk, that is, those patients with combined upper airway instability and hypoventilation.

As described in U.S. Pat. No. 6,223,064 (assigned to the present inventor and incorporated herein by reference), the underlying cyclic physiologic process, which drives the perpetuation of a cluster of airway closures, can be exploited to recognize upper airway instability in real time. The underlying cyclic process, which defines the behavior of the unstable upper airway, is associated with precipitous changes in ventilation and attendant precipitous changes in monitored parameters, which reflect and/or are induced by such ventilation changes. For example, cycling episodes of airway collapse and recovery produces sequential precipitous changes in waveform output defining analogous cluster waveforms in the oximetry pulse tracing, the airflow amplitude tracing, the oximetry $SpO_2$ tracing, the chest wall impedance tracing and the EKG pulse rate or R to R interval tracing.

The use of central hospital monitors generally connected to a plurality (often five or more) of patients through telemetry is a standard practice in hospitals. The central monitor is not, however, typically involved in the diagnosis of sleep apnea, for which the application of additional monitors is needed. The present inventors are not aware of any of the central patient monitors (such as those in wide use which utilize central telemetry), which provide the above functionality. The use of additional monitors to diagnose sleep apnea is inefficient because it requires additional patient connections, is not automatic, and is often unavailable. According to one aspect of the present invention, the afore-referenced conventional hospital monitors may be adapted to provide a measurement and count of airflow attenuation and/or oxygen desaturation and to compare that output with the chest wall impedance to routinely identify the presence of obstructive sleep apnea and to produce an overnight summary and formatted output. The summary and formatted output, which may be over read by the physician, may meet the standard of the billing code in that it includes airflow, oximetry, chest impedance, and EKG or body position. Embodiments of the present invention may use conventional apnea recognition algorithms (as are well known in the art), such as the apnea recognition system of U.S. Pat. No. 6,223,064 (hereby incorporated by reference), or another suitable system for recognizing sleep apnea.

The present inventors discovered and recognized that the addition of such functionality to central hospital monitors could result in improved efficiency, patient care, reduced cost and potentially enhanced physician and hospital revenue. The business of diagnosing sleep apnea has long required additional equipment relative to the standard hospital monitor and would be improved by the conversion and programming of central hospital monitors to provide this functionality. Moreover, the method of using the processor of a central hospital monitor to interactively detect obstructive sleep apnea and provide processor-based interpretive indication of obstructive output and to output a summary suitable for interpretation to make a diagnosis of obstructive sleep apnea can result in the automatic diagnosis of sleep apnea for many patients who may be unaware of their condition. The present invention may also allow patient monitoring companies, which manufacture the central hospital monitors, to enter the sleep apnea diagnostic market and to exploit that entry by providing a telemetry connection of positive pressure devices to the primary processor or secondary processor of the carried telemetry unit so that positive pressure can be adjusted by the patient monitor. The present invention may facilitate growth in the field of selling positive pressure devices by providing an opportunity for hospital monitoring companies to create specialized interfaces for the transport of telemetry data between patient monitors and/or the associated telemetry unit to the positive pressure devices. Moreover, market growth may be enhanced because more potential customers of positive pressure treatment may be identified.

According one aspect of the present invention, the recognition of sequential precipitous changes can be achieved by analyzing the spatial and/or temporal relationships between at least a portion of a waveform induced by at least a first apnea and at least a portion of a waveform induced by at least a second apnea. This can include the recognition of a cluster, which can comprise a high count of apneas with specified identifying features which occur within a short time interval along said waveform (such as 3 or more apneas within about 5-10 minutes) and/or can include the identification of a waveform pattern defined by closely spaced apnea waveform or waveform clusters. Further, the recognition can include the identification of a spatial and/or temporal relationship defined by waveform clusters, which are generated by closely spaced sequential apneas due to cycling upper airway collapse and recovery. Using the above discoveries, typical standard hospital monitors can be improved to provide automatic recognition of apnea clusters indicative of upper airway instability and to provide an automatic visual or audible indication of the presence of such clusters and further to provide a visual or audible output and severity of this disorder thereby rendering the timely recognition and diagnosis of upper airway instability and obstructive sleep apnea a typical occurrence in the hospital.

FIG. 5a illustrates the re-entry process driving the propagation of apnea clusters. The physiologic basis for these clusters has been previously described in U.S. Pat. Nos. 5,891,023 and 6,223,064 (the disclosure of each of which is incorporated by reference as if completely disclosed herein). This cycle is present when the airway is unstable but the patient is capable of arousal. In this situation, in the sleeping or sedated patient, upon collapse of the airway, the patient does not simply die, she rescues herself and precipitously opens the airway to recover by hyperventilation. However, if the airway instability remains after the arousal and rescue is over, the airway collapses again, only to result in another rescue event. This cycle produces a cluster of closely spaced apneas with distinct spatial, frequency and temporal waveform relationships between and within apneas wherein the physiologic process re-enters again and again to produce a clustered output. In accordance with aspects of the present invention, an apnea cluster is comprised of a plurality (two or more) of closely spaced apneas or hypopneas. Analysis of three or more apneas is desirable. Embodiments of the present invention include recognition of apnea clusters along signals derived from sensors outside the body or from sensors within the body, for example in association with pacemakers, catheters, or other indwelling or implanted devices or sensors wherein the signals are indicative of parameters including $SpO_2$, pulse (including pulse characteristics as derived for example from the plethesmographic pulse defined, for example, by a red pleth signal, an IR pleth signal, and ratio of ratios, to name a few), chest wall impedance, airflow (including but not limited to exhaled carbon dioxide ($CO_2$) and air temperature (for example measured by a thermistor), and sound. Additional parameters that may be analyzed include the plethesmographic pulse, blood pressure, heart rate, ECG (including, for example, QRS morphology, pulse rate, R to R interval plots and timed plots of ST segment position to name a few), chest wall and/or abdominal movements, systolic time intervals, cardiac output. Additional examples include continuous cardiac outputs as by $CO_2$ analysis, chest impedance, and thermodilution, esophageal and plevd process parameters, genioglossal tone, accessory, EEG signals, EMG signals, and other signals, that provide a cluster pattern indicative of a condition that is of interest from a diagnostic perspective. All of these parameters comprise respiratory parameters since they manifest, for example, circulatory, movement, electrical and electrochemical patterns of variations in response to respiratory patterns of variations due to pathophysiologic instabilities.

The present invention further includes a system for defining the physiologic status of a patient during critical illness based on the comparison of a first parameter along a first monitored time interval defining a first timed data set to at least one other parameter along a second time interval, defining a second timed data set. The second time interval corresponds to the first time interval and can actually be the first time interval or another time interval. The second time interval corresponds to the effected physiologic output of the second parameter as inclined by the output of the first parameter during the first time interval. For example the first time interval can be a five to fifteen minute segment of timed airflow and the time interval can be a slightly delayed five to fifteen minute segment of timed oxygen saturation derived from the airflow which defined the dataset of the first time interval.

According another aspect of the present invention, the microprocessor identifies changes in the second parameter that are unexpected in relationship to the changes in the first parameter. For example, when the microprocessor identifies a pattern indicative of a progressive rise in minute ventilation associated with a progressive fall in oxygen saturation, a textual warning can be provided indicating physiologic divergence of the oxygen saturation and minute ventilation. For example, the term "divergent oxygen saturation" can be provided on the patient monitor indicating that an unexpected change in oxygen saturation has occurred in association with the ventilation output. The occurrence of such divergence is not necessarily a life threatening condition but can be an early warning of significant life threatening conditions such as pulmonary embolism or sepsis. If the patient has an attached apparatus which allows the actual minute ventilation to be quantitatively measured rather than trended then, divergence can be identified even when the oxygen saturation does not fall as defined by plotting the timed output of ventilation indexing oximetry as by formulas discussed in the U.S. patent applications (of one of the present inventors) entitled Medical Microprocessor System and Method for Providing a Ventilation Indexed Value (U.S. Application Ser. No. 60/201,735) and Microprocessor System for the Simplified Diagnosis of Sleep Apnea (U.S. application Ser. No. 09/115,226) (the disclosure of each of which is incorporated herein by reference as if completely disclosed herein). Upon the identification of divergence, the time series of other parameters such as the temperature, while blood cell count and other lab tests can be included to identify the most likely process causing, the divergence.

One of the reasons that the identification of pathophysiologic divergence is important is that such identification may provide earlier warning of disease. In addition, if the patient progresses to develop significantly low levels of a given parameter, such as oxygen saturation or pulse, it is useful to be able to go back and identify whether or not the patient experienced divergence of these parameters earlier since this can help identify whether it is a primary cardiac or pulmonary process which is evolving and indeed the time course of the physiologic process is provided by both diagnostic and therapeutic. Consider, for example, a patient experiencing significant drop in oxygen saturation and cardiac arrest. One purpose of the present invention is to provide an output indicative of whether or not this patient experienced a cardiac arrhythmia which precipitated the arrest or whether some antecedent pulmonary process occurred which caused the drop in oxygen saturation which then ultimately resulted in the cardiac arrhythmia and arrest. If the patient is being monitored by chest wall impedance, oximetry and EKG, all three parameters can be monitored for evidence of pathophysiologic divergence. If, according to the present invention, the processor identifies divergence of the oxygen saturation in association with significant rise in minute ventilation, then consideration for bedside examination, chest x-ray, arterial blood gas measurement can all be carried out so that the relationship between cardiac and pulmonary compensation in this patient can be identified early rather than waiting until a threshold breach occurs in one single parameter. Since, with the use of conventional monitors, threshold breach of an alarm can be severely delayed or prevented by an active compensatory mechanism, such as hyperventilation, one advantage of the present invention is that the processor can provide warning as much as four to eight hours earlier by identifying pathophysiologic divergence rather than waiting for the development of a threshold breach.

Another example of the value of monitor based automatic divergence recognition, according to embodiments of the present invention is provided by a patient who has experienced a very mild breach of the alarm threshold in association with significant physiologic divergence such as a patient whose baseline oxygen saturation is 95% in association with a given baseline amplitude and frequency of minute ventilation as identified by an impedance monitor. For this patient, the fall in oxygen saturation over a period of two hours from 95% to 89% might be perceived by the nurse or house officer as representing only a mild change which warrants the addition of simple oxygen treatment by nasal cannula but no further investigation. However, if this same change is associated with marked physiologic divergence wherein the patient has experienced significant increase in the amplitude and frequency of the chest impedance, the microprocessor identification of significant pathophysiologic divergence can give the nurse or house officer cause to consider further performance of a blood gas, chest x-ray or further investigation of this otherwise modest fall in the oxygen saturation parameter.

Excessive sedation is unlikely to produce physiologic divergence since sedation generally results in a fall in minute ventilation, which will be associated with a fall in oxygen saturation if the patient is not receiving nasal oxygen. The lack of pathophysiologic divergence in association with a significant fall in oxygen saturation can provide diagnostic clues to the house officer.

In accordance with embodiments of the present invention, a processor-based system can automatically output an indication of pathophysiologic divergence relating to timed data sets derived from sensors which measure oxygen saturation, ventilation, heart rate, plethesmographic pulse, and/or blood pressure to provide automatic comparisons of linked parameters in real time, as will be discussed. The indication can be provided in a two or three-dimensional graphical format in which the corresponding parameters are presented summary graphical format such as a timed two-dimensional or three-dimensional animation. This allows the nurse or physician to immediately recognize pathophysiologic divergence.

According to another aspect of exemplary embodiments of the present invention, the comparison of signals can be used to define a mathematical relationship range between two parameters and the degree of variance from that range. This approach has substantial advantages over the simple comparison of a given signal with itself along a time series to determine variability with respect to that signal, which has been shown to correlate loosely with a diseased or aged physiologic system. Such an approach is described in Griffin U.S. Pat. No. 6,216,032, the disclosure of which is incorporated by reference as is completely disclosed herein. As appreciated by those of ordinary skill in the art, the signal variability processing method, which has been widely used with pulse rate, lacks specificity since variance in a given signal may have many causes. According to embodiments of the present invention, a plurality of signals are tracked to determine if the variability is present in all of the signals, to define the relationship between the signals with respect to that variability, and to determine if a particular signal (such as airflow, for example) is the primary (first) signal to vary with other signals tracking the primary signal. With respect to analysis of signal variability, airway instability, sepsis, stroke, and congestive heart failure are all associated with a high degree of heart rate variability and this can be determined in relation to a baseline or by other known methods. In accordance with embodiments of the present invention, the general variability of a plurality of signals is determined and these are matched to determine if a particular signal has a greater variability than the other signals, and more importantly the dynamic relationship between the signals is determined to identify the conformation of that variability. In this respect for example, the pulse in sepsis in a neonate may show a high degree of variability, by confirming that this variability is associated with a general multi-parameter conformation rather than a conformation of rapidly expanding and contracting parameters, as is typical of airway instability. In this way, the etiology of the pulse variability is much better identified.

FIGS. 2a and 2b are graphical representations of parametric models that may be constructed in accordance with embodiments of the present invention to assist in the recognition of non-conformities of a range of parameters. The parameters, which may represent time series data, may be defined to correspond with data that is variable in response to certain conditions such as sleep apnea or sepsis. The shape of each region of the geometric figures illustrated in FIGS. 2a and 2b may be defined to represent a range of normal values for each parameter (oxygen saturation including arterial and venous), airflow, pulse, inflammation indicators, blood pressure and chest movement in FIG. 2a) that is being evaluated. As illustrated in FIGS. 2a and 2b, the shape of one or more of the parametric representations may vary over time, indicating relational nonconformity with respect to expected normal time series data. The degree and pattern of divergence from the predetermined normal range may serve to indicate the presence of a malady such as sleep apnea or sepsis. Examples of analytical tools that may be employed as at least one component of an embodiment of the present invention include time domain analysis, frequency domain analysis, neural network analysis, preprocessing signals to remove artifacts, phase analysis, pattern recognition, ratiometric analysis, wavelet analysis, filtering (average, median, ACF, ADC), histogram analysis (stochastic distribution), variability analysis, entropy analysis, data fusion, fractal analysis transformations, combine or convolve signals and peak detector analysis.

As illustrated in FIGS. 2a and 2b, variability may be defined in relation to which parameters are changing, whether they are changing together in a particular category of conformation indicative of a specific disease process, and the extent to which they follow anticipated subordinate behavior is identified. According to another aspect of an exemplary embodiment of the present invention, the time series of the parameter "relationship variance" and the time series of the "relationship variability" may be analyzed as part of a data matrix. Those of ordinary skill in the art will appreciate that the shape of the region representing a collection of parameters of interest may be defined to correspond to a wide range of geometries. For example, the parametric representation may be defined to have a cross section of a circle (see, for example, FIGS. 1a and 1b), a rectangle or any suitable parameter to facilitate analysis of the data representative of that parameter.

As illustrated in FIG. 2a, airflow and heart rate increases begin to develop early in the state of sepsis. In FIG. 2a, oxygen saturation does not vary much outside its normal range even though airflow begins to increase because the peak value of the oxygen saturation vale to limited. As septic shock evolves, variability increases and the tight relationship between airflow and oxygen saturation begins to break down (see FIG. 2b). In one embodiment of the present invention, this relationship is analyzed, as time series of the calculated variance of the airflow, variance of the heart rate, and variance of the oxygen saturation, along with the streaming time series of objects of the original measured values. Timed calculated variability thereby comprises components of a data matrix of objects having a particular geometric shape. Furthermore, a time series of the variance from a given relationship and the variability of that variance may be derived and added to the data matrix. By way of example, an index of the magnitude value of airflow in relation to the magnitude value of oxygen saturation and/heart rate is calculated for each data point (after adjusting for the delay) and a time series of this index is derived. Then, a time series of the calculated variability of the index is derived and added to the data matrix. The slope or trend of the index of "airflow" and oxygen saturation will rise significantly as septic shock evolves and this can be correlated with the slope of the variability of that index. In comparison with septic shock, in airway instability, the time series of these parameters show a high degree of variability generally but a relatively low degree of variance of the indexed parameters associated with that variability (since despite their precipitous dynamic behavior, these parameters generally move together maintaining the basic relationships of physiologic subordinance). In addition to heart rate, a time series of the plethesmographic pulse (as amplitude, ascending slope, area under the curve or the like) variability and variance (as with continuous blood pressure or airflow) can be derived and incorporated with the data matrix for analysis and comparison to determine variability and variance relationships as well as to define the general collective conformation of the dynamic relationships of all of these parameters.

According to another aspect of an embodiment of the present invention, the analysis of subsequent portions of a time-series can automatically be adjusted based on the output of the analysis of preceding portions of a time-series. By way of example, with timed waveforms, such as $SpO_2$, in clinical medicine, two differing conditions may occur intermittently: a first condition may occur in which additional processing of acquired data is desirable intermittently with a second condition in which the additional processing of data is not desirable. For example, the application of smoothing algorithms if they are not needed may result in modification of the slope of an oxygen desaturation and the slope of resaturation. Improper smoothing may also affect the relative relationship between the desaturation and resaturation slopes. Embodiments of the present invention may be adapted to perform additional processing such as smoothing when it is desirable and omit the additional processing when the additional processing is not desirable. Subsequently, the data signal is processed with cluster analysis technology for the recognition of airway instability. The cluster analysis technology may be adjusted to account for the effect of averaging on the slopes and the potential for averaging to attenuate mild desaturations.

In an exemplary embodiment of the present invention, a microprocessor system is provided for the recognition of specific dynamic patterns of interaction between a plurality of corresponding and related time series. The system comprises a processor programmed to process a first time series to produce a lower-level time series of sequential time series fragments derived from the first time series, process the lower-level time series to produce a higher-level time series comprised of sequential time series fragments from the lower-level time series, process a second time series, the second time series being related to the first time series, produce a second lower-level time series of sequential time series fragments derived from the second time series, and identify a dynamic pattern of interaction between the first time series and the second time series. The system can be further programmed to process the lower-level time series of the second time series to produce a higher-level time series derived from sequential time series fragments of the second lower-level time series. The system can be programmed to process a third time-series, the third time series being related to at least one of the first and the second time series, to produce a third lower-level time series of sequential time series fragments derived from said third time series. The system can be programmed to process the higher-level time series to produce a complex-level time series derived from sequential time series fragments of said higher-level time series.

The time series fragments of the first and second time series can be stored in a relational database. The fragments of the higher-level time series can comprise objects that inherit the characteristics of the objects of the lower-level time series from which they are derived. The first and second time series can comprise datasets of physiologic data points and the system can comprise a patient monitoring system wherein the dynamic pattern of interaction comprises pathophysiologic divergence.

As set forth below, data obtained from embodiments of the present invention may be employed to initiate or control a wide range of actions, depending on the condition being identified and other design considerations. Examples of diagnostic activities that may be performed responsive to data analysis performed by embodiments of the present invention include the identification of patterns indicative of airway obstruction or instability, hypoventilation, hyperventilation and Chenyne-Stokes respiration among others. Another exemplary use for embodiments of the present invention is to identify variations between similar conditions, such as the difference between central and obstructive sleep apnea. Examples of therapeutic activities that may be controlled or initiated responsive to data analysis performed in accordance with embodiments of the present invention include providing an audiovisual alarm, waking a patient, providing a remote notification, sending human intervention, altering setting of life support event (ventilator), writing a severity index to a display device such as a Digicalc, switching display modes of a display device, showing a list of options, printing a warning, performing genioglossal stimulation, performing phrenic nerve stimulation, performing diaphragm stimulation (implantable pacemaker), titrating a CPAP or bi-level pressure device, triggering another process, administering respiratory stimulant drugs, administering theophylline (caffeine or the like), reducing or ceasing administration of narcotics, reducing administration of $O_2$ or closing a control loop to processes such as $FiO_2$, CPAP, PCA or PEEP. A number of examples of the application of embodiments of the present invention are set forth below.

In one exemplary embodiment of the present invention, the system comprises a monitor having a plurality of sensors for positioning adjacent a patient and a processor programmed to produce a first timed waveform based on a first physiologic parameter of the patient, produce a second timed waveform based on a second physiologic parameter which is generally subordinate to the first physiologic parameter, so that the second parameter normally changes in response to changes in the first parameter, identify pathophysiologic divergence of at least one of the first and second physiologic parameters in relationship to the other physiologic parameter. The system can be further programmed to output an indication of the divergence, calculate an index of the divergence and/or provide an indication based on the index. The first parameter can, for example, comprise an indication of the magnitude of timed ventilation of a patient which can, for example, be the amplitude and/or frequency of the variation in chest wall impedance and/or the amplitude and/or frequency of the variation in nasal pressure and or the amplitude and frequency of the variation of at least one of the tidal carbon dioxide and/or the volume of ventilation or other measurable indicator. The second parameter can, for example, comprise a measure of oxygen saturation and can be pulse oximetry value or other measurable indicator of arterial oxygenation such as a continuous or intermittent measurement of partial pressure of oxygen.

Another embodiment of the present invention may include a method of monitoring a patient comprising monitoring a patient to produce a first timed waveform of a first physiologic parameter and a second timed waveform of a second physiologic parameter, the second physiologic parameter being physiologically subordinate to the first physiologic parameter, identifying a pattern indicative of divergence of at least one of the waveforms in relation to a physiologically expected pattern of the one of the other of the waveforms and outputting an indication of the divergence. The first timed waveform can be, for example defined by a time interval of greater than about 5-20 minutes. The first and second time series can, for example, be physiologic time series derived from airflow and pulse oximetry. The processor can comprise a primary processor, and the system can include a secondary processor and at least one of a diagnostic and treatment device, the primary processor being connectable to the secondary processor, the secondary processor being programmed to control at least one of the diagnostic and treatment device, the secondary processor being programmed to respond to the output of said primary processor. The primary processor can be programmed to adjust the program of the secondary processor. The treatment device can be, for example an airflow delivery system controlled by a secondary processor, the secondary processor being programmed to recognize hypopneas, the primary processor adjusting the program of the secondary processor based on the identifying. In another embodiment, the treatment device can be an automatic defibrillator. The secondary processor can be mounted with at least one of the treatment and diagnostic device, the primary processor being detachable from the connection with the secondary processor. In one embodiment, the primary processor is a hospital patient monitor adapted to monitor and analyze a plurality of different patient related signals, which may include electrocardiographic signals. The primary processor may comprise a polysomnography monitor capable of monitoring a plurality of different signals including encephalographic signals.

Embodiments of the present invention may comprise a monitor capable of organizing the complexity of the actual operative dynamic interactions of all of the signals both with respect to the absolute values, the degree of relative variation, and rate of variation across along and across multiple levels of the processed output and, more specifically, along and across multiple levels of multiple signals. Embodiments of the present invention may facilitate organization of interactive complexity defining the physiologic outputs generated by the affected physiologic systems, to recognize specific types and ranges of interactive pathophysiologic time series occurrences, and analysis of the components and evolution of such occurrences, thereby providing a timely output that reflects the true interactive, multi-system process impacting the patient or to take automatic action base on the result of said analysis.

Embodiments of the present invention may provide an iterative processing system and method that analyzes both waveforms and timed laboratory data to produce an output corresponding to the dynamic evolution of the interactive states of perturbation and compensation of physiologic systems in real time. As a result, accurate information about the physiologic state of the patient may be obtained.

Embodiments of the present invention may provide an iterative object oriented waveform processing system, which can characterize, organize, and compare multiple signal levels across a plurality of signals by dividing each waveform level of each signal into objects for discretionary comparison within a relational database, object database or object-relational database. Embodiments of the present invention may provide a diagnostic system, which can convert conventional hospital-based central telemetry and hard wired monitoring systems to provide automatic processor based recognition of sleep apnea and airway instability. Such systems may be adapted to output data sets in a summary format so that this can be over read by a physician. In this manner, maladies such as sleep apnea can be detected in a manner similar to that of other common diseases such as hypertension and diabetes.

Embodiments of the present invention may provide a diagnostic system, that can convert conventional hospital-based central telemetry and hard wired monitoring systems to provide processor based recognition of maladies such as sleep apnea and airway instability though the recognition of patterns of closely spaced apneas and/or hypopneas both in real time and in overnight interpretive format.

Embodiments of the present invention may provide a system that is adapted to identify map, and link waveform clusters of apneas from simultaneously derived timed signals of multiple parameters that include chest wall impedance, pulse, airflow, exhaled carbon dioxide, systolic time intervals, oxygen saturation, EKG-ST segment level, or the like to enhance the real-time and overnight diagnosis of sleep apnea. In addition, embodiments of the present invention may be adapted to provide timely, real-time indication such as a warning or alarm of the presence of apnea and/or hypopnea clusters so that nurses can be aware of the presence of a potentially dangerous instability of the upper airway during titration of sedatives and/or narcotics.

Embodiments of the present invention may provide a system for the recognition of airway instability for combined cluster mapping of a timed dataset of parameters such as nasal oral pressure in conjunction with tidal $CO_2$ to identify clusters of conversion from nasal to oral breathing and to optimally recognize clusters indicative of airway instability in association with tidal $CO_2$ measurement indicative of hypoventilation.

An exemplary embodiment of the present invention may be employed to identify pathophysiologic divergence of a plurality of physiologically linked parameters along a timed waveform over an extended period of time to provide earlier warning or to provide reinforcement of the significance of a specific threshold breach. Exemplary embodiments of the present invention may be employed to identify an anomalous trend of a first respiratory output in relation to a second respiratory output wherein said first output is normally dependent on said second output to identify divergence of said first respiratory output in relationship to the expected trend said first respiratory output based on the trend of said second output.

An exemplary embodiment of the present invention may be adapted to plot the prolonged slope of a first respiratory output in relationship to the prolonged slope of a second respiratory output and to identify divergence of said first respiratory output in relation to the slope second respiratory output. Further, exemplary embodiments of the present invention may be adapted to automatically trigger testing (and comparison of the output) of a secondary intermittently testing monitor based on the recognition of an adverse trend of the timed dataset output of at least one continuously tested primary monitor.

Exemplary embodiments of the present invention may be adapted to provide recognition of lower airway obstruction (as with bronchospasm or chronic obstructive pulmonary disease) by exploiting the occurrence of the forced exhalation during the hyperventilation phase of recovery intervals after and/or between intermittent upper airway obstruction to identify obstructive flow patterns within the forced exhalation tracing and thereby identify lower airway obstruction superimposed on clustered upper airway obstruction. Additionally, embodiments of the present invention may automatically customize treatment algorithms or diagnostic algorithms based on the analysis of waveforms of the monitored parameters. Finally, exemplary embodiments of the present invention may include providing a method of linking a time series of expense and/or billing data to a time series of patient related outputs and exogenous actions applied to the patient so that the expense of each aspect of the patients care can be correlated with both the procedures and medications administered as well as the patient output both with respect to dynamic patterns of interaction and specific laboratory values or comparative results.

Embodiments of the present invention may comprise a digital object processing system that functions to provide multidimensional waveform object recognition both with respect to a single signal and multiple signals. Such a system may be employed to identify and compare objects. Objects defined along one or more signals, including different signals may then be analyzed, identified and compared and defined by, and with, objects from different levels, if desired.

FIG. 1a is a diagram of a three-dimensional cylindrical data matrix 1 in accordance with embodiments of the present invention comprising corresponding, streaming, time series of objects from four different timed data sets. The cylindrical data matrix 1 shown in FIG. 1a provides a representation of a relational data processing structure of multiple time series. As this representation shows, a plurality of time series of objects are organized into different corresponding streams of objects, which can be conceptually represented as the cylindrical data matrix 1, comprising processed, analyzed, and objectified data with time defining the axis along the length of the cylindrical matrix 1. In this example, the cylindrical data matrix 1 is comprised of four time series streams of processed objects, each stream having three levels. Each of the time series and their respective levels are matched and stored together in a relational database, object database or object-relational database. Each streaming time series of objects as from a single signal or source (e.g. airflow or oximetry, as in a matrix of physiologic signals) is represented in the main cylinder 1 by a smaller cylinder (2, 3, 4, 5) and each of these smaller cylinders is comprised of a grouping of ascending levels of time series of streaming objects (6, 7, 8) with the higher levels being derived from the level below it. The streaming objects in each ascending time series level are more complex with each new level, and these more complex objects contain the simpler objects of the lower levels as will be described.

Figure 1B:
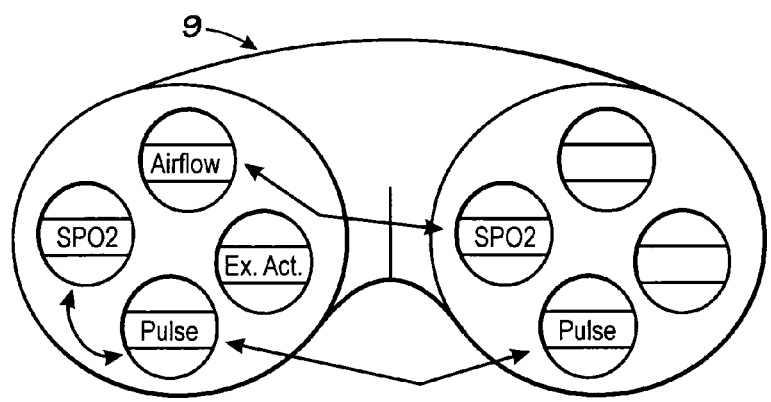
FIG. 1b is a diagram of a portion of the diagram shown in FIG. 1a curved back upon itself to show the flexibility of object comparison between levels and different data sets within the same time period and across different levels of different data sets at different time periods to identify a dynamic pattern of interaction between the data sets in accordance with embodiments of the present invention.

FIG. 1b shows a cross section 9 of the cylindrical data matrix 1 (FIG. 1a) curved back upon itself to illustrate an advantage of organizing the data in this way. Each object from each grouping can be readily compared and matched to other objects along the grouping and can further be compared and matched to other objects from each other grouping. Furthermore, an object from one level of one signal at one time can be readily compared to an object from another level of a different signal at a different time. The time series of streaming objects in FIG. 1b are airflow, SPO₂, pulse, and a series of exogenous actions. This is a typical data structure, which would be used according to the present invention to monitor a patient at risk for sudden infant death syndrome and this will be discussed below in more detail.

Using this data structure, highly complex patterns and subtle relationships between interactive and interdependent streams of objects can be readily defined by searching the matched object streams. This allows for the recognition of the dynamic pattern interaction or conformation of the matrix of analyzed streaming interactive objects.

FIG. 2a is a diagram of a three-dimensional representation of collective conformation of corresponding time series of objects of pulse (which can be heart rate and/or pulse amplitude or another pulse object derived of one or more of the many pulse characteristics), oxygen saturation, airflow, chest wall movement, blood pressure, and inflammatory indicators during early infection, organized in accordance with embodiments of the present invention. FIG. 2b is a diagram of a representation of the dynamic multi-parameter conformation shown in FIG. 2a, but extended through the evolution of septic shock to the death point. Each particular expected conformation will be defined by the specific parameters chosen and the manner in which they are analyzed. In an extension of the example a time series of expenditures would reflect a significant increase in the slope of resource (as financial or other recourses), which begins at a recognition point. If no recognition point occurs (i.e. the patient dies without the condition being diagnosed), the resource object time series may have a flat or even decreasing slope. The recognition of a specific dynamic pattern of interaction occurrence falling within a specified range may be used to determine the presence and severity of a specific of a biologic or physical process. A correlation with a time series of recourse allocation (such as timed expenditures) and a time series of exogenous actions (such as pharmaceutical therapy or surgery) can be used to determine the cost and causes of a given dynamic pattern of interaction and to better define the efficacy of intervention. The conformation of FIGS. 2a and 2b can be seen as comprising a progressive expansion, evolving to divergence of the parameters and eventual precipitous collapse and death. This can be readily contrasted with the conformation of the cylindrical analyzed data matrix 1 (FIG. 1a) derived from the same analysis of the same time series grouping during the state of evolving airway instability associated with excessive sequential or continuously infused dosing of sedation or narcotics. In this case, the pattern is one of precipitous, cyclic, and convergent expansion and contraction with eventual terminal contraction and death.

The following discussion presents an exemplary embodiment of the present invention for application to the patient care environment to achieve organization and analysis of physiologic data and particularly physiologic signals and timed data sets of laboratory data from patients during a specific time period such as a hospitalization or perioperative period.

The interaction of physiologic signals and laboratory data is particularly complex, and requires a widely varied analysis to achieve comprehensive recognition of the many dynamic patterns of interaction indicative of potential life threatening pathophysiologic events. This wide variation is due, in part, to the remarkable variation in both patient and disease related factors. Such analysis is best performed in real-time to provide timely intervention. To accomplish this level of organization and DPI identification through multiple levels of each data set or waveform and then across multiple levels of multiple data sets or waveforms, the system processes and orders all of the datasets from each system of the patient into a cylindrical matrix with each of the smaller cylinders containing the levels in a specific ascending fashion. An illustrative example of one exemplary method sequence for organizing the data set of a single smaller cylinder (comprised of a single signal of airflow) is shown in FIGS. 3a-3i.

Figures 3A, 3B:
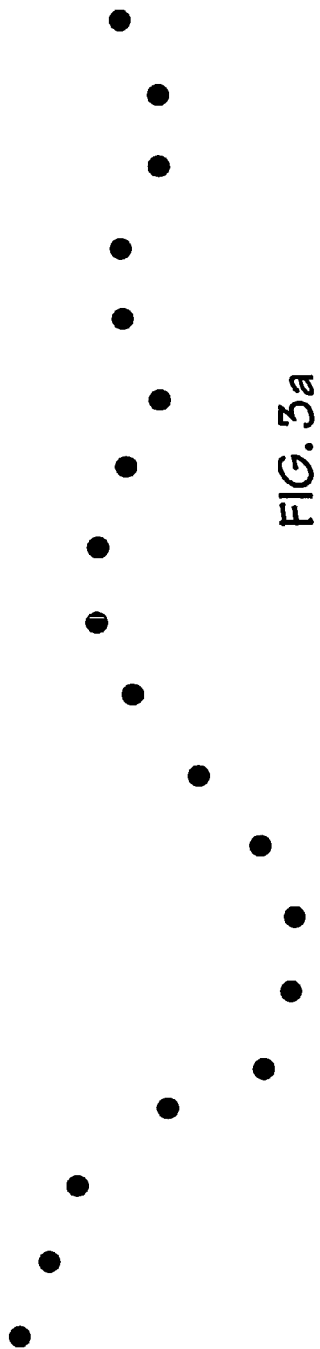
FIG. 3a is a diagram of a time series of raw data points.
FIG. 3b is a diagram of a time series of dipole objects.
Figure 3C:
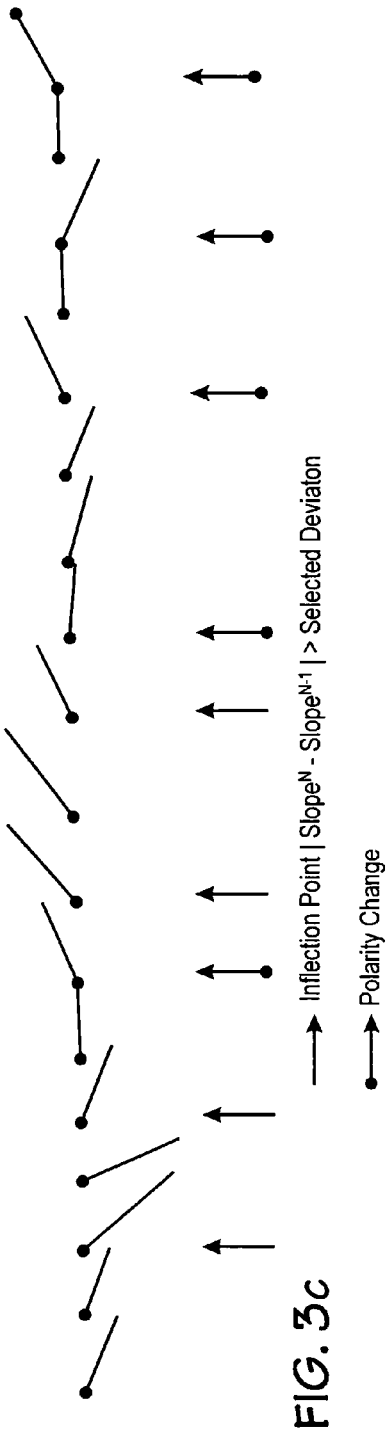
FIG. 3c is a diagram of a time series of a slope set of the dipole objects shown in FIG. 3b with the spatial attributes of the points removed to highlight relative change in accordance with embodiments of the present invention.
Figure 3D:
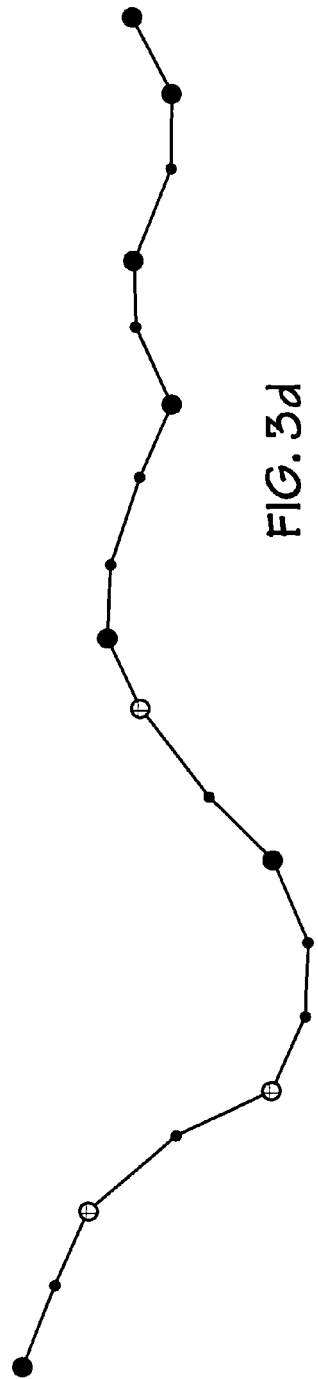
FIG. 3d is a diagram of a time series with critical boundary points from which the wave pattern can be segmented and the objects can be derived and associated properties calculated in accordance with embodiments of the present invention.
Figure 3G:
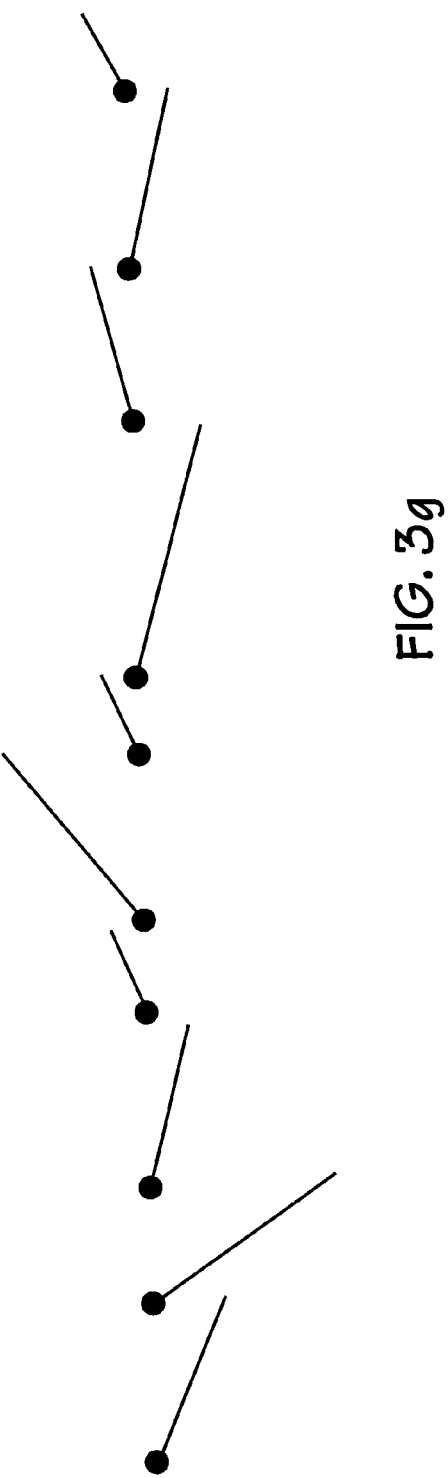
FIG. 3g is a diagram of a representation for the manipulation by the user for slope deviation specification in accordance with embodiments of the present invention.

According to this method, a processor executing instructions in accordance with an embodiment of the present invention derives from a time series of raw data points (FIG. 3a) a series of dipole objects with their associated polarities and slopes (FIG. 3b). As shown in FIG. 3c these dipoles can be represented as a slope set which removes the spatial attributes of the points and highlights relative change. As shown in FIG. 3c, various boundary types can be used to separate the dipoles into composite sequential objects and the figure shows three illustrative boundary types: pattern limits, inflection points, and polarity changes. As shown in FIG. 3d, the system now has the critical boundary points from which the wave pattern can be segmented and the composite objects can be derived and associated properties calculated. Although this is represented in FIG. 3d as linear segments, each composite object is actually comprised of the original set of dipoles so that the user can choose to consider it a straight segment with one slope or a curved segment defined by the entire slope set of the segmented object. FIG. 3e shows how the "trend" composite objects can be identified to provide a simplified linear trend (or polarity) analysis.

Though the "trend" object set is useful as shown in FIG. 3e, the time series can be segmented into other composite objects derived from the utilization of more or different user-defined boundary types. This can be useful even if the curved shapes can be analyzed in the simpler trend analysis because the selection of object boundaries at specific ranges or deflections helps to organize the objects as a direct function of changes in the physiologic output. In the example below, all three boundary types are employed to derive a wave pattern wire frame. The wire frame provides a simplified and very manageable view of the pattern and has boundary attributes that can be vary useful in waveform pattern searching. This type of object segmentation can be shown (FIG. 3f) as a set of object slopes with associated durations with the spatial relationships removed. As is shown in FIG. 3h this provides a representation for the manipulation by the user for object slope or duration deviation specification. Such deviations may be specified specifically to individual segment objects or may be globally designated. Deviations may or may not be designated symmetrically. Multiple deviations can be specified per segment with scoring attributes (weighted deviations) to provide even more flexibility to the user to search for and correlate derived patterns. These two figures below shots specified deviations per segment (but not weighted deviations) for slope and duration.

In the above exemplary manner, the time series can be organized with its associated objects and user-specified deviations, all of which are stored and categorized in a relational database, object database or object-relational database. Also as will be discussed, once processed, portions of such a time series can then be applied as target search objects to other waveforms to search for similar objects and to score their similarity.

FIG. 3h is representative of the user selection of linear ranges of variations. Those skilled in the art will recognize that complex curved shape variations can be specified in a similar way through the selection of specific ranges in variations of the dipole slope data set (FIG. 3c) defining the ranges of the curved target search object. It should be noted that, while the dipole set shown appears linearized, in fact, it can be seen that the dipoles can contain all of the information in the data points so that any curve present in the original raw data can be reproduced. It is cumbersome to input such ranges for each dipole so this can be provided by specifying a curved shape and then moving a pointer adjacent a curved shape to identify a range of shapes defining a curved target search object.

Figure 4:
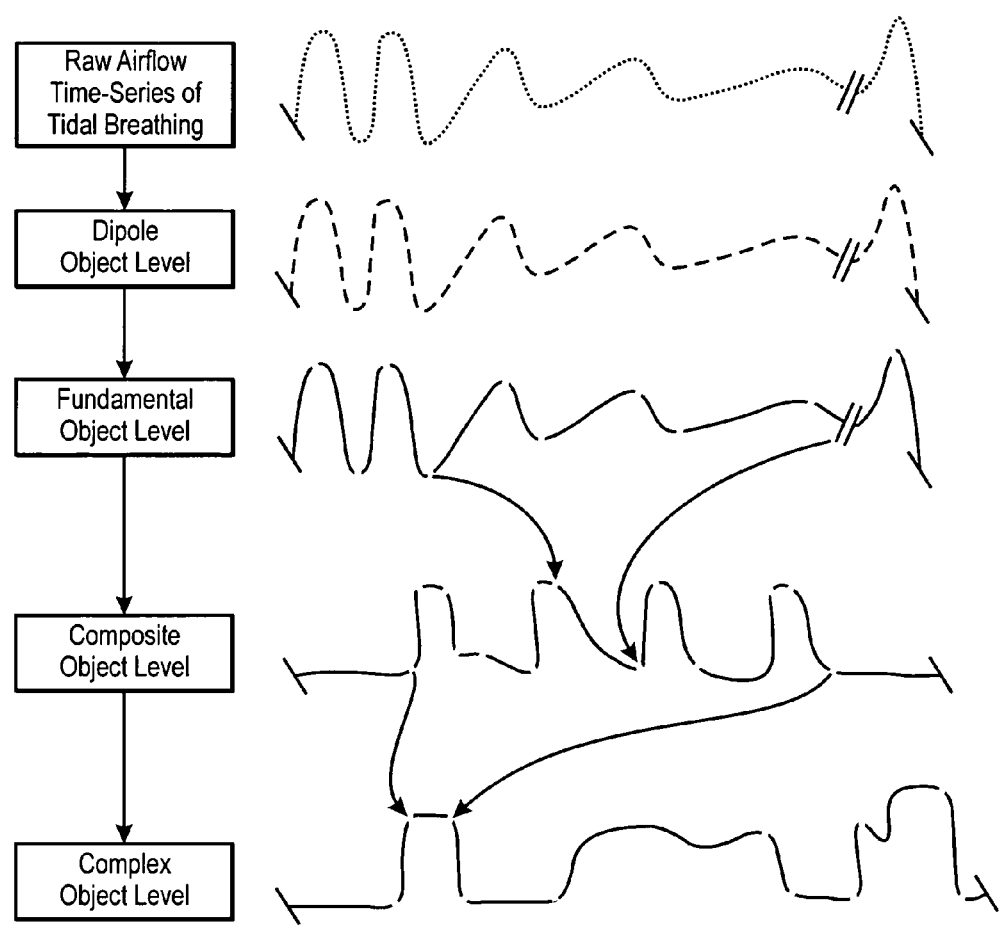
FIG. 4 is a graphical representation of an organization of the waveforms shown in FIGS. 3a-3g into ascending object levels in accordance with embodiments of the present invention.

FIG. 4 is a graphical representation of an organization of the waveforms shown in FIGS. 3a-3h into ascending object levels in accordance with embodiments of the present invention. The graphs shown in FIG. 4 illustrate the ascending object processing levels according to embodiments of the present invention, which are next applied to order the objects. These levels may be defined for each signal and comparisons can be made across different levels between different signals. The first level is comprised of the raw data set. The data from this first level are then converted by the processor into a sequence of fundamental objects called dipoles to form the second (fundamental object) level. In accordance with embodiments of the present invention, these dipole objects, which will ultimately define complex multi-signal objects, are comprised of these sequential fundamental objects having the simple characteristics of slope polarity, and duration. At this level, the dipoles can be processed to achieve a "best fit" dipole matching of two or more signals (as will be discussed) and are used render the next level, called the "composite object level."

The composite object level is comprised of sequential and overlapping composite objects, which are composed of a specific sequence of slope dipoles as defined by selected search criteria. Each of these composite objects has similar primary characteristics of a slope duration, and polarity to the fundamental objects. However, for the composite objects, the characteristic of slope can comprise a time series characteristic given as a slope dataset. The composite object level also has the characteristic of "intervening interval time-series" defined by a time series of the intervals between the recognized or selected composite objects. At this level, a wide range of discretionary index characteristics can be derived from the comparison of basic characteristics of composite objects. Examples of such index characteristics include: a "shape characteristic" as derived from any specified portion of the slope dataset of the object, a "positional characteristic" as derived from, for example, the value of the lowest or highest points of the object, or a "dimensional value characteristic" as derived by calculating the absolute difference between specified data points such as the value of the lowest and the highest values of the object, or a "frequency characteristic" such as may be derived from performing a Fourier transform on the slope dataset of the object.

The next analysis level is called the "complex object level." In that level, each sequential complex object comprises plurality of composite objects meeting specific criteria. A complex object has the same categories of primary characteristics and derived index characteristics as a composite object. A complex object also has the additional characteristics of "composite object frequency" or "composite object order" which can be used as search criteria defined by a selected frequency or order of composite object types, which are specified as defining a given complex object. A complex object also has additional higher-level characteristics defined by the time-series of the shapes, dimensional values, and positional characteristics of its component composite objects. As described for the composite objects, similar index characteristics of the complex objects can be derived from these characteristics for example; a "shape characteristic" derived from the mean rate of change along the dataset of the mean slopes of composite objects. Alternatively characteristics or index characteristics may be combined with others. For example, a shape characteristic may be combined with a frequency characteristic to provide a time series of a mathematical index of the slopes and the frequencies of the composite objects.

The next level, termed the "global objects level" is then derived from the time series of complex objects. At this level global characteristics are derived from the time series datasets of complex objects (and all of their characteristics). At the global objects level, the processor can identity specific patterns over many hours of time. An example of one specific pattern which is readily recognizable at this level would be a regular monotonous frequency of occurrence of one substantially complex object comprised of composite objects having alternating polarities, each with progressively rising or falling slope datasets. This pattern is typical of Cheyene-Stokes Respirations and is distinctly different from the pattern typical of upper airway instability at this global object level. Additional higher levels can be provided if desired as by a "comprehensive objects level" (not shown) which can include multiple overnight studies wherein a comprehensive object is comprised of a dataset of "global objects."

While FIG. 3b and FIG. 4 illustrate the levels of object derivations of a ventilation signal, in another example, a similar hierarchical architecture can be derived for the timed data set of the pulse waveform (as from an arterial pressure monitor or a plethesmographic pulse). Here the fundamental level is provided by the pulse tracing itself and includes all the characteristics such as ascending and descending slope, amplitude, frequency or the like. This signal also includes the characteristic of pulse area (which, if applied to a precise signal such as the flow plot through the descending aorta, is analogous to tidal volume in the fundamental minute ventilation plot). When the pulse signal is plethesmographic, it is analogous to a less precise signal of ventilation such as nasal pressure or thermister derived airflow. With these less precise measurements, because the absolute values are not reliable indicators of cardiac output or minute ventilation, the complex spatial relationships along and between signals become more important than any absolute value of components of the signal (such as absolute amplitude of the ascending pulse or inspiration curve). In other words, the mathematical processing of multiple signals that are simply related to physiologic parameters (but are not a true measurement of those parameters) is best achieved by analyzing the complex spatial relationships along and between those signals. To achieve this purpose, in accordance with embodiments of the present invention, as with ventilation, the pulse signal is organized into a similar multi-level hierarchy of overlapping time series of objects. Subsequently, these are combined and compared with the processed objects of respiration to derive a unified object time series defined by multiple corresponding data sets.

Figure 5C:
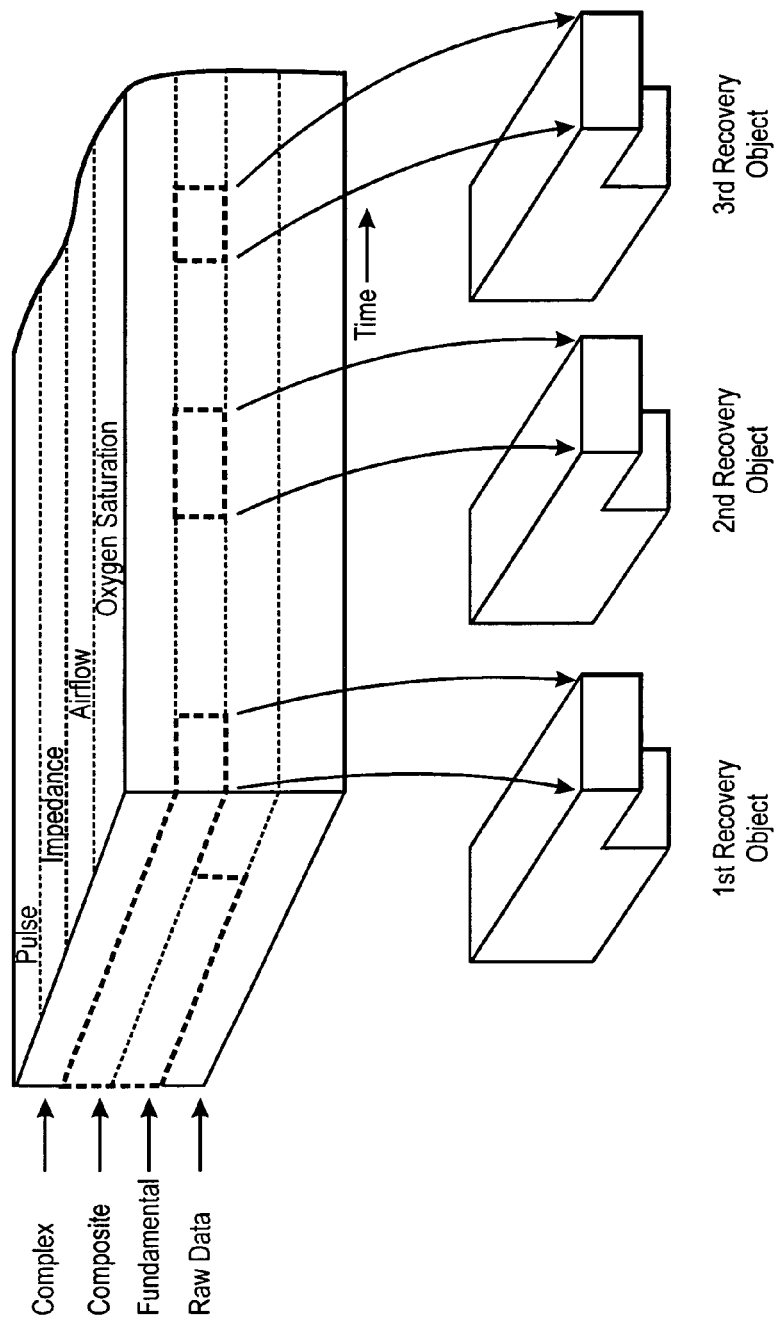
FIG. 5c is a diagram showing a representation of a portion of a multi-signal object as derived from the multiple corresponding time series of FIG. 5b with three multi-signal recovery objects up to the composite object level identified for additional processing according to embodiments of the present invention.
Figure 6A:
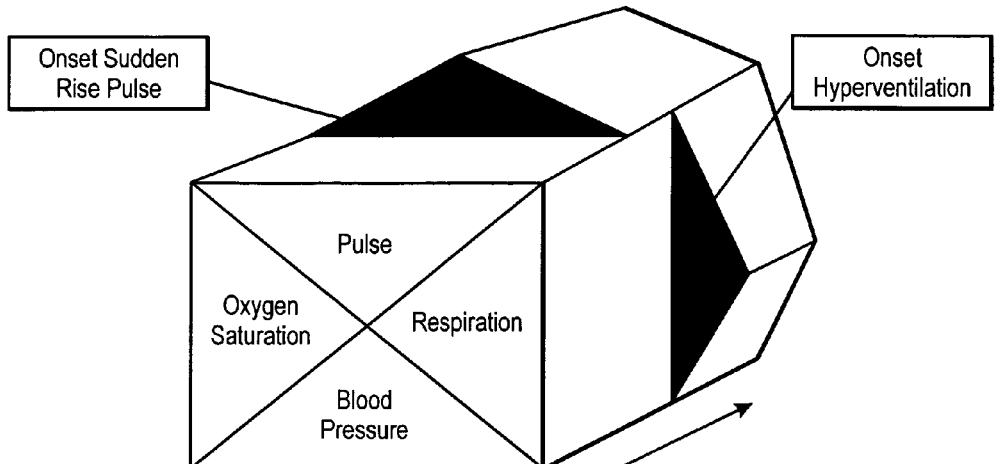
FIG. 6a is a three-dimensional graphical representation of an output for clinical monitoring for enhanced representation of the dependent and dynamic relationships between patient variables, which may be referred to as a "monitoring cube"
Figure 6B:
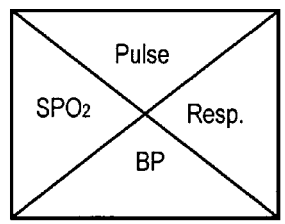
FIG. 6b is a two-dimensional graphical representation of an output of the "monitoring cube" during a normal physiologic state.
Figure 6C:
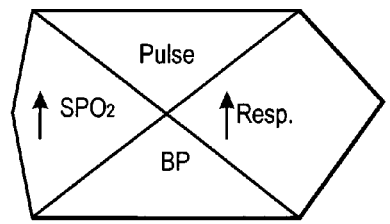
FIG. 6c is a two-dimensional graphical representation of an output of the "monitoring cube" showing physiologic convergence during an episode of volitional hyperventilation.
Figure 6D:
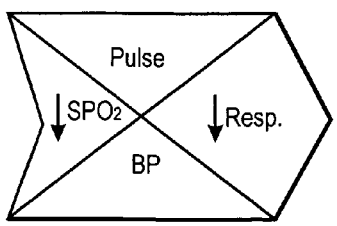
FIG. 6d is a two-dimensional graphical representation of an output of the "monitoring cube" showing pathophysiologic divergence as with pulmonary embolism.
Figure 6E:
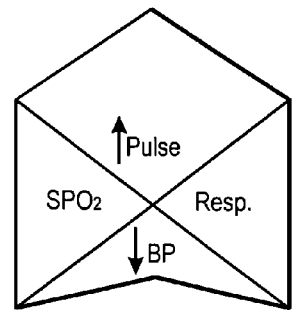
FIG. 6e is a two-dimensional graphical representation of an output of the "monitoring cube" showing a concomitant increase in blood pressure and heart rate, the cube being rotated in accordance with embodiments of the present invention to see which increase came first.
Figure 7:
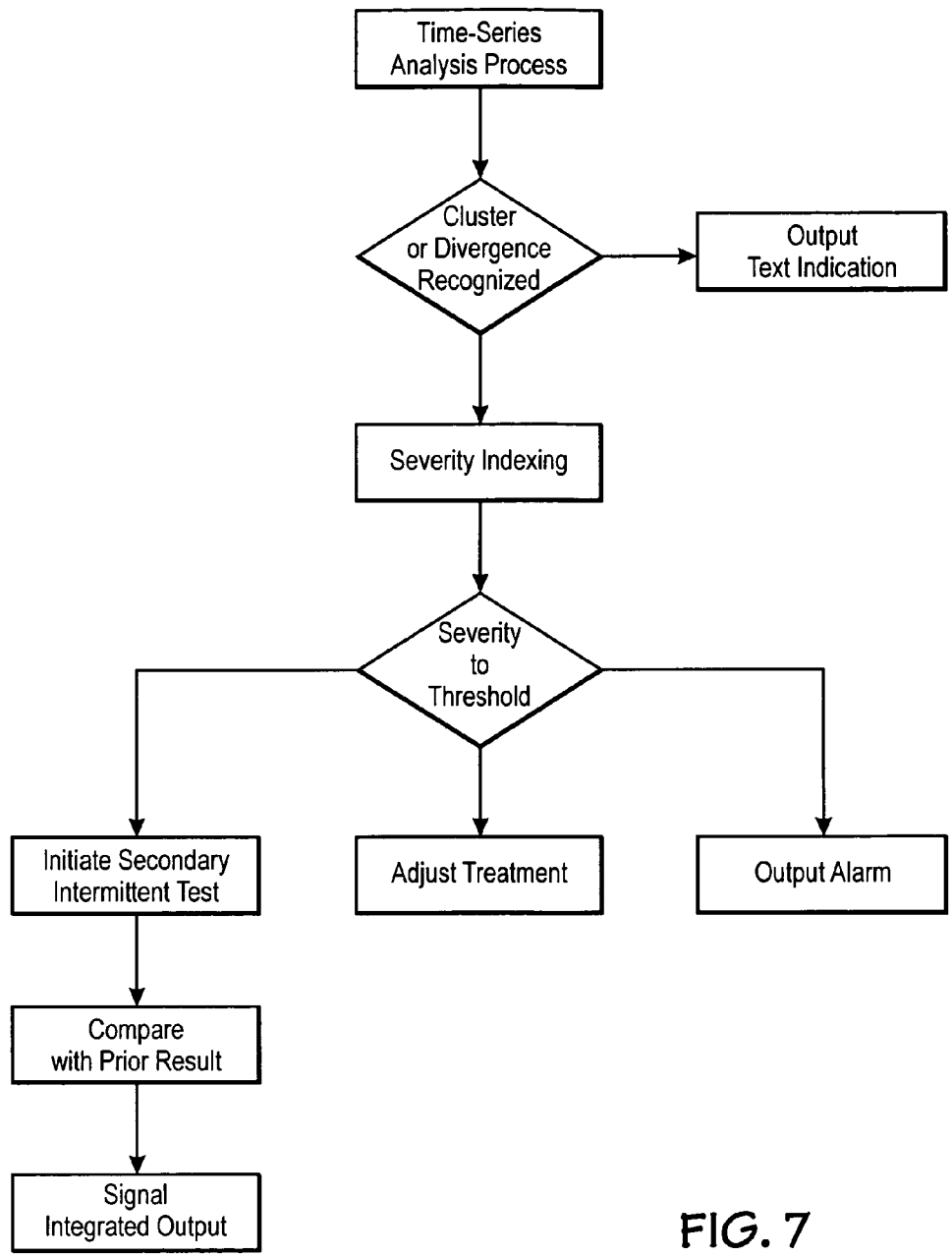
FIG. 7 is a schematic of a processing system for outputting and/or taking action based on the analysis of the time series processing in accordance with embodiments of the present invention.

FIG. 5a shows an exemplary pathophysiologic process associated with a characteristic dynamic pattern of interaction. As discussed previously, this cyclic process is induced by upper airway instability. FIG. 5b shows four corresponding signals derived from monitoring different outputs of the patient during a time interval wherein the dynamic process of FIG. 5a is operative. The basic signals shown in FIG. 5b are pulse, chest wall impedance, airflow, and oxygen saturation (SPO2). According to the present invention, these signals are processed into time series fragments (as objects) and organized into the object levels as previously discussed. For the purpose of organizing and analyzing complex interactions between these corresponding and/or simultaneously derived signals, similar ascending processes are applied to each signal. As shown in FIG. 5c, these streaming objects, many of which overlap, project along a three-dimensional time series comprised of multiple levels of a plurality of corresponding signals. A "multi-signal object" is comprised of at least one object from a first signal and at least one object from another signal. The multi-signal object shown in FIG. 5c has the primary and index characteristics derived from each component signal and from the spatial, temporal, and frequency relationships between the component signals. As illustrated, the objects defining a multi-signal object can include those from analogous or non-analogous levels. With this approach even complex and subtle dynamic patterns of interaction can be recognized.

This type of representation may be difficult to analyze in a clinical environment, but is useful for the purpose of general representation of the data organization. At such a level of complexity, a complete representation of the time series does not lend itself well to a two-dimensional graphical (and in some cases a three-dimensional) representation. Along the time series of sequential multi-signal objects, the spatial characteristics of these multi-signal objects change as a function of a plurality of interactive and different characteristics derived from the different signals.

The mathematical power of this approach to characterize the achieved organization of the complexity of the timed behavior of a physiologic system is illustrated by the application of this method to characterize the codependent behavior of ventilation and arterial oxygen saturation and plethesmographic pulse. While these variables are codependent in that a change in one variable generally causes a change in the other two, they are also each affected differently by different pathologic conditions and different preexisting pathologic changes. For example, the multi-signal objects comprising a time series of ventilation and arterial oxygen saturation and plethesmographic pulse in a sedated 50-year-old obese smoker with asthma and sleep apnea are very different than those of a sleeping 50 year-old patient with Cheyene Stokes Respiration and severe left ventricular dysfunction. These differences are poorly organized or represented by any collection of two-dimensional graphical and/or mathematical representations. Despite this, throughout this disclosure, many of the signal interactions (such as those relating to pathophysiologic divergence) will be discussed as a function of a simplified two-dimensional component representation for clarity based on older standards of mathematical thought. However, it is one of the express purposes of the present invention to provide a mathematically robust system for the organization and analysis of the complex mathematical interactions of biologic and other systems through the construction of time series sets of multidimensional and overlapping objects.

To illustrate the complexity ordered by this approach, consider the components of just one of the three simple recovery objects shown in FIGS. 5b and 5c. This single recovery object includes, by way of example, the exemplary characteristics, each of which may have clinical relevance when considered in relation to the timing and characteristics of other objects, set forth in Table 1:

TABLE 1

1. Amplitude, slope, and shape of the oxygen saturation rise event at the composite level
2. Amplitude, slope, and shape of the ventilation rise event at the composite level which contains the following characteristics at the fundamental level:
    a. Amplitude, slope, and shape of the inspiration rise object
    b. Amplitude, slope, and shape of the expiration fall object
    c. Frequency and slope dataset of the breath to breath interval of tidal breathing objects
    d. Frequency and slope data sets of the amplitude, slope, and shape of the pulse rise and fall events
3. Amplitude, slope, and shape of the pulse rise event at the composite level which contains the following exemplary characteristics at the fundamental level
    a. Amplitude, slope, and shape of the plethesmographic pulse rise event
    b. Amplitude, slope, and shape of the plethesmographic pulse fall event
    c. Frequency and slope datasets of beat-to-beat interval of the pulse rate
    d. Frequency and slope data set of the amplitude, slope, and shape of the pulse rise and fall events As is readily apparent, it is not possible for a health care worker to timely evaluate the values or relationships of even a modest number of these parameters. For this reason, the development of an output based on the analysis of these time series of objects to be presented in a succinct and easily interpreted format is a desirable aspect of an embodiment of the present invention.

FIG. 6 shows several variations of a three-dimensional graphical representation of an output for clinical monitoring for enhanced representation of the dependent and dynamic relationships between patient variables. This representation may be referred to as a "monitoring cube." These types of monitoring cubes may be adapted for display on a hospital monitor, for example, for animation of the summarized relationships between multiple interacting objects.

Such an animation can be shown as a small icon next to the real-time numeric values typically displayed on present monitors. Once a baseline is established for a patient, either for example as the patient's baseline settings for a selected or steady state time period (of for example 10-15 minutes) or by a selected or calculated set of normal ranges, the cube may be illustrated as a square. For example, the patient may initially have parameters out of the normal ranges and never exhibit a square output. After the square for this patient is established, the cube is built from the evolving time series of these parameters. A given region of the cube can be enlarged or reduced as the particular value monitored increases or decreases respectively. The relationship between these variables can be readily seen even if they remain within the normal range. Moreover, a system adapted according to embodiments of the present invention may display distortions to the individual constituent components of the square (see FIGS. 6b-6e) to illustrate the deviation of those particular constituent components from predetermined normal ranges. The computer can flag with a red indicator a cube that is showing pathophysiologic divergence when compared with the baseline values even though none of the values are at a typical alarm threshold. If other abnormalities (such as the development of pulse irregularity or a particular arrhythmia or ST segment change, this can be flagged on the cube so that the onset of these events can be considered in relation to other events. If preferred the time series components of the cube and their relationships to occurrences on other monitored time series can be provided in a two-dimensional timeline.

Using this approach, time series relationships of multiple physiologic events can be characterized on the screen with, for example, a small dynamic animated icon in a succinct and easily understood way. There are many other alternative ways to animate a summary of the dynamic relationships and some of these will be discussed later in the disclosure.

One of the longstanding problems associated with the comparison of outputs of multiple sensors to derive simultaneous multiple time series outputs for the detection of pathophysiologic change is that the accuracy and/or output of each sensor may be affected by different physiologic mechanisms in different ways. Because of this, the value of matching an absolute value of one measurement to an absolute value of another measurement is degraded. This is particularly true if the measurement technique or either of the values is imprecise. For example, when minute ventilation is measured by a precise method such as a pneumotachometer, then the relationship between the absolute values of the minute ventilation and the oxygen saturation are particularly relevant. However, if minute ventilation is being trended as by nasal thermister or nasal pressure monitoring or by chest wall impedance then the absolute values become much less useful. However, according to one aspect of embodiments of the present invention, the application of the slope dipole method, the relationship between a plurality of simultaneously derived signals can be determined independent of the relationships of the absolute values of the signals. In this way, simultaneously derived signals can be identified as having convergence consistent with physiologic subordination or divergent shapes consistent with the development of a pathologic relationship or inaccurate data acquisition.

As noted, with physiologically linked signals, a specific occurrence or magnitude of change in one signal in relationship to such a change in another signal may be more important and much more reproducible than the absolute value relationships of the respective signals. For this reason, the slope dipole method provides an important advantage to integrate and analyze such signals. Using this signal integration method, two simultaneously acquired physiologic linked signals are compared by a processor over corresponding intervals by matching the respective slope dipoles between the signals. Although the exact delay between the signals may not be known, the processor can identity this by identifying the best match between the dipole sets. Embodiments of the present invention may consider this to be a "best match" constrained by preset limits. For example, with respect to ventilation and oximetry, a preset limit could be provided in the range of 10-40 seconds although other limits could be used depending on the hardware, probe site and averaging, intervals chosen. After the best match is identified, the relationships between the signals are compared (for example, the processor can compare the slope dipole time series of oxygen saturation to the slope dipole time series of an index of the magnitude of ventilation). In this preferred embodiment, each slope dipole is compared. It is considered preferable that the dipoles of each respective parameter relate to a similar duration (for example. 1-4 seconds). With respect to airflow, calculation of the magnitude value of airflow may require sampling at a frequency of 25 hertz or higher, however, the sampling frequency of the secondary plot of the magnitude value of the index can, for example, be averaged in a range of one hertz to match the averaging interval of the data set of oxygen saturation. Once the signals have been sufficiently matched at the dipole level, they can be further matched at the composite level. In accordance with embodiments of the present invention, most object matching across different signals is performed at the fundamental level or higher, however timing matching can be performed at the dipole level and this can be combined with higher level matching to optimize a timing match.

Figure 9:
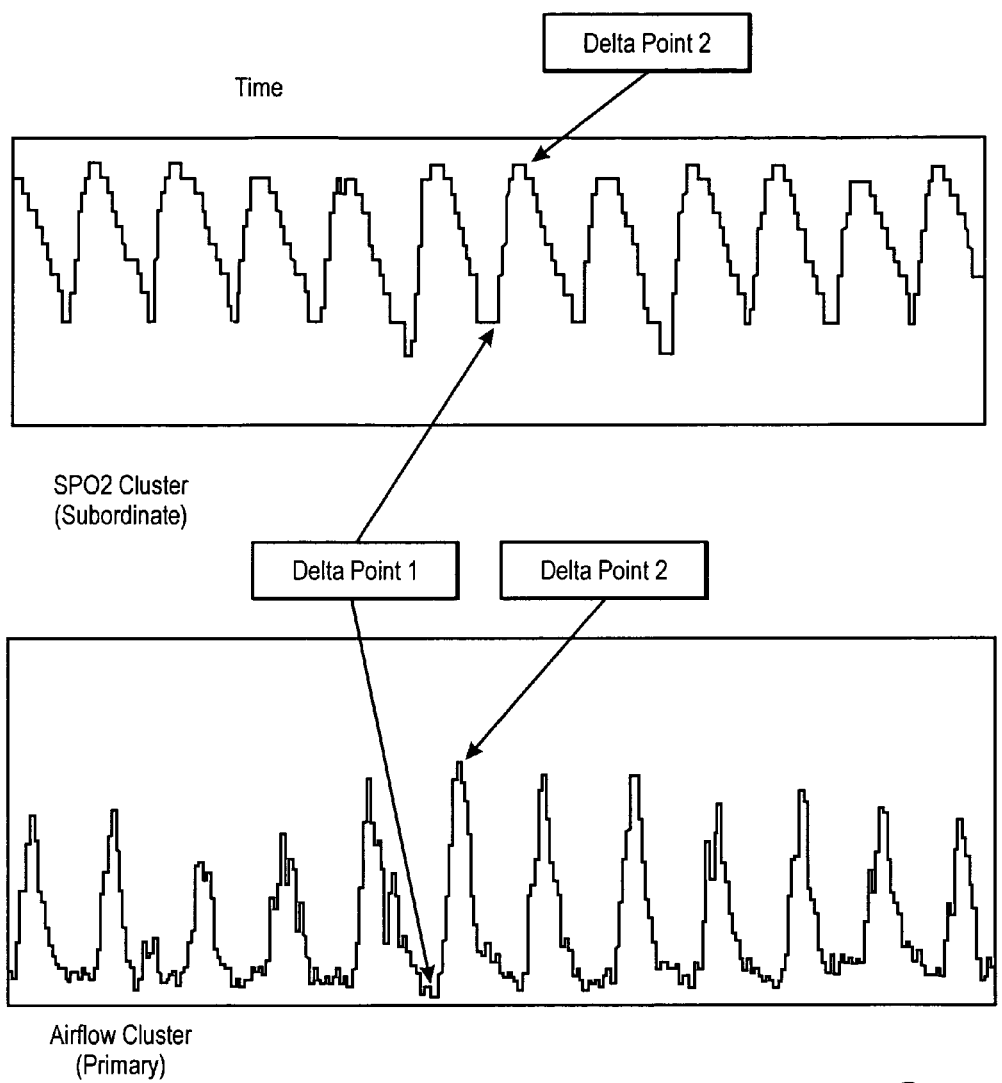
FIG. 9 is a graphical representation of corresponding data at the raw data level of airflow and oxygen saturation wherein a subordinate saturation signal segment demonstrates physiologic convergence with respect to the primary airflow signal segment.
Figure 10:
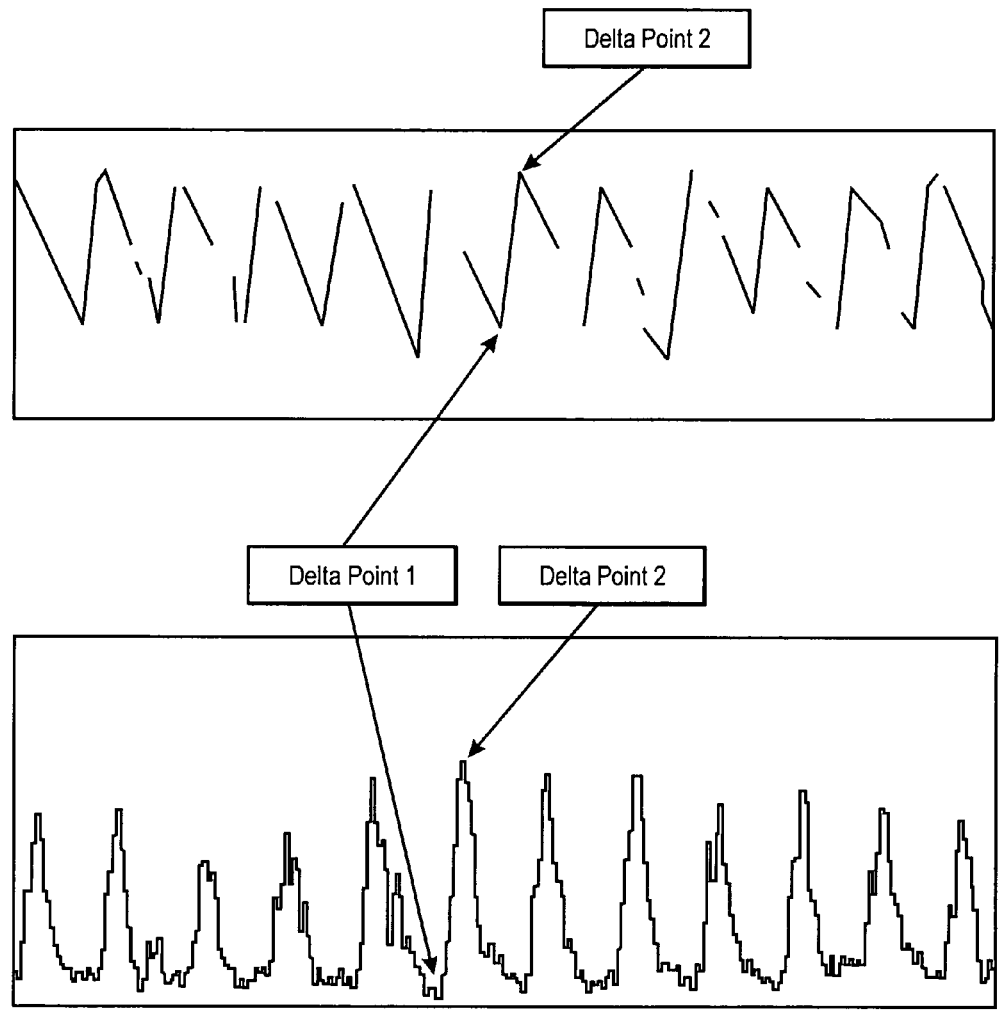
FIG. 10 is a graphical representation of the raw data level of FIG. 9 converted to the composite level, the data comprising a time series of sequential composite objects derived from the data sets of airflow and oxygen saturation signals.
Figure 11:
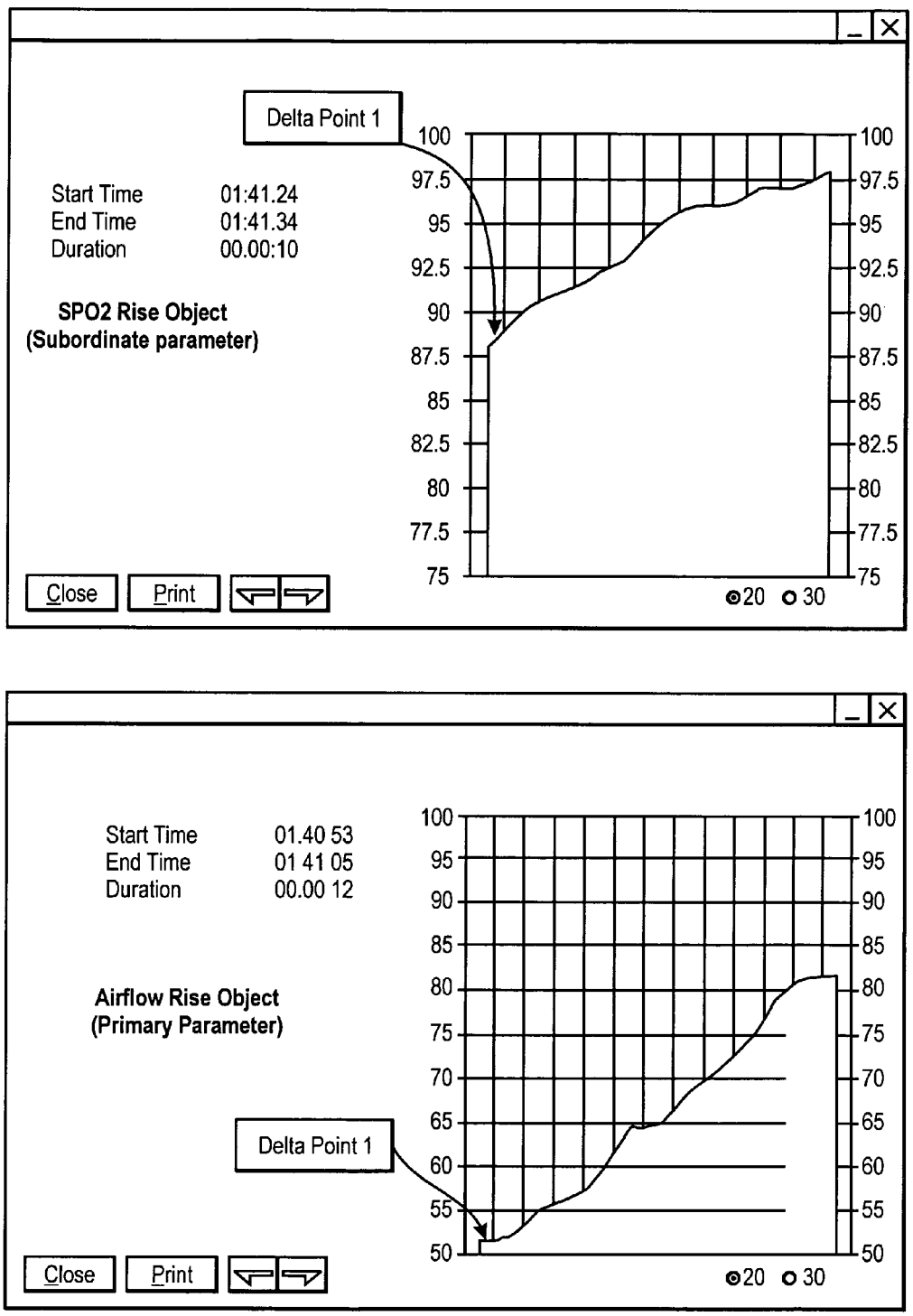
FIG. 11 is a graphical representation of a selected composite subordinate object of oxygen saturation from FIG. 10 matched with its corresponding primary composite object of airflow, as they are stored as a function of dipole datasets in a relational database, object database or object-relational database in accordance with embodiments of the present invention.

FIGS. 9, 10, and 11, show schematic mapping of matched clusters of airway instability (of the type shown in FIG. 5b) where clusters are recognized and their components matched at the composite object level. When the objects are matched, the baseline range relationship between the signals can be determined. This baseline range relationship can be a magnitude value relationship or a slope relationship. The signals can then be monitored for variance from this baseline range, which can indicate pathology or signal inaccurate. The variance from baseline can be, for example, an increase in the relative value of ventilation in relation to the oximetry value or a greater rate of fall in oxygen saturation in relation to the duration and/or slope of fall of ventilation. In another example, the variance can include a change from the baseline delay between delta points along the signals.

With multiple processed signals as defined above, the user, who can be the program developer, can then follow the following to complete the process of searching for a specific pattern of relationships between the signals:
1. Specify a search wave pattern
2. Analyze and divide the search pattern into objects
3. Input the allowed deviation (if any) from the search pattern or the objects comprising it.
4 Input additional required relationships (if any) to other objects in the target waveform.
5. Apply the search pattern or selected component objects thereof to a target waveform.

Various methods of identification may be employed to provide a wave pattern to the system. For example, users may:
1. Choose from a menu of pattern options.
2. Select dimensional ranges for sequential related patterns of ascending complexity.
3. Draw a wave pattern within the system with a pointing or pen device.
4. Provide a scanned waveform.
5. Provide a data feed from another system.
6. Describe the pattern in natural language.
7. Type in a set of points.
8. Highlight a sub-section of another waveform within the system.

In accordance with embodiments of the present invention, the system can be automated such that search is automatically applied once the criteria are established. Also, the method of identification of the search pattern can be preset. For example, the occurrence of a specific sequence of objects can be used as a trigger to select a region (which can be an object of the types previously described) as the specified search pattern, the processor can automatically search for other such patterns in the rest of the study. The result of any of these inputs would be a set of points with or without a reference coordinate system definition as shown in FIGS. 3a-3h.

After receiving search criteria, the system begins its analysis of the target set of points to derive a series of object sets. These sets will be used to identify key properties of the wave pattern. These objects (and their boundaries) will provide a set of attributes which are most likely to be significant in the wave pattern and that can be acted upon in the following ways:

1. To provide parameters on which sets of rules may be applied for the identification of expected conditions.
2. To provide parameters that can be associated with specifically allowable deviations and/or a globally applied deviation.
3. To provide parameters than can be used to score the relative similarity of patterns within the target waveform.

In such a manner, a search can be carried out for specific pathophysiologic anomalies. This can be carried out routinely by the software or on demand.

One example of the clinical utility of the application of the object processing and recognition system to physiologic signals is provided by identification of upper airway instability. As discussed in the aforementioned patents and application, events associated with airway instability are precipitous. In particular, the airway closure is precipitous and results in a rapid fall in ventilation and oxygen saturation. Also the subsequent airway opening airway is precipitous, and because ventilation drive has risen during closure the resulting ventilation flow rate (as represented by a measurement of airflow deflection amplitude) rises rapidly associated with recovery. Also, after the period of high flow rate associated with the recovery the flow rate precipitously declines when the chemoreceptors of the brain sense ventilation overshoot. In this way, along a single tracing of timed airflow deflection amplitude, three predictable precipitous relatively linear and unidirectional waveform deflections changes have occurred in a particular sequence in a manner analogous to the tracing of the $SpO_2$ or pulse rate. Subsequent to this, the unstable airway closes suddenly propagating the cluster of cycles in all of these waveforms.

As noted above, a hallmark of airway instability is a particular cluster timed sequence of precipitous, unidirectional changes in the timed data set. For this reason, the first composite object to be recognized is defined by a precipitous unidirectional change in timed output of one of the above parameters. The system then recognizes along the fundamental sequential unipolar composite objects and builds the composite level comprised of time series of these composite objects. One presently preferred embodiment uses the following method to accomplish this task. A unipolar "decline object" is a set of consecutive points over which the parameter level of the patient is substantially continually falling. A unipolar "rise object" is a set of consecutive points over which the parameter is substantially continually increasing. A "negative pattern" is a decline together with a rise object wherein the rise follows the decline within a predetermined interval. A "positive pattern" is a rise together with a decline wherein the decline follows the rise within a predetermined interval. How closely these composite objects can follow each other is a specifiable parameter. At the complex object level, a cluster is a set of consecutive positive or negative patterns that appear close together. How closely these patterns must follow each other to qualify, as a cluster is a specifiable parameter.

In operation, a system constructed in accordance with embodiments of the present invention may proceed in several phases. As an example, in a first phase, decline and rise objects are identified. In a second phase, negative and positive patterns are identified. In a third phase, clusters of negative and/or positive patterns are identified. In a fourth phase, a relationship between the events and patterns is calculated and outputted. In a fifth phase, a diagnosis and severity indexing of airway or ventilation instability or sleep/sedation apnea is made. In a sixth phase, a textual alarm or signal is outputted and/or treatment is automatically modified to eliminate cluster. The process may then be repeated with each addition to the dataset in real-time or with stored timed datasets.

Embodiments of the present invention may apply either a linear or iterative dipole slope approach to the recognition of waveform events. Since the events associated with airway collapse and recovery are generally precipitous and unipolar, the linear method suffices for the recognition and characterization of these nonlinear waves. However, the iterative dipole slope approach is particularly versatile and is preferred in situations wherein the user would like an option to select the automatically identification of a specific range of nonlinear or more complex waves. Using the iterative dipole slope method, the user can select specific consecutive sets of points from reference cases along a waveform as by sliding the pointer over a specific waveform region. Alternatively, the user can draw the desired target waveform on a scaled grid. The user can also input or draw range limits thereby specifying an object or set of objects for the microprocessor to recognize along the remainder of the waveform or along other waveforms. Alternatively, the processor can automatically select a set of objects based on pre-selected criteria (as will be discussed). Since the iterative dipole process output is shape-dependent (including frequency and amplitude) but is not necessarily point dependent, it is highly suited to function as a versatile and discretionary engine for performing waveform pattern searches. In accordance with embodiments of the present invention, the waveform can be searched by selecting and applying objects to function as Boolean operators to search a waveform. The user can specify whether these objects are required in the same order. Recognized object sequences along the waveform can be scored to choose the degree of match with the selected range. If desired, (as for research analysis of waveform behavior) anomalies within objects or occurring in one or more of a plurality of simultaneously processed tracings can be identified and stored for analysis.

For the purpose of mathematically defining the presently preferred object system, according to the present invention, for recognition of digital object patterns let $o_1, o_2, \ldots, o_m$ be original data points. The data can be converted to a smoother data set, $x_1, x_2, \ldots, x_n$, by using a moving n average of the data points as a 1-4 second average for cluster recognition or as a 15-30 second average for the identification of a pathophysiologic divergence. For the sake of clarity of presentation, assume that $x_i$ is the average of the original data points for the $i^{th}$ second. A dipole is defined to be a pair of consecutive data points. Let $d_i=(x_i, x_{i+1})$ be the $i^{th}$ dipole, for $i=1, 2, \ldots, n-1$. The polarity, say $p_i$ of the $i^{th}$ dipole is the sign of $x_{i+1}-x_i$, (i.e. $p_i=1$ if $x_{i+1}>x_i$, $p_i=0$ if $x_{i+1}=x_i$, and $p_i=-1$ if $x_{i+1}<x_i$). For the purpose of automatic recognition of user specified, more complex nonlinear waveforms, the data can be converted to a set of dipole slopes, $z_1, z_2, \ldots, z_n$. Let $z_i=(x_{i+1}-x_i,)$ be the $i^{th}$ dipole slope, for $i=1, 2, \ldots, n-1$.

As an exemplary way to recognize a decline event by applying the iterative slope dipole method in accordance with embodiments of the present invention, let, $\{z_1, z_2, \ldots, z_n\}$ be a set of consecutive dipole slopes. Then $\{z_1, z_2, \ldots, z_n\}$ is a decline if it satisfies the following conditions:

1. $z_1, z_2, \ldots, z_n$ are less than zero i.e., the parameter level of the patient is continually falling over the set of dipole slopes. This condition may be partially relaxed to adjust for outliers, as by the method described below for the linear method.
2. The relationship of $z_1$ to $z_2$, $z_2$ to $z_3$, ... $z_{n-1}$ to $z_n$ is/are specified parameter(s) defining the shape of the decline object, these specified parameters can be derived from the processor based calculations of the dipole slopes made from a user selected consecutive data set or from a set drawn by the user onto a scaled grid.

To recognize a rise event a similar method is applied wherein $z_1, z_2, \ldots, z_n$ are greater than zero. Complex events, which include rise and fall components are built from these more composite objects. Alternatively, a specific magnitude of change along a dipole slope dataset can be used to specify a complex object comprised of two composite objects separating at the point of change (a waveform deflection point). In one application the user slides the cursor over the portion of the wave, which is to be selected, and this region is highlighted and enlarged and analyzed with respect to the presence of more composite objects. The dimensions of the object and the slope data set, which defines it, can be displayed next to the enlarged waveform. If the object is complex (as having a plurality of segments of differing slope polarity or having regions wherein the slope rapidly changes as by a selectable threshold) then each composite object is displayed separately with the respective dimensions and slope data sets. In this way the operator can confirm that this is the actual configuration desired and the user is provided with a summary of the spatial and dimensional characteristics of the composite objects, which define the actual selected region. The operator can select a range of variations of the slope data set or chance the way in which the composite objects are defined, as by modifying the threshold for a sustained change in slope value along the slope dataset. (For example, by allotting at least one portion of the slopes to vary by a specified amount, such as 10%, by inputting graphically the variations allowed. If the operator "OKs" this selection, the processor searches the entire timed dataset for the composite objects, building the selected object from the composite objects if identified To recognize a decline event by applying the linear method according to the present invention, let $\{x_i, x_{i+1}, \ldots, x_r\}$ be a set of consecutive points and let $s=(x_r-x_i)/(r-i)$ be the overall slope of these points. Although the slope could be defined by using linear regression or the like, the previous definition allows for improved fidelity of the output by allotting rejection based on outlier identification. Then $\{x_i, x_{i+1}, \ldots x_r\}$ is a decline if it satisfies the following conditions:

1. $x_i > x_{i+1} > \ldots x_r$, i.e. the parameter level of the patient is continually falling over the set of points. This condition may be partially relaxed to adjust for outliers, as described belong.
2. $r-i \geq D_{min}$, where $D_{min}$ is a specified parameter that controls the minimum duration of a decline.
3. $s_{min} \leq s \leq s_{max}$, where $s_{min}$ and $s_{max}$ are parameters that specify the minimum and maximum slope of a decline, respectively.

The set {97, 95, 94, 96, 92, 91, 90, 88}, does not satisfy the current definition of a decline even though the overall level of the parameter is clearly falling during this interval. The fourth data point, 96, is an outlier to the overall pattern. In order to recognize this interval as a decline, the first condition must be relaxed to ignore outliers. The modified condition 1 is:

1. *Condition 1 with Outlier Detection
   a. i>xi+1,
   b. xi>xi+1 or xi+1>xj+2 for j=i+1, . . . , r−2.
   c. xr−1>$x_r$.

To recognize a rise event, let $\{x_i, x_{i+1}, \ldots, x_r\}$ be a set of consecutive points and let $s=(x_r-x_i)/(r-i)$ be the overall slope of these points. Then $\{x_i, x_{i+1}, \ldots, x_r\}$ is a rise if it satisfies the following conditions:

1. $x_i < x_{i+1} < \ldots < x_r$, i.e., the parameter level of the patient is continually rising over the set of points. This condition may be partially relaxed to adjust for outliers, as described below.
2. $r-i \geq D_{min}$, where $D_{min}$ is a specified parameter that controls the minimum duration of rise.
3. $s_{min} \leq s \leq s_{max}$, where $s_{min}$ and $s_{max}$ are parameters that specify the minimum and maximum slope of a decline, respectively.

Similar to declines, the first condition of the definition of a rise is relaxed in order to ignore outliers. The modified condition 1 is:

Condition 1 with Outlier Detection
   a. xi<xi+1.
   b. xj<xj+1 or xj+1<xj+2 for j=i+1, . . . , r−2.
   c. xr−1<xr.

To recognize a negative pattern the program, iterates through the data and recognize events and then identifies event relationships to define the patterns. The system uses polarities (as defined by the direction of parameter movement in a positive or negative direction) to test for condition (1*) rather than testing for greater than or less than. This simplifies the computer code by permitting the recognition of all decline and rise events to be combined in a single routine and ensures that decline events and rise events do not overlap, except that they may share an endpoint. The tables below show how condition (1*) can be implemented using polarities.

| Equivalent Condition 1* For Decline Event | |
|---|---|
| Condition 1* | Equivalent Condition |
| a. $x_i > x_{i-1}$ | $p_i = -1$ |
| b. $x_i > x_{j-1}$ or $x_{j-1} > x_{j-2}$ | $P_j = -1$ or $P_{j+1} = -1$ |
| c. $x_{r-1} > x_r$ | $P_{r-1} = -1$ |

| Equivalent Condition 1* For Rise Event | |
|---|---|
| Condition 1* | Equivalent Condition |
| a. $x_i < x_{i\,1}$ | $p_i = 1$ |
| b. $x_i < x_{j-1}$ or $x_{j-1} < x_{j-2}$ | $P_j = 1$ or $P_{j+1} = 1$ |
| c. $x_{r-1} < x_r$ | $P_{r-1} = 1$ |

Exemplary pseudocode for a combined microprocessor method, which recognizes both unipolar decline events and unipolar rise events, is shown below. In this exemplary code, E is the set of events found by the method, where each event is either a decline or a rise.

```
EVENT RECOGNITION i = 1
Exent_polarity = p_1
for j = 2 to n−2
    if (p_j .≠ event_polarity) and (p_{i+1} .≠ event_polarity)
        r = j
        X = {x_p,.....x_j}
        if event_polarity = 1
            Add X to E if it satisfies rise conditions (2) and (3) elseif
                event_polarity = −1
            Add X to E if it satisfies decline conditions (2) and (3)
        endif
        i = j
        event_polarity = p_i
    Endif
endfor
Add X={ x_i, . . . , x_n} to E if it satisfies either the rise or decline
conditions
```

Next, A specific pattern is recognized by identifying a certain sequence of consecutive events, as defined above, which comply with specific spatial relationships. For example, a negative pattern is recognized when a decline event, say D={$x_i$, ..., $x_j$}, together with a rise event, say R={$x_k$, ..., $x_m$}, that closely follows it. In particular, D and R must satisfy k−i≤$t_{dr}$, where $t_{dr}$ is a parameter, specified by the user, that controls the maximum amount of time between D and R to qualify as a negative pattern.

The exemplary pseudocode for the microprocessor system to recognize a negative pattern is shown below. Let E={$E_1$, $E_2$, ..., $E_q$} be the set of events (decline events and rise events) found by the event recognition method, and let DR be the set of a negative pattern.

---
NEGATIVE PATTERN RECOGNITION
---
```
for h = 1 to q−1
    Let D = {x_i,..., x_j,} be the event E_h
    if D is a decline event
        Let R = {x_k,...,X_m,} be the event E_{h+1}
        if R is a rise event
            gap = k − j
            if gap ≤ t_dr
                Add (D,R) to the list of negative patterns
            endif
        endif
    endif
endfor
```
---

As noted, a cluster is a set of consecutive negative or positive patterns that appear close together. In particular, let C={$DR_i$, $DR_{i+1}$, ..., $DR_k$} be a set of consecutive negative patterns. s.sub.j be the time at which $DR_j$ starts, and $e_j$ be the time at which $DR_j$ ends. Then C is a cluster if it satisfies the following conditions:

1. $s_{j+1} − e_j ≤ t_c$, for j=i, ..., k−1, where $t_c$ is a parameter, specified by the user, that controls the maximum amount of time between consecutive negative patterns in a cluster.
2. k−i−1≤$c_{min}$, where $e_{min}$ is a parameter, specified by the user, that controls the minimum number of negative patterns in a cluster.

The pseudocode for the algorithm to recognize clusters of negative patterns is shown below. Let DR={$DR_1$, $DR_2$, ..., $DR_r$} be the set of negative patterns found by the above pattern recognition method.

---
CLUSTER RECOGNITION (OF NEGATIVE PATTERNS)
---
```
f = 1:
    for h = 2:r
        Let R = {x_i,...,X_m,} be the rise in DR_{h−1}
        Let D = {x_i,...,X_j,} be the in decline in DR_h
        gap = i − m
        if gap > t_c
            g = h − 1
            if g − f + 1 ≥ c_min
                Add DR_1,..., DR_{i1},..., DR_g to the list of clusters
            endif
            f = h
        endif
    endfor
    g = r
    if g − f − 1 ≥ c_min
        Add DR_{i − DRi−1}. .... DR_g to the list of clusters
Endif
```
---

In accordance with embodiments of the present invention, this object based linear method maps the unique events, patterns and clusters associated with airway instability because the sequential waveform events associated with airway closure and reopening are each both rapid, substantially unipolar and relatively linear. Also the patterns and clusters derived are spatially predictable since these precipitous physiologic changes are predictably subject to rapid reversal by the physiologic control system, which is attempting to maintain tight control of the baseline range. Because timed data sets with predictable sequences of precipitous unidirectional deflections occur across a wide range of parameters, the same digital pattern recognition methods can be applied across a wide range of clustering outputs, which are derived from airway instability. Indeed, the basic underlying mechanism producing each respective cluster is substantially the same (e.g. clusters of positive pulse rate deflections or positive airflow amplitude deflections). For this reason, this same system and method can be applied to a timed data set of the oxygen saturation, pulse rate (as for example determined by a beat to beat calculation), amplitude of the deflection of the chest wall impedance waveform per breath, amplitude of deflection of the airflow signal per breath (or other correlated of minute ventilation), systolic time intervals, blood pressure, deflection amplitude of the nasal pressure, the maximum exhaled $CO_2$ per breath, and other signals. Additional details of the application of this digital pattern recognition method to identify clusters are provided in patent application Ser. No. 09/409,264, which is assigned to the present inventors.

Next, for the purpose of building the multi-signal object, a plurality of physiologically linked signals are analyzed for the purpose of recognizing corresponding patterns and corresponding physiologic convergence for the optimal identification of the cluster cycles. For example, a primary signal such as airflow is analyzed along with a contemporaneously measured secondary signal such as oxygen saturation as by the method and system discussed previously. As discussed previously, for the purpose of organizing the data set and simplifying the analysis, the raw airflow signal is processed to a composite object level. For example, the composite level of airflow can be a data set of the amplitude and/or frequency of the tidal airflow as by thermister or pressure sensor, or another plot, which is indicative of the general magnitude of the timed tidal airflow. In an exemplary embodiment, a mathematical index (such as the product) of the frequency and amplitude is preferred, because such an index takes into account the important attenuation of both amplitude and frequency during obstructive breathing. Furthermore, both the frequency and amplitude are often markedly increased during the recovery interval between apneas and hypopneas. It is not necessary that such a plot reflect exactly the true value of the minute ventilation but rather, it is important that the plot reflect the degree of change of a given level of minute ventilation. Since these two signals are physiologically linked, an abrupt change in the primary signal (airflow) generally will produce readily identifiable change in the subordinate signal (oxygen saturation). As previously noted, since the events which are associated with airway collapse are precipitous, the onset of these precipitous events represent a brief period of rapid change which allows for optimal detection of the linkage between the primary signal and the subordinate signal.

The signals can be time matched by dipole slopes at the fundamental level. In addition, in one exemplary embodiment of the present invention, the point of onset of precipitous change is identified at the composite object level of the primary signal and this is linked to a corresponding point of a precipitous change in the composite object level of the subordinate signal. This condition is referred to herein as a "delta point." As shown in FIGS. 9, 10, and 11, a first delta point is identified in the primary signal and in this example is defined by the onset of a rise object. A corresponding first delta point is identified in the subordinate signal and this corresponds to the onset of a rise object in the subordinate signal. A second delta point is identified which is defined by the point of onset of a fall object in the primary signal and which corresponds to a second delta point in the subordinate signal defined by the onset of a fall event in the secondary signal. The point preceding the second delta point (the "hyperventilation reference point") is considered a reference indicating an output associated with a degree of ventilation, which substantially exceeds normal ventilation and normally is at least twice normal ventilation. When applying airflow as the primary signal and oximetry as the subordinate signal, the first delta point match is the most precise point match along the two integrated waveforms and therefore comprises a ("timing reference point") for optimally adjusting for any delay between the corresponding objects of the two or more signals. The mathematical aggregate (such as the mean) of an index of the duration and slope, and/or frequencies of composite rise and fall objects of the fundamental level of tidal ventilation along a short region adjacent these reference points can be applied as a general reference for comparison to define the presence of relative levels of ventilation within objects along other portions of the airflow time series. Important fundamental object characteristics at these reference points are the slope and duration of the rise object or fall object because these are related to volume of air, which was moved during the tidal breath. The fundamental objects comprising the tidal breaths at the reference hyperventilation point along the composite level are expected to have a high slope (absolute value) and a high frequency. In this way, both high and low reference ranges are determined for the signal. In another exemplary embodiment, these points can be used to identify the spatial shape configuration of the rise and fall objects at the fundamental level during the rise and fall objects at the composite level.

As shown in FIGS. 9 and 10, using this method at the composite object level, a first object (FIG. 11) can then be identified in the primary signal between the first delta point and the second delta point which is designated a recovery object. As also shown in FIG. 11, the matched recovery object is also identified in the subordinate signal as the point of onset of the rise object to the point of the onset of the next subsequent fall object. In an exemplary embodiment, the recovery object is preceded by the apnea/hypopnea object which is defined by the point of onset of the fall object to the point of onset of the next rise object in both the primary and subordinate signals.

Figure 12:
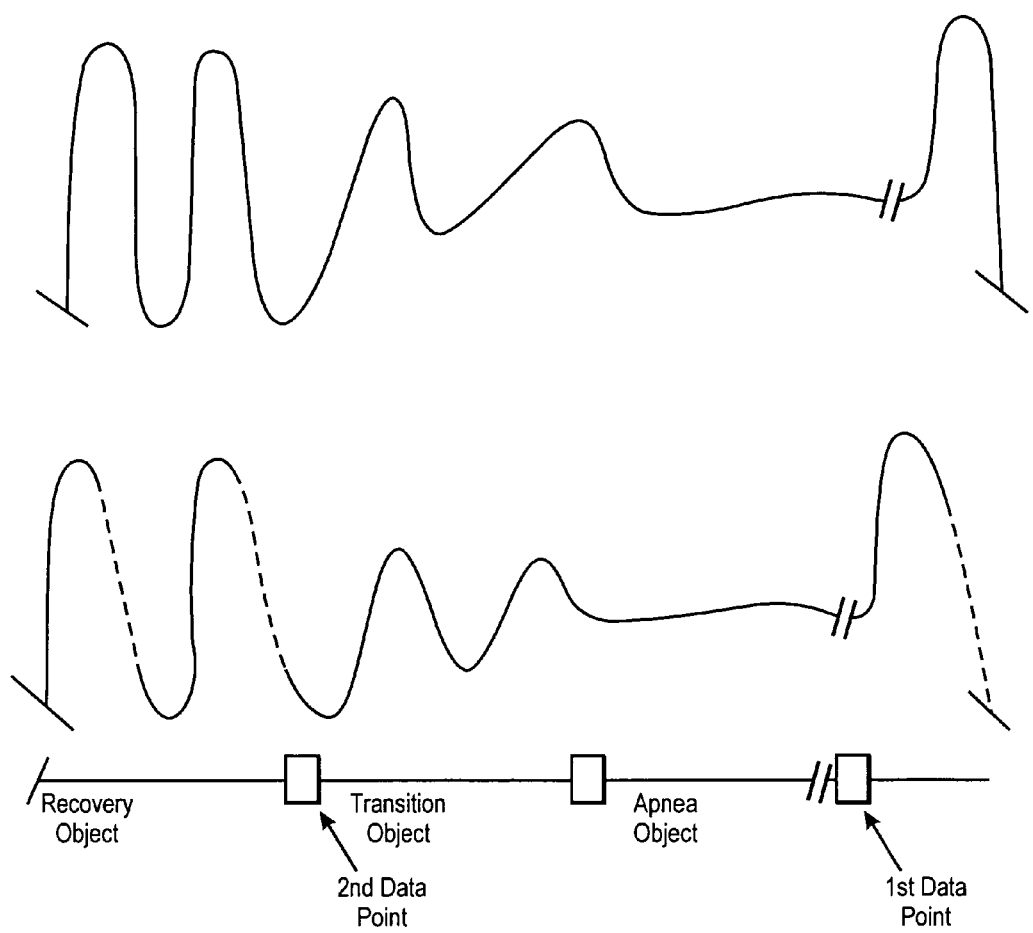
FIG. 12 is a graphical representation of a comparison between two data sets of airflow wherein at the fundamental level the second data set shows evidence of expiratory airflow delay during the recovery object, wherein the recovery object is recognized at the composite level in accordance with embodiments of the present invention.

As shown in FIG. 12, a recovery object recognized at the composite level can used to specify a region for comparison of sequential objects at the fundamental object level. Here, upon recognition of the presence of a recovery object (where it is anticipated that the ventilation effort will be high) the ratio of the slope of exhalation objects to the slope of inhalation objects can be compared within the recovery object and the time series derived from these comparisons can be plotted if desired. During upper airway obstruction, the inspiration is slowed to a greater degree than exhalation. The magnitude change of the ratio during the clusters of apneas provides an index of the magnitude of upper airway narrowing (which selectively slows inhalation during the clustered apnea/hypopnea objects). However, during the recovery object or at the "hyperentilation reference point", the upper airway should be wide open for both inhalation and exhalation and this can be used as a reference because, during this time. The absolute slope of the fundamental objects during recovery can then be compared to the absolute slope of the fundamental objects during other times along the night to provide an indication of upper or looser airway narrowing.

When airflow is the primary signal and oximetry the subordinate, the most reliable delta point is the point of onset of a rapid rise in ventilation (in a patient with an oxygen saturation, at the point of onset point, of less than 96-97%). Patients with very unstable airways will generally have relatively short recovery objects. Other patients with more stable airways may have a multi-phasic slope of decline in airflow during the recovery objects herein, for example, there is an initial precipitous decline event in the airflow parameter and then a plateau or a much more slight decline which can be followed by a second precipitous decline to virtual absence of ventilation. Using the slope dipole method these composite objects can be readily separated such that the occurrence of multiple composite objects (especially wherein the slopes are close to zero) or a single object with a prolonged slowly falling slope dataset occurring immediately after the first data point, can be identified. These patients generally have longer recovery intervals and more stable airways. The identification of a decline object associated with decline from the hyperventilation phase of recovery followed by a plateau and/or a second decline object associated with the onset of apnea is useful to indicate the presence of a greater degree of airway stability. Accordingly, with the airflow signal, a third delta point (FIG. 12) designated a "airflow deflection point" can often be identified in the airflow tracing corresponding to the deflection point at the nadir of drop in airflow at the end of the recovery. This point is often less definable than the second delta point and for this reason matching the second delta points in the airflow and oximetry signals is preferred although with some tracings a match between the airflow deflection point and the second delta point in the oximetry dataset provides a better match.

If a significant decline in airflow is identified after the "airflow deflection point" then the region of the intervening decline object and the next delta point (onset of the next recovery) is designated a reference "ventilation nadir region". If the region or object(s) from the second delta point to ventilation deflection point is very short (as 0-3 breaths) and the ventilation nadir region has a mean slope close to or equal to zero (i.e. the region is relatively flat) and the deflection amplitude is close to zero or otherwise very small indicating now or very little ventilation, then the airway is designated as highly unstable.

Another example of object processing at the fundamental object level, according to the present invention, includes the processor-based identification of fluttering of the plateau on the pressure signal to recognize partial upper airway obstruction. During the nasal pressure monitoring a fluttering plateau associated with obstructive breathing often occurs intervening a rise event and a fall event of tidal breathing. Since the plateau objects are easily recognizable at the fundamental level and readily separated using the present object recognition system the plateau can be processed for the tiny rise and fall objects associated with fluttering and the frequency of these objects can be determined. Alternatively, a Fourier transform can be applied to the plateau objects between the rise and fall events of the nasal pressure signal to recognize the presence of fluttering or another method can be utilized which provides an index of the degree of fluttering of the plateau objects.

Since reduced effort also lowers the slope of exhalation and inspiration, the configuration (as defined by the slope dataset of the dipoles defining the fundamental objects of both inspiration and expiration at the reference objects) can be applied as reference fundamental object configurations defining the presence of hyperventilation or hypopnea. This process is similar to the selection process for identifying search objects described earlier but in this case the input region is preselected. In an example, the range of characteristics of the objects at the fundamental level derived from one or more tidal breaths occurring prior to the second airflow delta point can be used to designate a reference hyperventilation objects range. Alternatively, the object-based characteristics, defined by of the range of characteristics of the objects derived from one or more tidal breaths occurring prior to the first airflow delta point can be used designate a reference hypopnea objects range. The processor can then automatically assess object ranges along other points of the tracing. In this way, the processor can apply an artificial intelligence process to the identification of hypopneas by the following process:

1. Identify the region wherein a hypopnea is expected (as for example two to three tidal breaths prior to the first airflow delta point).
2. Select this as a region for objects processing to define the characteristics of hypopneas in this patient.
3. Process the region using the slope dipole method to define the range of fundamental objects comprising the target region.
4. Compare the identified range of objects to other analogous objects along to tracing to identify new objects having similar characteristics.
5. Using the criteria derived from the objects defining the target region search the processed waveform for other regions having matching sequences of new objects and identify those regions.
6. Provide an output based on said identification and/or take action (e.g. increase CPAP) based on said identification.

These processing methods exploit the recognition that certain regions along a multi-signal object (as within a cluster) have a very high probability of association with certain levels of ventilation. The objects defining those regions can then be used as a reference or as an opportunity to examine for the effects of a given level of ventilation effort on the flow characteristics. Patients with obstructive sleep apnea will have a fall in the slopes of fundamental inspiration objects during decline objects at the composite level indicative of upper airway occlusion. Also, as shown in FIG. 12, patients with asthma or chronic obstructive lung disease will have a reduced slope of the exhalation when compared to the slope of inhalation during the rise objects between apneas at the base level. According to one embodiment of the present invention, the time series of the ratio of the slope of inhalation objects to exhalation objects is included with the basic time series. Patients with simple, uncomplicated obstructive apnea will have clusters of increasing slope ratios with the ratio rising to about one during the recovery objects. Patients with combined obstructive apnea and asthma or chronic obstructive lung disease will have a greater rise in slope ratios during the recovery objects to into the range of 2-3 or greater, indicating the development of obstructive lower airways during the rapid breathing associated with recovery.

Figure 8:
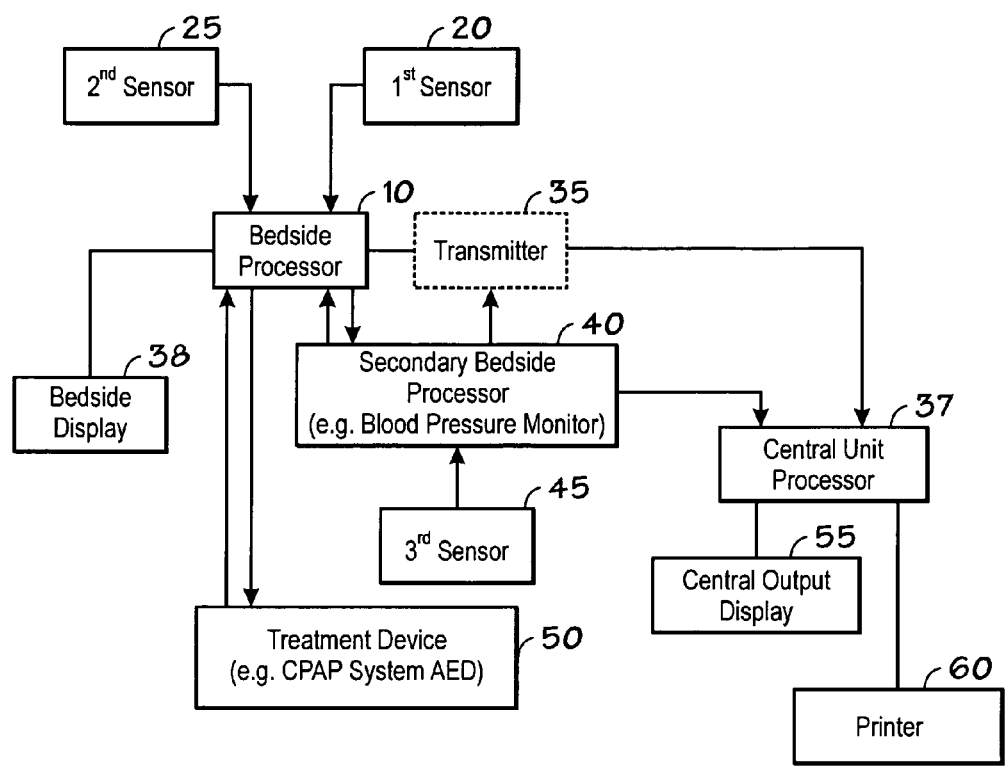
FIG. 8 is a schematic of a monitor and automatic patient treatment system in accordance with embodiments of the present invention.

A system for processing, analyzing and acting on a time series of multi-signal objects in accordance with one embodiment of the present invention is shown in FIG. 8. The examples provided herein show the application of this system for real time detection, monitoring, and treatment of upper airway and ventilation instability and for the timely identification of pathophysiologic divergence. The system includes a portable bedside processor 10, which may comprise a microprocessor, having at least a first sensor 20 and a second sensor 25, which may provide input for at least two of the signals discussed above. The system includes a transmitter 35 to a central processing unit 37. The bedside processor 10 may include an output screen 38, which provides the nurse with a bedside indication of the sensor output. The bedside processor 10 can be connected to a controller of a treatment or stimulation device 50 (which can include, for example, a positive pressure delivery device, an automatic defibrillator, a vibrator or other tactile stimulator, a drug delivery system such as a syringe pump or back to the processor to adjust the analysis of the time-series inputs), the central unit 37 preferably includes an output screen 55 and printer 60 for generating a hard copy for physician interpretation. In accordance with embodiments of the present invention, the system allows recognition of conditions such as airway instability, complications related to such instability, and pathophysiologic divergence in real time from a single or multiple inputs. Moreover, embodiments of the present invention may be programmed or otherwise adapted to identify recurring patterns in a wide range of signals to identify conditions associated with those recurring patterns. In the embodiment illustrated in FIG. 8, the bedside processor 10 is connected to a secondary processor 40 which can be a separate unit. The secondary processor 40 may be adapted to perform measurements intermittently and/or on demand. Examples of measurements that may be performed include non-invasive blood pressure monitoring or monitoring with an ex-vivo monitor, which draws blood into contact with a sensor on demand for testing to derive data points for addition to the multi-signal objects. The secondary processor 40 includes at least one sensor 45. The output of the bedside processor can be transmitted, for example, to a central processor 37. which may comprise a hospital monitoring station, or to the bedside monitor 10 to render a new object output, action, or analysis. In an exemplary embodiment of the present invention, the method of hypopnea recognition discussed previously can be coupled with a treatment device 50 such as a CPAP auto-titration system.

The previously described method for detecting hypopneas may be desirably adapted to identify milder events because, while the configuration of each tidal breath of the hypopnea may be only mildly different, there is a cumulative decline in ventilation or increase in airway resistance which often, eventually directly triggers a recovery object or indirectly triggers the occurrence of a recovery object via an arousal response. The recovery objects being a precipitous response to a mild but cumulative decline on airflow is easier to recognize and is exploited to specify timing of the target processing as noted above.

A potential problem with conventional CPAP is that CPAP systems typically operate with pre-selected criteria for recognition of a hypopnea (such as 50% attenuation of a breath or group of breaths when compared with a certain number of preceding breaths). These systems generally determine the correct pressures for a given patient by measuring parameters derived from the algorithms which monitor parameters through the nasal passage. Unfortunately, the nasal passage resistance is highly variable from patient to patient and may be variable in a single patient from night to night. These simplistic single parameter systems are even less suitable in a hospital environment where many confounding factors (such as sedation or the like) may severely affect the performance of a conventional auto-titration system. Since most auto-titration system monitors their effectiveness through nasal signals their algorithms are limited by this wide variability of nasal resistance from patient to patient. Studies have shown that, while apneas can be detected, the detection of hypopneas by these devices is often poor. This becomes even more important for the detection of mild hypopneas, which can be very difficult to reliably detect (without an unacceptably high false positive rate) through a nasal signal alone. Indeed these milder hypopneas are more difficult characterize and not readily definable as a set of function of a set of predetermined rules for general application to all patients. In an exemplary embodiment of the present invention, the system customizes hypopnea recognition to match a given patient's nasal output.

Figure 16:
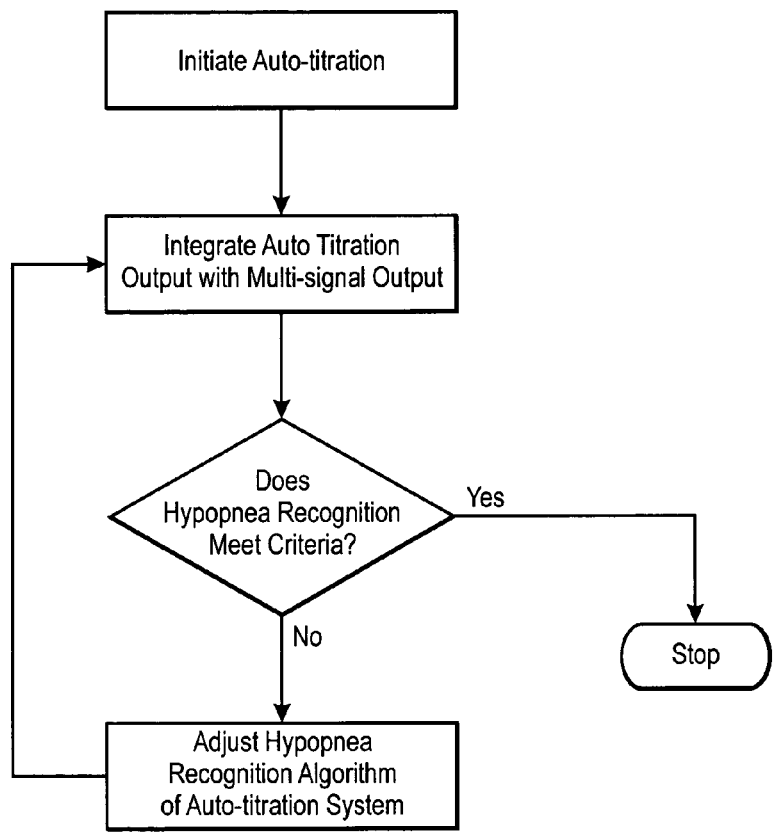
FIG. 16 is a diagram of a system for customizing a constant positive airway pressure (CPAP) auto-titration algorithm based on the analysis of multiple corresponding signals in accordance with embodiments of the present invention.

An exemplary embodiment of a process in accordance with the present invention suitable for deployment in an auto-titration system is illustrated in FIG. 16. Such a system adjusts its titration algorithm (which can be any of the conventional algorithms) based on the configurations of the multi-signal object, which can include oximetry data, chest wall movement, EEG data sets or the like. In the illustrated system, for example, the initial titration algorithm is applied with the data set of CPAP pressure becoming part of the multi-signal object. The object time series at the composite level is monitored for the presence of persistent clusters (especially clustered recovery objects or clustered EEG arousals). If persistent clusters are identified, then the region of the cluster occurrences is compared to the identified hypopnea region derived from the conventional method. If this region is as recognized as hypopneas, then the pre-selected pressure for a given increment in titration is further incremented by 1-2 cm so that conventional titration occurs at higher-pressure levels. The process may be repeated until all clusters are eliminated. If EEG arousals worsen with this increase, then the increment can be withdrawn. If, on the other hand, the algorithm did not recognize this region as a hypopnea, the threshold criteria for a hypopnea is reduced until the clusters are eliminated (some cases require a baseline fixed pressure of 2-3 or more cm). The illustrative embodiment shown in FIG. 16 relates to a CPAP auto-titration system which uses the multi-signal object dataset during one or more auto-adjusting learning nights to customize a treatment response to a given triggering threshold or the triggering threshold to a given treatment response. The application of a learning night can prevent inappropriate or unnecessary adjustments and can provide important information about treatment response while assuring that the basic algorithm itself is customized to the specific patient upon whom it is applied. This may be useful when using hospital-based monitors where the monitor is coupled with the processor of the CPAP unit for the learning nights while in the hospital. Alternatively, learning nights can be provided at home by connecting a primary processor for processing multiple signals with the processor of the CPAP unit for a few nights to optimize the algorithm for later use. In the hospital, components can be used to attempt to provide optimal titration. Using object-based cluster analysis of tracing of chest wall impedance and oximetry, the titration can be adjusted to assure mitigation of all clusters. In the alternative, if all clusters are not mitigated by the titration then, a nurse or other caregiver may be warned that these clusters are refractory that central apnea should be considered, particularly if the impedance movements during the apneas are equivocal or low. If, for example, the patient's oxygen saturation falls (after adjusting for the delay) in response to an increase in pressure, the pressure can be withdrawn and the nurse warned that desaturation unresponsive to auto-titration is occurring. If needed, ventilation can be automatically initiated. The self-customizing auto-titration system can include a pressure delivery unit capable of auto adjusting either CPAP or BiPAP such that such a desaturation in response to CPAP can trigger the automatic application of BiPAP.

Figure 13:
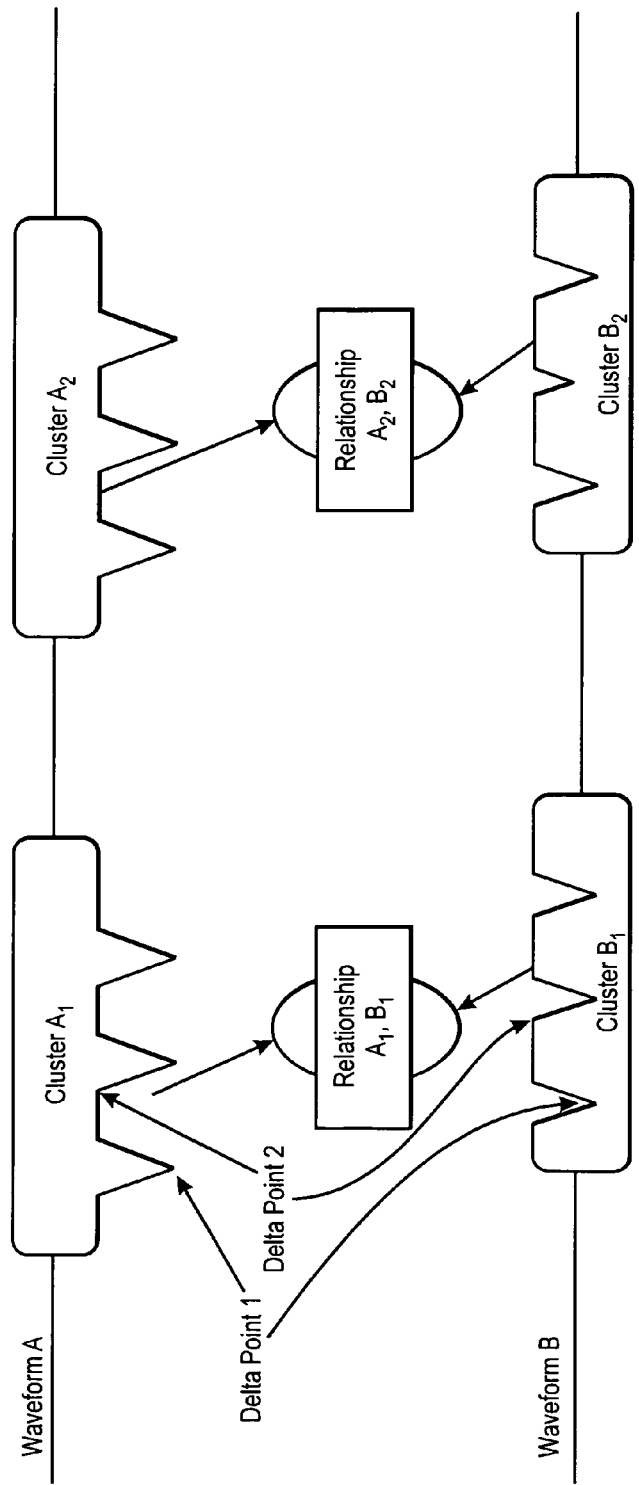
FIG. 13 is a diagram of a schematic object mapping at the composite level of corresponding signals of airflow and oxygen saturation in accordance with embodiments of the present invention.
Figure 14:
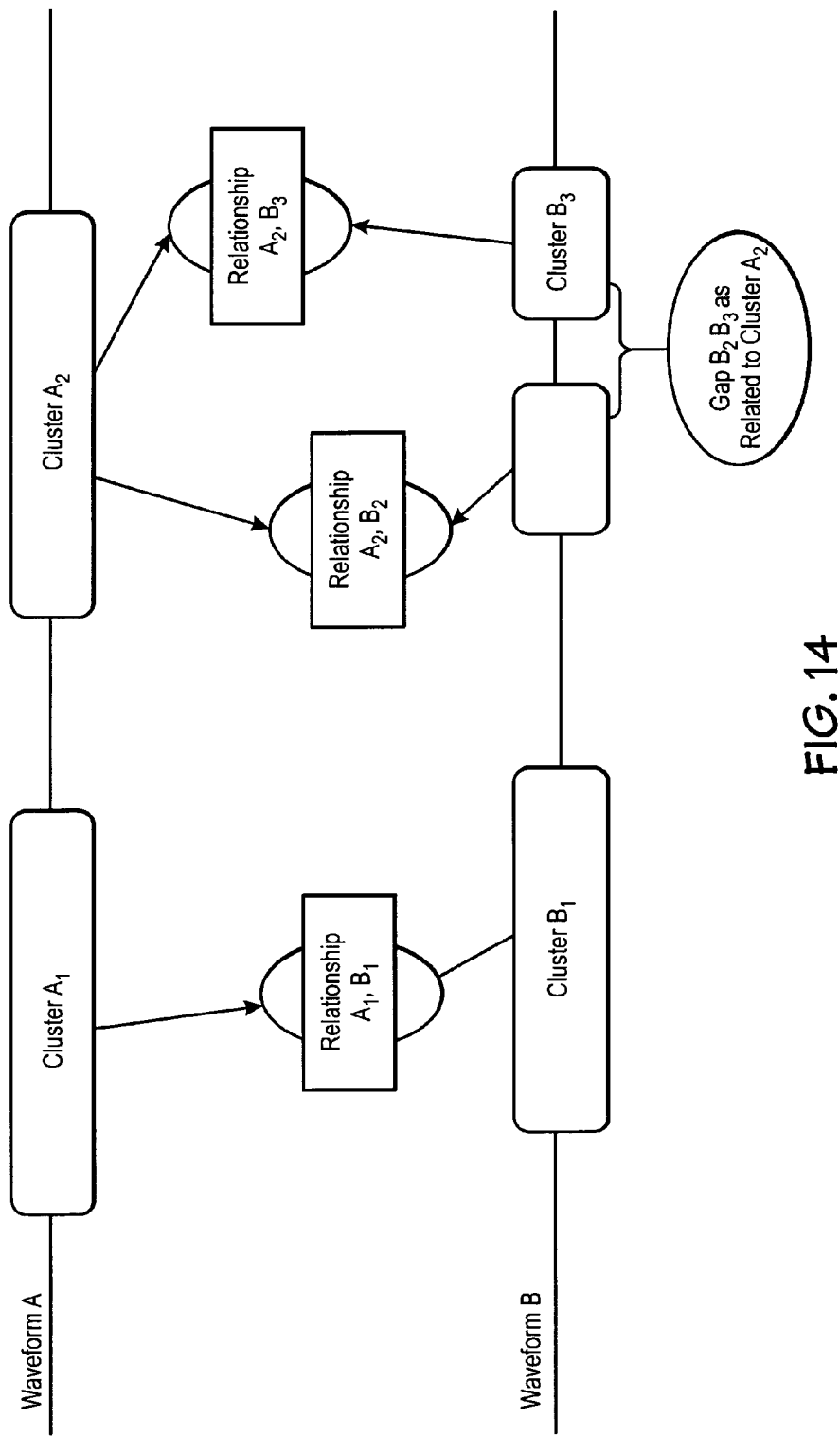
FIG. 14 is a diagram of a schematic object mapping at the composite level of two simultaneously measured parameters with a region of anticipated composite objects in accordance with embodiments of the present invention.
Figure 15:
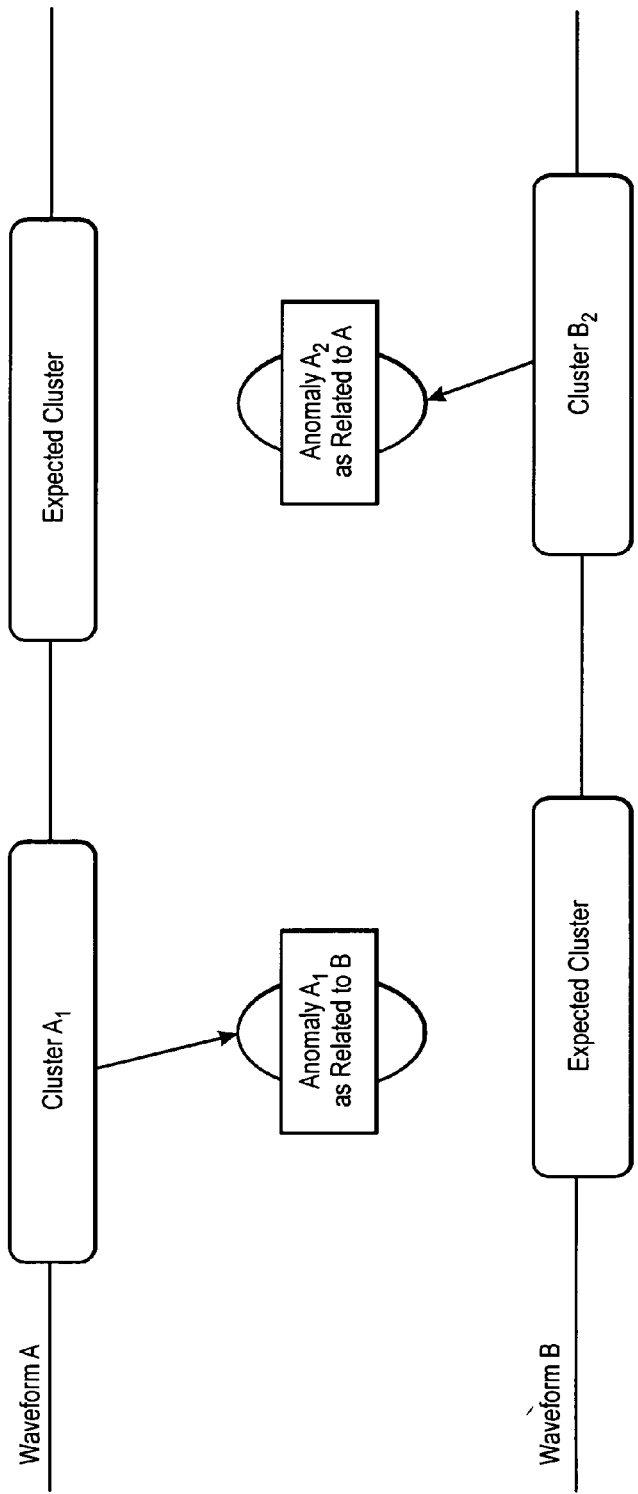
FIG. 15 is a diagram of a schematic object mapping and scoring at the composite level of two simultaneously measured parameters with the region of anticipated composite objects in accordance with embodiments of the present invention.

In accordance with embodiments of the present invention, clusters of hypopneas can generally be reliably recognized utilizing a single parameter. However, when significant signal noise or reduced gain is present, the object-based system can combine matched clusters within a time series of multi-signal objects in the presence of sub-optimal signals by providing a scoring system for sequential objects. FIGS. 13, 14 and 15 are diagrams of schematic object mappings at the composite level in accordance with embodiments of the present invention. The schematics in those figures represent basic cluster matching in situations wherein sub-optimal signals may be present. The multi-signal objects defining the matched clusters of paired timed datasets of airflow and oximetry include a matched sequence of negative cycle objects in the airflow signal and corresponding negative cycle object in the oximetry signal. Each cycle object is defined by a set of coupled rise and fall objects meeting criteria and occurring within a predetermined interval of each other (as discussed previously). The occurrence of a cycle object in either dataset meeting all criteria is given a score of one (1). The cycles are counted in sequence for each multi-signal cluster object. For the purpose of illustration, in accordance with embodiments of the present invention, the occurrence of a score of three (3) in any one signal (meaning that a sequence of three (3) cycles meeting criteria have occurred within a specified interval) provides sufficient evidence to identify a cluster object. When two (2) simultaneous signals are processed, a total score of four (4), derived from adding the number of cycles meeting criteria in each signal, is sufficient to indicate the presence of a cluster object. In this manner, the cluster is continued by a sequential unbroken count greater than three (3) with one signal, or greater than four (4) with two signals. Once the presence of a cluster object has been established along the time series, at any point along the cluster object the sequential count along one signal can be converted to a continuation of the sequential count along another signal allowing the cluster object to continue unbroken. The failure of the occurrence of a cycle meeting criteria within either signal within a specified interval (for example about 90-120 seconds, although other intervals may be used) breaks the cluster object. A new cluster object is again identified if the count again reaches the thresholds as noted above. It can be seen that this scoring method takes into account the fact that artifact often affects one signal and not another. Therefore, if either signal alone provides a sufficient score, the presence of a cluster object is established. In addition, the effect of brief episodes of artifact affecting both signals is reduced by this scoring method. In this way, artifact, unless prolonged, may cause the cluster object to be broken but as soon as the artifact has reduced sufficiently in any one or more signals the process of scoring for a new cluster object will restart.

Another CPAP auto-titration system in accordance with embodiments of the present invention includes a processor and at least one sensor for sensing a signal transmitted through the nose. Examples of such signals include a pressure signal indicative of airflow, sound, impedance or the like. An oximeter, which can be detachable or integrated into the CPAP unit, is connected with the processor. The processor detects hypoventilation, using output from both the flow sensor and the oximeter, when the oximeter is attached. In an embodiment in which with the oximeter is detachable, the processor detects hypoventilation using the flow sensor without oximetry when the oximeter is not attached.

In accordance with embodiments of the present invention, the multi-signal object time series can be used for identifying pathophysiologic divergence. Pathophysiologic divergence can be defined at the fundamental, composite, or complex level object. An example of divergence at the fundamental level is provided by the relationship between an airflow rise object (inspiration) and a fall object (expiration). Along a time series of matched expiration and inspiration objects, the occurrence of a marked increase in amplitude of inspiration is commonly associated with an increase in the ratio of the absolute value of inspiration slope to the absolute value of the slope of exhalation. Should this value increase, this provides evidence suggesting pathophysiologic divergence. Alternatively, in an exemplary embodiment of the present invention, the evaluation time period can be much longer. In one embodiment, the objects defining the data set of the first time interval is compared to the objects defining the data set of the second corresponding time interval. This comparison is performed in a similar manner to the aforementioned comparison of corresponding cluster objects noted above. The specific parameters, which are compared, are parameters having known predictable physiologic linkages wherein a change of first physiologic parameter is known to induce a relatively predictable change in a second physiologic parameter. The second parameter is, therefore, a physiologically subordinate of the first parameter. As shown in FIG. 11, the first parameter can be a measure indicative of the timed volume of ventilation and the second parameter can be the timed arterial oxygen saturation. Here, as shown in FIG. 11, a progressive rise in minute ventilation is expected to produce rise in oxygen saturation. The alveolar gas equation, the volume of dead space ventilation and the oxyhemoglobin disassociation curve predict the rise in oxygen saturation by known equations. However, in accordance with embodiments of the present invention, it is not necessary to know the absolute predicted value of oxygen saturation rise for a given change in minute ventilation but rather the processor identifies and provides an output indicating whether or not an expected direction of change in the subordinate one parameter occurs in association with a given direction of change in the primary parameter. For example, with respect to arterial oxygen saturation and ventilation, embodiments of the present invention may determine whether or not an expected direction and/or slope of change of oxygen saturation occur in association with a given direction and/or slope change in minute ventilation. The time course of the rise in ventilation of FIG. 11 is short however, as the time period lengthens the relationship is strengthened by the greater number of corresponding measurements and the greater measurement time. When minute ventilation slopes or trends upward over a sustained period, after the anticipated delay there would be an expected moderate upward change in oxygen saturation if the saturation is not already in the high range of 97-100%. If, on the other hand, if the oxygen saturation is falling during this period, this would suggest that the patient is experiencing a divergent pathophysiologic response which may warrant further investigation. Automatic recognition of falling or unchanged oxygen saturation in association with a rising minute ventilation can provide earlier warning of disease than is provided by the simple non-integrated monitoring and analysis of these two wave forms.

In accordance with embodiments of the present invention, it is not necessary to be exact with respect to the measurement of minute ventilation. Minute ventilation can be trended by conventional methods, without an absolute determination of the liters per minute for example, by plotting a measure of the amplitude and frequency of a nasal oral thermister or by the application of impedance electrodes on the chest, thereby monitoring the amplitude and frequency of tidal chest movement. Alternatively, conventional impedance or stretch sensitive belts around the chest and abdomen or other measures of chest stall and/or abdominal movement can be used to monitor tidal ventilation and then this can be multiplied by the tidal rate of breathing to provide a general index of the magnitude of the minute ventilation. In an exemplary embodiment of the present invention, the minute ventilation is trended on a time data set over a five to thirty minute interval along with the oxygen saturation.

In the exemplary embodiment of the present invention shown in FIG. 8, pathophysiologic divergence of timed output may be identified. As discussed previously, the monitor includes a microprocessor 5, the first sensor 20, a second sensor 25, and an output device 30, which can be a display a printer or a combination of both. The processor 5 may be programmed to generate a first timed waveform of the first parameter, derived from the first sensor 20, and a second timed waveform of second parameter, derived from the second sensor 25. Using the multi-signal processing system, described previously the processor 5, may be adapted to compare the objects of the first timed output to the objects of the second timed output to identify unexpected divergence of the shape of the first timed output to the shape of the second timed output and particularly to recognize a divergence in directional relationship or polarity of one timed output of one parameter in relationship to another timed output of another related parameter. In an exemplary embodiment, this divergence comprises a fall in the slope of the oxygen saturation (for example, as defined by the recognition of a "decline object", as discussed previously) in relationship to a rise (referred to as a "rise object") in the slope of the corresponding minute ventilation. In another example, the processor integrates three signals to identify divergence. The processor identifies the relationship of other signals such as heart rate or R-to-R interval or a measure of the pulse magnitude (as the amplitude, slope of the upstroke, or area under the curve of the plethesmographic pulse). In particular, a rise object in minute ventilation may be identified in association with a decline object in oxygen saturation and a decline object in heart rate or pulse amplitude. These outputs can be plotted on a display 30 for further interpretation by a physician with the point of pathophysiologic divergence of one parameter in relationship to another parameter identified by a textural or other marker.

The identification of pathophysiologic divergence can result in significant false alarms if applied to the short time intervals used for rise and decline objects which are used for detection of cluster objects (and also the short averaging intervals for this purpose). In particular, if the identification of divergence is applied for short intervals, such as one (1) to two (2) minutes, a significant number of false episodes of divergence may be identified. In accordance with embodiments of the present invention, clear evidence of a trend in one measured parameter in relationship to a trend of another measured parameter may be provided so that it is likely that divergence has indeed occurred. This can be enhanced by the evaluation of the prolonged general shape or polarity of the signal so that it is considered preferable to identify divergence over segments of five to thirty minutes. The averaging of many composite objects to identify a rise object at the complex object level helps mitigate such false alarms. For this reason, the expected time course of a divergence type must be matched with the resolution (or averaging times) of the objects compared.

According to an exemplary embodiment of the present invention, to enhance the reliability of the analysis of the timed data set, the averaging interval for this purpose, can be adjusted to avoid excessive triggering of the intermittent monitoring device. In one exemplary embodiment, the averaging interval is increased to between thirty and ninety seconds or only the analysis of complex objects can be specified. Alternative methods may be used to identify a rise and fall objects such as the application of line of best-fit formulas, as previously discussed. Elimination of outlier data points to define larger composite objects can also be applied as also previously discussed or by other methods. In this way, the identification of a trend change, which evolves over a period of five to fifteen minutes, can be readily identified. The identification of divergence can produce a textual output, which can be maintained for a finite period until the secondary parameter corrects or a threshold period of time has elapsed. For example, if a rise in minute ventilation is identified over a predetermined interval period (such as about ten minutes) to define a rise object and a fall in oxygen saturation is identified over a corresponding period to define a fall object, the processor identifies the presence of divergence and can produce a textual output which can be provided on the bedside display or central processing display. This textual output can be maintained for a finite period, for example, one to two hours, unless the oxygen saturation returns to near its previous value, at which time the textual output may be withdrawn from the display.

In this manner, the presence of pathophysiologic divergence is readily identified. However, since divergence is defined by divergent rise and fall objects of corresponding physiologically linked parameters, its duration is necessarily limited since these slopes cannot continue to diverge indefinitely. It is important to carry forward the identification of prior divergence in the patient's display for at least a limited period of time so that the nurse can be aware that this event has occurred. For example, a "fall object" identified in the secondary, signal such as a fall in oxygen saturation from 95% to 90% over a period of ten minutes occurring in association with a rise object in the primary signal, such as, for example, a doubling of the amplitude of the airflow or chest wall impedance deflection over a period of ten minutes can produce an identification of pathophysiologic divergence that can be linked to the outputted saturation so that the display shows a saturation of 90% providing an associated textual statement "divergence-TIME". This identification of divergence can, over a period of time, be withdrawn from the display or it can be immediately withdrawn if the oxygen saturation corrects back close to 95%.

As discussed previously and as also illustrated in FIG. 8, in another exemplary embodiment of the present invention, a change in the configuration of the multi-signal time series can be used to trigger the addition of one or more additional signals to the multi-signal time series, such as a non-invasive blood pressure. In this manner, a system can identify whether pathophysiologic divergence is occurring with respect to the new, less frequently sampled signal. For example, the trending rise in heart rate should not be generally associated with a fall in blood pressure. If, for example over a period of 5 to 20 minutes, a significant rise in heart rate (as for example a 25% rise and at least 15 beats per minute) is identified by the processor, the monitor can automatically trigger the controller of a non-invasive blood pressure monitor to cause the measurement of blood pressure to be immediately taken. The output of the non-invasive blood pressure monitor is then compared by the processor to the previous value which was recorded from the blood pressure monitor and, if a significant fall in blood pressure (such as a fall in systolic of 15% and more) is identified in association with the identified rise in heart rate which triggered the test, a textual warning can be provided indicating that the patient is experiencing pathophysiologic divergence with respect to heart rate and blood pressure so that early action can be taken before either of these values reach life-threatening levels. According to another embodiment of the present invention, a timed dataset of the pulse rate is analyzed, if a significant change (for example, a 30-50% increase in the rate or a 30-50% decrease in the interval or a 50-75% increase in the variability of the rate), then the blood pressure monitor can be triggered to determine if a significant change in blood pressure has occurred in relation to the change in pulse rate or the R-to-R interval. This can be threshold adjusted. For instance, a significant rise in heart rate of 50%, if lasting for a period of two and a half minutes, can be used to trigger the intermittent monitor. On the other hand, a more modest rise in heart rate of, for example, 25% may require a period of five or more minutes before the intermittent monitor is triggered.

In another embodiment, also represented in FIG. 8, identification by the bedside processor 5 of a sustained fall in oxygen saturation can be used to trigger an ex-vivo monitor 40 to automatically measure the arterial blood gas parameters. Alternatively, a significant rise in respiratory rate (for example, a 100% increase in respiratory rate for five minutes) can suffice as a trigger to automatically evaluate either the blood pressure or an ex-vivo monitor of arterial blood gasses.

There are vulnerabilities of certain qualitative indexes of minute ventilation in relationship to divergence, the effect of which may be reduced by embodiments of the present invention serves to enhance the clinical applicability of the output. For example, a rise in the signal from chest wall impedance can be associated with a change in body position. Furthermore, a change in body position could result in a fall of oxygen saturation due to alteration in the level of ventilation, particularly in obese patients. Such alterations can be associated with an alteration in the ventilation perfusion matching in patients with regional lung disease. Therefore, a change in body position could produce a false physiologic divergence of the signals when the multi-signal time series includes chest wall impedance and oximetry. For this reason, in accordance with embodiments of the present invention, additional time series components may be employed, such as information provided by a position sensor. Alternatively, if position information is not available, a more significant fall in one parameter may be used in association with a more significant divergent rise in another. By way of example, a significant fall in oxygen saturation of, for example, 4-5% in association with a doubling of the product of the amplitude and frequency of the impedance monitor would provide evidence that this patient is experiencing significant pathophysiologic divergence and would be an indication for a textual output indicating that pathophysiologic divergence has occurred. The thresholds for defining divergence, in accordance with embodiments of the present invention, may be selectable by the physician or nurse. When the time series output of a position monitor is incorporated into the system with a significant position-related change in one or more parameters, the position monitor provides useful additional information.

In accordance with embodiments of the present invention, the magnitude of pathophysiologic divergence can be provided on the central display 38 or bedside display 30. In some cases, as discussed previously, a mild degree of pathophysiologic divergence may not represent a significant change and the nurse may instead want to see an index of the degree of pathophysiologic divergence. A bar graph or other variable indicator, which can be on the order of the monitoring cubes of illustrated in FIGS. 6a-6e, can provide this. In one embodiment the monitoring cube can be selectively time-lapsed to observe the previous relational changes between parameters. Alternatively, the animated object can be rotated and scaled to visually enhance the represented timed relationships and points of divergence.

In one embodiment of the present invention, the multi-signal time series output is placed into a format useful for reviewing events preceding an arrest or for physician or nurse education. In this format, the output controls an animation of multiple objects which, instead of being parts of a hexagon or cube, are shaped into an animated schematic of the as the physiologic system being monitored. The animation moves over time and in response to the signals in one preferred embodiment. The type of signals (or the reliability of such signals) determines which components of the schematic are "turned on" and visible. One example includes a multi-signal object defined by outputs of airflow, thoracic impedance, oximetry, and blood pressure, rendering a connected set of animation objects for the lungs, upper airway, lower airway, heart, and blood vessels which can be animated as set forth below in Table 2:

TABLE 2

Each inspiration causing an animated enlargement of the lungs tracking the inspiration slope
Each expiration causing an animated reduction in size of the lungs tracking the expiration slope
Each animated systolic beat of the heart tracks the QRS or upstroke of the oximetry output
The color of the blood in the arteries and left heart tracks the oxygen saturation
The diameter of the lower airway (a narrowing diameter can be highlighted in red) tracks the determination of obstruction by the slope ratio in situations of hyperventilation (as discussed previously)
The patency of the upper airway (a narrowing or closure can be highlighted in red) tracks the determination of upper airway obstruction (as discussed previously)
The magnitude of an animated pressure gauge tracks the blood pressure This provides "physiologic animation" which can be monitored in real-time but will generally be derived and reviewed from the stored multi-signal objects at variable time scales. This is another example of an embodiment of the present invention providing a quickly, easily understood and dynamic animated output of a highly complex, interactive time series derived form a patient. The animation can be reviewed at an increased time lapsed rate to speed through evolution of a given patients outputs or can be slowed or stopped to see the actual global physiologic state at the point of arrhythmia onset.

In another example, a patient with a drop in oxygen saturation of 4% and a doubling of the product of the frequency and amplitude of the chest wall impedance tidal variation may have a single bar presented on the monitor, whereas a patient with a 6% drop wherein the product of the impedance amplitude and frequency has tripled may have a double bar, and so on. This allows reduction in the occurrence of false alarms by providing a bar indicator of the degree of divergence that has occurred. A similar indicator can be provided for clustering, indicative of the severity of airway or ventilation instability. It should be noted that very mild clustering may simply represent the effect of moderate sedation, and not, therefore, represent a cause for great concern (although it is important to recognize that it is present). Such a clustering could be identified with a single bar, whereas more severe clustering would generate a larger warning and, it very severe, an auditory alarm. When the clustering becomes more severe and demonstrates greater levels of desaturation and/or shorter recovery intervals, the bar can be doubled.

In another embodiment, which could be useful for neonates, the time series of multi-signal objects is derived entirely from a pulse oximeter. Each object level for each signal and further a multi-signal object time series of the oxygen saturation and pulse (as for example can be calculated below) is derived. This particular multi-signal time series has specific utility for severity indexing of apnea of prematurity. The reason for this is that the diving reflex in neonates and infants is very strong and causes significant, cumulative bradycardia having a progressive down slope upon the cessation. In addition, the apnea is associated with significant hypoxemia, which also causes a rapid down slope due to low oxygen storage of these tiny infants. Even a few seconds of prolongation of apnea causes profound bradycardia because the fall in heart rate like that of the oxygen saturation does not have a reliable limit or nadir but rather falls throughout the apnea. These episodes of bradycardia cluster in a manner almost identical to that of the oxygen saturation, the pulse in the neonate being a direct subordinate to respiration.

In neonates, oxygen delivery to the brain is dependent both upon the arterial oxygen saturation and the cardiac output. Since bradycardia is associated with a significant fall in cardiac output, oxygen delivery to the neonatal brain is reduced both by the bradycardia and the fall in oxygen saturation. It is critical to have time series measurements, which relate to cumulative oxygen delivery (or the deficit thereof) both as a function of pulse and oxygen saturation. Although many indices can be derived within the scope of the present invention, the presently preferred index is given as the "Saturation Pulse". Although many calculations of this index are possible, in one exemplary embodiment of the present invention, the index is calculated as:

$$SP = R(SO2-25)$$

Where:
SP is the saturation pulse in "% beats/sec"
R is the instantaneous heart rate in beats per second, and
SO2 is the oxygen saturation of arterial blood in %.

The saturation-pulse is directly related to the brain oxygen delivery. The $SpO_2$-25 is chosen because 25% approaches the limit of extractable oxygen in the neonatal brain. The index is preferably counted for each consecutive acquisition of saturation and pulse to produce a continuous time series (which is an integral part of a multi-signal time series of oxygen saturation and pulse). This index can be calculated for the time interval of each apnea and each cluster to derive an apnea or cluster index of saturation-pulse during apnea and recovery in a manner analogous to that described in U.S. Pat. No. 6,223, 064, which is hereby incorporated by reference herein. This provides an enhanced tool for severity indexing of apnea of prematurity in infants. Both the duration and the absolute value of any decrement in saturation-pulse are relevant. If desired, the average maximum instantaneous and cumulative deficit of the pulse saturation index can be calculated for each cluster (as by comparing to predicted normal or automatically calculated, non apnea related baseline values for a given patient).

In this way, in accordance with embodiments of the present invention, a general estimate of oxygen delivery over time to the infant brain is provided using a non-invasive pulse oximeter. This estimate is derived through the calculation of both oxygen saturation and pulse over an extended time series deriving a cumulative deficit specifically within clusters of apneas to determine index of the total extent of global decrease in oxygen delivery to the brain during apnea clusters. The deficit can be calculated in relation to either the baseline saturation and pulse rate or predicted normals.

The processor can provide an output indicative of the pulse saturation index, which can include an alarm, or the processor can trigger an automatic stimulation mechanism to the neonate, which will arouse the neonate thereby aborting the apnea cluster. Stimulation can include a tactile stimulator such as a vibratory stimulator or other device, which preferably provides painless stimulation to the infant, thereby causing the infant to arouse and abort the apnea cluster.

In another embodiment of the present invention, the recognition of a particular configuration and/or order of objects can trigger the collection of additional data points of another parameter so that these new data points can be added to and compared with the original time series to recognize or confirm an evolving pathophysiologic process. One application of this type of system is shown in FIG. 8 and illustrated further in FIG. 17. The time series of pulse, oxygen saturation, and/or cardiac rhythm can be used to trigger an automatic evaluation of blood pressure by a non-invasive blood pressure device. The bedside processor, upon recognition of tachycardia by evaluation of the pulse or EKG tracing, automatically causes the controller of the secondary monitoring device 40 to initiate testing. The nurse is then immediately notified not only of the occurrence, but also is automatically provided with an indication of the hemodynamic significance of this arrhythmia. In this situation, for example, the occurrence of an arrhythmia lasting for at least twenty seconds can trigger the automatic comparison of the most recent blood pressure antecedent the arrhythmia and the subsequent blood pressure, which occurred after the initiation of the arrhythmia. The processor identifies the time of the initial blood pressure, which occurred prior to the point of onset of the arrhythmia, and the time of evaluation of the blood pressure after the onset of the arrhythmia. These parameters may be provided in a textural output so that the nurse can immediately recognize the hemodynamic significance of the arrhythmia. Upon the development of a pulseless arrhythmia, a printed output is triggered which provides a summary of the parameter values over a range (such as the 5-20 minutes) prior to the event as well as at the moment of the event. These are provided in a graphical format to be immediately available to the nurse and physician at the bedside during the resuscitation efforts so that the physician is immediately aware if hyperventilation, or oxygen desaturation preceded the arrhythmia (which can mean that alternative therapy is indicated.

In accordance with another aspect of the present invention, if the patient does not have a non-invasive blood pressure cuff monitor attached, but rather has only a pulse oximeter or an impedance based non-invasive cardiac output monitor and an electrocardiogram attached, then the multi-level time series plethsmographic pulse objects can be used to help determine the hemodynamic significance of a given change in heart rate or the development of an arrhythmia. In this manner, the identification of significant change in the area under the curve associated with a significant rise in heart rate or the development of an arrhythmia can comprises a multi-signal object indicative of potential hemodynamic instability.

If the multi-signal object includes a new time series of wide QRS complexes of this occurrence is compared to the area under the plethesmographic pulse to determine the presence of "pulseless" or "near pulseless" tachycardia. It is critical to identify early pulseless tachycardia (particularly ventricular tachycardia) since cardioversion of pulseless tachycardia may be more effective than the cardioversion of ventricular fibrillation. On the other hand, ventricular tachycardia associated with an effective pulse, in some situations, may not require cardioversion and may be treated medically. Timing in both situations is important since myocardial lactic acidosis and irreversible intracellular changes rapidly develop and this reduces effective cardioversion. It is, therefore, very important to immediately recognize whether or not the significant precipitous increase in heart rate is associated with an effective pulse.

Figure 17:
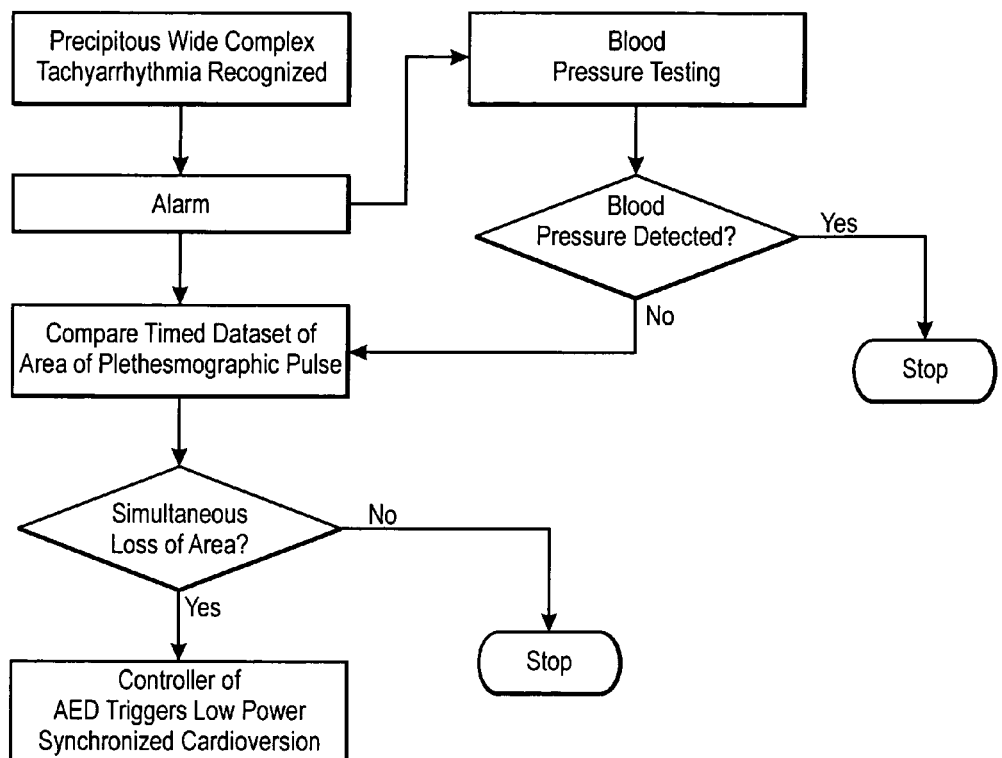
FIG. 17 is a diagram of a system for comparing multiple signals and acting on the output of the comparison in accordance with embodiments of the present invention.

The plethesmographic tracing of the oximeter can provide indication of the presence or absence of an effective pulse. However, displacement of the oximeter from the proper position on the digit can also result in loss of the plethesmographic tracing. For this reason, in accordance with embodiments of the present invention, the exact time in which the wide QRS complex time series developed is identified and related to the time of the loss of the plethesmographic pulse. If the plethesmographic pulse is lost immediately upon occurrence of a sudden increase of heart rate (provided that the signal does not indicate displacement), this is nearly definitive evidence that this is a pulseless rhythm and requires cardioversion. The oxygen saturation and thoracic impedance portion of the multi-signal object is also considered relevant for the identification of the cause of arrhythmia. At that moment, an automatic external cardioversion device can be triggered to convert the pulseless rhythm. In an alternative embodiment, as also shown in FIG. 17, a blood pressure monitor, which can be a non-invasive blood pressure monitor integrated with the automatic defibrillator, can be provided. Upon the recognition of a precipitous increase in heart rate, this event can trigger automatic non-invasive blood pressure evaluation. If the non-invasive blood pressure evaluation identifies the absence of significant blood pressure and pulse confirmed by the absence of a plethesmographic pulse, then the processor can signal the controller of the automatic cardio version unit to apply and electrical shock to the patient based on these findings. It can be seen that multiple levels of discretionary analysis can be applied. A first level of analysis could be the identification of a precipitous development of a wide complex tachyarrhythmia in association with simultaneous loss of plethesmographilc pulse which can trigger an automatic synchronized external cardio version before the patient develops ventricular fibrillation. A second level of analysis could include confirmation by another secondary measurement such as loss of blood pressure, the lack of the anticipated cycle of chest impedance variation associated with normal cardiac output as with a continuous cardiac output monitor, or other quality or confidence indicator.

It can be seen that even without the EKG time series component object an analysis of the multi-signal object can be applied to compare the area under the curve of the plethesmographic pulse tracing generated by a pulse oximeter to a plot of peak-to-peak interval of the pulse tracings. The sudden decrease in the peak-to-peak interval or increase in pulse rate in association with a sudden decrease in the plethesmographic area is strong evidence that the patient has experienced a hemodynamically significant cardiac arrhythmia. In the alternative, a moderate and slowly trending upward increase in heart rate in association with a moderate and slowly trending downward plot of the area of the plethesmographic pulse would be consistent with intervascular volume depletion, or ineffective cardiac output resulting from significant sympathetic stimulation which is reducing the perfusion of the extremities as with as congestive heart failure. During such a slow evolution, it would also be anticipated that the frequency of tidal respirations would increase.

Those skilled in the art will recognize that the information provided from the data and analysis generated from the above-described system can form the basis for other hardware and/or software systems and has wide potential utility. Devices and/or software can provide input to or act as a consumer of the physiologic signal processing system of the present invention's data and analysis.

Table 3, set forth below, provides a non-exhaustive list of examples of exemplary ways that the present physiologic signal processing system can interact with other hardware or software systems:

TABLE 3

1. Software systems can produce data in the form of a waveform that can be consumed by the physiologic signal processing system
2. Embedded systems in hardware devices can produce a real-time stream of data to be consumed by the physiologic signal processing system
3. Software systems can access the physiologic signal processing system representations of populations of patients for statistical analysis
4. Software systems can access the physiologic signal processing system for conditions requiring hardware responses (e.g. increased pressure in a CPAP device), signal the necessary adjustment and then analyze the resulting physiological response through continuous reading of the physiologic signal processing system data and analysis It is anticipated that the physiologic signal processing system will be used in these and many other ways. To facilitate this anticipated extension through related hardware and software systems the present system will provide an application program interface (API). This API can be provided through extendable source code objects, programmable components and/or a set of services. Access can be tightly coupled through software language mechanisms (e.g. a set of C++ modules or Java classes) or proprietary operating system protocols (e.g. Microsoft's DCOM, OMG's CORBA or the Sun Java Platform) or can be loosely coupled through industry standard non-proprietary protocols that provide real-time discovery and invocation (e.g. SOAP [Simple Object Access Protocol] or WSDL [Web Service Definition Language]).

In accordance with an exemplary embodiment of the present invention, the physiologic signal processing system with the API as defined becomes a set of programmable objects providing a feature-rich development and operating environment for future software creation and hardware integration.

Although embodiments in accordance with the present invention have been described, which relate to the processing of physiologic signals, it is also critical to recognize the present streaming parallel objects based data organization and processing method can be used to order and analyze a wide range of dynamic patterns of interactions across a wide range of corresponding signals and data sets in many environments. The invention is especially applicable to the monitoring of the variations or changes to a physical system, biologic system, or machine subjected to a specific process or group of processes over a specific time interval.

Embodiments of the present invention may provide a general platform for the organization and analysis of a very wide range of datasets during hospitalization or a surgical procedure. For example, in addition to the time series of the monitored signals parameters, which may be sampled at a wide range (for example between about 500 hertz and 0.01 hertz), previously noted, the cylindrical data matrix can include a plurality of time series of laboratory data, which may be sampled on a daily basis or only once during the hospitalization. These data points or time series are stored as objects and can be included in the analysis. These objects can include, for example, the results of an echocardiogram wherein a timed value ejection fraction of the left ventricle is provided as an object in the matrix for comparison with other relationships. In application, the presence of a low ejection fraction object along the matrix with a particular dynamic cyclic variation relationship between airflow and oxygen saturation time series can, for example, provide strong evidence of periodic breathing secondary to congestive heart failure and this identified relationship can be provided for the healthcare worker in a textual output. In another example, medication data is included in data matrix. For example, in a patient receiving digoxin and furosemide (a diuretic), the daily serum potassium time series is compared to a time series indicative of the number and severity of ventricular arrhythmias such as premature ventricular contractions. A fall in the slope of the potassium time series in association with a rise in slope of such an arrhythmia indication time series could for example produce an output such as "increased PVCs—possibly secondary to falling potassium, consider checking digoxin level." In another example, a first time series of the total carbon dioxide level and a second time series of the anion gap can be included in the general streaming object matrix and compared to the time series of airflow. If a rise in the slope or absolute values of the airflow is identified with a fall in the slope or absolute value along the total carbon-dioxide time series and a rise the slope or absolute values alone the anion gap time series, the processor can provide an automatic identification that the airflow is rising and that the cause of a rise in airflow may be secondary to the development of a potentially life threatening acidosis, providing an output such as "hyperventilation—possibly due to evolving anion gap acidosis". In another example, the daily weight or net fluid balance is included with the total carbon dioxide and anion gap in the cylindrical data matrix. The identification of a fall in slope of airflow or absolute value along with a fall in slope of the oxygen saturation, and a fall in slope of the fluid balance and weight can generate an output such as "possible hypoventilation-consider contraction alkalosis."

Alternatively with a matrix made up of the same parameters, a rise in the slope or absolute values of the airflow time series and a rise in the pulse time series may be recognized in comparison with a fall in the time series of the total carbon dioxide, a flat slope of the time series of the anion gap, and a rise in the slope or absolute values of the fluid balance time series, confirmed by a trending rise in slope of the weight time series, and a notification can be provided as "hyperventilation—potentially secondary to expansion acidosis or congestive heart failure." In one exemplary embodiment of the present invention, the cylindrical data matrix becomes the platform upon which substantially all relevant data derived during a hospitalization is stored and processed for discretionary and automatic comparison. Initial input values, which can be historical input, can also be included to set the initial state of the data matrix. For example, if the patient is known to have a history congestive heart failure, and that condition is accounted for as an initial data point at the start of the matrix, a particular conformation in the initial matrix may be considered in the analysis. The data matrix provides a powerful tool to compare the onset of dynamic changes in parameters with any external force acting on the organism whether this force is pharmacological, a procedure, related to fluid balance, or even simple transportation to other departments for testing. In one exemplary embodiment, as shown in FIG. 1b, a time series of action applied to the patient is included in a time series that may be referred to as an "exogenous action time series." This time series includes a set of streaming objects indicating the actions being applied to the patient throughout the hospitalization. In this example, within the exogenous action time series, a time series component indicative of dynamic occurrence of a particular invasive procedure, such as the performance of bronchoscopy, is included. This "bronchoscopic procedure object" may, for example, comprise a time series component along the exogenous action time series of 15 minutes within the total matrix derived from the hospitalization. The dynamic relationships of the parameters along the matrix are compared with the onset of the procedure (which comprises an object onset), dynamic patterns of interaction evolving subsequent to the onset of the procedure can be identified and the temporal relationship to the procedure object identified and outputted in a similar manner as has been described above for other objects. The dynamic patterns of interaction can be interpreted with consideration of the type of procedure applied. For example, after a 15 minute time series associated with a bronchoscopic procedure, the occurrence of a progressive increase in slope of the airflow time series associated with a significant decrease in the slope of the inspiration to expiration slope ratio time series suggests the development of bronchospasm secondary to the bronchoscopy and can initiate an output such as "hyperventilation post-bronchoscopy with decreased I:E—consider bronchospasm."

A larger surgical procedure comprises a longer cylindrical data matrix and this can comprise a perioperative matrix, which can include the portion of time beginning with the administration of the first preoperative medication so that dynamic patterns of interaction are compared with consideration of the perioperative period as a global time series object within the matrix. The preoperative period, the operative period, and the post operative period may be identified as different time-series segments of the matrix within the total hospital matrix. Using this object-based relational approach, a "dynamic pattern" of interaction occurring within this procedure-related data stream or subsequent to it can be easily recognized. The dynamic pattern may then be temporally correlated with the procedure so that the dynamic relationships between a procedure and plurality of monitored time series outputs and/or laboratory data are stored, analyzed, and outputted. In another example, the continuous or intermittent infusion of a pharmaceutical such as a sedative, narcotic, or inotropic drug comprises a time series which has as one of its timed characteristics the dose administered. This new time series is added to the cylindrical matrix and the dynamic relationships between monitored signals and laboratory data is compared. For example after the initiation of Dobutamine (an inotropic drug) the occurrence of a rising slope of pulse rate or a rising slope of premature ventricular contraction frequency, or the occurrence of an object of non-sustained ventricular tachycardia, can be recognized in relation to onset the time series of medication infusion or a particular rise in the slope or absolute value of the of the dose of this medication. In another example, the occurrence of a dynamic clustering of apneas such as those presented in FIGS. 10, 11, and 5c in relation to a rise in slope, or a particular absolute value, of the time series of the sedative infusion can be identified and the pump can be automatically locked out to prevent further infusion. An output such as "Caution—pattern suggestive of mild upper airway instability at dose of 1 mg Versed" may be displayed and/or printed. If, in this example, the nurse increases the dose to 2 mg and the pattern shows an increase in severity, an output such as "Pattern suggestive of moderated upper airway instability at dose of 2 mg/hr. of Versed-dose locked out" may be displayed and/or printed. To maintain Versed dose at the 2 mg level in this patient, the nurse or physician would have to override the lockout. Upon an override, the processor then tracks the severity of the clusters and, if the clusters reach a additional severity threshold then an output such as "Severe upper airway instability—Versed locked out" may be displayed and/or printed.

The anticipated range of time series for incorporation into the cylindrical relational matrix of streaming objects include multiple pharmaceutical time series, exogenous action time series, monitored signal time series (which can include virtually any monitored parameter or its derivative), fluid balance, weight, and temperature time series. Time series or single timed data points of laboratory values (including chemistry, hematology, drug level monitoring), and procedure based outputs (such as echocardiogram and pulmonary function test outputs) may also be included. Interpreted radiology results may also be incorporated as data points and once the digital signal for such testing can be reasonably summarized to produce a time series, which reliably reflects a trend (such as the degree of pulmonary congestion). Such outputs can also be included in the data matrix as time series for comparison with for example the net fluid balance and weight time series. An additional time series can be the provided by nursing input, for example, a time series of the pain index, or Ramsey Scale based level of sedation. This time series can be correlated with other monitored indices of sedation or anesthesia as is known in the art.

The cylindrical matrix of processed, analyzed, and objectified data provides a useful tool for the purpose of doing business to determine, much more exactly, the dynamic factors, occurrences, and patterns of relationships, which increase expense in any timed process. In the example of the hospital system discussed above, the expense data is structured as a time series of objects with the data point value represented by the total expense at each point. Expense values can be linked and/or derived from certain procedures or laboratory tests, for example the time series of the hemoglobin can be associated with a corresponding time series of the calculated expense for that test. In an exemplary embodiment, the plurality of time series of expenses for each monitored laboratory tests are combined to produce a global expense time series. Individual time series for the expense of each class of exogenous actions (such as pharmaceutical, and procedural time series) may also be provided and can then be combined to form one global expense time series. This may be incorporated into the cylindrical data matrix to provide discretionary comparison with dynamic expense variables and dynamic patterns of relationships of other variables. This allows the hospital to determine the immediate expense related to the occurrence of an episode of ventricular fibrillation. This expense can be correlated with, for example, the timeliness of treatment, the application of different technologies, or the presence of a specific dynamic pattern of interaction of the signals. In other words, the immediate cost, and resources expended over, for example, the 24 hours following the episode of ventricular fibrillation, can be compared with the true behavior and duration of the pathophysiologic components relating the ventricular fibrillation episode.

In a further example consider a patient monitored with an embodiment of the present invention deriving a cylindrical data matrix comprised of streaming and overlapping objects of airflow, chest wall impedance, EKG, oximetry, and global expense. The occurrence of the procedure for insertion of the central line represents an object (which need not have a variable value) along a segment of the cylinder. If the patent develops a pneumothorax, the processor can early identify and warn of the development of pathophysiologic divergence with respect to the airflow (and/or chest wall impedance) and the oxygen saturation (and/or pulse). In addition to earlier recognition, the expense related to this complication, the timeliness of intervention, the magnitude of pathophysiologic perturbation due to the complication, and the resources expended to correct the complication can all be readily determined using the processor method and data structure of the present invention.

In a further example, consider a patient monitored with an embodiment of the present invention deriving a cylindrical data matrix comprised of streaming and overlapping objects of airflow, chest wall impedance, EKG, oximetry, and global expense. The occurrence of the procedure for insertion of the central line represents an object (which need not have a variable value) along a segment of the cylinder. If the patent develops a pneumothorax, the processor can early identify and warn of the development of pathophysiologic divergence with respect to the airflow (and/or chest wall impedance) and the oxygen saturation (and/or pulse). In addition to earlier recognition, the expense related to this complication, the timeliness of intervention, the magnitude of pathophysiologic perturbation due to the complication, and the resources expended to correct the complication can all be readily determined using the processor method and data structure in accordance with embodiments of the present invention.

Many other additional new component time series and "cylinders of ascending parallel time series" may be added to the matrix. During the implementation of the present invention it is anticipated that many subtle relationships between the many components will become evident to those skilled in the art and these are included within the scope of this invention.

Many indices of instability are definable within the scope of this teaching. One example of a useful mathematical relationship calculated by a system in accordance with an exemplary embodiment of the present invention may be derived as set forth below.

The percentage of time during the selected measurement interval wherein the airway is functionally unstable (and cycling) can be defined by the ratio:

$$Tu/Tt$$

where Tu is a time unstable, and Tt is a time total.
However all unstable time is not equal. To quantify the severity of instability within Tu the following formula is applied:

$$Tr/Tc$$

where Tr is a time of recovery and Tct is a time of closure.

For example, when SPO2 is the parameter under test, this would be (Duration of SPO2 Fall)/(Duration from beginning of next SPO2 rise to beginning of next fall). From this can be derived a "ratio of instability ratios" as:

$$VII=[Tu/Tt]/[Tr/Tc]$$

where VII is the Ventilation Instability Index (or Hypoventilation Instability Index or Instability Index).

This Instability Index is parameter nonspecific and is applicable to a wide range of discretionary time intervals and to the time interval selected for the test, which may be selectable, for example, using a menu. The index can then be adjusted for the parameter under test (e.g. SPO2 or Pulse) rendering, for example, a desaturation instability index, a heart rate instability index or a pulse amplitude instability index to name a few. Indeed, the instability index can be calculated and adjusted for non-medical signals such as signals of movement, signals of electromagnetic energy, biologic time series, mechanical time series, and financial signals, such as a time series of a financial index to name a few.

In one example of this adjustment we multiply the VVI by the mean perturbation amplitude of the target event under test (for example the Desaturation instability index is calculated as:

$$DVII=(D)Tu/Tt]/[Tr/Tc]$$

Where D=mean amplitude of the fall events within the clusters (note that dPulse amplitude, or dheart rate would be used for those indices if desired).

In one example, DAVII can be calculated as: (10) (D) [Tu/Tt]/[Tr/Tc]. For this example, it is desirable that the recovery (interapnea interval) is not the mean interapnea interval for the time period under test but rather the mean interapnea interval within the unstable (cycling) time and excludes recovery time between clusters.

In one exemplary embodiment, the analysis system determines an "SPO2 Wake-Sleep Gradient," an "SPO2 Wake-REM gradient" and/or an "SPO2 Non REM-REM gradient." To achieve this, the system can, for example, determine a baseline value of SPO2 (as, for example, over a 5 second to 15 minute period of resting wakefulness, although other time periods may be used) and then determine the SPO2 value during a period of sleep, (or a period a particular sleep stage such as REM) wherein the SPO2 value is not exhibiting a cluster pattern (for example this may be the average of the SPO2 over a 5 second to 15 minute period of REM). This determination can for example be the point or range of points immediately preceding the onset of the first cluster after sleep onset. According to one aspect of the present invention, the difference between the awake SPO2 and the sleep SPO2 is outputted as by print or other output. This value is different than the average value of SPO2 during wakefulness or a sleep stage, which includes cluster related values. The SPO2 Wake-Sleep Gradient can be a useful indication of the stability of ventilatory control during sleep. For example, patients with SPO2 Wake-Sleep Gradients of 4%-8% or more are often exhibiting a significant decline in ventilation control in response to assumption of a given sleep state especially if this decline is progressive on sleep onset, and/or ends with the onset of a cluster. This sleep onset related fall in ventilation and/or SPO2 which ends in the onset of a cluster pattern may be called a "Pattern of Transitional Instability" and provides evidence concerning the phenotype of the patient's sleep disordered breathing, as defined by suboptimal central ventilation control during sleep. Such patients may be at risk for exhibiting severe worsening later in sleep with incomplete arousals especially during REM sleep. A Wake-Sleep Gradient and the detection of the Pattern of Transitional Instability can be similarly achieved by analysis of airflow parameters (as, for example, by CO2 or minute ventilation to name a few) and for transcutaneous parameters such as CO2 and/or PO2.

In another embodiment, an implanted pacemaker may be programmed to record the ventilation patterns with a sampling rate sufficient to detect the instability clusters. The recording can be continuous or intermittent and can be triggered by an internal clock or by an action or inaction of the patient (for example, as by sensors recognizing the assumption of a specific type or range of body positions, such as horizontal body position, or a sensor detecting a lack of movement (as by incorporated atigraphy)). In one embodiment, the pacemaker stores the ventilation data sets for automatic or manual retrieval by an external pacemaker interrogator. The datasets are then analyzed for detection and severity indexing of Cheynne Stokes respirations or sleep apnea, which can be useful in monitoring the severity of heart failure. This provides a method for monitoring heart failure and for detecting sleep disordered breathing in patients with indwelling pacemakers. The interrogator can include memory for storage of the ventilation datasets and software for analyzing those data sets for sleep disordered breathing as by detecting clusters. In one method, a pulse oximeter probe is applied to a body part and the overnight time series of oxygen derived from the oximeter and the timed datasets of EKG, ST segment position, and ventilation derived from the pacemaker are compared with a contemporaneously time series from the oximeter.

In an exemplary embodiment of the present invention, a signal pattern viewer is provided. This viewer is preferably accessible directly from the patient's medical record in the hospital information system or from, for example, the display of a mechanical ventilator. When a healthcare worker requests access, the viewer component loads and accesses the physiologic time series data from a local database or through services to a centralized data repository into which the time series from the patient monitors are continuously or intermittently updated and stored. The view component processes and analyzes the physiologic time series data and the image of the processed signals is then displayed. In one example, this image can be a pre-selected grouping of processed and analyzed parallel time series of different parameters or can be a group of parameters indicated through a set of user gestures. Upon loading, the processor can then output a series of two-dimensional cross-sections defining three-dimensional representation of the parameters. This can be accomplished, for example by displaying the parameters in different quadrants of a two-dimensional representation, which can be rendered with the points connected to enhance the image. The incremental distance values from the center of the all the intersecting quadrants can be defined for each parameter by placing the normal ranges equidistant form the center.

In one embodiment, the three-dimensional representation is tubular in appearance, but with flat sides of a predetermined color (for example, green), the sides equal to the number of parameters in the group when the values are normal. The respective walls of the tube bow in or out if one or more of the parameters deviate from the normal range and the walls turn a different color (for example, yellow) and then yet another color (for example, red) when the values fall or rise to threshold levels. A bi-directional arrow may be shown across the tube between two parameters when a relational breach or pathophysiologic divergence is identified. The system may be adapted to provide the healthcare worker with the option to move through the three-dimensional representation along the time axis with each sequential cross-section appearing on the display in a manner similar to the scrolling through CT scan images provided to heath care workers today. For example, with each user gesture, the user requests advancement along the time axis (the longitudinal axis of the tube) to the next sequential cross-section image or layer. The two-dimensional image represents a plurality of data points of different parameters in a predefined spatial relationship that visually and simultaneously displays both the relationship to other parameters and the relationship to normal values with each cross-sectional image. This provides immediate visual cues to the healthcare worker of the relational state of the parameters to normality and to other parameters. Upon scrolling the timing of these relationships and detected deviations form normality (which may be relational) are dynamically evident with rapid iteration, which can be automated providing a pseudo animation of the three-dimensional representation (as by scrolling back and forth). Examples of parameters that can be included within the representation include the parameters previously discussed as well as body dimension characteristics (for example, weight), temperature, laboratory values (such as hemoglobin or white blood cell count), and financial (or resource) expenditure to name a few. In another embodiment the viewer emulates the instant or a series of prior medical monitor representations (such as, for example an oximeter or ventilator). This allows a physician, for example, to view the patient's medical records in a remote location through ubiquitous standard secure internet protocols to see a simulation of the monitor, which would otherwise be visible only at the bedside. The viewer may also provide a reanimation of the patients signals as will be discussed. Different options for viewing the signals in these and other ways may be selectable by the user, as by a pull down window, so that the user can choose to render and view the various time series in his or her preferred viewing mode.

Another exemplary embodiment of the invention may be adapted to assist in the classification of the type of a patient's sleep-disordered breathing by iterating though the patterns outputted and or responses of the patterns to therapy to define the best match. For the purpose of illustration, an exemplary embodiment of the present invention may be adapted to prioritize and weight a plurality of characteristics associated with a condition of interest such as sleep-disordered breathing. Parameter patterns associated with the plurality of characteristics and/or appropriate treatment responses may be characterized along at least one time series. An iterative operation may be performed on the characteristics to compare the patterns and treatment responses (such as a prolonged fall in SPO2 terminated by a cluster) to each type grouping. The best matching type may be identified and an output of an indication based on the best matching type provided. The treatment of a patient may be adjusted based on the identification of the best matching type.

By way of example, the patterns of sleep-disordered breathing may be divided into five primary types, each with a grouping of different characteristics. In one embodiment, the processor is programmed to detect at least one of the characteristics below and to take at least one of the following actions based on the detection of the characteristic or combination of characteristics: output an indication of the characteristic, output an indication of the most likely type or combination of types of sleep disordered breathing, output an indication of the therapy most likely to be effective, automatically adjust treatment to the therapy most likely to be effective, provide a graded auditory or visual alarm. The five types of sleep disordered breathing are:

Type I. Upper Airway Instability—Obstructive Sleep Apnea, characterized by:
1. Paroxysmal reentry derived clusters often with precipitous onset and termination.
2. Variable length of paroxysmal clusters.
3. Paroxysmal clusters are commonly separated by intervals of stable time having variable lengths.
4. Variable amplitude of reciprocations (SPO2 often falls below about 85% or less).
5. Very precipitous reciprocation recoveries.
6. SPO2 "fall to rise" slope ratio commonly less than about 1.
7. Elimination of clusters is generally complete with CPAP alone.
8. Complete reciprocations even during REM (fall to rise amplitude ratio of greater than 0.8 and usually about 1) and/or the peak of the recovery exceeding 85-90.
9. Severity of clusters and amplitude of reciprocations increase during REM.
10. Severity of clusters and amplitude of reciprocations increase with various body positions.
11. Periods of prolonged slow reciprocations with brisk recoveries occasionally occur between typical rapidly cycling clusters (as due to obstructive hypoventilation).
12. Cluster Pattern is often defined by regular reciprocations but reciprocations also can be irregularly irregular.
13. Nasal oxygen alone reduces but generally fails to eliminate moderate or severe SPO2 clusters.

14. Nasal oxygen alone fails to improve (and may increase) the severity of airflow clusters.
15. Low or normal Baseline awake SPO2.

Type II. Hypo-sensitivity/Hypo-responsive Induced Ventilation Instability (Primary hypoventilation represents a rare pure form of this process), characterized by:
1. Cyclic Periods of prolonged reciprocations with slow declines (greater than 3 minutes but often 10-20 minutes or more) with brisk recoveries may occur generally without rapidly cycling clusters.
2. Spontaneous precipitous recovery and/or precipitous recovery upon the occurrence of a stimulus to the patient such as an auditory alarm.
3. Increased SPO2 and or CO2 wake-sleep gradient.
4. Incomplete reciprocations (for example with an amplitude ratios of less than about 0.8 and/or a peak of the recoveries being less than 85-90) are common, especially during REM.
5. Variable (often high) amplitude of reciprocations (SPO2 often falls below 85% during reciprocation).
6. Precipitous recoveries (but sometimes incomplete).
7. Amplitude of desaturation component of reciprocations often increases with REM.
8. Elimination of prolonged reciprocations is often incomplete with even high levels of CPAP (indicates a central component).
9. Complete elimination of SPO2 clusters and low SPO2 often achieved with BIPAP but often requires an IPAP-EPAP difference of greater than 4, full face mask, and backup rate.
10. SPO2 "fall to rise" slope ratio less than 1 and generally very low such as for example 0.1 or 0.2 or less.
11. Sustained falls in SPO2 often responds completely to low flow oxygen alone but the falls in airflow or other ventilation signals may be unaffected or worsened by oxygen alone.
12. Low or normal Baseline awake SPO2.

Type III PolymorphicIII (Complicated) Sleep Apnea (generally a combination of type I one and type II), characterized by:
1. Incomplete reciprocations (for example with amplitude ratios of about 0.8 or less and or recovery peaks of leas than about 90-85 or less)) are common, especially during REM.
2. Periods of prolonged reciprocations with slow declines (greater than 3 minutes but often 10-20 minutes or more) with brisk recoveries may occur between rapidly cycling clusters.
3. A plot of the amplitude of the peaks can look similar to a plot of a Type II patient indicating progressively weaker functional arousal (physiologic recovery) response followed by improvement in the functional arousal (physiologic recovery) response.
4. Increased SPO2 wake-sleep gradient (high delta).
5. Highly unstable nadirs and unstable peaks.
6. Clusters often begin after prior progressive (often slow) fall in SPO2 of 4-8% or more.
7. Variable (often high) amplitude of reciprocations (SPO2 often falls below 85% during reciprocation).
8. Precipitous Recoveries (but sometimes incomplete).
9. Cluster pattern is often regular but also can be irregularly irregular.
10. SPO2 "fall to rise" slope ratio less than 1 is most common.
11. Low or normal baseline awake SPO2 (low 90s or high 80s is typical).

Type IV Delayed Response Induced Ventilation Instability (e.g. Cheyenne Stokes Respiration), characterized by:
1. Monotonous "waxing and waning" pattern often with slow and/or prolonged reciprocation recoveries.
2. Regularly, regular pattern with monotonous (often about 40-70 second) cycle length for most of the night with 15-30 minute periods of stability due to REM sparing.
3. Clusters often begin with the onset of sleep without prior fall in SPO2.
4. SPO2 "fall to rise" slope ratio often near about 1 (but also commonly less than 1).
5. Partial reduction in reciprocation amplitude may occur with CPAP.
6. Increase in reciprocation amplitude with BiPAP.
7. REM sparing.
8. Both Airflow and SPO2 Cluster are often very responsive to nasal oxygen alone.

Type V Hyper-sensitivity/Hyper-responsive Induced Ventilation Instability, characterized by:
1. Clusters begin with the onset of sleep without prior fall in SPO2.
2. Clusters of central apneas often with obstruction at end of the apneas low amplitude of reciprocations (desaturation often fails to fall below about 90%).
3. Precipitous recoveries of reciprocations.
4. Clusters more severe with high CPAP or BiPAP.
5. REM sparing may occur.
6. Often high awake baseline SPO2.
7. SPO2 clusters (but not airflow clusters) are often eliminated by low flow oxygen.

Additional categories of breathing may be employed if desired, such as: Type VI. Non-Hypoventilation induced Hypoxemia, characterized by:
1. SPO2 fall is associated with at rise in minute ventilation (pathophysiologic divergence)
2. Sustained (greater than 3 minute and often 20-60 minute or more) falls in SPO2
3. Slow SPO2 recoveries
4. Often responds completely to oxygen but may require high flow (46 liters per minute)
5. Often fails to respond to CPAP or BiPaP Considerable overlap between the types of sleep disordered breathing commonly occurs.

In another exemplary embodiment, the system detects a cluster pattern of timing delay or of spatial variation between similar physiologic events measured at different sites on the body. Such a cluster patterns is induced, for example, by a rise in sympathetic tone which reduces the diameter of the tiny blood vessels in the fingers thereby causing a delay or slope attenuation at a second sensing site in comparison with a first sensing site wherein the second site receives blood flow from vessels which are narrower or longer than at a first site. In an example, the method can include the application of a first pulse oximetry probe to a first site and a second pulse oximetry probe to a second site the second site being more remote form the heart than the first site. The first site can, for example the thumb, ear, or forehead and the second site can be, for example the third digit or another digit. For example a combination of the thumb and third digit may be used since the middle finger generally has considerably longer small vessel supply through the palmar arch and the digit itself.

A time series of the plethesmographic pulse is derived from both sites in parallel and a cluster pattern of variance between matching characteristics of the plethesmographic pulse (for example the characteristics noted in the previous listing) is defined. For example, a time series of the delay between the upstroke onset, and/or peak of the pulse waveform at the second site in comparison with the first site. In another example, a time series is provided comprised of the difference in slope of pulse waveform at the second site and the first site (for example, of the difference in slope of the upstroke at each site). These relational time series can then be analyzed to monitor sympathetic tone, which rises for example with drug infusion or hemorrhage and for detection of clusters to indicate the presence of clusters of variations in sympathetic tone or the presence of sleep apnea or other disease processes.

The time series of delay can also be rendered for time series of different parameters, for example the delay between matching characteristics of the arterial pulse waveform and the pleth waveform or the onset of the QRS and the onset of the rise of the pleth waveform. In one embodiment, a single oximeter is used with the output triggering light delivery split or with rapidly alternating light delivery to each probe to allow the pleth to be derived from each site with a single pulse oximetry unit. In another embodiment, a plurality of oximeters are used and each time series is analyzed in parallel to derive the time series of the delay or variation difference or to otherwise track the delay or variation difference.

In one exemplary embodiment, a system especially useful for home detection of sleep apnea comprises or includes a very small, low power, battery-operated pulse oximeter, which may be patient mountable to the hand, wrist, forearm, upper arm, head adjacent the ear, nose, forehead, around the neck or the like. The oximeter preferably includes a transmitter, or has sufficient memory for storage of at least 7-8 hours of a time series of high fidelity pethesmographic pulse waveforms along with a high fidelity time series of the SPO2 with or without a time series of the heart rate. The SPO2 data is desirably recorded or transmitted with a sampling rate of about 0.5-1 hertz, although a slower or faster sampling rate can be used depending on system design considerations. As an example, the plethesmographic pulse could be recorded or transmitted with a sampling rate of 25 hertz or higher with a transmission of data in packets to a receiver updating every five seconds to save power. The pluralities of stored time series recordings may then be downloaded into an analysis program for analysis and viewing using, for example, a modem or a direct connection. The plurality of time series are then analyzed for clusters for the detection and characterization of sleep disordered breathing. In one embodiment, this oximeter can be connectable (for example removably dockable or integrally combined with) a pressure or flow sensing device (as may be deployed with a nasal cannula and/or with a positive pressure delivery device). The system may desirably include sufficient memory to record parallel high-fidelity time-series of airflow to produce an additional parallel time series for downloading with the time series grouping from the oximeter. One exemplary method includes detecting pathophysiologic occurrences that may represent abnormal patient conditions. Another exemplary method may comprise generating a plethesmographic output, generating an SPO2 output, programming a processor to compare the at least one component of plethesmographic output to at least one component of the SPO2 output to detect a pathophysiologic occurrence or the like.

The component of both the plethesmographic pulse and SPO2 compared can include, for example, the patterns or frequency of the variation of amplitude, slope of the upstroke, area under the curve, cycling, timing, or rate to name a few and these can be compared for example using the processing methods discussed supra or by another method.

In another exemplary embodiment, a nasal cannula (such as a dual lumen nasal cannula capable of both delivering oxygen and sensing airflow, pressure waveforms and or CO2 waveforms) is deployed in connection with a processor for storing a time series of airflow, pressure waveforms and or CO2 preferably with a parallel time series indicative of the flow rate of oxygen delivered to or flowing to the cannula. The time series of parameters derived from this multi-function cannula is then analyzed for clusters indicative of ventilation instability in relation to oxygen flow (or to identify disconnect of the nasal cannula from the nose). The analysis can be provided in real-time and can, for example, be triggered by automatically by a patient-related action or physiologic output as by an actigraph or body position indicator or manually by the patient.

Another exemplary embodiment for relational processing comprises a mechanical ventilator with integrated circulatory monitoring. In this embodiment, at least one time series of at least one parameter derived from a mechanical ventilator such as the 840 Ventilator manufactured by Nellcor Puritan Bennett, (and which can also include a positive pressure delivery device such as a CPAP unit or Bilevel ventilator) is analyzed in combination with a parallel time series derived from the flow of blood in at least one blood vessel. For example, a time series of the minute ventilation and/or the inspiration to expiration (I:E) ratio can be monitored in combination with a time series of the blood pressure from an invasive or noninvasive monitor, heart rate, cardiac output or another circulatory parameter. The processor can then output the relationship between pattern of the circulatory parameter and patterns of variations of the parameter derived from the mechanical ventilator. In one embodiment, the mechanical ventilator is configured to receive signal indicative of at least one circulatory parameter and a relationship between circulatory parameters and the ventilation parameters are displayed on the operator facing ventilator display as well as the changes in circulatory parameters in association with changes in ventilator output. For example, this display can be of the types discussed previously for the signal viewer embedded in the patient's medical record.

For example, parallel time series of minute ventilation and heart rate (as for example derived from an oximeter that functions as a circulatory monitor), pulse amplitude, and or blood pressure to name a few, may be displayed on the ventilator screen to assist the operator in defining ventilator parameter settings, which are optimal both from a circulatory and respiratory perspective. In one embodiment, the ventilator is configured to trigger or to queue the manual triggering of a measurement of blood pressure prior to initiating a change in ventilator settings and then again within a short period of time after the change. A difference in the blood pressure is identified on the ventilator display. When the ventilation indexing oximeter is included as part of the mechanical ventilator the detection of SPO2, minute ventilation divergence can be derived along with the detection of alterations in circulation in response to changes in the ventilator settings. In another embodiment, the variation in amplitude of the pulse pressure or variation in amplitude of the plethesmographic pulse in association with the inspiration and expiration cycle is determined and for example plotted as a time series of the variation. In another example, the amplitude of the plethesmographic pulse can be plotted in parallel with volume time curve or pressure time curve or another ventilation time series on the display of the mechanical ventilator. The operator therefore has immediate visualization of the effect of any change in ventilation (or change in intravascular volume) on a plethesmographic pulse parameter (such as the amplitude, area under the curve, or slope of the upstroke to name a few). In one embodiment, the ventilator has an input for a high fidelity plethesmographic pulse (for example, from a pulse oximeter), a high fidelity pressure tracing from an arterial line, an input from a noninvasive blood pressure device, which if the device uses a compression cuff can include a high fidelity plethesmographic tracing from the arm under the cuff during partial and/or complete inflation and the actual systolic and diastolic blood pressure readings. With this embodiment, parallel vascular pressures and pulmonary pressures are provided (preferably in real time) on the ventilator display. Indices and differences derived of these values can also be presented and chosen for example from a menu on the display. In another exemplary embodiment, outputs that relate to oxygen delivery such as intermittent or continuous cardiac output, mixed venous or central venous oxygen saturation, or the arterial to mixed venous saturation difference are inputted to the ventilator and provided as analyzed time series on the ventilator display. In one embodiment, the processor is programmed to automatically detect a relationship of a vascular or oxygen delivery parameter in relation to a ventilation parameter (such as a 30% variation in plethesmographic amplitude) in relation to the variation in positive airway pressure associated with inspiration and expiration.

Figure 18:
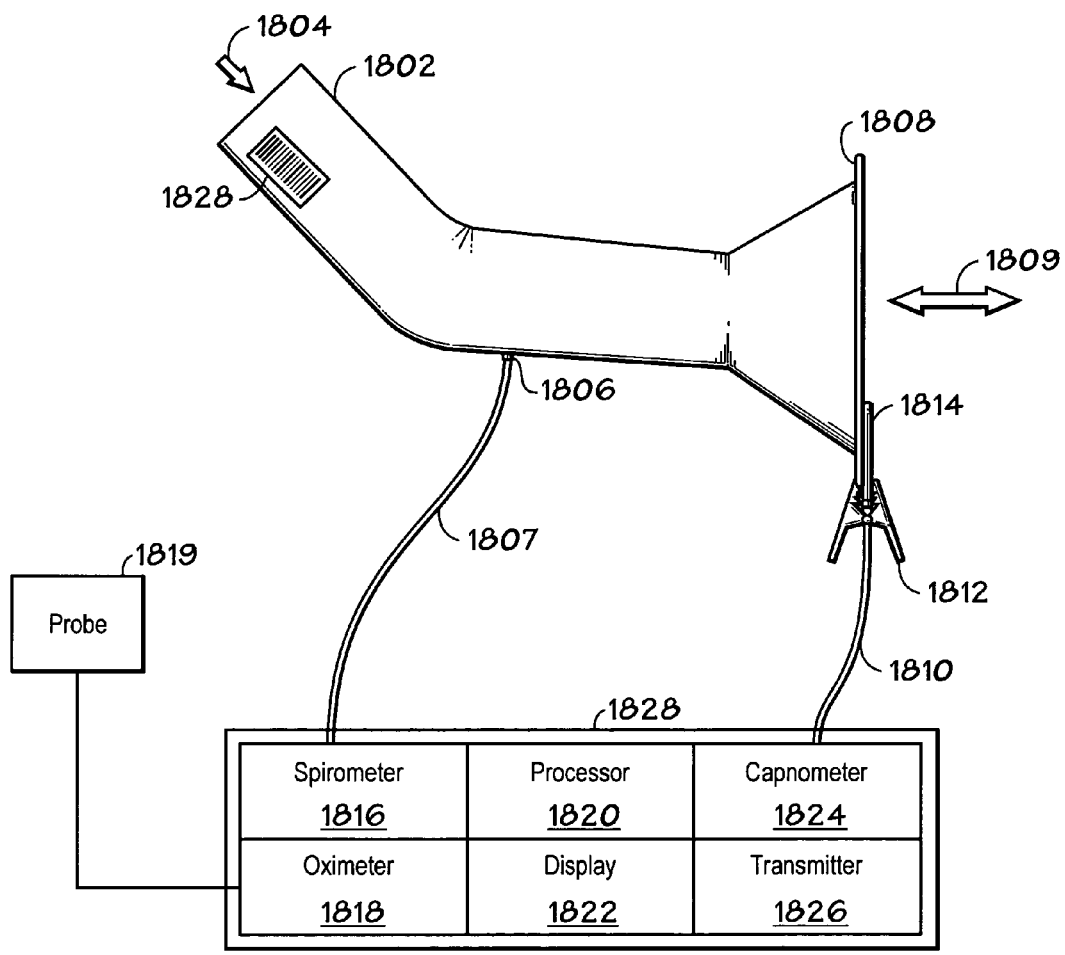
FIG. 18 is a block diagram of a spirocapnoximetry system in accordance with an exemplary embodiment of the present invention; and analyzed in accordance with an exemplary embodiment of the present invention.

Another exemplary embodiment for relational processing is comprised of a spirocapnometer. FIG. 18 is a block diagram of a spirocapnometer in accordance with an exemplary embodiment of the present invention. The spirocapnometer is generally referred to by the reference number 1800. The spirocapnometer 1800 comprises a flow tube 1802. The flow tube 1802 receives a gas flow 1804 from the mouth of a patient. The patient's lips provide a seal around the end of the flow tube 1802. The flow tube 1802, which may comprise a disposable penumotachometer, includes a pressure sensing port 1806. The pressure sensing port 1806 is connected to a tube 1807, which delivers a portion of the gas flow 1804 to a spirocapnometer 1816.

The flow tube 1802 may have a flange covered with a screen or filter 1808. The flow tube 1802 may additionally comprise a pilot tube 1810 that is adapted to deliver a portion of the gas flow 1804 to a capnometer 1824. The pilot tube 1810 may be clipped onto the flange of the flow tube 1802 by a clip 1812. A tip 1814 of the pilot tube 1810 may face up, in, or out and can have a very small diameter lumen. If desired, a flow detecting mask, as may be provided for example by incorporating a flow tube into the lower port of a soft plastic mask (the lower port of these masks is now conventionally used to attach a medication nebulizer) may be provided.

The spirocapnometer 1800 may comprise a housing 1828 that houses a plurality of instruments. The housing 1828 may house the spirocapnometer 1816 and the capnometer 1824, as well as one or more of an oximeter 1818, a processor 1820, a display device 1822 and a transmitter 1826 (such as a telemetry transmitter). The housing 1828 may assume a wide range of configurations, including a handheld configuration or a fixed configuration, such as for positioning on a rolling stand.

The exemplary embodiment illustrated in FIG. 18 can provide continuous and spot assessment of respiratory status in the emergency room or on the awards. A flow sensor that is preferably disposable (such as a pneumotachometer of a spirometer) is connected with a capnometer to produce a spiro-capnometer. This device provides for the derivation of a time series of exhaled CO2 along with the time series of flow during a forced exhalation maneuver, which can include an exhalation of the expiratory reserve volume or vital capacity maneuver and desirably using a simple disposable pneumotachometer. In one method the patient is asked to breathe normally and then at the end of a normal tidal exhalation is asked to exhale till complete emptying rendering an end forced exhaled CO2 (EFCOs) which is not preceded by a large inspiration (thereby preventing the dilution associated with the maximum inhalation). The CO2 monitor can be a side-stream capnometer connected to an accessory port on the disposable pneumotachometer or other flow sensor or can be a mainstream capnometer with light emitter and transmitter connectable to at least one window on or connected with the tube of a disposable pneumotachometer or other flow sensor. This system provides an exhaled CO2 waveform with the spirometry data collection and further enhances the value of the exhaled CO2 evaluation since the forced and/or slow vital capacity maneuvers are associated with near complete emptying of the lung (except for residual volume) so that a plateau of CO2 more indicative of the PaCO2 is derived. The system thereby provides a measurement of the "end vital capacity CO2" (EVCO2) rather than the conventional end tidal CO2 (ETCO2). Because of the dilution of the large preceding tidal volume, the EVCO2 is not considered as useful as the EFCO2. In the absence of a high respiratory rate or shallow breathing a high EFCO2 to ETCO2 gradient is suggestive of airway obstruction. In one embodiment, the processor 1820 is programmed to detect the plateau as by identifying a minimum slope of CO2 rise during exhalation and/or the highest CO2 value and report these values along with the forced vital capacity and exhaled CO2 waveform adjacent the volume time curve derived of the FVC maneuver. For example, the reported EFCO2 can be the CO2 identified when exhalation flow falls to about zero or the slope of the exhaled CO2 falls to about zero.

As illustrated in FIG. 18, the spirocapnometry system 1800 can be integrated with the pulse oximeter 1818 to provide for other measurements such as a simultaneous SPO2 and the ventilation indexed oximetry value. The method can include determining the resting minute ventilation and the oxygen saturation value corresponding to the resting minute ventilation and then determining the exhaled carbon dioxide at the end of a maximal exhalation maneuver (as for example performed after or immediately at the end of resting minute ventilation measurement). The EFCO2 value can then be used to calculate the ventilation oximetry index instead of the minute ventilation or both can be used. A method for directly comparing exhaled CO2 and SPO2 and for calculating a ventilation adjusted and/or exhaled carbon dioxide adjusted oximetry value is discussed in U.S. Pat. No. 6,609,016 by the present inventor (which is incorporated herein by reference as if completely disclosed herein). When implemented with a spirometer, a capnometer and an oximeter, the system 1800 may be referred to as a SpiroCapnOximetry (SCO) system. The system 1800 can be combined in a single small compact housing configured to be hand carried to the patient's bedside or can be modular with the spirometer, capnometer and oximeter connectable (such as dock able, by cable connection, or by transmission-reception connection) or connectable to a central processor (as, for example, by cabling or direct docking or by transmission-reception based connection). Alternatively, the SpiroCapnometer can be employed alone without the oximeter. Additional sidestream or mainstream gas sampling can be added to detect and quantify, and characterize the patterns of other exhaled gases such as nitric oxide, carbon monoxide, or oxygen to name a few.

When implemented as a spirocapnoximetry system, the system 1800 can be combined with other monitors such as an electrocardiogram and blood pressure monitor as, for example, mounted on a rolling stand for immediate bedside availability in the emergency room. The system is particularly suitable for the evaluation of shortness of breath in the emergency room and on the wards providing a dyspnea evaluation montage, with which the patient can be followed by multiple spot checks, or on a continuous basis. The montage displayed or exported by the processor 1820 can include, for example, the FVC, FEV1, peak flow, end vital capacity CO2 (EVCO2), EFCO2, end tidal CO2 (ETCO2), the EFCO2-ETCO2 difference, flow volume loop, resting SPO2 (RSPO2), hyperventilation SPO2 (HSPO2), the HSPO2-RSPO2 difference, the resting heart rate, resting respiratory rate, I:E ratio, the resting minute ventilation, the ventilation indexed oximetry (VOI) value (calculated using the minute ventilation to estimate the paCO2 or by using the measured EFCO2 as a surrogate value for the PaCO2 applied in the formula) or the like. An adjustment of 2-3 mm may be added to the EFCO2 or another adjustment may be made by the processor for example if the exhaled CO2 fails to reach plateau at the end of the forced exhalation maneuver. Examples of other data that may be exported include the inspiration to expiration variation of plethesmographic pulse (the variation can be the amplitude, slope, or area under the curve or slope etc.) to name a few.

One exemplary method using the oximeter 1818 for detecting pathophysiologic occurrences abnormal patient comprises generating a plethesmographic output comprised of a time series indicative of the waveform of a plurality of the patient's pulse, generating a capnographic output comprised of a time series indicative of the waveform of a plurality of the patients tidal breaths, programming the processor 1820 to compare the plethesmographic output with the capnographic output to detect a pathophysiologic occurrence. All of these can be generated and displayed along with a programmed interpretation within a few minutes with a simple bedside resting minute ventilation measurement and subsequent FVC maneuver. In one embodiment, these values and the associated time series are uploaded automatically to the patient's medical records to subsequently become part of the time series viewer discussed supra. The time series of these values can then analyzed and viewed in the central patient record along with the time series of other monitored parameters. An application program may be adapted to analyze and view physiologic datasets as accessible from a primary program used to view the patient's electronic medical records. A link may be embedded in a user interface of the primary program to induce loading and operation of the application program. The application program, when launched, may acquire at least one time series of physiologic data and transmit the time series to a central processor for storage in a database. The application program may be linked to the database. When the link is activated (e.g. clicked), the relevant dataset may be loaded, analyzed and displayed.

In one exemplary embodiment, the patient monitor system 1800 may be adapted to evaluate a patient using the display 1822. The spirometer 1816 may be attached to the flow tube 1802 for measuring, at least, exhaled flow and producing at least a first output indicative of the vital capacity. The capnometer 1824 may additionally be connected to the flow tube 1802. The system 1800 may be adapted to produce a second output indicative of the patient's exhaled carbon dioxide. The processor 1820 may be programmed to determine an indication of the exhaled cabon dioxide value, which relates to the vital capacity. The monitor 1800 can further including the processor 1820 being programmed to receive an input indicative of a body dimension of the patient such as the height, weight, body surface area and/or the age and sex of the patient. The oximeter 1818 (if included in the system 1800) may be adapted to determine an oxygen saturation value for connection with the patient, the processor 1820 being programmed to compare the carbon dioxide value, which relates to the vital capacity to the oxygen saturation value.

In another embodiment, the flow tube 1802 defines a resistance to flow or otherwise has an obstruction such as a spinning member. The flow tube 1802 may employ ultrasonic or other methods for determining flow though the tube, the tube having a first end for receiving exhaled flow from a patient and a second end for venting the exhaled flow. The spirometer 1816 or other flow meter may be connectable with the flow tube 1802, the spirometer 1816 being programmed to receive an input derived from a measure responsive to the resistance or to the other parameters used to determine flow through the flow tube 1802. In this manner, the system 1800 may determine the flow rate through the flow tube 1802 using the input and to determine the vital capacity of the patient. A carbon dioxide monitor (such as the capnometer 1824) may be connectable with the flow tube 1802 for monitoring the carbon dioxide flowing through the flow tube 1802. The processor 1820 may be programmed to determine an indication of the time series of exhaled carbon dioxide and to determine an indication of the exhaled carbon value, which relates to the end of forced exhalation or to the vital capacity. At least a portion of the flow tube 1802 can be disposable or, preferably, the entire flow tube 1802 can be disposable. The flow tube 1802 can be marked and/or coded (for example, with a bar code 1828 or another method) with a calibration value, which for example can relate to the resistance to flow through the flow tube 1802. For example, the flow tube 1802 can be of the disposable type marketed by Nellcor Puritan Bennett for use the Renaissance II Spirometer. A small side port can be provided along the flow tube 1802 for attachment of (for example) a cannula of a micro-stream capnometer of the type marketed by Oridian. Alternatively, to avoid the need to modify the presently manufactured flow tube, the small pilot tube 1810 (illustrated in FIG. 18) or cannula may be attached as by adhesive between the screen and the housing such that the lumen of the gas sampling pilot tube 1810 or cannula projects adjacent the flow stream at the distal end of the flow tube. In one embodiment, the gas sampling pilot tube 1810 includes the clip 1812 for clipping onto the flow tube 1802 adjacent the distal end with the end of the pilot tube 1810 projecting adjacent the exhaled flow stream emitted from the flow tube 1802. In one embodiment, the clip 1812 comprises a pilot tube holding clip into which the pilot tube 1810 is fixedly bonded or otherwise snapped and which holds the projecting pilot tube 1810 such that it projects about 1-10 millimeters or more from the distal end of the flow tube 1802 so that the end of exhalation is detected by the capnometer 1824 even if the patient does not inhale. The pilot tube 1802 can be laterally shielded to prevent dilution of the exhaled gas stream by ambient airflow. In another embodiment, the pilot tube is connected to the flow tube 1802 along the length of the tube so that the lumen of the pilot tube is positioned adjacent to or within the lumen of the flow tube. In this embodiment, the onset of inhalation is detected by the washout of CO2. When a nasal cannula is applied and connected with the capnometer instead of a flow tube, the patient can be periodically asked (or the monitor can be programmed to ask the patient) to exhale to residual volume through the nose with the mouth closed and these peak CO2 values resulting for the forced exhalation can be used to calculate Ventilation indexing SPO2 values as by the previously discussed formulas.

The present invention provides method for evaluating a patient, comprising disposing a flow tube of a flow meter adjacent a patient and measuring using the flow meter, the exhaled flow through the flow tube to determine at least a first output indicative of the vital capacity; disposing a capnometer in connection with at least a portion of the flow tube, the capnometer being capable of producing a second output indicative of the carbon dioxide exhaled through the flow tube and using a processor, determining an indication of the exhaled carbon dioxide value which relates to the vital capacity.

If the capnometer is combined with a mechanical ventilator as by providing an capnometry input into the mechanical ventilator, the ventilator can be programmed so that the operator can select manual or automatic (as every 15 minutes for example) the determination of the end forced exhalation CO2 as will be described. Upon manual or automatic queue, the processor 1820 delays the next breath until exhalation flow falls to about zero or the slope of the exhaled CO2 falls to about zero through a forced exhalation of the patient in the manual mode (EFCO2) and at passive end of a prolonged exhalation in the manual or automatic mode. The measurement of the CO2 (such as the highest CO2) is identified at either of these points. In one embodiment, the ventilator is programmed to allow passive exhalation to functional residual capacity.

In another embodiment a nebulizer or other medication generating device is provided connected with the flow sensor tube (as for use with a disposable vane spirometer or the like) so that the patient can inhale medication while the minute ventilation and the patterns of tidal breathing such as the inspiratory to expiratory time or slope ratio is continuously monitored. The nebulizer of such a system can be driven by an oxygen cannula and the processor can adjust the calculated minute ventilation for the added flow rate of oxygen automatically or this can be accomplished manually. This is particularly suitable for continuous delivery of albuterol or other inhaled bronchodilator.

In another embodiment, the capnometer 1824 may be used in combination with the oximeter 1818 to assess the relationship between ventilation, SPO2, and the plethesmograph output of the oximeter (such as the photoplethesmograph). The capnograph can be employed to determine the respiration rate and this can be compared with the SPO2 to identify pathophysiologic divergence between the SPO2 and the respiration rate or the end tidal CO2 (ETCO2) as previously discussed. For example, a falling ETCO2 coupled with a falling SPO2 comprises pathophysiologic divergence of the ETCO2 and SPO2. Furthermore, a rising respiratory rate (as derived for example from the capnograph) coupled with a falling SPO2 or a rising CO2 comprises pathophysiologic divergence. The system 1800 can include a side-stream capnometer or mainstream capnometer.

According to one aspect of the present invention, the time-series of the primary capnographic breath by breath output is compared with a time series of the plethesmograph, a relationship between a change in at least one component of the plethesmographic pulse (such as a fall in amplitude, fall in the area under the curve, or slope of the upstroke, to name a few) with a portion of the inspiration-expiration curve of the capnograph can be used to asses the influence of time series of CO2, a time series of nasal pressure can be compared to provide the inspiration-expiration curve for comparison. In an example, the percent variation of the plethesmographic pulse amplitude or area under the curve (AUC) during or at the end of inspiration and the plethesmographic pulse amplitude or AUC during or at the end of expiration.

According to one embodiment of the invention, the tidal nasal pressure and tidal CO2 can be monitored using the same cannula as for example by attaching a pressure transducer to the nasal tubing used for collecting the CO2 sample. This can be achieved for example by providing an accessory tubing bifurcation adjacent the nasal prongs or distally adjacent the capnometer, which leads to the pressure transducer. Alternatively, the pressure transducer can be built into the capnometer so that the monitor provides both outputs. In one embodiment, the output from the capnometer is provided with a contemporaneous output of the nasal pressure or other nasal flow sensor and at least one component of the time-series of the nasal pressure or flow sensor is analyzed and compared with the capnographic breath by breath time series to compare a change or pattern of change in the nasal pressure or flow sensor (such as a rise or fall in amplitude, a rise or fall in the area under the curve, or change in the slope of the upstroke, to name a few) with a change or pattern of change in the capnograph (such as the amplitude peak value, a rise or fall in amplitude, a rise or fall in the area under the curve, or a change in the slope of the upstroke, to name a few).

In another embodiment, a method for monitoring sleep disordered breathing comprises a disposing a nasal, oral, and/or nasal oral cannula (for example of the type marketed by Oridian for delivery of oxygen during monitoring of end tidal) in simultaneous connection with a pressure transducer and a side stream CO2 sensor (for example, connecting the nasal pressure monitor to the portion of the tubing which is positioned at the neck or at the proximal end of or otherwise along the oxygen delivery portion of the tubing. The tubing connected to the transducer can be accessory tubing connected to the main oxygen delivery lumen or can be the main oxygen delivery tubing itself. The nasal pressure is then monitored along with a contemporaneous measurement of carbon dioxide. The processor 1820 can be programmed to detect a fall in the amplitude of tidal nasal pressure coupled with a rise in amplitude of the tidal carbon dioxide value and to output an indication such as "evidence of reduced drive or obstructive hypoventilation" if the nasal pressure has an obstructive shape this can be so indicated. In the alternative, if the processor 1820 detects a rise in the amplitude of the tidal nasal pressure coupled with a rise in amplitude of the tidal carbon dioxide the processor can output an indication of pathophysiologic divergence of nasal pressure and CO2. The development of a rising CO2 and rising tidal nasal pressure suggests a late declining respiratory state and portends an adverse outcome without timely intervention. The cluster patterns of nasal pressure and CO2 (as discussed previously) can likewise be detected using the combined pressure-CO2 monitoring described above.

In another embodiment, a direct or indirect capnometer is coupled with the flow tube connected with a patient during cardiopulmonary resuscitation. According to an exemplary embodiment of the present invention, a plurality of time series derived of the capnometer is outputted and analyzed by the processor as by the methods discussed previously. The time-series of the maximum CO2 per breath (as for example the ETCO2) is compared with the slope of plateau of the CO2 per breath. If the ETCO2 is falling at the same time the slope is rising or if the slope exceeds about zero and the CO2 is low (such as less than about 12-15), then the processor may produce an indication so that the operator is warned that the CO2 value may be low due to a high minute ventilation or an excessive respiratory rate during CPR. This can prevent the erroneous use of a low ETCO2 due to excessive ventilation as an indication to terminate CPR efforts. In addition, the processor-based detection of a slope exceeding about zero can trigger an indication that the breathing rate should be slowed. In one embodiment, the processor 1820 may be programmed to provide an indication (such as a flash, a vibration or a sound, to name a few) when there is no longer any objective evidence that the patient is passively exhaling (indicating that exhalation is complete) so that the operator has objective evidence (such as a positive CO2 slope or continued exhaled gas flow at a flow sensor) of ongoing exhalation or the end of exhalation so that the operator can consider delaying the administration of the next breath until the patient has completely exhaled to reduce the adverse potential for auto-PEEP. In an automated system for delivering breaths during CPR, the processor 1820 may be programmed to determine the end of exhalation and so that the operator can obtain a more accurate reflection of the true state of circulation using the end expiration CO2 monitor and so that auto-PEEP is minimized. In this respect, the system 1800 provides for the detection of the exhaled CO2 value at the end for passive exhalation (at functional residual capacity) which value should be less affected by breathing rate and tidal volume. The potential for auto-PEEP, which can severely compromise circulation and lower the ETCO2 values during CPR is discussed in more detail in U.S. patent application Ser. No. 10/080,387, entitled "Asthma Resuscitation System and Method," filed Feb. 25, 2002 and assigned to the present inventor (the contents of which is incorporated herein by reference as if completely disclosed herein).

In one exemplary embodiment, the monitor is configured to detect functional arousal threshold failure. An example of a method for using an oximeter for detecting arousal threshold failure includes generating at least one time series of a at least one physiologic parameter, detecting at least one reciprocation having a threshold value, defining the threshold value, determining the presence of arousal threshold failure based on the value. The threshold value can be a duration or length, such as an apnea or a desaturation duration, a nadir (such as a desaturation nadir), or a peak (such as an exhaled carbon dioxide peak).

Another exemplary embodiment includes generating at least one time series of at least one physiologic parameter, detecting at least a first reciprocation having a first threshold value (or a value indicative of, or resulting from of the first threshold value), defining a value associated with the first threshold value, determining at least a second reciprocation having a second threshold value, (or a value indicative of, or resulting from the second threshold value) determining the presence of arousal threshold failure based on the relationship between the first threshold value at the second threshold value. The relationship of the plurality of threshold values can be, for example a magnitude difference between absolute values of the nadirs, a magnitude difference between absolute values of the decline events, a slope of consecutive nadirs, a duration of a nadir range, a frequency or range of patterns of nadir values, to name a few. In still another exemplary embodiment, a plurality of threshold values are determined and a baseline mathematical relationship, such as an average range, of the threshold value is identified. The presence of functional arousal threshold failure (or recovery threshold failure) is detected upon the identification of a threshold value, which is sufficiently lower (for example 10% lower), higher or longer than the threshold baseline. Alternatively, the presence of threshold failure can be detected upon the identification of a value indicative of the minimum threshold value (such a nadir SPO2 value of about 65-75).

Figure 19:
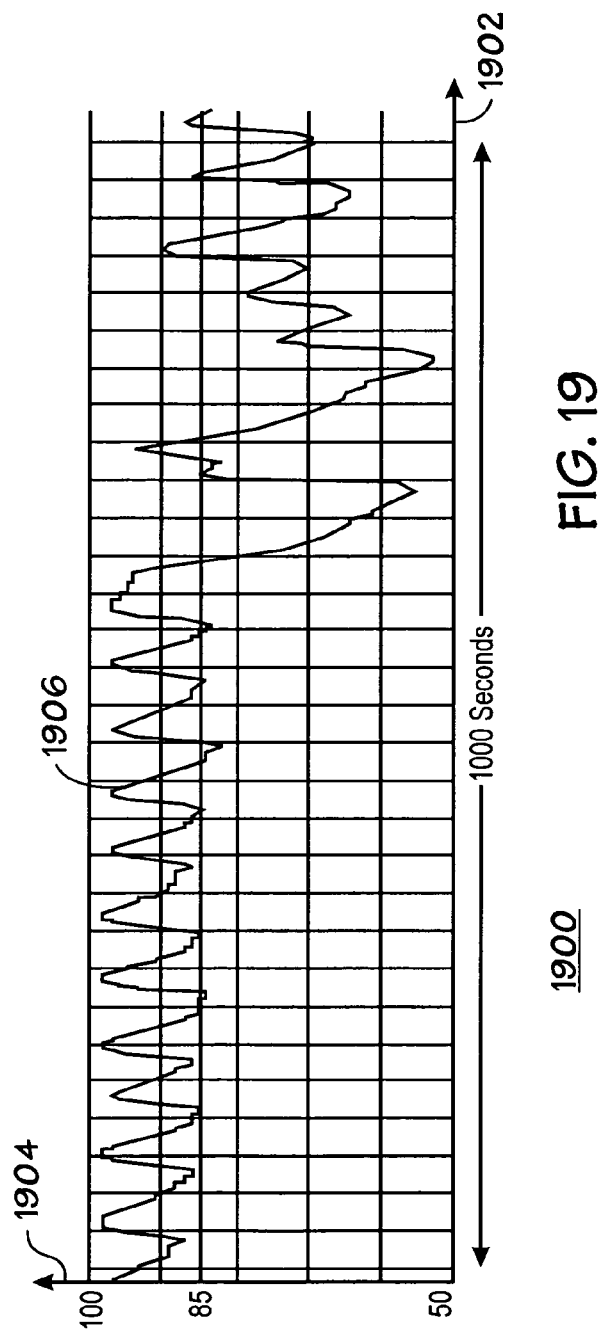
FIG. 19 is a graph showing an example of functional arousal threshold failure, which may be detected and analyzed in accordance with an exemplary embodiment of the present invention.

FIG. 19 is a graph showing an example of functional arousal threshold failure, which may be detected and analyzed in accordance with an exemplary embodiment of the present invention. The graph, which is generally referred to by the reference number 1900, shows a 1000 second time series of SPO2 values along an x-axis 1902. A y-axis 1904 shows a percentage SPO2 value. A waveform 1906 shows a cluster pattern typical of obstructive sleep apnea. Note that 11 consecutive reciprocations are shown with baseline average decline length of about 35 seconds and a baseline average nadir SPO2 value of about 80. The 12th reciprocation has a decline length of about 90 seconds and a nadir SPO2 value of about 55%.

An exemplary embodiment of the present invention may include a processor programmed to identify the 12th reciprocation (or the decline component of the 12th reciprocation) as indicative of arousal threshold failure and to output an indication based on the identification. In another exemplary embodiment of the present invention, the monitor is configured to detect functional arousal response failure (or recovery response failure). This type of failure can be due to absolute arousal response failure (wherein the arousal response is weak or absent) or relative arousal response failure (wherein the arousal response is weak relative to the magnitude of the perturbation which triggered the arousal). An example of a method for using an oximeter for detecting arousal response failure in accordance with an exemplary embodiment of the present invention includes generating at least one time series of at least one physiologic parameter, detecting at least one reciprocation having a response value, defining the response value, determining the presence of arousal response failure based on the value. The response value can be for example, a magnitude or a relationship between a magnitude and another value (such as a relationship between the fall magnitude and a rise magnitude), a duration, a length, an area or another such value. For example a response value may be the airflow recovery or resaturation duration, a peak value (such as a resaturation peak value or a relationship between a peak and another value), or a nadir or a relationship between a peak and another value (such as a transcutaneous carbon dioxide nadir) or an area, such as the recovery area (area under the curve from the onset of resaturation to the onset of the next fall). In an example readily applied to, for example an SPO2 time series, the processor can be programmed to detect a threshold value indicative of the peak value and/or a magnitude of rise event and to provide an indication, for example to highlight the region of recovery failure and to output a text warning indicative of "Severe Recovery Failure" along with the instability index value which is calculated for the recovery failure and the surrounding associated patterns. The indication of the type of adverse pattern for example "Unstable Hypoventilation Type III" can also be outputted. The instrument, such as a pulse oximeter can be programmed to provides the function of automatically detecting the instability pattern type, the severity, and a range of failure modes, and to take action such as to provide an indication the instability pattern type, the severity, and a range of failure modes and or to control therapy to treat the instability or reduce medication which may be inducing the instability or provide medication which may reduce the instability. For example, a patient controlled analgesia pump may have a port for connection with or connected with a reservoir containing a narcotic reversing agent and for automatically injecting or warning the nurse to consider injecting the reversing agent upon the identification of a profoundly adverse pattern. The PCA device might for example require the mounting of a vial of a reversing agent or an indication that such an agent is mounted before the device can be activated. to deliver IV analgesia.

Another exemplary embodiment of the present invention includes generating at least one time series of at least one physiologic parameter, detecting at least a first reciprocation having a first response value, defining a value associated with the first response value, determining at least a second reciprocation having a second response value, determining the presence of arousal response failure based on the relationship between the first response value at the second response value. In one exemplary embodiment, a plurality of response values are determined and a baseline mathematical relationship, such as an average range, of the response value is identified. The presence of response arousal failure is detected upon the identification of a response value, which is sufficiently lower (for example 10% lower), higher or longer than the response baseline. Alternatively, the presence of response arousal failure is detected upon the identification of a value indicative of the maximum response value (such a peak SPO2 recovery value of about 92-84).

FIG. 19 also shows an example of arousal response failure. Note that 11 consecutive reciprocations are present with baseline peaks of 94 and SPO2 fall-to-rise amplitude ratios of about one. The 12th reciprocation has a peak of about 90 and then the 13th reciprocation has a peak of about 60. The processor, detecting this low peak, can output an indication in response to the low peak, which can, for example, be an alarm indication that the patient has evidence of arousal response failure. A "low peak" which triggers an alarm may for example be programmatically fixed as peak below between about 90 and 80 or may be selectable from a menu. As discussed previously, the ratio of the SPO2 fall magnitude to the subsequent rise magnitude may also be used to trigger the detection of arousal (recovery) response failure. In addition, the absolute value of the peak and/or the absolute magnitude of the fall, and or the fall to rise magnitude ratio may be used in combination. For example, the processor may be programmed to require a fall magnitude of at least 4%-6% or higher before any peak value or magnitude ratio is considered indicative of response failure. In another example the processor may be programmed to require a fall of at least 4%-6% below a given threshold (such as 90%) before any peak value or magnitude ratio is considered indicative of response failure.

In one exemplary embodiment of the present invention, a time series of the peaks (for example as the highest point of each rise object) is plotted and analyzed as by the aforementioned methods for falls and or reciprocations of the peaks. The detection of a significant relative or absolute fall of the SPO2 peaks can be used to trigger an indication of arousal response failure. In another exemplary embodiment, a time series of the nadirs (for example, as the lowest point of each fall object) is plotted and analyzed as by the aforementioned methods and falls and or reciprocations of the nadirs are analyzed and detected. The detection of a significant relative or absolute fall of the nadirs can be used to trigger an indication of arousal response failure. Other parameters may be used instead of SPO2 (or in combination with SPO2) to detect these failures.

Arousal response failure can also be detected by programming the processor to determine a measure of physiologic perturbation, resulting from an apnea and or hypopnea (examples include the magnitude of fall in oxygen saturation, the magnitude of rise in CO2, to name a few) determining a measure of response to the perturbation (examples include; the number of recovery breaths which follow the apnea or hypopnea, the change in amplitude or duration of the EEG arousal of the EEG in response to the apnea to name a few). The processor can be programmed to compare (for example, by calculating an index) the perturbation and the response. A time series of this index can then be analyzed either manually or automatically to detect a relative reduction in arousal response.

In another exemplary embodiment of the present invention, both the duration of the attenuation of the plethesmographic pulse amplitude and the magnitude of the desaturation are used together to determine severity. If clustered pulse amplitude attenuations are present and especially if prolonged (for example more than 30 seconds) then the threshold for outputting an indication of based on the detection of an associated cluster of desaturations can be reduced. For example, if 30-second amplitude attenuations are present, then an alert indication (such as an alarm) may be triggered by clusters of 4% desaturation, whereas if only 15-second amplitude attenuations are present, then the alert trigger threshold may be set at 8%. In this way the duration of the amplitude attenuations (which is a marker for apnea length) is used as a marker of severity along with the magnitude of the desaturation to reduce the potential for oxygen to hide the severity of sleep disordered breathing when the magnitude of oxygen saturation is used alone. The pattern, or a threshold measure of the plethesmographic pulse amplitude can be compared with the pattern, or a threshold measure of the SPO2 (or ratio of ratios) to detect a pathophysiologic occurrence. For example, the processor may be programmed to identify ventilation instability upon the detection of three or more desaturations of greater than or equal to 2% SPO2 coupled with a cluster of three or more plethesmographic pulse amplitude attenuations of 15 seconds or more wherein the recovery between the pulse attenuations is less then or equal to 120 seconds.

In one exemplary embodiment of the present invention, the processor is programmed to produce a different output in response to the detection of a threshold breach and the detection of a cluster pattern. For example, the output in response to a threshold breach may be a continuous auditory alarm whereas the output in response to the detection of a cluster (as by detection of a plurality of threshold breaches) may be a textual output or a discontinuous or periodic auditory alarm. The processor can be programmed to produce a different alarm or signal output for each channel or for different patterns or different severities of the same pattern along the same channel.

In one exemplary embodiment of the present invention, the processor can be further programmed to detect a plurality of threshold breaches or directional crossings within a time interval to detect a cluster. The crossings may be differentiated based on the direction of crossing. For example, a fall crossing may be detected and recorded as different than a rise crossing. In one exemplary embodiment, the number of crossings of a threshold is determined for the fall and/or the rise and/or for a coupled fall and rise (which can be designated as comprising a single set of crossings). A plurality of different threshold crossings can be set, for example providing a different threshold for the fall and the rise and/or for a rise following a fall a specified period (such as a time period). In one embodiment, the various threshold crossings of the above events or reciprocations are selectable from a menu. Different threshold levels can be set for different severity of clusters. For example, a plurality of crossings of 90% saturation may produce a different severity index and/or a different indication (such as an alarm) than a plurality of crossings of 80% saturation. Further, this may be different than a plurality of crossings of 75% saturation or a plurality of crossings of which a at least one of the crossings reach a selected threshold or which progress through thresholds of increasing severity. In addition to providing a level for each crossing threshold, which may be different for fall than a rise, the severity may be adjusted based on the baseline of saturation prior to the fall or for the absolute or relative magnitude of the fall or rise. The absence of a threshold rise crossing after a fall crossing wherein the rise crossing fails to occur within a period (as, for example, a period of time or after a threshold magnitude of desaturation area such as a desaturation second product) may also be used to indicate severity. The relationships between the crossings (as for example the pattern of the crossings, the patterns of the levels of crossings, and/or the time interval or desaturation area between the crossings) can be used to trigger an indication such as an alarm. The relationships and patterns of falls, rises, and reciprocations, have been discussed extensively previously. Various exemplary embodiments employing simple or more complex analysis of threshold crossings to achieve a processor based analysis, result, and/or alarm of signal patterns similar or that achieved with more robust pattern analysis (as disclosed, for example, in U.S. patent application Ser. No. 10/150,582) are included within the scope of this teaching.

In another exemplary embodiment of the present invention, the instability index may be adjusted for the occurrence of threshold failure or recovery (such as arousal) failure. In an example, the detection of recovery failure may result in the increase in the instability index by a multiple factor of two with the minimum value after the increase being raised to the minimum level selected for high severity. Alternatively, a graded factor can be applied such that the detection of a plurality of incomplete recoveries or the detection of severely reduced peaks or the detection of a prolonged period with incomplete recoveries can produce a greater instability index multiple or index adjustment value than the detection of less severe threshold or recovery failures. The adjustment can be provided in real time so that the nurses are notified or drug infusion (such as a narcotic) automatically or manually reduced or stopped upon a threshold breach or a specific pattern of the severity index.

In one exemplary embodiment, a time series of the severity index, as adjusted for various precipitous adverse occurrences (such as recovery or threshold failure), is analyzed (for example objectified as by the preciously disclosed method methods) and the various alarms and indications are outputted based on the pattern of the instability index time series. For example, the system may be programmed such that a sudden sustained rise event may induce one output (one type of indication or treatment adjustment whereas a reciprocation (rise followed by a fall) may produce another. In this way, the pattern of the time series of the severity instability.

In an exemplary embodiment for automatic treatment adjustment (such as drug infusion or CPAP titration), the detection of an occurrence of threshold failure after upward titration of a medication or CPAP, as for example after titration to CPAP levels above 15, can cause an action such as an indication or an alarm or a modification such as a reduction in the therapy (such as the drug dose or level of CPAP). The preoperative detection of the occurrence of threshold failure or recovery failure may be used to determine the operative or anesthesia risk. In one exemplary embodiment of the present invention, a patient is monitored preoperatively using a pulse oximeter for recovery and/or threshold failure and then an adjustment in risk is assigned the patient based on the detection of recovery and/or threshold failure. The patient can be further monitored for recovery and/or threshold failure postoperatively and therapy can be manually or automatically adjusted based on the detection of recovery and/or threshold failure.

In an exemplary embodiment, precipitous state related threshold failure is differentiated from progressive or evolving threshold failure. For example, a state-related threshold failure is detected when a fall event of a time-series of the SPO2 reciprocation nadirs declines precipitously (as with for example a slope of 5-15% per minute) and/or when a negative reciprocation of time series of the nadirs is sustained (for example greater than 3-5 minutes).

Figure 20:
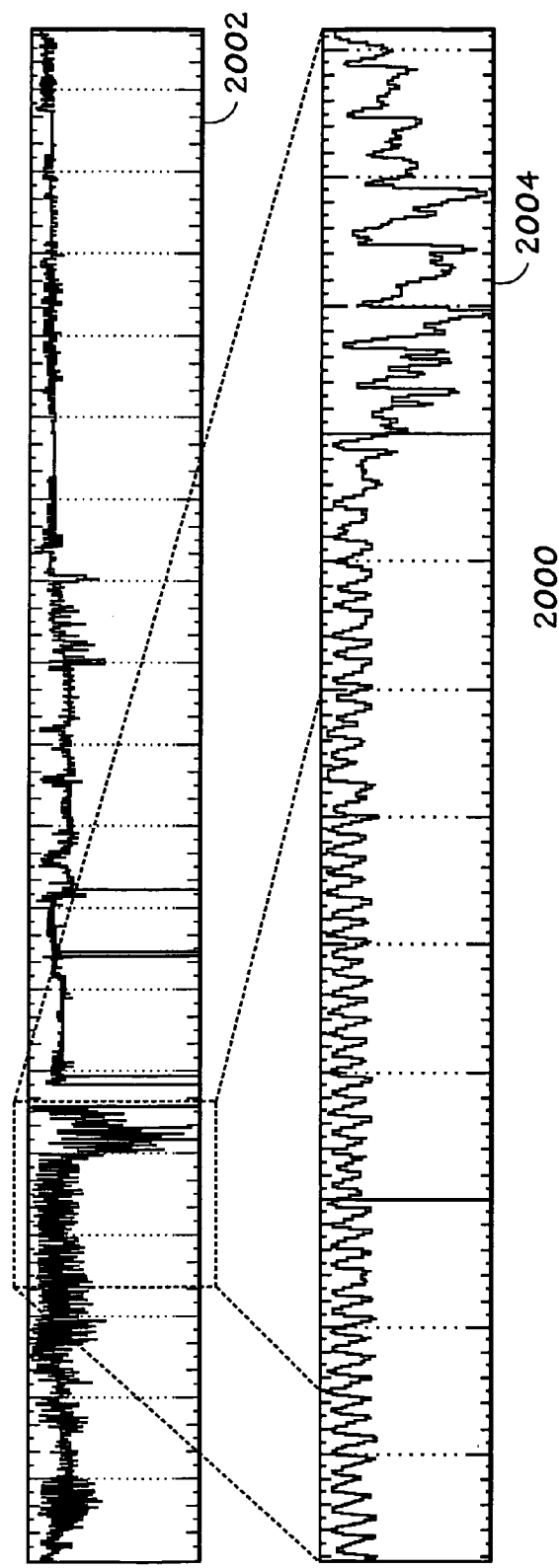
FIGS. 20 and 21 are graphs showing exemplary segments of a time series and expanded snapshots of different portions of data represented by the time series segment.
Figure 21:
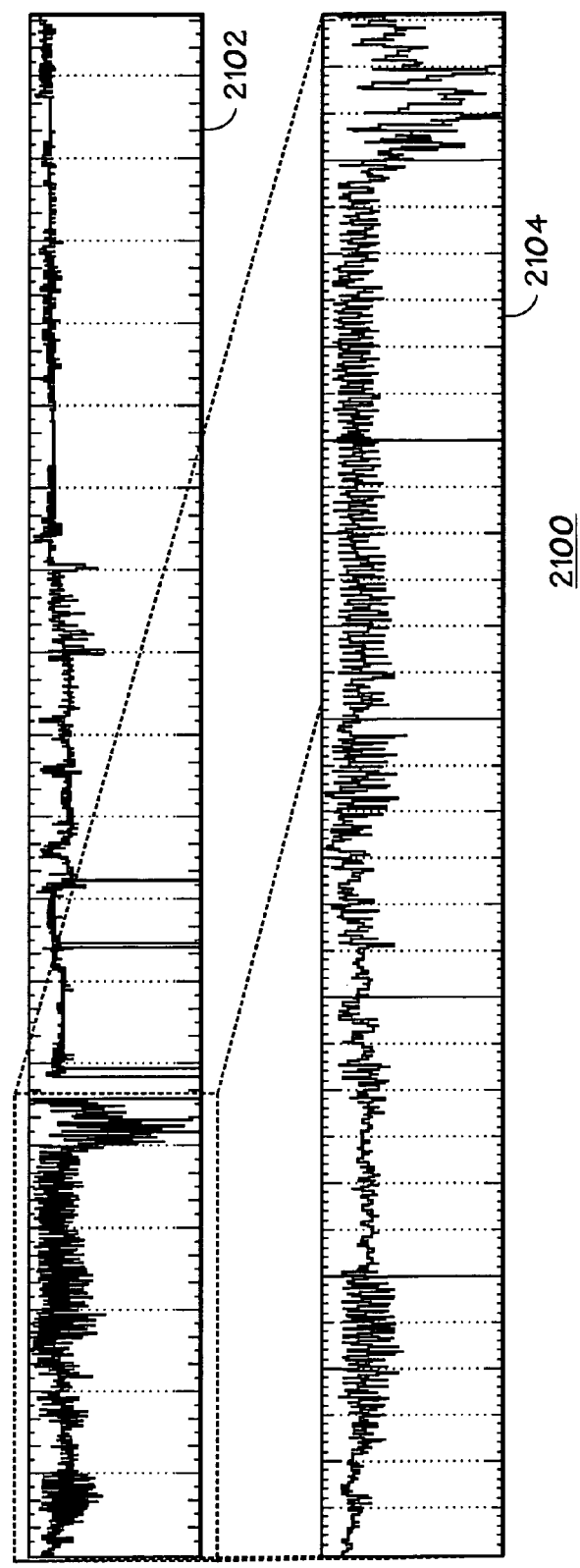

FIG. 20 is a graph showing an exemplary segment of a time series and an expanded snapshot of a portion of data represented by the time series segment. The graph is generally referred to by the reference number 2000. The segment of the time series is referred to by the reference number 2002 and the expanded portion of the time series is referred to by the reference number 2004. FIG. 21 is a graph showing an exemplary segment of a time series and a different expanded snapshot of a portion of data represented by the time series segment. The graph is generally referred to by the reference number 2100. The segment of the time series is referred to by the reference number 2102 and the expanded portion of the time series is referred to by the reference number 2104.

In one exemplary embodiment of a system according to the present invention, the simulation of the real-time environment can be accomplished through the storage and representation of a series of snapshots of data and analysis. A true representation of real-time conditions of a monitored patient at a particular time (in the example called a real-time point) can be derived by generating an analysis of a subset of a time series. In an example, the snap analysis accomplishes this by extracting a contiguous set of points from a time series (such as the time series segments 2002 or 2102) into a second time series (such as the expanded time series portions 2004 or 2104) and performing an analysis against this subset. This analysis executed as if the subset of data is all of the data available, thus recreating real-time conditions. This snap analysis can be performed against a single channel of data (e.g. oximetry) or against any number of related channels. Since data is stored with a timestamp (e.g. start time) the subset of data can be extracted by describing a specific start and end time. The analysis can be performed in the exact same way it is against a full night of data including the consideration of inter-channel properties.

In an exemplary embodiment of the present invention, three options exist for executing a snap analysis although more can be provided if preferred. In this example, the three options are: window, window-plus-thumbnail and past-omniscience. A window snap analysis can specify both a start time and an end time that is other than the start and end time of the entire night of data. The past omniscient analysis specifies an end time (or a given termination time) and assumes that the analysis can see everything up to that point. Past omniscience will provide for comprehensive analysis when given adequate resources for data storage. All data up to the point specified (representing the real-time point) is available for analysis.

The window options can be applied, for example, when data storage resources or processing power does not allow the analysis of all data since the beginning of data collection. A start point can be indicated as well, or a time span (e.g. 30 minutes) may be specified to indicate limit the data that would be available in a limited-resource real-time environment. The window-plus-thumbnail option specifies a start point (specifically or as an offset from the real-time point), but also provides a data-structure containing information about data previous to the start point that can be used to more accurately calculate values that depend on information derived from an entire time series (e.g. area above the curve, number of clusters, or the like). The data stored in the thumbnail may include index values as applied to previous data and/or component values that would be used to create those indices such that data is differentiated sufficiently to calculate indices that apply to the entire time series previous to the real-time point with little or no loss of fidelity.

Figure 22:
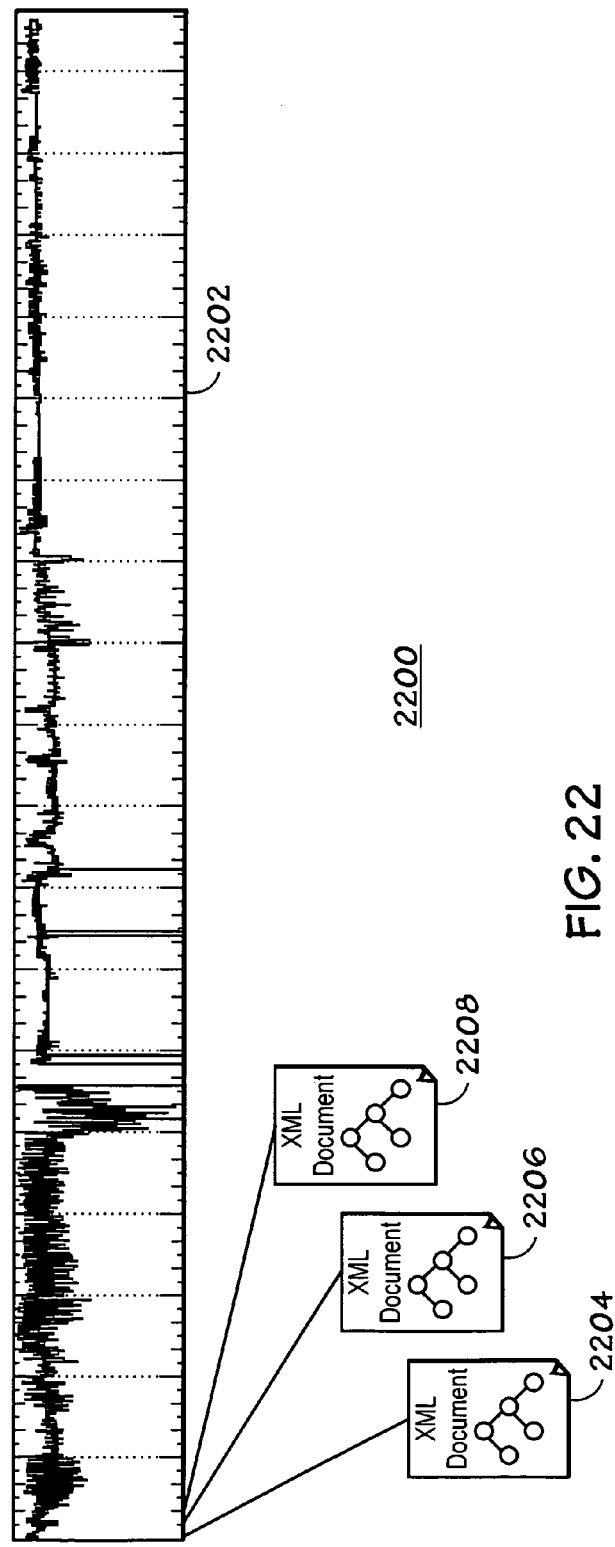
FIG. 22 is a graph showing a time series, along with a plurality of thumbnails in accordance with an exemplary embodiment of the present invention.

FIG. 22 is a graph showing a time series, along with a plurality of thumbnails in accordance with an exemplary embodiment of the present invention. The graph is generally referred to by the reference number 2200. A time series 2202 may be indicative of a physiological parameter of a patient. A plurality of thumbnails 2204, 2206 and 2208 may be derived from the time series 2202 to allow closer analysis of the underlying time series data. The thumbnails 2204, 2206 and 2208 may comprise XML (Extensible Markup Language) documents.

In one exemplary embodiment, each analysis is reduced to a set of relevant values stored in a single data structure—the analysis thumbnail. Each analysis object may have a separate thumbnail. For example, the thumbnails 2204, 2206 and 2208 may correspond to events, reciprocations and/or clusters or the like, each with relevant values stored. Higher-order thumbnails contain a collection of lower-order thumbnails such that individual values can be iterated and/or aggregated as necessary. For example, a cluster thumbnail contains a set of reciprocation thumbnails. Further, a reciprocation thumbnail contains a pair of event thumbnails. This hierarchical form of the data fits well within an XML document.

Thumbnails allow for an abstraction of data for indexing, transmission and efficient storage. The thumbnail can remain in memory, for example, without requiring storage for all data points in a time series. The thumbnails of a high volume of cases can be reviewed with statistical analysis tools to identify correlations.

In one exemplary embodiment of the present invention, a snap analysis is provided that renders an accurate simulation of the state of the patient from the perspective of a real-time point. A set of snap analyses provides a simulation of the changes of that state over time. The analysis thumbnail allows for an abstract representation of the state of the patient from the perspective of a real-time point. A collection of analysis thumbnails provides a sampling of those representations over time. Given a particular sample rate (e.g. about 0.5-10 minutes minute although other rates can be used), a series of snap analyses can be stored assuming each successive time (e.g. minute) being the real-time point. Each analysis can be abstracted into a thumbnail and stored in a collection of analyses thumbnails.

The execution of an analysis per sample rate (e.g. per minute) can put a significant strain on resources. In-memory versions of channels and associated time series are required to allow the rapid creation of these objects.

Figure 23:
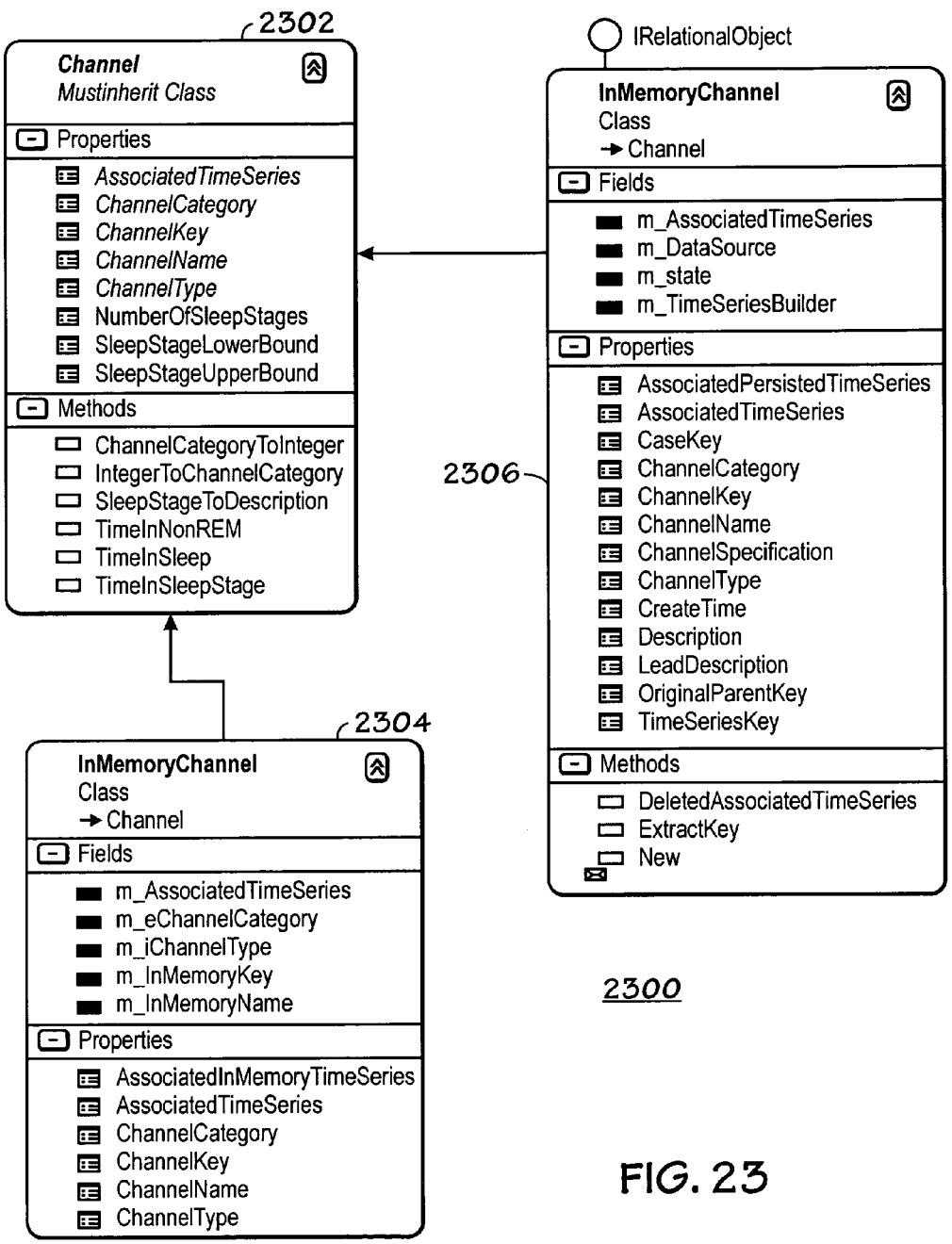
FIG. 23 is a block diagram of a hierarchical channel object in accordance with an exemplary embodiment of the present invention.

FIG. 23 is a block diagram of a hierarchical channel object in accordance with an exemplary embodiment of the present invention. The diagram is generally referred to by the reference number 2300. As illustrated in FIG. 23, an exemplary embodiment of the present invention may be adapted to mitigate resource consumption by providing a process wherein a channel has been refactored into an abstract class (herein called "channel") and two sub-classes (herein called "persistent channel" and "in-memory channel" respectively). In FIG. 23, the channel object is identified by the reference number 2302. The in-memory channel object is identified by the reference number 2304 and the persistent channel is identified by the reference number 2306. The persistent channel 2306 may be database-aware and can represent a channel that has been stored in the database as part of a case. The in-memory channel 2304 may be a lightweight class with no ties to the database. In-memory channels can be created from persistent channels (with a subset, or window of the time series).

In one exemplary embodiment of the present invention, the analysis builder classes have been refactored to be polymorphic (i.e. to work against either in memory or database-generated channels. In a similar way, the time series may be refactored to support persistent and in-memory versions of the class.

In one example, a real time analysis object is made up of three elements:
1. A selected sample rate that indicates the granularity of the analyses collection;
2. A snap analysis style—either window, window-plus-thumbnail or past-omniscient; and
3. A collection of snapshot thumbnails abstracted from snap analyses executed at the real-time points indicated by the selected sample rate This object can be stored along with a standard analysis to provide a simulation of what could have been ascertained in real time.

The user of the software can simulate moving through the time series, which may represent a night of sleep study data, and understand the real-time conditions. This can be used for training purposes or for the analysis, as discussed below, of alarming mechanisms.

Figure 24:
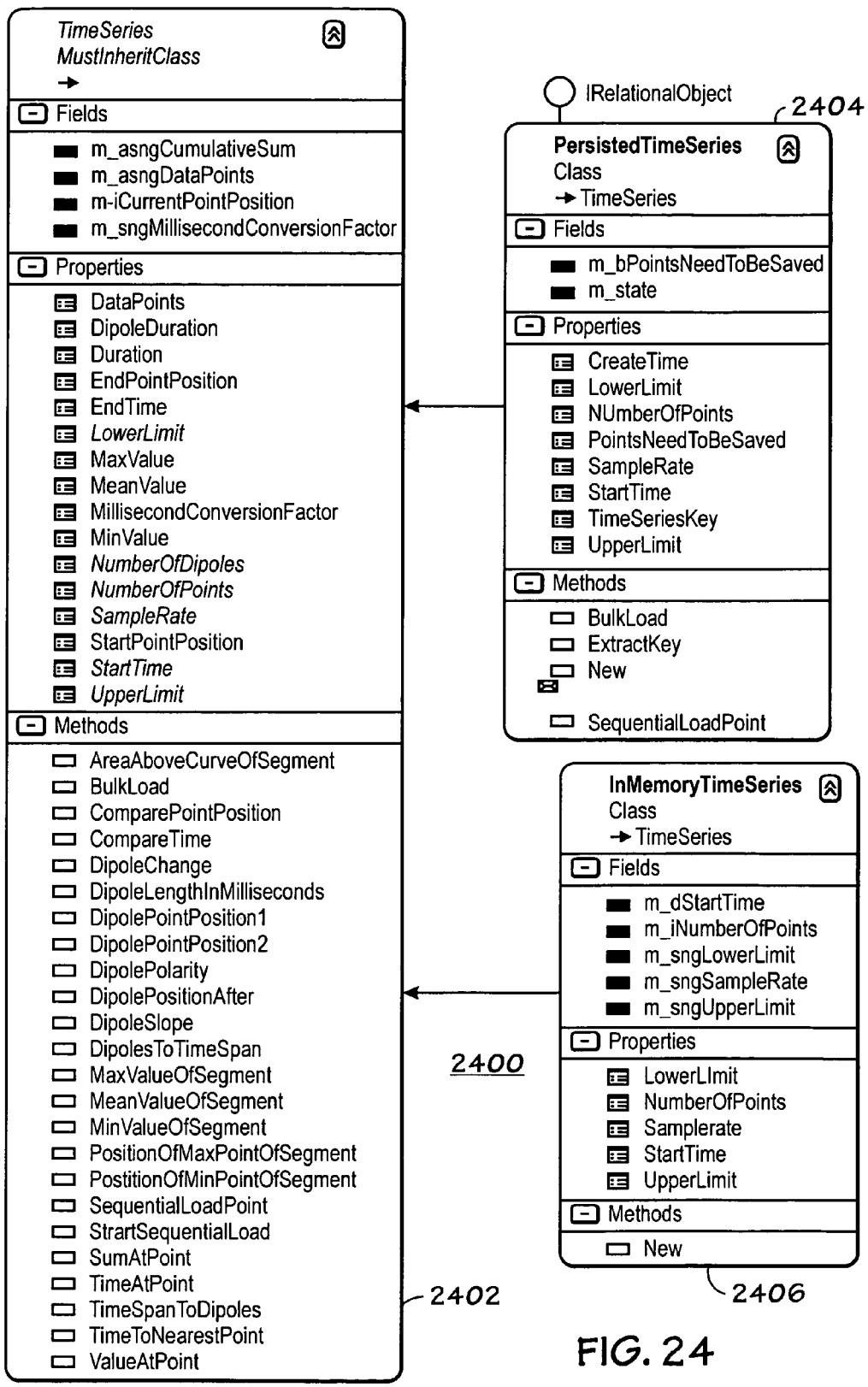
FIG. 24 is a block diagram of a hierarchical time series object in accordance with an exemplary embodiment of the present invention.

FIG. 24 is a block diagram of a hierarchical time series object in accordance with an exemplary embodiment of the present invention. The diagram is generally referred to by the reference number 2400. The exemplary time series object illustrated in FIG. 24 comprises a timeseries object 2402, a PersistedTimeSeries object 2404 and an InMemoryTimeSeries object 2406.

Once a real time analysis object such as the time series object 2400 is available, a new type of time series can be derived, displayed, manipulated, and transformed. A real time analysis object is a collection of data structures associated with contiguous data points. From this collection, any number of time series can be generated. Any value or calculation can be specified against the snap analysis thumbnail to generate a series of contiguous values. This set of contiguous values represents data parallel in the same time set of the original channel or set of channels from which they were derived. In other words, any function that can reduce a snap analysis thumbnail into a single value can create a new channel. This channel has exactly the same general properties and characteristics as any other channel within the system. Transformations could be applied (e.g. smoothing). The data can be displayed in a graphical format. For example, if the average recovery interval was considered critical in the real time analysis, the system could show a graphical representation of what the average recovery interval was at any sample real-time point in the time series. A significant increase in the recovery interval would be represented as an upward trend on the x-axis.

Examples for creating a separate channel can be accomplished by providing the following:
1. A real time analysis object. This will provide the sample rate and the collection of snap analysis thumbnails from which the values will be obtained.
2. A function that will derive a single value when applied to a snap analysis thumbnail. This can be the specification of a value within the thumbnail or a calculation using the values contained in the thumbnail. The time location can also be used—e.g. an algorithm may follow a different path with real-time points that are within the first 30 minutes of a case.
3. A range of the channel. This can be auto-generated as the minimum and maximum of the values actually obtained from the function or can be specified directly.

Since a real time analysis channel can have the same characteristics as any other channel, it can be subject to the same analysis as any other channel. Patterns of change can be identified using the same mechanism that generated the set of original analyses. For example, the system could identify a trend in the recovery interval and create an event from which can be derived all of the information associated with an event (e.g. slope and duration). Reciprocations, and even clusters could be identified in the same way.

In one exemplary embodiment, the real time analysis channel provides an effective mechanism for defining an alarm. An alarm could be based on the following examples although many other mechanisms are possible within the scope of this teaching:

1. The identification of a real time value falling into a particular range. Any number of ranges could be used with severities attached.
2. A function could be used to create a dynamic range. Threshold values could be variable dependent on the location within the time series (e.g. in the first 30 minutes) or be adjusted according to values earlier in the real time analysis.
3. The alarm could be based on the properties of objects within the analysis of the real time analysis channel (e.g. the duration and/or slope of a trend of the average recovery ratio).
4. The alarm could examine relationships within the final snap analysis thumbnail, which represents the most comprehensive analysis given a specific real-time point. For example, the alarm could look at whether the real-time point is in a cluster and the characteristics of the last five reciprocations. These relationships could be quantified and measured against a static or dynamic range.
5. An alarm may look at a combination of characteristics of the real-time channel and the final snap analysis thumbnail.
6. An alarm my look at a combination of a real time analysis channel and the parallel native channels (e.g. the change the average recovery channel along with the activity in the chest wall channel).

The representation of a separate channel provides an effective mechanism for reviewing results of an alarm. Experts can define an alarm and immediately test its veracity. The system can highlight sections of the time series (in either native channels or in the real time analysis channel) to indicate the results and severity of an alarm. Alternatively, a separate channel could display alarm results as a step function. If thresholds are used to trigger and determine the severity of an alarm, the threshold values could be indicated on the appropriate channels (either as a simple horizontal line or a curve if a function is used).

A set of representative cases could be manually marked by an expert with the identification and severity of an alarm. The system could run through the set of cases to identify how closely the algorithmic alarm correlates with the manual review of an expert.

The following program listing is an example of an XML representation of a channel analysis thumbnail:

```
<ChannelAnalysisThumbnail>
 <CaseName>Mono To Poly</CaseName>
 <CaseDescription>Patient exhibits a moderate SpO2 delta. Progresses from
monomorphic pattern to polymorphic with incomplete recovery
cluster.</CaseDescription>
 <CaseNumber>2</CaseNumber>
 <ChannelCategory>Oximetry</ChannelCategory>
 <ChannelType>0</ChannelType>
 <DurationInMilliseconds>33898000</DurationInMilliseconds>
 <NumberOfClusters>18</NumberOfClusters>
 <ClusterThumbnails>
  <ClusterThumbnail>
   <ClusterType>Symetrical Reciprocation Cluster</ClusterType>
   <CorrelatedToSleepStage>false</CorrelatedToSleepStage>
   <PercentageInArtifact>0</PercentageInArtifact>
   <PercentageInWake>0</PercentageInWake>
   <PercentageInStage1>0</PercentageInStage1>
   <PercentageInStage2>0</PercentageInStage2>
   <PercentageInStage3>0</PercentageInStage3>
   <PercentageInStage4>0</PercentageInStage4>
   <PercentageInNonREM>0</PercentageInNonREM>
   <PercentageInREM>0</PercentageInREM>
   <Morphology>Monomorphic</Morphology>
<MeanStartEventDurationInMilliseconds>25400</MeanStartEventDurationInMilliseconds>
<MeanEndEventDurationInMilliseconds>12360</MeanEndEventDurationInMilliseconds>
   <MeanStartEventMagnitude>-8.523999</MeanStartEventMagnitude>
   <MeanEndEventMagnitude>8.539998</MeanEndEventMagnitude>
   <MeanStartEventSlope>-0.341138542</MeanStartEventSlope>
   <MeanEndEventSlope>0.698189259</MeanEndEventSlope>
   <MeanReciprocationMaxValue>96.49201</MeanReciprocationMaxValue>
   <MeanReciprocationMinValue>87.564</MeanReciprocationMinValue>
   <MeanReciprocationMagnitude>8.928</MeanReciprocationMagnitude>
<MeanReciprocationDurationRatio>2.10189247</MeanReciprocationDurationRatio>
<MeanReciprocationMagnitudeRatio>1.01252</MeanReciprocationMagnitudeRatio>
   <MeanReciprocationSlopeRatio>0.5337045</MeanReciprocationSlopeRatio>
<MeanRecoveryDurationInMilliseconds>16917</MeanRecoveryDurationInMilliseconds>
   <MeanRecoveryRatio>0.762648046</MeanRecoveryRatio>
   <NumberOfReciprocations>25</NumberOfReciprocations>
   <ReciprocationThumbnails>
    <ReciprocationThumbnail>
     <StartEventDurationInMilliseconds>9000</StartEventDurationInMilliseconds>
     <StartEventSlope>-0.455555379</StartEventSlope>
     <EndEventDurationInMilliseconds>9000</EndEventDurationInMilliseconds>
     <EndEventSlope>0.366666168</EndEventSlope>
     <Magnitude>4.09999847</Magnitude>
```

```
    <SlopeRatio>1.24242544</SlopeRatio>
    <MagnitudeRatio>1.24242556</MagnitudeRatio>
    <DurationRatio>1</DurationRatio>
    <MajoritySleepStage>-1</MajoritySleepStage>
   </ReciprocationThumbnail>
    ...
  </ReciprocationThumbnails>
 </ClusterThumbnail>
  ...
</ChannelAnalysisThumbnail>
```

In one exemplary embodiment of the present invention, a trigger is used to enhance the detection of hypoventilation. A fall in SpO2 can commonly occur from hypoventilation or from a V/Q mismatch. A fall in SPO2 due to hypoventilation is often rapidly reversed by patient stimulation (for example by an auditory pulse oximetry alarm which wakes the patient up or by the fall itself or the rise in CO2 that accompanies the fall) whereas a fall in SPO2 from a V/Q mismatch is not rapidly reversed by patient stimulation. These represent various stimulus events, which can be detected to identify a response to the stimulus. One of the problems with the use of a SPO2 alarm is that fall in SPO2 may be reversed by the alarm induced by the fall or by the nurse who wakes the patient up upon responding to the alarm. This preempts the fall but this preemption may be early enough that the pattern of the SPO2 time series, which would have been evident if not preempted, is not available for analysis so that the nurse is not advised as to the nature of the fall. This may prevent the detection of dangerous types of unstable hypoventilation such as a type II and Type III instability discussed previously since the nurse may be inclined to simply add oxygen, which may not be the best choice of therapy. However, one exemplary embodiment of the present invention provides a processor which can record and/or receive an automatic or manual indication of the occurrence of a stimulation event and/or which can induce patient stimulation (such as an auditory alarm or a patient mounted vibration inducer). The processor may be programmed to identify the occurrence of a stimulation event (which may the externally applied or may represent a physiologic stimulus, such as a fall in oxygen saturation or a rise in CO2, from the patient under test) and to identify the occurrence of a pattern or value or range of values indicative of recovery, such as a recovery event subsequent to the stimulation event. The processor can be programmed to output an automatic indication of the occurrence of at least one precipitous recovery event within a short time interval (such as for example about 2-15 seconds) after the onset of the stimulation event. In this way the nurse is notified that the fall in SPO2 was likely due to unstable hypoventilation. Another problem is that the conventional bedside alarm may not be loud enough to awaken the patient so that preemption of a profound and potentially fatal episode of hypoventilation may depend on timely arrival of the nurse. To solve these problems upon detection of an episode of profound fall in SPO2, a very forceful (crisis alarm) stimulation can for example be delivered to the patient by a bedside monitor or by an attached headphone, a collar for auditory or vibration stimulation or another patient mounted stimulator. According to one embodiment of the invention, a patient receiving parenteral narcotics using a patient-controlled analgesia pump has the conventional basics alarm system for notifying the nurses as well as a second tier crisis alarm system and/or stimulator intended to stimulate and awaken the patient in the event of a life threatening decline in SPO2. Regardless of the cause of the stimulation, the detection of rapid "Stimulation Induced Oxygenation Recovery" ("SIOR") can provided as an automatic output by the processor. SIOR provides strong evidence that the cause of the fall in oxygen saturation is antecedent unstable hypoventilation and that oxygen therapy may not be the best choice.

One exemplary method for using an oximeter for detecting response of a patient to a stimulus can comprise generating at least one time series of at least one physiologic parameter derived from the oximeter, automatically detecting the stimulus, detecting at least one response subsequent to the stimulus, the response comprising at least one of a pattern and a value and outputting an indication of the response to the stimulus. The response can be a value indicative of the peak value, a value indicative of a magnitude value, such as a magnitude of a rise in oxygen saturation. The response value is a value indicative of a peak value of oxygen saturation and/or magnitude of rise in an oxygen saturation value (as for example defined by the nadir to peak difference) that follows the stimulus (such as the alarm) or which follows a manually applied stimulus by the nurse (in this situation, the processor can be programmed to receive an input, which may be a manual input, indicating the occurrence of a stimulus). The response value can be a value indicative of a change in a component of the plethesmographic pulse such as the rise in the plethesmographic pulse amplitude that follows the stimulus.

In another exemplary embodiment of the present invention, the monitor includes an alarm-response tracking system. One of the problems with present hospital environments is that personnel may respond slowly to alarms and the response time in a given hospital or on a given ward is generally unknown to the hospital administration. Yet the "Alarm-to-Bedside-Response-Time" (ABRT) may be an important factor in patient well-being. An exemplary embodiment of the present invention includes a user interface for inputting an indication that a response to the alarm has occurred. The processor may record and output at least two responses; The physiologic response of the patient subsequent to the alarm (including the presence or absence of SIOR and the delay between the response, if any), and the alarm and the nurse response subsequent to the alarm (including the delay between the response, if any and the alarm). Using these data sets, hospitals can identify delays by hospital ward, by shift, an by many other factors. One issue can be that the nurse, arriving at the bedside needs to examine the patient as quickly as possible and perhaps should not be delayed by having to input a bedside response into the monitor. However, it can be hospital policy that, if the patient is in distress or appears in crisis, that the response time need not be recorded. The processor can include an input that indicates that the nurse forgot to input the response or was too busy to do so. Since there are many non-distress alarms, these variations in recording should not affect the validity of the quality of the ABRT datasets.

In one exemplary embodiment of the present invention, a severity index is determined using a combination of a plurality of waveform features that are indicative of severity of instability. Examples of such indicia include a combination of one or more of the recovery threshold, the recovery response, and the duration of objects (such as events reciprocations or cluster) or other features. In an example, these features can include at least one value indicative of at least one nadir relationship, at least one value indicative of at least one peak relationship, and at least one value indicative of duration such as the area above at least a portion of a cluster. The nadir or peak relationship can be the absolute nadir or peak value, a difference between the nadir and/or peak value and another value or measure, a relationship between consecutive peaks and or nadirs, a relationship between the fall and rise amplitudes, or a relationship between ranges of a plurality of peaks and nadirs. These values can be weighted. For example, the calculation can be weighted such that a poor arousal response greatly affects the index. One example of a weighted instability index calculation is (98-Nadir)+4(94-Peak)+(area given in saturation seconds of desaturation below 98 over an interval of X minutes/60Y). For example, X can be about 3-15 minutes although other values may be used and Y any of a range of values including equal to X. The index can be provided, for example, on a numerical scale having in a range from 1 to 100 with the final calculation adjusted to that range proportionally or by considering all values in excess of 100 to be equal to 100. This index can be calculated, for example, for each a moving window of time. A few examples of moving window of time include:

- A series of contiguous sections of the time series with a fixed time interval. As an example, a series of 1-minute sections that are adjacent to each other but not necessarily intersecting.
- A series of contiguous or near contiguous sections of the time series with a variable time interval. As an example, a time interval that can change depending on characteristics within the time series, a response to a user gesture, according to a mathematical function, and/or randomly to name a few.
- A series of non-contiguous sections with a fixed time interval with a fixed or variable separation in between.
- A series of non-contiguous sections with a variable time interval. As an example, a time interval that can change depending on characteristics within the time series, a response to a user gesture, according to a mathematical function, and/or randomly to name a few.
- A series of overlapping windows. In an example, a sample point can be chosen for each X seconds (e.g. 10) and the previous Y minutes (e.g., 5) can be analyzed. The beginning of the window can be truncated such that for any sample point less than 5 minutes the window will be less than 5 minutes depending on the available data between the sample point and the beginning of the time series.
- Non-discrete windows. For example, windows that can conditionally include points outside of their boundary (e.g. the minimum point of a rise event that falls within the window which could be outside of the window boundary).

Since a low SPO2 is indicative of instability risk, which is not only the function of the oxygen deficit but also as a function of factors that allowed the SPO2 to fall to a low level and of factors (such as the commonly increased CO2), which accompanies a given low SPO2. The SPO2 value can be weighted for severity of the absolute value itself as, for example, the (100−SPO2 value) squared and then divided by 10. The value of a given measure or calculation may be weighted for the presence of a pattern such as a cluster pattern (as for example a threshold pattern of clusters) as detected by any method. Examples for the detection and/or quantification of a cluster pattern include, the detection of a threshold difference between a plurality maximum and minimum values detected within an interval as defined for example within a series of contiguous, but substantially non-intersecting, sections of the time series (e.g., minute sections), the detection of a temporal, spatial, or frequency pattern (as by a transform) indicative of threshold clustering, or the detection of a specific object such as clusters or a pattern of objects such as a plurality of reciprocations, or events to name a few. Maximum value may be defined as the maximum value or a conditionally identified maximum within a set of maximum values. For example, a series of minimum values could be derived from a moving window within a specified section of time and a specific maximum value could be conditionally determined according to thresholds, or through other characterizations of the waveform (for example if a particular section of the waveform is considered artifact, specific values may be discarded). Minimum value may be defined as a minimum value or a conditionally identified minimum value within a set of minimum values. An example of the weighting applied if clustering is detected follows. Using an oximeter, a time series of SPO2 values are determined, the processor is programmed to detect clusters and nadirs within clusters, the calculation 2(98-Nadir) can then be applied if a cluster is detected and the nadir is part of a fall event thereby indicating that the nadir value is a component of an unstable SPO2 pattern. These choices for severity indexing and various options for weighting can be provided in a menu, which is especially useful for the researcher. For example, the calculation 2 (98-Nadir) may be used if a cluster is detected prior to the determination of the Nadir and the nadir is part of a fall event (which indicates that the nadir value is a component of a unstable SPO2 pattern). These choices for severity indexing and weighting can be provided in a menu, which is especially useful for the researcher.

Alternatively, in another example, the window can vary with the objects such that a prolonged continuous cluster of a given cluster type can prolong the window as with the denominator (below the area calculation) being adjusted for the time and the nadir can be the mean nadir or the lowest nadir and/or the peak can be the mean peak or the lowest peak. In one example, a plurality of parallel time series of severity can be generated, each containing at least one component severity. For example, a time series indicative of a plurality of at least one nadir relationship can be generated parallel to a time series indicative of a plurality of at least one peak relationship. The patterns of each of these times series may be then be analyzed to define events, reciprocations, and clusters. A severity index can then be similarly calculated using the pattern relationships of one or more of the severity time series. The pattern relationships of one or more of the indices of severity can be quantified using pattern recognition and analysis software for example of the types disclosed previously. This is one example of providing a way to quantify the patterns, absolute values, and relationships of the components of the aggregate severity index to provide additional diagnostic utility.

The above system method for severity indexing can be applied to a broad range of physiologic signals. For example, a plethesmographic pulse time series (such as a time series of the amplitude of the plethesmographic pulse) can be similarly processed. In one exemplary embodiment, the time series of the SPO2 and the time series of the amplitude of the plethesmographic pulse are analyzed together in parallel. If oxygen is applied, the severity of the instability of the plethesmographic pulse is used as a marker of severity.

In one exemplary embodiment of the present invention, an interpretive oximeter is capable of at least one of a textual indication of the pattern detected and a severity index value (such as the severity index value associated with that pattern) which may be automatically displayed. For example, upon the detection of an incomplete recovery cluster, the processor may be programmed to output "Unstable Hypoventilation with Incomplete Recovery" and also display a severity index of 78, which displays for the caregiver the severity of the unstable hypoventilation pattern. In one exemplary embodiment, all detected patterns, (including the failure patterns) or a discretionary range of detected patterns, are stored for retrieval by the nurse as by providing a "review detected SPO2 or Pleth patterns" icon on the oximeter or central monitor.

In one exemplary embodiment, the severity indexing and/or alerts are adjusted for the presence of oxygen therapy (as by nasal cannula). The presence of oxygen therapy is inputted either manually of automatically. For example, the processor can include an input for manual designation of oxygen therapy on the display or can be programmed to receive the information relevant to the presence of oxygen from the patient's electronic chart, or the monitor may have a sensor which connects to the bedside oxygen source which automatically senses the flow of oxygen. In one example, oxygen delivery indicator, such as a flow-sensing monitor can be mounted on the oxygen gas port. The flow or pressure sensing monitor can have a connector for connecting to the oxygen gas port at one end, and the conventional gas delivery port at another end. This can be attached, as by threading onto the oxygen gas port when the oximeter is in use (or can be permanently connected to the rooms bedside the location occupied by the oximeter). The flow or pressure-sensing monitor includes a sensor, which identifies the presence of flow or pressure in the sensor, which is mounted at the port distal the oxygen flow valve. The presence of pressure sends a signal (such as an analog signal or digital signal) to the oximeter indicating the presence of oxygen flow (and the flow rate if desired). The processor is programmed to adjust the severity index and alarms for the presence of oxygen flow or pressure. This adjustment can be, for example, indicating all clusters as severe in the presence of oxygen or providing a weight for the presence of oxygen therapy (for example multiplying the severity index by about 3-4 or adding a value such as 50% of the maximum index to the calculated index. Alternatively the oxygen valve at the oxygen source can be an electronic valve, which provides an output such as a digital transmitted output of the flow rate being delivered or a flow sensor can be mounted on the flow tubing extending to the patient or otherwise along the flow path between the oxygen source and the patient internal airway. When a real-time oxygen delivery indicator is provided it can be combined with a nasal pressure and/or CO2 monitor so that both oxygen delivery, nasal catheter and/or mask position, and the pattern of patient response can be monitored.

As discussed previously, specific spatial, temporal, and frequency patterns vary as a function of specific pathophysiologic mechanisms, each of which produce a specific pattern type. Also, within each pathophysiologic mechanism, specific types of biologic failure modes can occur which produce specific patterns of deviation from the pattern type occurring without the failure. For this reason, an exemplary embodiment of the present invention generates an output, which renders a contemporaneous output of at least one of the detected adverse pattern type (if any), the detected failure mode and failure mode pattern type (if any), and sequential values or indicators indicative the magnitude, pattern, and/or trend of instability, such as a time series of instability integers (as, for example, derived form an aggregate analysis of the instability of the pattern). For the purpose of illustration, the factors derived of the patterns, which define clinical instability, can be divided into two main component classes: Class 1 can contain pattern components, which potentially induce or increase the probability of substantial adverse of an organ or organ system. Such adverse condition or injury include cardiac arrhythmias, cardiac ischemia, brain ischemia, enhanced thrombogenisis, and/or patient confusion to name a few. Examples of pattern subcomponents of Class 1 include high amplitude of the oxygen deficit as defined for example by a low SPO2 nadir, rapid progression of oxygen as defined for example by a steep slope SPO2 fall, high duration of the oxygen deficit as defined by a prolonged SPO2 fall, a short recovery interval, a high area above a portion of the SPO2 curve, the presence of cycling (which can result in autonomic stimulation and increased regional oxygen consumption) as detected by a wide range of measures, for example, frequency transforms, peak to trough detection, template comparison, to name a few. Class 2 can contain pattern sentinel components and subcomponents, which indicate an increased probability of progression of general instability as, for example, progression to stupor, coma, and/or respiratory arrest. A few examples of pattern subcomponents of Class 2 include variability of the arousal threshold (arousal threshold instability), increased arousal threshold (arousal threshold failure), and incomplete physiologic response to the perturbation (recovery failure).

The pattern components of the basic patterns of the pathophysiologic mechanisms and/or the pattern components indicative of a specific failure mode can be derived from a plurality of parameters and/or a plurality of processing methods. For example, an index combining a spatial pattern component of a time series of SPO2 may be combined with frequency component of the pleth to produce an aggregate component indicative of a magnitude of adverse perturbation. In another example, sequential measures of the maximum to minimum difference of the pleth amplitude (or pleth derived pulse rate) combined with sequential measures of the maximum to minimum difference of the SPO2 value, can be used to aggregate component indicative of the magnitude of perturbation. These pattern components and aggregate components may be detected and quantified by a wide range of techniques. Examples include, time series objectification, frequency transforms, template comparisons, adaptive methods, and/or the application of a moving window (for example a 20-180 second window) as with a set of rules for detecting minimum and maximum values and the spatial, temporal and/or frequency relationships such as the differences or distributions of or between these patterns to name a few.

One exemplary embodiment can produce a continuous instability index time series based on one or more, or at least, the following weighted factors; an indication of a minimum value or nadir relationship as, for example, a selected value minus the nadir value, an indication of a maximum value or peak relationship as for example a selected value minus the peak value, an indication of an area in relationship to the curve such as the product of the saturation seconds above the curve (and below a reference value if preferred which value can be varied with the detection of the presence of cycling). With any of these calculations, absolute value can be weighted for its difference from a normal or other reference value. For example, a greater weight (as a function of the value itself) can be applied to a SPO2 fall of 5 between 85 and 80 then a fall of 5 between 80 and 75. This is a useful weighting approach because, despite the presence of identical magnitudes of fall, the first fall of 5 is indicative of less inherent instability than the second fall of 5. Also, a greater increased severity weight (beyond the difference of 10) can be included in any subsequent calculation such that additional weight may be given to a data point having absolute SPO2 value of 70 then to a SPO2 data point having a value of 80 which weight is greater than the weight ascribable to their relative positions below 90. This type of weighting is particularly useful when the parameter comprises an absolute reference values (values in which the absolute range of normality is known) such as the CO2 or SPO2, the absolute value can be weighted for its difference from a normal or other reference value. An example of how such weighting can be derived discussed earlier for the SPO2 parameter. This type of value adjusted weighting can by used to derive an enhanced saturation seconds calculation where a given low SPO2 provides a greater weight than a higher value as a function of its absolute value, its difference from a reference value or by another method of weighting based on the relationship of the value to another value, a pattern, or a reference value. In this way, an instability index can be derived that is weighted as a direct function of the position of any given measured SPO2 or CO2 value in relation to a reference value or to the detection of a pattern such as a specific pattern of cycling. For example, an SPO2 value recognized at the nadir along a type IV pattern may be given less weight then an identical SPO2 value recognized at the peak along a type IV pattern. In another example, an SPO2 value recognized at the nadir along a type IV pattern may be given less weight then an identical SPO2 value recognized at the nadir along the more fundamentally unstable type III pattern. In each of these exemplary embodiments, the processor can be programmed to produce an automatic textual output of the aforementioned detected pattern type or types, an automatic textual output of any detected failure mode, such as arousal threshold failure or recovery failure, and a time series of the calculated aggregate or component severity index which relates to the severity of the pattern and the severity of the failure. In this way, the processor is programmed to output for the nurse in real time at the bedside and or central station, a display of the timed parameter, an automatic text indication of the pathophysiologic pattern types with reviewable archived text indications and the associated pattern, a text indication of the failure modes with reviewable archived text indications of failures and the associated failure pattern, and a timed numerical or other scale indication of the aggregate instability which is archived, reviewable at a range of scales, and analyzable for patterns of aggregate instability. The time series of aggregate instability can be incorporated into the cylindrical data matrix or otherwise used to compare the pattern or absolute values of aggregate instability with other parameter patterns, exogenous actions such as drug infusion, patient location (as by a time series output of a GPS recorder), or expense to name a few.

One exemplary embodiment comprises a monitor, a processor programmed to detect a maximum value, and to detect a maximum value below an expected or reference maximum value. The maximum value can be indicative of a recovery the maximum value below an expected or reference maximum value can be indicative of an incomplete recovery. The monitor can be an oximeter such as a pulse oximeter and the incomplete recovery can comprise an incomplete reciprocation as defined by a magnitude, slope, shape, timing or other relationship between a fall and a rise. In another example the incomplete recovery can comprise an incomplete reciprocation as defined by the absolute value of the peak or by a relationship between an absolute value of the peak or maximum value of the recovery and a reference value (such as a normal value). For example, the relationship can be a spatial relationship, a calculated difference, or a distance to name a few. The presence of a recovery can be detected by a wide range of methods or combinations of method or can be inferred (as, for example, by detecting a maximum value within a specified prolonged window or windows of time after a point wherein clustering is initially detected. In another example, the relative equivalent of a maximum value of at least one recovery within the window can be assumed if the detected minimum value within or adjacent the window is different, as by a pre-selected amount than a subsequent detected maximum value and wherein the detected maximum value is not the last value in the window.

One exemplary embodiment of the present invention comprises a monitor, a processor programmed to detect a minimum value, and to detect a minimum value below an expected or reference minimum value. The minimum value can be indicative of the nadir of a fall and the minimum value below an expected or reference minimum value can be indicative of clinically significant fall. One exemplary embodiment comprises a monitor, a processor programmed to detect a nadir and/or to detect a failing nadir (as with arousal threshold failure) or an unstable pattern of nadirs. The monitor can be an oximeter such as a pulse oximeter and presence of unstable nadirs can comprise nadir, which varies in relation to other nadirs as for example defined by a threshold pattern, slope, timing or shape of a plurality of nadirs. The nadirs can also be defined as a magnitude, slope, shape, timing or other relationship between a fall and a rise. The nadir can be defined, for example, by a relationship between an absolute value of the nadir, or minimum value of the fall, and a reference value (such as a normal value). For example, the relationship can be a spatial relationship, a calculated difference, or a distance to name a few. The presence of a fall and of a nadir can be detected by a wide range of methods or combinations of method or can be inferred (as, for example, by the detecting minimum value within a specified window of time, which is then assumed to be the relative equivalent of a minimum value of at least one fall within the window). In an example, this inference can be made if the detected minimum value within or adjacent the window is different, as by a pre-selected amount than the detected maximum value. The above approach is useful for parameters, which fall with increasing perturbation, such as SPO2; the CO2 often rises in association with the SPO2 falls induced by increasing levels of hypoventilation. For this reason, the peak of the CO2 in the above discussed processing can be used as indicative of the magnitude of the adverse event and the nadir to the recovery from the adverse event.

In an example using an oximeter, a method for monitoring a patient comprises, placing a probe of an oximeter adjacent a body part, outputting a time series of SPO2, detecting at least one of a plurality of minimum and maximum values of SPO2 along the time series, using at least one of the plurality minimum and maximum values, determining an index of the severity of a pathophysiolgic process such as unstable hypoventilation. The method can further comprise programmatically defining a moving window for the detection of the minimum and maximum values. The method can be similarly applied to CO2 monitors other monitors or to combined SPO2, CO2 and or other monitors.

In one embodiment, the processor is programmed to calculate a plurality of sequential and frequently updated values indicative of the global or near global instability of the patient which can be a time series of the patient's Global Instability Index (GII). The global instability index can be derived from the processing of the spatial, temporal, and frequency patterns and relationships of a plurality of numerical, spatial, temporal, and/or frequency derivatives of parameters such as oxygen saturation, exhaled carbon dioxide, respiratory rate, pulse, temperature, and blood pressure, to name a few. The global instability index can be derived of the patterns of at least one parameter compared with the pattern of at least another parameter and/or the absolute value of at least another parameter. The known presence of a potentially volatile disease or disorder or of a particular vulnerability can be induced to enhance the value of weighting. For example, if a patient is known to have coronary artery disease and/or a recent myocardial infarction the weight applied to the presence of clustering and/or to the nadir value of the SPO2 can be adjusted so that the patient with particular known vulnerability is identified as potentially more unstable by manifesting a higher or otherwise more severe real time index in the presence of clustering then a patient without this vulnerability. The nadir component can, for example, be doubled and then applied to derive SPO2 instability index which is then combined with derivatives of other parameters to output the global instability index. Alternatively, the SPO2 instability index could be weighted for the presence of coronary artery disease after it is calculated as a combined index or the global instability index could be weighted for the presence of coronary artery disease after it is calculated as a combined index. Additional volatile diseases include, for example, congestive heart failure, Type I diabetes, severe hypertension, sepsis, pulmonary embolism, pulmonary hypertension to name a few.

In one exemplary embodiment, a patient monitor is provided that comprises an instability detection and tracking monitor. The monitor preferably includes a large screen (which can be a pop-up screen) so that multiple time series and multiple instability indicators and/or instability time series can be displayed. For example, for the bedside version, a configuration with a large display as well as a large display-to-size ratio, similar to a tablet PC is suitable. A display that allows various time series to be scrolled up into view, is also acceptable to reduce size. The processor can be programmed to automatically move the most unstable time series into view upon, as on the occurrence of a threshold instability value or pattern. The instability monitor preferably includes a pulse oximeter and at least one ventilation monitor (such as a flow monitor, pressure monitor, impedance or other chest movement monitor, spirometer), and/or a CO2 monitor, and/or and at least one cardiovascular monitor (which can be the pleth portion of the pulse oximeter). The processor of the instability detection and tracking monitor may be programmed to define the SPO2 instability components and their subcomponents, the cardiovascular instability components and their subcomponents, and the ventilation instability components and their subcomponents. The processor can be programmed to determine sequential instability index calculations for each parameter and then to combine them to render sequential, unifying aggregate instability index calculations, which can be adjusted as discussed above for the presence of a disease, condition, other parameter, and/or pattern which is potentially fundamental destabilizing. In an example, each parameter specific instability index can render a value on a numerical scale between 1 and 100 as for example described for SPO2. Such a numerical may be finite or unbounded. The index of each of the parameters can be additive to render a global Instability index also with a value range of 1 to 100 (where index values above 100 are given as 100). In this way, a profound instability as potentially of any one parameter will trigger the maximum instability index whereas even a moderate instability, which is sufficient to cause substantial perturbation of all three, may trigger the maximum value. Also, combined patterns, such as the presence of divergence of SPO2 and respiratory rate may generate a minimum value to be added to the global instability index (such as 50), which is sufficient to reliably trigger the recommendation of a protocol, by the processor as discussed below.

In an exemplary embodiment, a threshold breach, trend or pattern of a parameter specific real-time or otherwise frequently updated instability index is used to trigger a protocol, which can be an assessment protocol, which for example calls for (or automatically triggers) additional testing, monitoring or treatment. The protocol can include a requisite entry based on the assessment of a health care worker such, for example, a review and confirmation of the SPO2 pattern before an the automatic positive airway pressure treatment and monitoring protocol is triggered. Using this embodiment, the processor can be programmed to identify an instability pattern type along a parameter, identify a failure pattern indicative of a specific failure mode (if any), determine a frequently updated instability index (which can be a time series of the instability index), identify a threshold level or pattern along the instability index, of the instability index of instability of a single parameter, trigger a protocol based at least one of the parameter, the detected pattern type (with or without health care worker confirmation of the pattern type), the failure mode, and the threshold level which triggered the protocol. The processor can be further programmed to; identify an instability pattern type along a plurality of parameters, identify a failure pattern along each of the parameters of at least one specific failure mode (if any), determine a frequently updated instability index for each parameter (which can be a time series of the instability index), add or otherwise combine the instability index to produce a global instability index, identify a threshold level or pattern along the global instability index or at least one of the instability index of the parameter, the detected pattern type (with or without health care worker confirmation of the pattern type), the failure mode, and the threshold level which triggered the protocol wherein the specific triggered protocol type triggered by the processor's determination of the detected pattern type (with or without health care worker confirmation of the pattern type). A typical protocol triggered by the processor, and outputted by the processor if desired, can include for example; review the patterns for confirmation of unstable hypoventilation "physician accepts pattern?", If yes, physician should also to review narcotic and sedative prescription and adjust as necessary, also if yes, call AutoPAP administration team (the processor can be programmed to automatically by the processor, fit mask and administer training, apply low acclimation pressures while patient is awake, review history, any patient history of CPAP use, if yes, apply minimum pressure as previously prescribed and maximum 5 cm higher, otherwise set min and max CPAP values at 5 and 12 respectively), connect autoCPAP output to the input port of the bedside instability tracking monitor (if wireless connection is not available), have patient notify nurse when ready to fall asleep, when patient is ready to fall asleep, apply mask and turn on the autoCPAP device with the 3 minute ramp, using the instability monitor connected with the autoCPAP device monitor the patterns. Call the AutoCPAP administration team if the SPO2 instability index is not reduced below 20 and global instability index of less than 30 or if the patterns are otherwise eliminated (this can be automatic as for example a notification at the respiratory therapist office such as "incomplete instability mitigation at bed 6 A, 8 north Tower" or at another station at a centralized control location. The protocol can also include secondary protocols based on the failure of correction of the instability index or the new development of a rising or otherwise high instability index despite the initiation of treatment.

Those skilled in the art will recognize that various changes and modifications can be made without departing from the invention. Many different pattern analysis methods, software tools, and mathematical calculations can be employed within the scope of the invention. In particular, it should be noted that the application of programming methods techniques such as, for example, adaptive programming, fuzzy logic, intentional programming, genetic algorithms and statistical processing are included in this teaching. While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A pulse oximeter, comprising:
a probe that is adapted to be attached to a body part of a patient to create a signal indicative of an oxygen saturation of blood of the patient; and
a processor that is adapted to receive the signal produced by the probe, to calculate an SPO2 value based on the signal, to detect a plurality of pattern types of SPO2 indicative of pathophysiologic events, to detect at least one SPO2 shape feature or value of a rise event of one of the pattern types of SPO2, and to recognize a condition of an arousal response failure based on the SPO2 shape feature or the value and produce a warning responsive to said recognizing.

2. The pulse oximeter recited in claim 1, comprising a display that is adapted to provide a visual indication corresponding to the warning.

3. The pulse oximeter recited in claim 2, wherein the visual indication comprises a text message.

4. The pulse oximeter recited in claim 1, wherein at least one of the plurality of pattern types is indicative of a recovery failure.

5. The pulse oximeter recited in claim 1, wherein at least one of the plurality of pattern types is indicative of a threshold failure.

6. The pulse oximeter recited in claim 1, the SPO2 shape feature comprising an SPO2 peak value.

7. The pulse oximeter recited in claim 1, the SPO2 shape feature comprising an SPO2 magnitude.

8. The pulse oximeter recited in claim 1, the SPO2 shape feature comprising a magnitude of the rise event in relationship to a magnitude of a corresponding fall event.

9. The pulse oximeter of claim 1, wherein the processor provides an output to initiate a therapeutic activity responsive to said recognizing.

10. The pulse oximeter of claim 9, wherein the therapeutic activity comprises a reduction of administration of a medication to the patient.

11. The pulse oximeter of claim 9, wherein the therapeutic activity comprises administration of a medication to the patient.

12. The pulse oximeter of claim 9, wherein the therapeutic activity comprises stimulating the patient.

13. The pulse oximeter of claim 1, wherein the processor provides an output to modify administration of a medication responsive to said recognizing.

14. A pulse oximeter, comprising:
a probe that is adapted to be attached to a body part of a patient to create a signal indicative of an oxygen saturation of blood of the patient; and
a processor that is adapted to receive the signal produced by the probe, to calculate an SPO2 value based on the signal, to detect a plurality of cluster pattern types of SPO2, to detect at least one SPO2 shape feature or value of a rise event of one of the pattern types of SPO2, and to recognize a condition of an arousal response failure based on the SPO2 shape feature or the value and produce a warning responsive to said recognizing.

15. The pulse oximeter recited in claim 14, comprising a display that is adapted to provide a visual indication corresponding to the warning.

16. The pulse oximeter recited in claim 15, wherein the visual indication comprises a text message.

17. The pulse oximeter recited in claim 14, wherein the at least one cluster pattern type is indicative of a recovery failure.

18. The pulse oximeter recited in claim 14, wherein the at least one of the plurality of pattern types is indicative of a threshold failure.

19. The pulse oximeter recited in claim 14 wherein the processor is adapted to calculate a plurality of sequential severity indices of the at least one cluster pattern type.

20. The pulse oximeter recited in claim 14, wherein the processor is adapted to calculate a time series of severity indices of the at least one cluster pattern type.

21. The pulse oximeter recited in claim 14, the SPO2 shape feature comprising an SPO2 peak value.

22. The pulse oximeter recited in claim 14, the SPO2 shape feature comprising an SPO2 magnitude.

23. The pulse oximeter recited in claim 14, the SPO2 shape feature comprising a magnitude of the rise event in relationship to a magnitude of a corresponding fall event.

24. A pulse oximeter, comprising:
a probe that is adapted to be attached to a body part of a patient to create a signal indicative of an oxygen saturation of blood of the patient; and
a processor that is adapted to receive the signal produced by the probe, to calculate an SPO2 value based on the signal, to detect a plurality of different cluster pattern types of SPO2, to detect at least one SPO2 shape feature or value of a rise event of one of the pattern types of SPO2, and to recognize a condition of an arousal response failure based on the SPO2 shape feature or the value and produce a warning responsive to said recognizing.

25. The pulse oximeter recited in claim 24, comprising a display that is adapted to provide a visual indication corresponding to the warning.

26. The pulse oximeter recited in claim 25, wherein the visual indication comprises a text message.

27. The pulse oximeter recited in claim 24, wherein at least one of the plurality of cluster pattern types is indicative of a recovery failure.

28. The pulse oximeter recited in claim 24, wherein at least one of the plurality of cluster pattern types is indicative of a threshold failure.

29. The pulse oximeter recited in claim 24 wherein the processor is adapted to calculate a plurality of sequential severity indices of at least one of the plurality of cluster pattern types.

30. The pulse oximeter recited in claim 24, wherein the processor is adapted to calculate a time series of severity indices of at least one of the plurality of cluster pattern types.

31. The pulse oximeter recited in claim 24, wherein the processor is adapted to determine an indication of severity of the detected cluster pattern type.

32. The pulse oximeter recited in claim 24, wherein the processor is adapted to display an indication of severity of the detected cluster pattern type.

33. The pulse oximeter recited in claim 24, wherein the processor is adapted to calculate a plurality of sequential severity indices of the detected cluster pattern type.

34. The pulse oximeter recited in claim 24, wherein the processor is adapted to calculate a time series of severity indices of the detected cluster pattern type.

35. The pulse oximeter recited in claim 24, the SPO2 shape feature comprising an SPO2 peak value.

36. The pulse oximeter recited in claim 24, the SPO2 shape feature comprising an SPO2 magnitude.

37. The pulse oximeter recited in claim 24, the SPO2 shape feature comprising a magnitude of the rise event in relationship to a magnitude of a corresponding fall event.

38. A method of monitoring a patient, comprising:
 receiving a signal indicative of an oxygen saturation of blood of the patient;
 calculating an SPO2 value based on the signal on a processor of a monitor;
 detecting a plurality of pattern types of SPO2 indicative of pathophysiologic events suggestive of arousal response failure;
 detecting at least one SPO2 shape feature or value of a rise event of one of the pattern types of SPO2;
 recognizing, via a processor, a condition of the arousal response failure based on the SPO2 shape feature or the value; and
 producing a warning responsive to said recognizing.

39. The method of claim 38, wherein the SPO2 shape feature comprises an SPO2 peak value.

40. The method of claim 38, wherein the SPO2 shape feature comprises an SPO2 magnitude.

41. The method of claim 38, wherein the SPO2 shape feature comprises a magnitude of the rise event in relationship to a magnitude of a corresponding fall event.

42. The method of claim 38, wherein the processor provides an output to initiate a therapeutic activity responsive to said recognizing.

43. The method of claim 42, wherein the therapeutic activity comprises a reduction of administration of a medication to the patient.

44. The method of claim 42, wherein the therapeutic activity comprises administration of a medication to the patient.

45. The method of claim 42, wherein the therapeutic activity comprises stimulating the patient.

46. A method of monitoring a patient, comprising:
 receiving a signal indicative of an oxygen saturation of blood of the patient;
 calculating an SPO2 value based on the signal on a processor of a monitor;
 detecting a plurality of cluster pattern types of SPO2 suggestive of arousal response failure;
 detecting at least one SPO2 shape feature or value of a rise event of one of the pattern types of SPO2;
 recognizing, via a processor, a condition of the arousal response failure based on the SPO2 shape feature or the value; and
 producing a warning responsive to said recognizing.

47. The method of claim 46, wherein the SPO2 shape feature comprises an SPO2 peak value.

48. The method of claim 46, wherein the SPO2 shape feature comprises an SPO2 magnitude.

49. The method of claim 46, wherein the SPO2 shape feature comprises a magnitude of the rise event in relationship to a magnitude of a corresponding fall event.

50. A method of monitoring a patient, comprising:
 receiving a signal indicative of an oxygen saturation of blood of the patient;
 calculating an SPO2 value based on the signal on a processor of a monitor;
 detecting a plurality of different cluster pattern types of SPO2 suggestive of arousal response failure;
 detecting at least one SPO2 shape feature or value of a rise event of one of the pattern types of SPO2;
 recognizing, via a processor, a condition of the arousal response failure based on the SPO2 shape feature or the value; and
 producing a warning responsive to said recognizing.

51. The method of claim 50, wherein the SPO2 shape feature comprises an SPO2 peak value.

52. The method of claim 50, wherein the SPO2 shape feature comprises an SPO2 magnitude.

53. The method of claim 50, wherein the SPO2 shape feature comprises a magnitude of the rise event in relationship to a magnitude of a corresponding fall event.

\* \* \* \* \*